US011634729B2

(12) United States Patent
Stevens

(10) Patent No.: US 11,634,729 B2
(45) Date of Patent: Apr. 25, 2023

(54) SEC MODIFIED STRAINS FOR IMPROVED SECRETION OF RECOMBINANT PROTEINS

(71) Applicant: Bolt Threads, Inc., Emeryville, CA (US)

(72) Inventor: Thomas Stevens, San Francisco, CA (US)

(73) Assignee: BOLT THREADS, INC., Emeryville, CA (US)

( * ) Notice: Subject to any disclaimer, the term of this patent is extended or adjusted under 35 U.S.C. 154(b) by 0 days.

(21) Appl. No.: 16/415,605

(22) Filed: May 17, 2019

(65) Prior Publication Data

US 2019/0390228 A1 Dec. 26, 2019

Related U.S. Application Data

(60) Provisional application No. 62/673,001, filed on May 17, 2018.

(51) Int. Cl.
*C12N 15/90* (2006.01)
*C07K 16/14* (2006.01)
*C12N 15/62* (2006.01)

(52) U.S. Cl.
CPC ............ *C12N 15/905* (2013.01); *C07K 16/14* (2013.01); *C12N 15/625* (2013.01)

(58) Field of Classification Search
CPC .................................................. C12N 15/905
See application file for complete search history.

(56) References Cited

U.S. PATENT DOCUMENTS

| 6,228,590 B1 * | 5/2001 | Baker |
| 2011/0021378 A1 | 1/2011 | Callewaert et al. |
| 2017/0029827 A1 | 2/2017 | Gasser et al. |
| 2018/0079788 A1 * | 3/2018 | Achmuller ............ C07K 14/395 |

FOREIGN PATENT DOCUMENTS

| WO | WO-2010135678 A1 * | 11/2010 | ........... C07K 14/395 |
| WO | 2015/042164 A2 | 3/2015 | |
| WO | 2019/070246 A1 | 4/2019 | |

OTHER PUBLICATIONS

Feldhiem et. al. Sec72p Contributes to the Selective Recognition of Signal Peptides by the Secretory I lypeptide Transl ation Complex 1994, The Journal of Cell Biology, vol. 126, No. 4, 935-943 (Year: 1994).*
Schutter et. al. Genome sequence of the recombinant protein production host Pichia pastoris. 2009. Nature Biotechnology vol. 27 No. 6 (Year: 2009).*
J.L. Cereghino, J.M. Cregg. Heterologous protein expression in the methylotrophic yeast *Pichia pastoris* FEMS Microbiology Reviews 24 (2000) 45-66 (Year: 2000).*
Delic et. al. Engineering of Protein Folding and Secretion—Strategies to Overcome Bottlenecks for Efficient Production of Recombinant Proteins. 2014. Antioxidants & Redox Signaling vol. 21, No. 3 (Year: 2014).*
GenBank: ADO95142.1. alpha-mating factor secretion signal peptide/hemagglutinin fusion protein. 2012. Accession ADO95142 (Year: 2012).*
Jiang et al. An interaction between the SRP receptor and the translocon is critical during cotranslational protein translocation. 2008. The Journal of Cell Biology, vol. 180, No. 6, 1149-1161 (Year: 2008).*
Accession XM_002491310, 2017. Komagataella phaffii GS115 Non-essential subunit of Sec63 complex (Sec63p, Sec62p, Sec6 6p and Sec7 2p) (PAS_chr2-1_0448), partial mRNA (Year: 2 017).*
Fahnstock et al. Microbial production of spider silk proteins. 2000 Reviews in Molecular Biotechnology 74 105-119 (Year: 2000).*
Feldheim et al. Sec72p Contributes to the Selective Recognition of Signal Peptides by the Secretory Polypeptide Translation Complex 1994 The Journal of Cell Biology, vol. 126, No. 4, 935-943 (Year: 1994).*
Feldheim and Schekman. "Sec72p Contributes to the Selective Recognition of Signal Peptides by the Secretory Polypeptide Translocation Complex"; J. Cell Bio.; vol. 126, No. 4, pp. 935-943, Aug. 15, 1994. PMID 8051213.
Ast et al.; "A Network of Cytosolic Factors Targets SRP-Independent Proteins to the Endoplasmic Reticulum"; Cell; vol. 152, No. 5, pp. 1134-1145, Feb. 2013. PMID 23452858.
Finke et al.; "A second trimeric complex containing homologs of the Sec6lp complex functions in protein transport across the ER membrane of S. cerevisiae"; EMBO J.; vol. 15, No. 7, pp. 1482-1494, 1996. PMID 8612571.
Jan et al.; "Principles of ER cotranslational translocation revealed by proximity-specific ribosome profiling"; Science vol. 346, No. 6210, Nov. 7, 2014. PMID 25378630.
Wittke et al.; "Recognition of a Subset of Signal Sequences by Ssh1p, a Sec61p-related Protein in the Membrane of Endoplasmic Reticulum of Yeast *Saccharomyces cerevisiae*"; Mol. Biol. Cell., vol. 13, No. 7, pp. 2223-2232, Jul. 2002. PMID 12134063.
Jaing et al.; "An interaction between the SRP receptor and the translocon is critical during cotranslational protein translocation"; J. Cell. Biol., vol. 180, No. 6, pp. 1149-1161, Mar. 24, 2008. PMID 18347066.
Delic et al. "The secretory pathway: exploring yeast diversity"; FEMS Microbiol. Rev., vol. 37, No. 6, pp. 872-914, Nov. 2013. PMID 23480475.
Uniprotkb Accession C4R0Q1. C4R0Q1_KOMPG (online) Nov. 22, 2017 [retrieved Aug. 29, 2019]. Available on the internet <https://www.uniprot.org/uniprot/C4ROQ1.txt?version-54>.

(Continued)

*Primary Examiner* — Scarlett Y Goon
*Assistant Examiner* — Tiffany Nicole Grooms
(74) *Attorney, Agent, or Firm* — Marshall, Gerstein & Borun LLP

(57) ABSTRACT

Disclosed herein are modified strains for improving secretion of recombinantly expressed products secreted from a host organism with improved growth and productivity characteristics, as well as methods of using the modified strains.

23 Claims, 16 Drawing Sheets

Specification includes a Sequence Listing.

(56) References Cited

OTHER PUBLICATIONS

Harty et al. Analysis of Sec61p and Ssh1p interactions in the ER membrane using the split-ubiquitin system. BMC Cell Biol Mar. 11, 2013 vol. 14 No. 14 pp. 1-12.

Uniprotkb Accession F2QQ76. F2QQ76_KOMPC. (online) Nov. 22, 2017 [retrieved Aug. 29, 2019]. Available on the internet: <https://www.uniprot.org/uniprot/F2QQ76.txt?version=40>.

Uniprot Accession C4QVV4. C4QVV4_KOMG. online) Nov. 22, 2017 [retrieved Aug. 29, 2019]. Available on the internet: <https://www.uniprot.org/uniprot/C4VV4.txt?version-55>.

PCT International Search Report and Written Opinion App. PCT/US19/32879 dated Sep. 20, 2019.

Fahnestock et al., Production of synthetic spider dragline silk protein in Pichia pastoris, Applied Microbiology and Biotechnology, 47(1):33-39 (1997).

Supplementary European Application No. 19804157.6, European Search Report and Opinion, dated Feb. 23, 2022.

Whittall et al., Host Systems for the Production of Recombinant Spider Silk, Trends in Biotechnology, 39(6):560-573 (2021).

Ji Hai-bing et al., "Gene cloning, expression and enzymatic properties of carboxypeptidase Y from Actinomyces elegans", Modern Food Science and Technology, 33(1):80-86 (2017).

UniProtKB/Swiss-Prot P07267 (2009).

UniProtKB/Swiss-Prot P01149 (2008).

\* cited by examiner

| Complex Membership | | | S. cerevisiae | P. pastoris | % ID (blastp) |
|---|---|---|---|---|---|
| SEC (heptameric) | SEC61 (trimeric) | SSH1 (trimeric) | SSH1 | PAS_chr1-4_0629 | 39% |
| | | | SSS1 | PAS_chr1-1_0023 | 52% |
| | | | SBH2* | PAS_chr2-2_0210 | 57% |
| | | SEC63 complex | SEC61 | PAS_chr1-3_0202 | 70% |
| | | | SEC62 | PAS_chr3_1014 | 35% |
| | | | SEC63 | PAS_chr4_0395 | 38% |
| | | | SEC66 | PAS_chr2-1_0433 | 41% |
| | | | SEC72 | PAS_chr2-1_0448 | 29% |

FIG. 1

Homology Arm Insertion into Nourseothricin Marker Plasmid

SEC MODIFIED STRAINS FOR IMPROVED SECRETION OF RECOMBINANT PROTEINS

CROSS-REFERENCE TO RELATED APPLICATIONS

This application claims the benefit of U.S. Provisional Application No. 62/673,001, filed May 17, 2018, the contents of which are incorporated by reference in its entirety.

SEQUENCE LISTING

The instant application contains a Sequence Listing which has been filed electronically in ASCII format and is hereby incorporated by reference in its entirety. Said ASCII copy, created on Jun. 25, 2019, is named BTT-019_Sequence_Listing.txt and is 261,196 bytes in size.

FIELD OF THE INVENTION

The present disclosure relates to methods of strain optimization to enhance secretion of proteins or metabolites from cells. The present disclosure also relates to compositions resulting from those methods. In particular, the disclosure relates to yeast cells selected or genetically engineered to enhance secretion of recombinant proteins expressed by the yeast cells, while minimizing or improving growth yields, and to methods of cultivating yeast cells for the production of useful compounds.

BACKGROUND OF THE INVENTION

The methylotrophic yeast *Pichia pastoris* is widely used in the production of recombinant proteins. *P. pastoris* grows to high cell density, provides tightly controlled methanol-inducible trans gene expression and is capable of secreting recombinant proteins into a defined media.

However, much of the expressed recombinant protein remains located intracellularly, which can make collection difficult and can negatively impact cell growth and longevity. Furthermore, recombinantly expressed proteins may be degraded in the cell before they are secreted, resulting in a mixture of proteins that includes fragments of recombinantly expressed proteins and a decreased yield of full-length recombinant proteins. What is needed, therefore, are tools and engineered strains to enhance secretion in *P. pastoris*, while mitigating any loss of or improving recombinant protein productivity, including maintaining growth characteristics, as many modifications can negatively impact the natural functioning of the cell.

What is needed, therefore, are modified organisms and methods of using these organisms to produce and secrete recombinant proteins while minimizing any negative effect on cell growth and productivity.

SUMMARY OF THE INVENTION

In some embodiments, provided herein is A *Pichia pastoris* microorganism, in which the activity of SEC72 has been eliminated or the sec72 gene has been deleted, and wherein said microorganism expresses a recombinant protein. In some embodiments, the microorganism further compress a recombinantly expressed SSH1 translocon complex.

In some embodiments, the SEC72 comprises a polypeptide sequence at least 95% identical to SEQ ID NO: 1. In some embodiments, the SEC72 comprises SEQ ID NO: 1. In some embodiments, the SEC72 is encoded by a sec72 gene. In some embodiments, the sec72 gene comprises a polynucleotide sequence at least 95% identical to SEQ ID NO: 2. In some embodiments, the sec72 gene comprises at least 15, 20, 25, 30, 40, or 50 contiguous nucleotides of SEQ ID NO: 2. In some embodiments, the sec72 gene comprises SEQ ID NO: 2. In some embodiments, the sec72 gene is at locus PAS_chr2-1_0448 of said microorganism.

In some embodiments, the SSH1 translocon complex comprises a first polypeptide sequence at least 95% identical to SEQ ID NO: 4, a second polypeptide sequence at least 95% identical to SEQ ID NO: 6, and a third polypeptide sequence at least 95% identical to SEQ ID NO: 8. In some embodiments, the SSH1 translocon complex comprises a first polypeptide comprising SEQ ID NO: 4, a second polypeptide comprising SEQ ID NO: 6, and a third polypeptide comprising SEQ ID NO: 8.

In some embodiments, the microorganism further comprises a recombinantly expressed translocon complex. In some embodiments, the translocon complex is expressed from a recombinant SSH1 gene, a recombinant SSS1 gene, and a recombinant SBH2 gene.

In some embodiments, the SSH1 gene comprises SEQ ID NO: 3. In some embodiments, the SSH1 gene comprises a polynucleotide sequence at least 95% identical to SEQ ID NO: 3. In some embodiments, the SSH1 gene comprises at least 15, 20, 25, 30, 40, or 50 contiguous nucleotides of SEQ ID NO: 3.

In some embodiments, the SSS1 gene comprises SEQ ID NO: 5. In some embodiments, the SSS1 gene comprises a polynucleotide sequence at least 95% identical to SEQ ID NO: 5. In some embodiments, the SSS1 gene comprises at least 15, 20, 25, 30, 40, or 50 contiguous nucleotides of SEQ ID NO: 5.

In some embodiments, the SBH2 gene comprises SEQ ID NO: 7. In some embodiments, the SBH2 gene comprises a polynucleotide sequence at least 95% identical to SEQ ID NO: 7. In some embodiments, the SBH2 gene comprises at least 15, 20, 25, 30, 40, or 50 contiguous nucleotides of SEQ ID NO: 7.

In some embodiments, expression of said recombinant SSH1 gene to increase levels of said SSH1 translocon in said microorganism above that expressed by the native organism improves the growth rate and/or fermentation performance of said microorganism.

In some embodiments, the translocon complex comprises an SSH1 protein, an SSS1 protein, and an SBH2 protein. In some embodiments, the SSH1 protein comprises a polypeptide sequence at least 95% identical to SEQ ID NO: 4. In some embodiments, the SSH1 protein comprises SEQ ID NO: 4. In some embodiments, the SSS1 protein comprises a polypeptide sequence at least 95% identical to SEQ ID NO: 6. In some embodiments, the SSS1 protein comprises SEQ ID NO: 6. In some embodiments, the SBH2 protein comprises a polypeptide sequence at least 95% identical to SEQ ID NO: 8. In some embodiments, the SBH2 protein comprises SEQ ID NO: 8.

In some embodiments, the activity of a YPS1-1 protease and a YPS1-2 protease in said microorganism has been attenuated or eliminated.

In some embodiments, the YPS1-1 protease comprises a polypeptide sequence at least 95% identical to SEQ ID NO: 10. In some embodiments, the YPS1-1 protease comprises SEQ ID NO: 10. In some embodiments, the YPS1-1 protease is encoded by a YPS1-1 gene. In some embodiments, the YPS1-1 gene comprises a polynucleotide sequence at least 95% identical to SEQ ID NO: 9. In some embodiments, the YPS1-1 gene comprises at least 15, 20, 25, 30, 40, or 50 contiguous nucleotides of SEQ ID NO: 9. In some embodiments, the YPS1-1 gene comprises SEQ ID NO: 9. In some embodiments, the YPS1-1 gene is at locus PAS_chr4_0584 of said microorganism.

In some embodiments, the YPS1-2 protease comprises a polypeptide sequence at least 95% identical to SEQ ID NO: 12. In some embodiments, the YPS1-2 protease comprises SEQ ID NO: 12. In some embodiments, the YPS1-2 protease is encoded by a YPS1-2 gene. In some embodiments, the YPS1-2 gene comprises a polynucleotide sequence at least 95% identical to SEQ ID NO: 11. In some embodiments, the YPS1-2 gene comprises at least 15, 20, 25, 30, 40, or 50 contiguous nucleotides of SEQ ID NO: 11. In some embodiments, the YPS1-2 gene comprises SEQ ID NO: 11. In some embodiments, the YPS1-2 gene is at locus PAS_chr3_1157 of said microorganism.

In some embodiments, the YPS1-1 gene or said YPS1-2 gene, or both, of said microorganism has been mutated or knocked out. In some embodiments, the activity of one or more additional proteases of said microorganism has been attenuated or eliminated.

In some embodiments, the recombinant protein expressed by said microorganism comprises at least one block polypeptide sequence from a silk protein. In some embodiments, the recombinant protein comprises a silk-like polypeptide. In some embodiments, the silk-like polypeptide comprises one or more repeat sequences $\{GGY\text{-}[GPG\text{-}X_1]_{n1}\text{-}GPS\text{-}(A)_{n2}\}_{n3}$ (SEQ ID NO: 13), wherein $X_1$=SGGQQ (SEQ ID NO: 14) or GAGQQ (SEQ ID NO: 15) or GQGPY (SEQ ID NO: 16) or AGQQ (SEQ ID NO: 17) or SQ; n1 is from 4 to 8; n2 is from 6 to 20; and n3 is from 2 to 20. In some embodiments, the silk-like polypeptide comprises comprises a polypeptide sequence encoded by SEQ ID NO: 21.

In some embodiments, the recombinant protein comprises a secretion signal peptide. In some embodiments, the secretion signal peptide is selected from the group consisting of: a PEP4 signal sequence, a CPY +4 signal sequence, a DAP2 signal sequence, and a MFα1 signal sequence. In some embodiments, the secretion signal peptide is selected from the group consisting of: SEQ ID NO: 84, SEQ ID NO: 86, SEQ ID NO: 88, and SEQ ID NO: 90.

Also provided herein, according to some embodiments, is a *Pichia pastoris* microorganism, wherein the activity of SEC72 of said microorganism has been eliminated or an sec72 gene comprising SEQ ID NO: 1 has been knocked out, wherein the microorganism comprises a recombinantly expressed SSH1 gene comprising SEQ ID NO: 3, a recombinantly expressed SSS1 gene comprising SEQ ID NO: 5, and a recombinantly expressed SBH2 gene comprising SEQ ID NO: 7, and wherein said microorganism comprises a silk-like polypeptide comprising a polypeptide sequence encoded by SEQ ID NO: 21.

Also provided herein, according to some embodiments, is a cell culture comprising a recombinant microorganism described herein.

Also provided, herein, according to some embodiments, is a cell culture comprising a recombinant microorganism as described herein, wherein said cell culture has an improved strain growth rate and fermentation performance under standard cell culture conditions as compared to a cell culture that does not comprise a recombinantly expressed SSH1 translocon complex.

Also provided, herein, according to some embodiments, is a cell culture comprising a recombinant microorganism as described herein, wherein said cell culture has an improved yield or specific productivity of said recombinant protein under standard cell culture conditions as compared to a cell culture of otherwise identical microorgansims that comprises a functional sec72 gene and does not comprise a recombinantly expressed SSH1 translocon complex, wherein each microorganism has the same number of copies of recombinant silk polypeptide genes.

Also provided herein, according to some embodiments, is a method of producing a recombinant protein, the method comprising: culturing the recombinant microorganism described herein in a culture medium under conditions suitable for expression of the recombinantly expressed protein; and isolating the recombinant protein from the microorganism or the culture medium.

In some embodiments, the recombinant protein is secreted from said microorganism, and isolating said recombinant protein comprises collecting a culture medium comprising said secreted recombinant protein.

In some embodiments, the microorganism has an increased yield or specific productivity of said recombinant protein as compared to an otherwise identical microorganism wherein said sec72 gene is not deleted.

In some embodiments, the microorganism has an increased yield or specific productivity of said recombinant protein as compared to an otherwise identical microorganism not comprising said recombinantly expressed SSH1 translocon complex, and wherein said sec72 gene is not deleted.

Also provided herein, according to some embodiments, is a method of modifying *Pichia pastoris* to improve the secretion of a recombinantly expressed protein, said method comprising knocking out a gene encoding an SEC72 protein. In some embodiments, the method of modifying *Pichia pastoris* to improve the secretion of a recombinantly expressed protein further comprises transforming said *Pichia pastoris* with a vector comprising genes encoding a recombinantly expressed SSH1 translocon complex.

In some embodiments, the recombinantly expressed protein comprises a silk-like polypeptide. In some embodiments, the silk-like polypeptide comprises one or more repeat sequences $\{GGY\text{-}[GPG\text{-}X_1]_{n1}\text{-}GPS\text{-}(A)_{n2}\}_{n3}$ (SEQ ID NO: 13), wherein $X_1$=SGGQQ (SEQ ID NO: 14) or GAGQQ (SEQ ID NO: 15) or GQGPY (SEQ ID NO: 16) or AGQQ (SEQ ID NO: 17) or SQ; n1 is from 4 to 8; n2 is from 6 to 20; and n3 is from 2 to 20. In some embodiments, the recombinantly expressed protein comprises a polypeptide sequence encoded by SEQ ID NO: 21.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead placed upon illustrating the principles of various embodiments of the invention.

FIG. 1 depicts groupings of genes in secretion complexes SEC, SEC61, SEC63, and SSH1. Also shown is a value of the homology between *S. cerevisiae* and *P. pastoris* translocon complex proteins.

DETAILED DESCRIPTION

Figure 2:
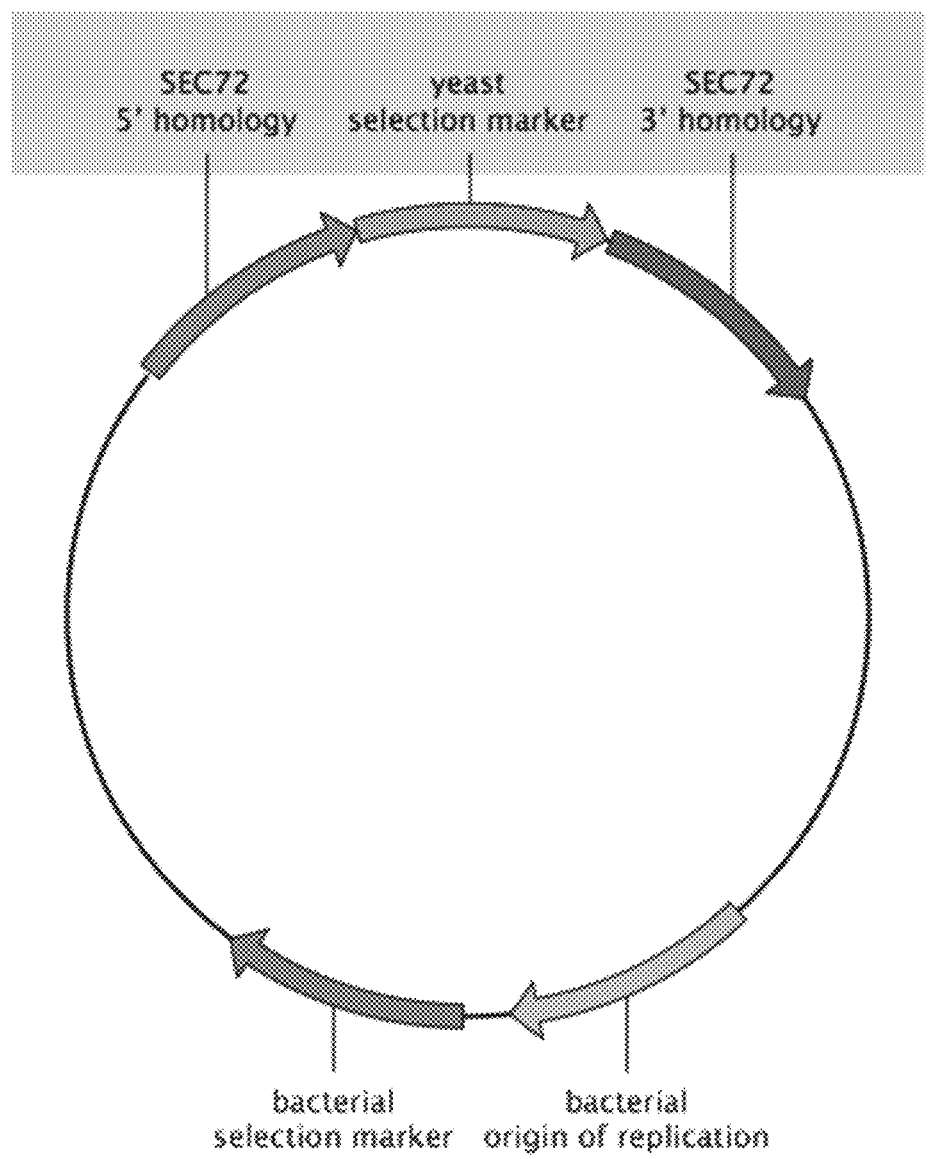
FIG. 2 is a plasmid map of a vector for SEC72 deletion comprising a yeast selection marker flanked by SEC72 homology arms.

The details of various embodiments of the invention are set forth in the description below. Other features, objects, and advantages of the invention will be apparent from the description and the drawings, and from the claims.

Definitions

Unless otherwise defined herein, scientific and technical terms used in connection with the present invention shall have the meanings that are commonly understood by those of ordinary skill in the art. Further, unless otherwise required by context, singular terms shall include the plural and plural terms shall include the singular. The terms "a" and "an" includes plural references unless the context dictates otherwise. Generally, nomenclatures used in connection with, and techniques of, biochemistry, enzymology, molecular and cellular biology, microbiology, genetics and protein and nucleic acid chemistry and hybridization described herein are those well-known and commonly used in the art.

The following terms, unless otherwise indicated, shall be understood to have the following meanings:

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hair-pinned, circular, or in a padlocked conformation.

Unless otherwise indicated, and as an example for all sequences described herein under the general format "SEQ ID NO:", "nucleic acid comprising SEQ ID NO:1" refers to a nucleic acid, at least a portion of which has either (i) the sequence of SEQ ID NO:1, or (ii) a sequence complementary to SEQ ID NO:1. The choice between the two is dictated by the context. For instance, if the nucleic acid is used as a probe, the choice between the two is dictated by the requirement that the probe be complementary to the desired target.

The term "recombinant" refers to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids.

An endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "recombinant" because it is separated from at least some of the sequences that naturally flank it.

A nucleic acid is also considered "recombinant" if it contains any modifications that do not naturally occur to the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990) (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)).

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 75%, 80%, 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

The nucleic acids (also referred to as polynucleotides) of this present invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product; see, e.g., Leung et al., *Technique*, 1:11-15 (1989) and Caldwell and Joyce, *PCR Methods Applic.* 2:28-33 (1992)); and "oligonucleotide-directed mutagenesis" (a process which enables the generation of site-specific mutations in any cloned DNA segment of interest; see, e.g., Reidhaar-Olson and Sauer, *Science* 241:53-57 (1988)).

The term "attenuate" as used herein generally refers to a functional deletion, including a mutation, partial or complete deletion, insertion, or other variation made to a gene sequence or a sequence controlling the transcription of a gene sequence, which reduces or inhibits production of the gene product, or renders the gene product non-functional. In some instances a functional deletion is described as a knockout mutation. Attenuation also includes amino acid sequence changes by altering the nucleic acid sequence, placing the gene under the control of a less active promoter, down-regulation, expressing interfering RNA, ribozymes or antisense sequences that target the gene of interest, or through any other technique known in the art. In one example, the sensitivity of a particular enzyme to feedback inhibition or inhibition caused by a composition that is not a product or a reactant (non-pathway specific feedback) is lessened such that the enzyme activity is not impacted by the presence of a compound. In other instances, an enzyme that has been altered to be less active can be referred to as attenuated.

The term "deletion" as used herein refers to the removal of one or more nucleotides from a nucleic acid molecule or one or more amino acids from a protein, the regions on either side being joined together.

The term "knock-out" as used herein is intended to refer to a gene whose level of expression or activity has been reduced to zero. In some examples, a gene is knocked-out via deletion of some or all of its coding sequence. In other examples, a gene is knocked-out via introduction of one or more nucleotides into its open reading frame, which results in translation of a non-sense or otherwise non-functional protein product.

The term "vector" as used herein is intended to refer to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply "expression vectors").

"Operatively linked" or "operably linked" expression control sequences refers to a linkage in which the expression control sequence is contiguous with the gene of interest to control the gene of interest, as well as expression control sequences that act in trans or at a distance to control the gene of interest.

The term "expression control sequence" refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "regulatory element" refers to any element which affects transcription or translation of a nucleic acid molecule. These include, by way of example but not limitation: regulatory proteins (e.g., transcription factors), chaperones, signaling proteins, RNAi molecules, antisense RNA molecules, microRNAs and RNA aptamers. Regulatory elements may be endogenous to the host organism. Regulatory elements may also be exogenous to the host organism. Regulatory elements may be synthetically generated regulatory elements.

The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription. Promoters may be endogenous to the host organism. Promoters may also be exogenous to the host organism. Promoters may be synthetically generated regulatory elements.

Promoters useful for expressing the recombinant genes described herein include both constitutive and inducible/repressible promoters. Where multiple recombinant genes are expressed in an engineered organism of the invention, the different genes can be controlled by different promoters or by identical promoters in separate operons, or the expression of two or more genes may be controlled by a single promoter as part of an operon.

The term "recombinant host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "wild-type" (i.e., "WT") as used herein refers to a comparative strain lacking the modification being discussed. It does not refer to the native, unmodified strain, but rather to a strain lacking a selected modification. For example, when comparing two versions of a recombinant strain modified to express a recombinant silk polypeptide, where one is a sec72 KO, the KO strain may be referred to as the $\Delta$sec72 strain, while the other version is referred to as "WT."

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

The term "polypeptide fragment" refers to a polypeptide that has a deletion, e.g., an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences.) As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, *Methods Mol. Biol.* 24:307-31 and 25:365-89 (herein incorporated by reference).

The twenty conventional amino acids and their abbreviations follow conventional usage. See *Immunology-A Synthesis* (Golub and Gren eds., Sinauer Associates, Sunderland, Mass., 2$^{nd}$ ed. 1991), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, N-methylarginine, and other similar amino acids and imino acids (e.g., 4-hydroxyproline). In the polypeptide notation used herein, the left-hand end corresponds to the amino terminal end and the right-hand end corresponds to the carboxy-terminal end, in accordance with standard usage and convention.

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is sometimes also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

A useful algorithm when comparing a particular polypeptide sequence to a database containing a large number of sequences from different organisms is the computer program BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62. The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, *Methods Enzymol.* 183:63-98 (1990) (incorporated by reference herein). For example, percent sequence identity between amino acid sequences can be determined using FASTA with its default parameters (a word size of 2 and the PAM250 scoring matrix), as provided in GCG Version 6.1, herein incorporated by reference.

Throughout this specification and claims, the word "comprise" or variations such as "comprises" or "comprising," will be understood to imply the inclusion of a stated integer or group of integers but not the exclusion of any other integer or group of integers.

Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Overview

Provided herein are recombinant strains and methods of improving secretion and productivity of recombinantly expressed proteins in yeast strains (e.g., P. pastoris).

Proteins destined for secretion must first cross the membrane of the endoplasmic reticulum (ER translocation). Multiple targeting pathways recruit elongating ribosomes or fully translated proteins to the ER membrane, which polypeptide chains enter via pore-forming protein complexes called translocons. Yeasts including S. cerevisiae and P. pastoris express two translocons, the SEC61 and SSH1 complexes. Each consists of a core trimeric complex, but the SEC61 translocon also associates with the tetrameric SEC63 complex. FIG. 1 shows the protein subunits contained within each of these translocon complexes.

SEC72 encodes a nonessential member of the SEC63 complex, but deletion of SEC72 (Δsec72) results in the accumulation of some secretory precursors. Surprisingly, herein we show that Δsec72 strains have improved secretion of recombinant silk polypeptides.

In some embodiments, the strains are modified to delete the sec72 gene (SEQ ID NO: 1). As we describe and shown herein, the deletion of sec72, which expresses SEC72 (SEQ ID NO: 2), an accessory factor for translocating proteins into the ER for secretion, unexpectedly assists silk secretion in bench-scale block model assays (up to +75%). This remained true across expression levels, signal sequences, and different silks.

In some embodiments, deletion of sec72 is effected using a plasmid having a 5' homology arm to sec72 and a 3' homology arm to sec72 flanking a yeast selection marker, e.g., as shown in FIG. 2. The Δsec72 deletion elicited transcriptional adaptation that could indirectly assist secretion. Sequences of the sec72 gene and the SEC72 protein are provided in Table 1.

TABLE 1 sec72 open reading frame and SEC72 protein sequences

| Description | SEQ ID NO: | Sequence |
|---|---|---|
| sec72 (PAS_chr2-1_0448) ORF sequence (5' to 3') | 1 | atgctaccattttcgtacgacgtgagctcaaagaaactgaaagtcaca ggtgactacgcagacttagaatatgacatacagcagctgaacaccttg agcggagagatcctggccaataaagcagatgttccttctccaccaagt aaggagtcgtttgacaagaaattgtcccacatggctcagaaattacac gagtcggctgtatccaacataaagacaggcaagtatcctgaggctatc aaattgttgacgacgggtcttgaaatggttaacagaaggcccaagtac gagagttttcagatgacgttgagtgaaatgacgatctttattgtcact agagctgacgcttacatgatgaatggagactttgaaggggcattcaat gatgcagatttactggtaacgctcctgccatccattccagataattac attagaagaggggtagcccttttcaagatggggagatacgttgatgca aaaaacaattttgagagaggactttcatttgacccagataatgcaaaa ttgaagaaggagttagattttgtgctgaagaagatcgacgaggagaat ggagagttatag |
| SEC72 (PAS_chr2-1_0448) Protein Sequence | 2 | MLPFSYDVSSKKLKVTGDYADLEYDIQQLNTLSGEILANKADVPSPPS KESFDKKLSHMAQKLHESAVSNIKTGKYPEAIKLLTTGLEMVNRRPKY ESFQMTLSEMTIFIVTRADAYMMNGDFEGAFNDADLLVTLLPSIPDNY IRRGVALFKMGRYVDAKNNFERGLSFDPDNAKLKKELDFVLKKIDEEN GEL |

In some observed cases, the sec72 deletion slowed strain growth, and fermentation production screens of Δsec72 strains struggled with glucose accumulation. Thus, also provided herein, according to some embodiments, are strains recombinantly overexpressing proteins that comprise the SSH1 translocon complex. As shown herein, overexpression of the SSH1 translocon complex in Δsec72 strains improved the strain growth rate and fermentation performance, while maintaining improved secretion. Runs of this combined deletion-overexpression strain with only 4 copies of of recombinant silk-like block polypeptide expressing genes (i.e., 18B) showed similar titers and improved specific productivity (+18%) over a strain with 6 copies of silk-like block polypeptide expressing genes (i.e., 18B).

Figure 3:
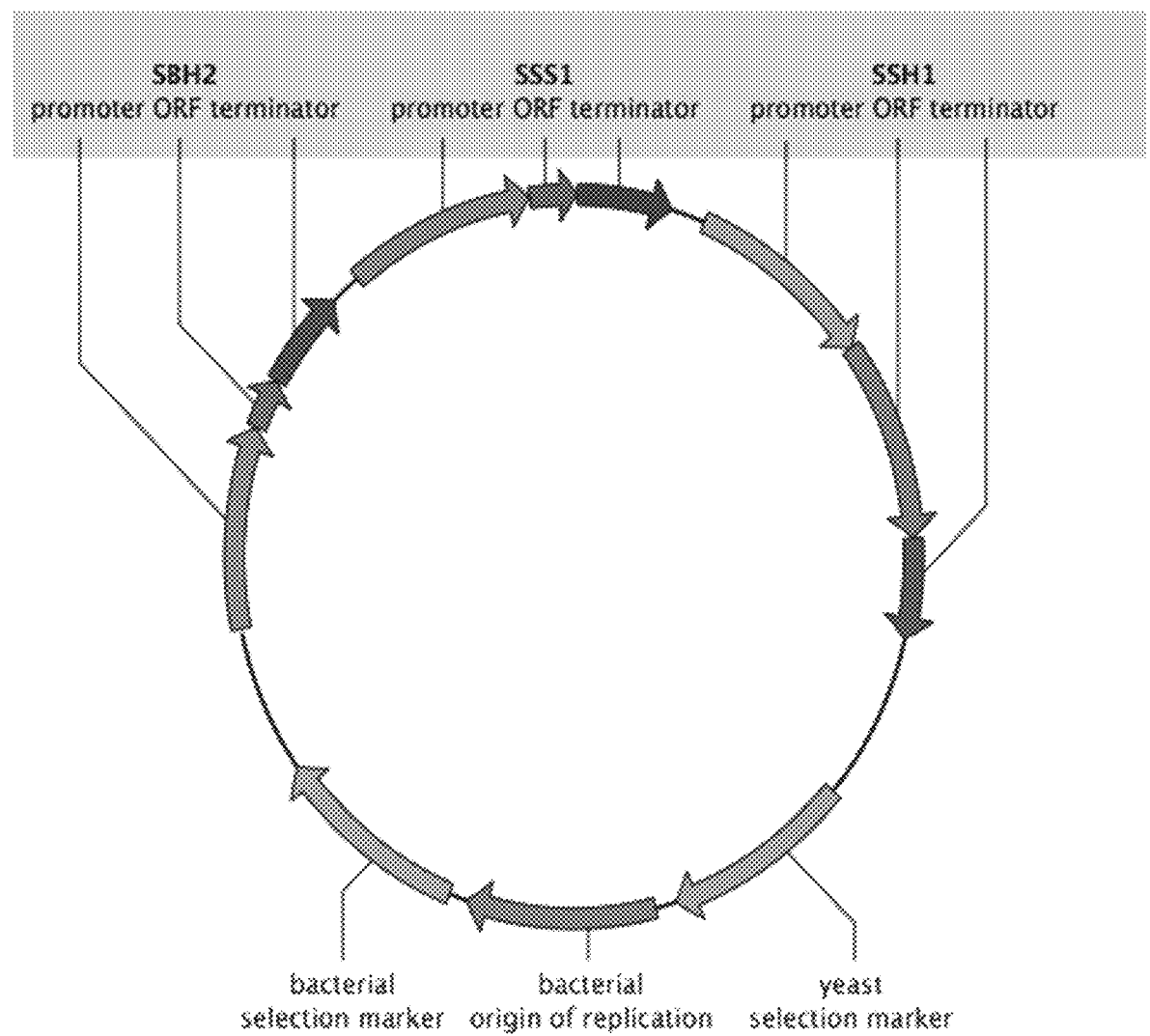
FIG. 3 is a plasmid map of a vector for overexpression of genes encoding proteins comprising the SSH1 complex. It includes a promoter, an open reading frame (ORF), and a terminator for SBH2, SSS1, and SSH1, as well as a yeast selection marker.

In some embodiments, the SSH1 translocon complex is overexpressed in host cells by inserting a plasmid comprising genes encoding recombinant SBH2, SSS1, and SSH1 (FIG. 3). Sequences for these genes and the expressed protein can be found in Table 2.

TABLE 2

Open reading frame and protein sequences for subunits of the SSH1 translocon complex.

| Description | SEQ ID NO: | Sequence |
|---|---|---|
| SSH1 (PAS_chr1-4_0629) ORF sequence | 3 | atggcggggttgcgttttttagacattgcaagaccatttgtcagctgg<br>atcccggaagttgaacttccttatgaaaactgggggttcgatgaaaag<br>ctgatttactcattttttcactgctgccatctatttgattctgtccctg<br>cctatatacggtgtcaaatcctctgaagtcgtggacccagttccccat<br>ttgcgttctgccttagggagtgagaagggaacattgctggagcttggg<br>ttactgcctgtgattacttcggcatttatcttgcagttgttggctggt<br>tggaaagttttcaaagtaaactttgatctggttagtgacagaatattg<br>ttccaaactttgcaaaagatcacttcagtcgttatcagcatcgtatat<br>gctgttcttctcacattttgtgactacttactccaggtgtgtccact<br>gataacgtcttgtggtcccaatttctgatcatcttacagatagtggtg<br>gtcaacttcttggttactctactcgttgaagtcattgacaaggattac<br>ggattttcttcaggagctctattgttgcttgcggtttattccgccacc<br>aacttcgttttttggcacgattggtcttagcaccgtcaacacctccaga<br>tcgaacgaatctattggtgctctgattcaattattccgcaatttgagc<br>tctaaaccaattggtgttgccatatatgactccttcttcagagtaaac<br>cttcctaacttgactcaattttatctggggattgccattatttgtgtt<br>tgtctgttcttgaataatgcaagatacgaagtaccaattaagccaaac<br>aaggttcgtgccatggcctcagcttacccaatcaagctacttttcaat<br>ggttctttgccacttctgtacacgtggactgtgctgtacaacttgaac<br>cttattggtttcttgtcttcaagcttaccaacttttctcttttaggg<br>aacttcaaagtggacccattcggcaacaactactacgaaattacatct<br>ggactgctgtatttattgactcctactttcaacgctgaagctggactt<br>ttacccaatgttgctaagccatttgttttcattgccttctatgttggt<br>gttagcacttctctttgctagatcgtggtccaacattaacgggtcgtca<br>ggcaaggacattgccaagttttttcaaggctcaaggaatctcattgtta<br>ggaaaaagagatgcctctgtgtctaaagagtttaacaccctagttcct<br>gttgcttctgcctctggagctttcctattgtcttttccagttgccgtc<br>gctgagttattgggtggctctggtgttccaacctctatcggaatcggt<br>cttttgagtggtttggctattttggaaactgttttgcaagaatggcaa<br>cagtctggaggtgcctcacagttctcccaatacttccagacttcttag |
| SSH1 (PAS_chr1-4_0629) Protein Sequence | 4 | MAGLRFLDIARPFVSWIPEVELPYENWGFDEKLIYSFFTAAIYLILSL<br>PIYGVKSSEVVDPVPHLRSALGSEKGTLLELGLLPVITSAFILQLLAG<br>WKVFKVNFDLVSDRILFQTLQKITSVVISIVYAVLLTFCDYFTPGVST<br>DNVLWSQFLIILQIVVVNFLVTLLVEVIDKDYGFSSGALLLLAVYSAT<br>NFVFGTIGLSTVNTSRSNESIGALIQLFRNLSSKPIGVAIYDSFFRVN<br>LPNLTQFYLGIAIICVCLFLNNARYEVPIKPNKVRAMASAYPIKLLFN<br>GSLPLLYTWTVLYNLNLIGFFVFKLTNFSLLGNFKVDPFGNNYYEITS<br>GLLYLLTPTFNAEAGLLPNVAKPFVFIAFYVGVSTFFARSWSNINGSS<br>GKDIAKFFKAQGISLLGKRDASVSKEFNTLVPVASASGAFLLSFPVAV<br>AELLGGSGVPTSIGIGLLSGLAILETVLQEWQQSGGASQFSQYFQTS |
| SSS1 (PAS_chr1-1_0023) ORF sequence | 5 | atgtcccaaaaagtcaccgacgtccctctggaatttgttaaggaaggt<br>tccaaattcatctctaaatgtactaaaccctctcagaaggagtactta<br>aagatagtaagagctgttggagttgggttttttaatgatgggcgtggtt<br>ggttacgttgtcaagctcattcatattccaatcagatatttgattgtt<br>taa |
| SSS1 (PAS_chr1-1_0023) Protein Sequence | 6 | MSQKVTDVPLEFVKEGSKFISKCTKPSQKEYLKIVRAVGVGFLMMGVV<br>GYVVKLIHIPIRYLIV |
| SBH2 (PAS_chr2-2_0210) ORF sequence | 7 | atggtaagtgtccagtttgatgagtgcagaatggttccaagttttaga<br>ccagttactaatatttaaagtctacagcaattccaggaggacagagaa<br>cgttagctaaaagaagagcagcaaacttggataagaaacaggatgaac<br>caaccctccgccagatctgccggtgctggaggttcttcgtctaccatgc<br>taaagttgtacacagacgagggcccaaggtttgaaagttgatcctttaa<br>ttgttcttgttcttgctgttggtttcattttcagtgtcattggtttgc<br>acgttgttgctaagctgacaggaaagttgatcaactaa |
| SBH2 (PAS_chr2-2_0210) Protein Sequence | 8 | MSTAIPGGQRTLAKRRAANLDKKQDEPTSARSAGAGGSSSTMLKLYTD<br>EAQGLKVDPLIVLVLAVGFIFSVIGLHVVAKLTGKLIN |

Protease Knock-Outs

In some embodiments, to attenuate a protease activity in *Pichia pastoris*, the genes encoding these enzymes are inactivated or mutated to reduce or eliminate activity. This can be done through mutations or insertions into the gene itself of through modification of a gene regulatory element. This can be achieved through standard yeast genetics techniques. Examples of such techniques include gene replacement through double homologous recombination, in which homologous regions flanking the gene to be inactivated are cloned in a vector flanking a selectable maker gene (such as an antibiotic resistance gene or a gene complementing an auxotrophy of the yeast strain). In some embodiments, the Nourseothricin selection plasmid shown in FIG. 4A can be used as a base plasmid, and homology arms (HA) flanking resistance cassettes (FIG. 4B and FIG. 4C) can be used, where the homology arms specifically target the desired protease to be knocked out. Description of protease knockouts and methods of modifying host cells to inhibit recombinant protein degradation are provided in U.S. application Ser. No. 15/724,196 and PCT Application No. PCT/US2017/054997, each of which are incorporated herein by reference in its entirety.

Alternatively, the homologous regions can be PCR-amplified and linked through overlapping PCR to the selectable marker gene. Subsequently, such DNA fragments are transformed into *Pichia pastoris* through methods known in the art, e.g., electroporation. Transformants that then grow under selective conditions are analyzed for the gene disruption event through standard techniques, e.g. PCR on genomic DNA or Southern blot. In an alternative experiment, gene inactivation can be achieved through single homologous recombination, in which case, e.g. the 5' end of the gene's ORF is cloned on a promoterless vector also containing a selectable marker gene. Upon linearization of such vector through digestion with a restriction enzyme only cutting the vector in the target-gene homologous fragment, such vector is transformed into *Pichia pastoris*. Integration at the target gene site is confirmed through PCR on genomic DNA or Southern blot. In this way, a duplication of the gene fragment cloned on the vector is achieved in the genome, resulting in two copies of the target gene locus: a first copy in which the ORF is incomplete, thus resulting in the expression (if at all) of a shortened, inactive protein, and a second copy which has no promoter to drive transcription.

Alternatively, transposon mutagenesis is used to inactivate the target gene. A library of such mutants can be screened through PCR for insertion events in the target gene.

The functional phenotype (i.e., deficiencies) of an engineered/knockout strain can be assessed using techniques known in the art. For example, a deficiency of an engineered strain in protease activity can be ascertained using any of a variety of methods known in the art, such as an assay of hydrolytic activity of chromogenic protease substrates, band shifts of substrate proteins for the selected protease, among others.

Attenuation of a protease activity described herein can be achieved through mechanisms other than a knockout mutation. For example, a desired protease can be attenuated via amino acid sequence changes by altering the nucleic acid sequence, placing the gene under the control of a less active promoter, down-regulation, expressing interfering RNA, ribozymes or antisense sequences that target the gene of interest, or through any other technique known in the art. In preferred strains, the protease activity of proteases encoded at PAS_chr4_0584 (YPS1-1) and PAS_chr3_1157 (YPS1-2) (e.g., polypeptides comprising SEQ ID NO: 10 and 12) is attenuated by any of the methods described above. In some aspects, the invention is directed to methylotrophic yeast strains, especially *Pichia pastoris* strains, wherein a YPS1-1 and a YPS1-2 gene (e.g., as set forth in SEQ ID NO: 9 and SEQ ID NO: 11) have been inactivated. In some embodiments, additional protease encoding genes may also be knocked-out in accordance with the methods provided herein to further reduce protease activity of a desired protein product expressed by the strain.

TABLE 3

Open reading frame nucleotide sequence and polypeptide sequence for proteases targeted for deletion in *P. pastoris*

| Description | SEQ ID NO: | Sequence |
|---|---|---|
| PAS_chr4_0584 (YPS1-1) ORF sequence (5' to 3') | 9 | atgttgaaggatcagttcttgttatgggttgctttgatagcgagcgtaccggtttc cggcgtgatggcagctcctagcgagtccgggcataacacggttgaaaacgagatg ccaaaaacgttgttggcgttcaacagttggacttcagcgttctgagggggtgattcc ttcgaaagtgcctcttcagagaacgtgcctcggcttgtgaggagagatgacacgct agaagctgagctaatcaaccagcaatcattctacttgtcacgactgaaagttggat cacatcaagcggatattggaatcctagtggacacaggatcctctgatttatgggta atggactcggtaaacccatactgcagtagccgttcccgcgtgaagagagatataca cgatgagaagatcgccgaatgggatcccatcaatctcaagaaaaatgaaacttctc agaataaaaattttgggattggctcgttggaactagcactagttctccttccacc gccacggcaactggtagtggtagtggtagtggtagtggtagtggtagtggtagtgc tgccacagccgtatcggtaagttctgcacaggcaacattggattgctctacgtatg gaacgtttgatcacgctgattcctcgacgttccatgacaataatacagactttttc atctcatacgctgataccacttttgcttcaggaatctggggttatgacgacgtcat tatcgacggcatagaggtgaaagaactttcctttcgccgttgcagacatgaccaatt cctctattggtgtgttaggtattggactgaaaggcctagaatccacatatgctagt gcatcttcggtcagtgaaatgtatcagtatgacaatttgccagccaagatggtcac cgatgggttgatcaacaaaaatgcatactccttgtacttgaactccaaggacgcct caagtggttccatcctctttggaggtgtggatcatgaaaaatattcgggacaattg ttgacagttccagtcatcaacacactcgcttccagtggttacagagaggcaattcg tttacaaattactttaaatggaatagatgtgaaaaagggttctgaccagggaactc ttttacaagggagatttgctgcattattggactctggagctacgctaacgtatgct ccttcttctgttttaaattcaattggccggaacctgggcggctcctatgattcgtc aagacaagcttataccattcgttgtgtttctgcatcagataccacttctctggtat tcaattttggggtgctacagtggaagttccctgtacgatctacagattgcaaca tattacaccgggggaagtgccacgcaatgtcttattggaatattcagctctggaag tgatgagtttgtgctcggtgataccttcttgaggtcagcctacgtggtttacgatc ttgatgggcttgaagtgtcgcttgcccaagccaacttcaacgaaaccgattctgat gttgaggctattacctccagtgtaccttccgctactcgtgcatccggatacagttc tacatggtctggttctgccagcggtacagtttacacttcggttcagatggaatccg gtgctgcttccagctccaactcttctggatcgaatatgggttcctcttcctcatcg tcctcttcatcgtcctcgacttccagtggagacgaagaaggagggagctccgccaa cagggtcccctcagctaccttctctctgtttggtagttattctcggcgtgtgta tagtatag |

TABLE 3-continued

Open reading frame nucleotide sequence and polypeptide sequence for proteases targeted for deletion in *P. pastoris*

| Description | SEQ ID NO: | Sequence |
|---|---|---|
| PAS_chr4_0584 (IPS1-4) Polypeptide Sequence | 10 | MLKDQFLLWV ALIASVPVSG VMAAPSESGH NTVEKRDAKN VVGVQQLDFS<br>VLRGDSFESA SSENVPRLVR RDDTLEAELI NQQSFYLSRL KVGSHQADIG<br>ILVDTGSSDL WVMDSVNPYC SSRSRVKRDI HDEKIAEWDP INLKKNETSQ<br>NKNFWDWLVG TSTSSPSTAT ATGSGSGSGS GSGSGSAATA VSVSSAQATL<br>DCSTYGTFDH ADSSTFHDNN TDFFISYADT TFASGIWGYD DVIIDGIEVK<br>ELSFAVADMT NSSIGVLGIG LKGLESTYAS ASSVSEMYQY DNLPAKMVTD<br>GLINKNAYSL YLNSKDASSG SILFGGVDHE KYSGQLLTVP VINTLASSGY<br>REAIRLQITL NGIDVKKGSD QGTLLQGRFA ALLDSGATLT YAPSSVLNSI<br>GRNLGGSYDS SRQAYTIRCV SASDTTSLVF NFGGATVEVS LYDLQIATYY<br>TGGSATQCLI GIFSSGSDEF VLGDTFLRSA YVVYDLDGLE VSLAQANFNE<br>TDSDVEAITS SVPSATRASG YSSTWSGSAS GTVYTSVQME SGAASSSNSS<br>GSNMGSSSSS SSSSSSTSSG DEEGGSSANR VPFSYLSLCL VVILGVCIV |
| PAS_chr3_1157 (YPS1-2) ORF sequence (5'to 3') | 11 | atgatcatcaaccacttggtattgacagccctcagcattgcactagcaagtgcgca<br>actccaatcgcctttcaaggctaacaagttgccattcaaaaagtttatcattccaa<br>cgacccaaaggaccgtttaattaagagagatgactacgagtccctcgacttgagac<br>acatcggagtcttgtacactgcagagatccaaattggatctgacgaaactgaaatt<br>gaggtcattgtcgacactggttctgccgacttgtgggtcatcgattccgacgctgc<br>cgtctgtgagttatcctacgatgagattgaggccaatagcttttcctcggcttctg<br>ccaaattcatggacaagatagctcctccatcacaagagctcctggatgggctgagt<br>gagtttggatttgctctcgatggtgaaatttctcaatacctagccgataaatctgg<br>acgtgtttcgaaaagagaggaaaatcaacaagatttcaacattaaccgtgacgagc<br>ctgtgtgtgaacagtttggttccttcgattctagttcttccgacactttccaaagc<br>aacaattcagcttttggtattgcttaccttgatggaaccactgctaacggaacttg<br>ggtcagggacacagtccgcatcggcgactttgccatcagccaacagagtttgcct<br>tagtcaacatcacagataactacatgggaatcttgggtctcggtcctgctacccaa<br>caaaccaccaatagtaacccaattgcagcaaacagatttacttatgatggtgttgt<br>ggattcattgcggtcccaaggatttatcaattcagcatcgttttctgtttacttgt<br>ctccagatgaagataacgagcacgacgaattcagcgacggagaaattttatttggt<br>gctattgatagggccaagatagacgggccatttagacttttcccatatgtcaatcc<br>ttacaaaccagtttaccccgatcaatatacttcctacgttacagtgtccacaattg<br>cggtgtcttcgtcagatgaaactctcattattgaaagacgtcctcgtttggcatta<br>atcgatacaggtgccaccttctcctatttgccaacctacccattgattcgtttagc<br>gtttccatccatggaggctttgaatatgtttctcaattgggactatttgtcattc<br>gtacaagttctctgtctgttgctagaaataaggtgattgagttcaagtttggtgaa<br>gacgttgtgatccaatcccagtttctgatcatctattggacgtctcaggcctttt<br>tactgatggccaacaatactccgcattaactgtacgtgaaagtcttgacggacttt<br>ccattctaggtgatacattcatcaaatcggcctacttattctttgacaatgaaaac<br>agccagctgggtattggtcagatcaacgtcactgatgacgaggatattgaggtggt<br>cggtgatttcactattgaacgagacccagcctactcctctacttggtctagcgatt<br>tacctcatgaaacacccactagggctttgagtactgcttcaggggaggccttggt<br>accggaataaacacggccacaagtcgtgcaagttctcgttccacatctggctctac<br>ttcacgaacttcttctacatctggctctgcttctggtacttcttcaggtgcatctt<br>ctgctactcaaaatgacgaaacatccactgatcttggagctccagctgcatcttta<br>agtgcaacgccatgtctttttgccatcttgctgctcatgttgtag |
| PAS_chr3_1157 (YPS1-2) Polypeptide Sequence | 12 | MIINHLVLTA LSIALANDYE SLDLRHIGVL YTAEIQIGSD ETEIEVIVDT<br>GSADLWVIDS DAAVCELSYD EIEANSFSSA SAKFMDKIAP PSQELLDGLS<br>EFGFALDGEI SQYLADKSGR VSKREENQQD FNINRDEPVC EQFGSFDSSS<br>SDTFQSNNSA FGIAYLDGTT ANGTWVRDTV RIGDFAISQQ SFALVNITDN<br>YMGILGLGPA TQQTTNSNPI AANRFTYDGV VDSLRSQGFI NSASFSVYLS<br>PDEDNEHDEF SDGEILFGAI DRAKIDGPFR LFPYVNPYKP VYPDQYTSYV<br>TVSTIAVSSS DETLIIERRP RLALIDTGAT FSYLPTYPLI RLAFSIHGGF<br>EYVSQLGLFV IRTSSLSVAR NKVIEFKFGE DVVIQSPVSD HLLDVSGLFT<br>DGQQYSALTV RESLDGLSIL GDTFIKSAYL FFDNENSQLG IGQINVTDDE<br>DIEVVGDFTI ERDPAYSSTW SSDLPHETPT RALSTASGGG LGTGINTATS<br>RASSRSTSGS TSRTSSTSGS ASGTSSGASS ATQNDETSTD LGAPAASLSA<br>TPCLFAILLL ML |

Production of Recombinant Strains

Provided herein are methods of transforming a strain to reduce activity, e.g., using vectors to deliver recombinant genes or to knock-out or otherwise attenuate endogenous genes as desired. These vectors can take the form of a vector backbone containing a replication origin and a selection marker (typically antibiotic resistance, although many other methods are possible), or a linear fragment that enables incorporation into the target cell's chromosome. The vectors should correspond to the organism and insertion method chosen.

Once the elements of a vector are selected, construction of the vector can be performed in many different ways. In an embodiment, a DNA synthesis service or a method to individually make every vector may be used.

Once the DNA for each vector (including the additional elements required for insertion and operation) is acquired, it must be assembled. There are many possible assembly methods including (but not limited to) restriction enzyme cloning, blunt-end ligation, and overlap assembly [see, e.g., Gibson, D. G., et al., Enzymatic assembly of DNA molecules up to several hundred kilobases. Nature methods, 6(5), 343-345 (2009), and GeneArt Kit (http://tools.invitrogen.com/content/sfs/manuals/geneart_seamless_cloning_and_assembly_man.pdf)]. Overlap assembly provides a method to ensure all of the elements get assembled in the correct position and do not introduce any undesired sequences.

The vectors generated above can be inserted into target cells using standard molecular biology techniques, e.g., molecular cloning. In an embodiment, the target cells are already engineered or selected such that they already contain the genes required to make the desired product, although this may also be done during or after further vector insertion.

Depending on the organism and library element type (plasmid or genomic insertion), several known methods of inserting the vector comprising DNA to incorporate into the cells may be used. These may include, for example, transformation of microorganisms able to take up and replicate DNA from the local environment, transformation by electroporation or chemical means, transduction with a virus or phage, mating of two or more cells, or conjugation from a different cell.

Several methods are known in the art to introduce recombinant DNA in bacterial cells that include but are not limited to transformation, transduction, and electroporation, see Sambrook, et al., Molecular Cloning: A Laboratory Manual (1989), Second Edition, Cold Spring Harbor Press, Plainview, N.Y. Non-limiting examples of commercial kits and bacterial host cells for transformation include NovaBlue Singles™ (EMD Chemicals Inc., NJ, USA), Max Efficiency® DH5α™, One Shot® BL21 (DE3) *E. coli* cells, One Shot® BL21 (DE3) pLys *E. coli* cells (Invitrogen Corp., Carlsbad, Calif., USA), XL1-Blue competent cells (Stratagene, CA, USA). Non limiting examples of commercial kits and bacterial host cells for electroporation include Zappers™ electrocompetent cells (EMD Chemicals Inc., NJ, USA), XL1-Blue Electroporation-competent cells (Stratagene, CA, USA), ElectroMAX™ *A. tumefaciens* LBA4404 Cells (Invitrogen Corp., Carlsbad, Calif., USA).

Several methods are known in the art to introduce recombinant nucleic acid in eukaryotic cells. Exemplary methods include transfection, electroporation, liposome mediated delivery of nucleic acid, microinjection into to the host cell, see Sambrook, et al., Molecular Cloning: A Laboratory Manual (1989), Second Edition, Cold Spring Harbor Press, Plainview, N.Y. Non-limiting examples of commercial kits and reagents for transfection of recombinant nucleic acid to eukaryotic cell include Lipofectamine™ 2000, Optifect™ Reagent, Calcium Phosphate Transfection Kit (Invitrogen Corp., Carlsbad, Calif., USA), GeneJammer® Transfection Reagent, LipoTAXI® Transfection Reagent (Stratagene, CA, USA). Alternatively, recombinant nucleic acid may be introduced into insect cells (e.g. sf9, sf21, High Five™) by using baculo viral vectors.

Transformed cells are isolated so that each clone can be tested separately. In an embodiment, this is done by spreading the culture on one or more plates of culture media containing a selective agent (or lack of one) that will ensure that only transformed cells survive and reproduce. This specific agent may be an antibiotic (if the library contains an antibiotic resistance marker), a missing metabolite (for auxotroph complementation), or other means of selection. The cells are grown into individual colonies, each of which contains a single clone.

Colonies are screened for desired production of a protein, metabolite, or other product, for reduction in protease activity, for growth, or for increase in secretion activity. In an embodiment, screening identifies recombinant cells having the highest (or high enough) product production titer or efficiency. This includes a decreased proportion of degradation products or an increased total amount of desired polypeptides secreted from a cell and collected from a cell culture.

This assay can be performed by growing individual clones, one per well, in multi-well culture plates. Once the cells have reached an appropriate biomass density, they are induced with methanol. After a period of time, typically 24-72 hours of induction, the cultures are harvested by spinning in a centrifuge to pellet the cells and removing the supernatant. The supernatant from each culture can then be tested for to determine whether desired secretion amounts have been achieved.

Silk Sequences

In some embodiments, the modified strains described herein recombinantly express a silk-like polypeptide sequence. In some embodiments, the silk-like polypeptide sequences are 1) block copolymer polypeptide compositions generated by mixing and matching repeat domains derived from silk polypeptide sequences and/or 2) recombinant expression of block copolymer polypeptides having sufficiently large size (approximately 40 kDa) to form useful fibers by secretion from an industrially scalable microorganism. Large (approximately 40 kDa to approximately 100 kDa) block copolymer polypeptides engineered from silk repeat domain fragments, including sequences from almost all published amino acid sequences of spider silk polypeptides, can be expressed in the modified microorganisms described herein. In some embodiments, silk polypeptide sequences are matched and designed to produce highly expressed and secreted polypeptides capable of fiber formation. In some embodiments, knock-out of protease genes or reduction of protease activity in the host modified strain reduces degradation of the silk like polypeptides. In some embodiments, knock-out of sec72 and overexpression of an SSH1 translocon complex improves secretion while mitigating defects in growth, maintaining, or improving growth of the strain.

Provided herein, in several embodiments, are compositions for expression and secretion of block copolymers engineered from a combinatorial mix of silk polypeptide domains across the silk polypeptide sequence space, wherein the block copolymers have minimal degradation. In some embodiments provided herein are methods of secreting block copolymers in scalable organisms (e.g., yeast, fungi, and gram positive bacteria) with minimal degradation. In some embodiments, the block copolymer polypeptide comprises 0 or more N-terminal domains (NTD), 1 or more repeat domains (REP), and 0 or more C-terminal domains (CTD). In some aspects of the embodiment, the block copolymer polypeptide is >100 amino acids of a single polypeptide chain. In some embodiments, the block copolymer polypeptide comprises a domain that is at least 80%, 81%, 82%, 83%, 84%, 85%, 86%, 87%, 88%, 89%, 90%, 91%, 92%, 93%, 94%, 95%, 96%, 97%, 98%, or 99% identical to a sequence of a block copolymer polypeptide as disclosed in International Publication No. WO/2015/042164, "Methods and Compositions for Synthesizing Improved Silk Fibers," incorporated by reference in its entirety.

Several types of native spider silks have been identified. The mechanical properties of each natively spun silk type are believed to be closely connected to the molecular composition of that silk. See, e.g., Garb, J. E., et al., Untangling spider silk evolution with spidroin terminal domains, *BMC Evol. Biol.*, 10:243 (2010); Bittencourt, D., et al., Protein families, natural history and biotechnological aspects of spider silk, *Genet. Mol. Res.,* 11:3 (2012); Rising, A., et al., Spider silk proteins: recent advances in recombinant production, structure-function relationships and biomedical applications, *Cell. Mol. Life Sci.,* 68:2, pg. 169-184 (2011); and Humenik, M., et al., Spider silk: understanding the structure-function relationship of a natural fiber, *Prog. Mol. Biol. Transl. Sci.,* 103, pg. 131-85 (2011). For example:

Aciniform (AcSp) silks tend to have high toughness, a result of moderately high strength coupled with moderately high extensibility. AcSp silks are characterized by large block ("ensemble repeat") sizes that often incorporate motifs of poly serine and GPX. Tubuliform (TuSp or Cylindrical) silks tend to have large diameters, with modest strength and high extensibility. TuSp silks are characterized by their poly serine and poly threonine content, and short tracts of poly alanine. Major Ampullate (MaSp) silks tend to have high strength and modest extensibility. MaSp silks can be one of two subtypes: MaSp1 and MaSp2. MaSp1 silks are generally less extensible than MaSp2 silks, and are characterized by poly alanine, GX, and GGX motifs. MaSp2 silks are characterized by poly alanine, GGX, and GPX motifs. Minor Ampullate (MiSp) silks tend to have modest strength and modest extensibility. MiSp silks are characterized by GGX, GA, and poly A motifs, and often contain spacer elements of approximately 100 amino acids. Flagelliform (Flag) silks tend to have very high extensibility and modest strength. Flag silks are usually characterized by GPG, GGX, and short spacer motifs.

The properties of each silk type can vary from species to species, and spiders leading distinct lifestyles (e.g. sedentary web spinners vs. vagabond hunters) or that are evolutionarily older may produce silks that differ in properties from the above descriptions (for descriptions of spider diversity and classification, see Hormiga, G., and Griswold, C. E., Systematics, phylogeny, and evolution of orb-weaving spiders, *Annu. Rev. Entomol.* 59, pg. 487-512 (2014); and Blackedge, T. A. et al., Reconstructing web evolution and spider diversification in the molecular era, *Proc. Natl. Acad. Sci. USA.,* 106:13, pg. 5229-5234 (2009)). However, synthetic block copolymer polypeptides having sequence similarity and/or amino acid composition similarity to the repeat domains of native silk proteins can be used to manufacture on commercial scales consistent silk-like fibers that recapitulate the properties of corresponding natural silk fibers.

In some embodiments, a list of putative silk sequences can be compiled by searching GenBank for relevant terms, e.g. "spidroin" "fibroin" "MaSp", and those sequences can be pooled with additional sequences obtained through independent sequencing efforts. Sequences are then translated into amino acids, filtered for duplicate entries, and manually split into domains (NTD, REP, CTD). In some embodiments, candidate amino acid sequences are reverse translated into a DNA sequence optimized for expression in *Pichia* (*Komagataella*) *pastoris*. The DNA sequences are each cloned into an expression vector and transformed into *Pichia* (*Komagataella*) *pastoris*. In some embodiments, various silk domains demonstrating successful expression and secretion are subsequently assembled in combinatorial fashion to build silk molecules capable of fiber formation.

Silk polypeptides are characteristically composed of a repeat domain (REP) flanked by non-repetitive regions (e.g., C-terminal and N-terminal domains). In an embodiment, both the C-terminal and N-terminal domains are between 75-350 amino acids in length. The repeat domain exhibits a hierarchical architecture. The repeat domain comprises a series of blocks (also called repeat units). The blocks are repeated, sometimes perfectly and sometimes imperfectly (making up a quasi-repeat domain), throughout the silk repeat domain. The length and composition of blocks varies among different silk types and across different species. Table 1 lists examples of block sequences from selected species and silk types, with further examples presented in Rising, A. et al., Spider silk proteins: recent advances in recombinant production, structure-function relationships and biomedical applications, *Cell Mol. Life Sci.,* 68:2, pg 169-184 (2011); and Gatesy, J. et al., Extreme diversity, conservation, and convergence of spider silk fibroin sequences, *Science,* 291: 5513, pg. 2603-2605 (2001). In some cases, blocks may be arranged in a regular pattern, forming larger macro-repeats that appear multiple times (usually 2-8) in the repeat domain of the silk sequence. Repeated blocks inside a repeat domain or macro-repeat, and repeated macro-repeats within the repeat domain, may be separated by spacing elements. In some embodiments, block sequences comprise a glycine rich region followed by a polyA region. In some embodiments, short (~1-10) amino acid motifs appear multiple times inside of blocks. For the purpose of this invention, blocks from different natural silk polypeptides can be selected without reference to circular permutation (i.e., identified blocks that are otherwise similar between silk polypeptides may not align due to circular permutation). Thus, for example, a "block" of SGAGG (SEQ ID NO: 23) is, for the purposes of the present invention, the same as GSGAG (SEQ ID NO: 24) and the same as GGSGA (SEQ ID NO: 25); they are all just circular permutations of each other. The particular permutation selected for a given silk sequence can be dictated by convenience (usually starting with a G) more than anything else. Silk sequences obtained from the NCBI database can be partitioned into blocks and non-repetitive regions.

TABLE 4

Samples of Block Sequences

| Species | Silk Type | Representative Block Amino Acid Sequence |
|---|---|---|
| *Aliatypus gulosus* | Fibroin 1 | GAASSSSTIITTKSASASAAADASAAATASAASRSSANAAASAFAQS FSSILLESGYFCSIFGSSISSSYAAAIASAASRAAAESNGYTTHAYA CAKAVASAVERVTSGADAYAYAQAISDAISHALLYTGRLNTANANSL ASAFAYAFANAAAQASASSASAGAASASGAASASGAGSAS (SEQ ID NO: 26) |
| *Plectreurys tristis* | Fibroin 1 | GAGAGAGAGAGAGAGAGSGASTSVSTSSSSGSGAGAGAGSGAGSGAG AGSGAGAGAGAGGAGAGFGSGLGLGYGVGLSSAQAQAQAQAAAQAQA QAQAQAYAAAQAQAQAQAQAQ (SEQ ID NO: 27) |

TABLE 4-continued

Samples of Block Sequences

| Species | Silk Type | Representative Block Amino Acid Sequence |
|---|---|---|
| Plectreurys tristis | Fibroin 4 | GAAQKQPSGESSVATASAAATSVTSGGAPVGKPGVPAPIFYPQGPLQ<br>QGPAPGPSNVQPGTSQQGPIGGVGGSNAFSSSFASALSLNRGFTEVI<br>SSASATAVASAFQKGLAPYGTAFALSAASAAADAYNSIGSGANAFAY<br>AQAFARVLYPLVQQYGLSSSAKASAFASAIASSFSSGTSGQGPSIGQ<br>QQPPVTISAASASAGASAAAVGGGQVGQGPYGGQQQSTAASASAAAA<br>TATS<br>(SEQ ID NO: 28) |
| Araneus gemmoides | TuSp | GNVGYQLGLKVANSLGLGNAQALASSLSQAVSAVGVGASSNAYANAV<br>SNAVGQVLAGQGILNAANAGSLASSFASALSSSAASVASQSASQSQA<br>ASQSQAAASAFRQAASQSASQSDSRAGSQSSTKTTSTSTSGSQADSR<br>SASSSASQSASASAFAQQSSASLSSSSSFSSAFSSATSISAV<br>(SEQ ID NO: 29) |
| Argiope aurantia | TuSp | GSLASSFASALSASAASVASSAAAQAASQSQAAASAFSRAASQSASQ<br>SAARSGAQSISTTTTTSTAGSQAASQSASSAASQASASSFARASSAS<br>LAASSSFSSAFSSANSLSALGNVGYQLGFNVANNLGIGNAAGLGNAL<br>SQAVSSVGVGASSSTYANAVSNAVGQFLAGQGILNAANA<br>(SEQ ID NO: 30) |
| Deinopis spinosa | TuSp | GASASAYASAISNAVGPYLYGLGLFNQANAASFASSFASAVSSAVAS<br>ASASAASSAYAQSAAAQAQAASSAFSQAAAQSAAAASAGASAGAGAS<br>AGAGAVAGAGAVAGAGAVAGASAAAASQAAASSSASAVASAFAQSAS<br>YALASSSAFAMAFASATSAGYLGSLAYQLGLTTAYNLGLSNAQAFAS<br>TLSQAVTGVGL<br>(SEQ ID NO: 31) |
| Nephila clavipes | TuSp | GATAASYGNALSTAAAQFFATAGLLNAGNASALASSFARAFSASAES<br>QSFAQSQAFQQASAFQQAASRSASQSAAEAGSTSSSTTTTTSAARSQ<br>AASQSASSSYSSAFAQAASSSLATSSALSRAFSSVSSASAASSLAYS<br>IGLSAARSLGIADAAGLAGVLARAAGALGQ<br>(SEQ ID NO: 32) |
| Argiope trifasciata | Flag | GGAPGGGPGGAGPGGAGFGPGGGAGFGPGGGAGFGPGGAAGGPGGPG<br>GPGGPGGAGGYGPGGAGGYGPGGVGPGGAGGYGPGGAGGYGPGGSGP<br>GGAGPGGAGGEGPVTVDVDVTVGPEGVGGGPGGAGPGGAGFGPGGGA<br>GFGPGGAPGAPGGPGGPGGPGGPGGPGGVGPGGAGGYGPGGAGGVGP<br>AGTGGFGPGGAGGFGPGGAGGFGPGGAGGFGPAGAGGYGPGGVGPGG<br>AGGFGPGGVGPGGSGPGGAGGEGPVTVDVDVSV<br>(SEQ ID NO: 33) |
| Nephila clavipes | Flag | GVSYGPGGAGGPYGPGGPYGPGGEGPGGAGGPYGPGGVGPGGSGPGG<br>YGPGGAGPGGYGPGGSGPGGYGPGGSGPGGYGPGGSGPGGYGPGGSG<br>PGGYGPGGYGPGGSGPGGSGPGGSGPGGYGPGGTGPGGSGPGGYGPG<br>GSGPGGSGPGGYGPGGSGPGGFGPGGSGPGGYGPGGSGPGGAGPGGV<br>GPGGFGPGGAGPGGAAPGGAGPGGAGPGGAGPGGAGPGGAGPGGAGP<br>GGAGGAGGAGGSGGAGGSGGTTIIEDLDITIDGADGPITISEELPIS<br>GAGGSGPGGAGPGGVGPGGSGPGGVGPGGSGPGGVGPGGSGPGGVGP<br>GGAGGPYGPGGSGPGGAGGAGGPGGAYGPGGSYGPGGSGPGGAGGP<br>YGPGGEGPGGAGGPYGPGGAGGPYGPGGAGGPYGPGGEGGPYGP<br>(SEQ ID NO: 34) |
| Latrodectus hesperus | AcSp | GINVDSDIGSVTSLILSGSTLQMTIPAGGDDLSGGYPGGFPAGAQPS<br>GGAPVDFGGPSAGGDVAAKLARSLASTLASSGVFRAAFNSRVSTPVA<br>VQLTDALVQKIASNLGLDYATASKLRKASQAVSKVRMGSDTNAYALA<br>ISSALAEVLSSSGKVADANINQIAPQLASGIVLGVSTTAPQFGVDLS<br>SINVNLDISNVARNMQASIQGGPAPITAEGPDFGAGYPGGAPTDLSG<br>LDMGAPSDGSRGGDATAKLLQALVPALLKSDVFRAIYKRGTRKQVVQ<br>YVTNSALQQAASSLGLDASTISQLQTKATQALSSVSADSDSTAYAKA<br>FGLAIAQVLGTSGQVNDANVNQIGAKLATGILRGSSAVAPRLGIDLS<br>(SEQ ID NO: 35) |

TABLE 4-continued

Samples of Block Sequences

| Species | Silk Type | Representative Block Amino Acid Sequence |
|---|---|---|
| Argiope trifasciata | AcSp | GAGYTGPSGPSTGPSGYPGPLGGGAPFGQSGFGGSAGPQGGFGATGG<br>ASAGLISRVANALANTSTLRTVLRTGVSQQIASSVVQRAAQSLASTL<br>GVDGNNLARFAVQAVSRLPAGSDTSAYAQAFSSALFNAGVLNASNID<br>TLGSRVLSALLNGVSSAAQGLGINVDSGSVQSDISSSSSFLSTSSSS<br>ASYSQASASSTS<br>(SEQ ID NO: 36) |
| Uloborus diversus | AcSp | GASAADIATAIAASVATSLQSNGVLTASNVSQLSNQLASYVSSGLSS<br>TASSLGIQLGASLGAGFGASAGLSASTDISSSVEATSASTLSSSASS<br>TSVVSSINAQLVPALAQTAVLNAAFSNINTQNAIRIAELLTQQVGRQ<br>YGLSGSDVATASSQIRSALYSVQQGSASSAYVSAIVGPLITALSSRG<br>VVNASNSSQIASSLATAILQFTANVAPQFGISIPTSAVQSDLSTISQ<br>SLTAISSQTSSSVDSSTSAFGGISGPSGPSPYGPQPSGPTFGPGPSL<br>SGLTGFTATFASSFKSTLASSTQFQLIAQSNLDVQTRSSLISKVLIN<br>ALSSLGISASVASSIAASSSQSLLSVSA<br>(SEQ ID NO: 37) |
| Euprosthenops australis | MaSp1 | GGQGGQGQGRYGQGAGSS<br>(SEQ ID NO: 38) |
| Tetragnatha kauaiensis | MaSp1 | GGLGGGQGAGQGGQQGAGQGGYGSGLGGAGQGASAAAAAAAA<br>(SEQ ID NO: 39) |
| Argiope aurantia | MaSp2 | GGYGPGAGQQGPGSQGPGSGGQQGPGGLGPYGPSAAAAAAAA<br>(SEQ ID NO: 40) |
| Deinopis spinosa | MaSp2 | GPGGYGGPGQQGPGQGQYGPGTGQQGQGPSGQQGPAGAAAAAAAAA<br>(SEQ ID NO: 41) |
| Nephila clavata | MaSp2 | GPGGYGLGQQGPGQQGPGQQGPAGYGPSGLSGPGGAAAAAAA<br>(SEQ ID NO: 42) |

Fiber-forming block copolymer polypeptides from the blocks and/or macro-repeat domains, according to certain embodiments of the invention, is described in International Publication No. WO/2015/042164, incorporated by reference. Natural silk sequences obtained from a protein database such as GenBank or through de novo sequencing are broken up by domain (N-terminal domain, repeat domain, and C-terminal domain). The N-terminal domain and C-terminal domain sequences selected for the purpose of synthesis and assembly into fibers include natural amino acid sequence information and other modifications described herein. The repeat domain is decomposed into repeat sequences containing representative blocks, usually 1-8 depending upon the type of silk, that capture critical amino acid information while reducing the size of the DNA encoding the amino acids into a readily synthesizable fragment. In some embodiments, a properly formed block copolymer polypeptide comprises at least one repeat domain comprising at least 1 repeat sequence, and is optionally flanked by an N-terminal domain and/or a C-terminal domain.

In some embodiments, a repeat domain comprises at least one repeat sequence. In some embodiments, the repeat sequence is 150-300 amino acid residues. In some embodiments, the repeat sequence comprises a plurality of blocks. In some embodiments, the repeat sequence comprises a plurality of macro-repeats. In some embodiments, a block or a macro-repeat is split across multiple repeat sequences.

In some embodiments, the repeat sequence starts with a Glycine, and cannot end with phenylalanine (F), tyrosine (Y), tryptophan (W), cysteine (C), histidine (H), asparagine (N), methionine (M), or aspartic acid (D) to satisfy DNA assembly requirements. In some embodiments, some of the repeat sequences can be altered as compared to native sequences. In some embodiments, the repeat sequences can be altered such as by addition of a serine to the C terminus of the polypeptide (to avoid terminating in F, Y, W, C, H, N, M, or D). In some embodiments, the repeat sequence can be modified by filling in an incomplete block with homologous sequence from another block. In some embodiments, the repeat sequence can be modified by rearranging the order of blocks or macrorepeats.

In some embodiments, non-repetitive N- and C-terminal domains can be selected for synthesis. In some embodiments, N-terminal domains can be by removal of the leading signal sequence, e.g., as identified by SignalP (Peterson, T. N., et al., SignalP 4.0: discriminating signal peptides from transmembrane regions, *Nat. Methods*, 8:10, pg. 785-786 (2011).

In some embodiments, the N-terminal domain, repeat sequence, or C-terminal domain sequences can be derived from *Agelenopsis aperta, Aliatypus gulosus, Aphonopelma seemanni, Aptostichus* sp. AS217, *Aptostichus* sp. AS220, *Araneus diadematus, Araneus gemmoides, Araneus ventricosus, Argiope amoena, Argiope argentata, Argiope bruennichi, Argiope trifasciata, Atypoides riversi, Avicularia juruensis, Bothriocyrtum californicum, Deinopis Spinosa, Diguetia canities, Dolomedes tenebrosus, Euagrus chisoseus, Euprosthenops australis, Gasteracantha mammosa,*

*Hypochilus thorelli, Kukulcania hibernalis, Latrodectus hesperus, Megahexura fulva, Metepeira grandiosa, Nephila antipodiana, Nephila clavata, Nephila clavipes, Nephila madagascariensis, Nephila pilipes, Nephilengys cruentata, Parawixia bistriata, Peucetia viridans, Plectreurys tristis, Poecilotheria regalis, Tetragnatha kauaiensis*, or *Uloborus diversus*.

Figure 5:
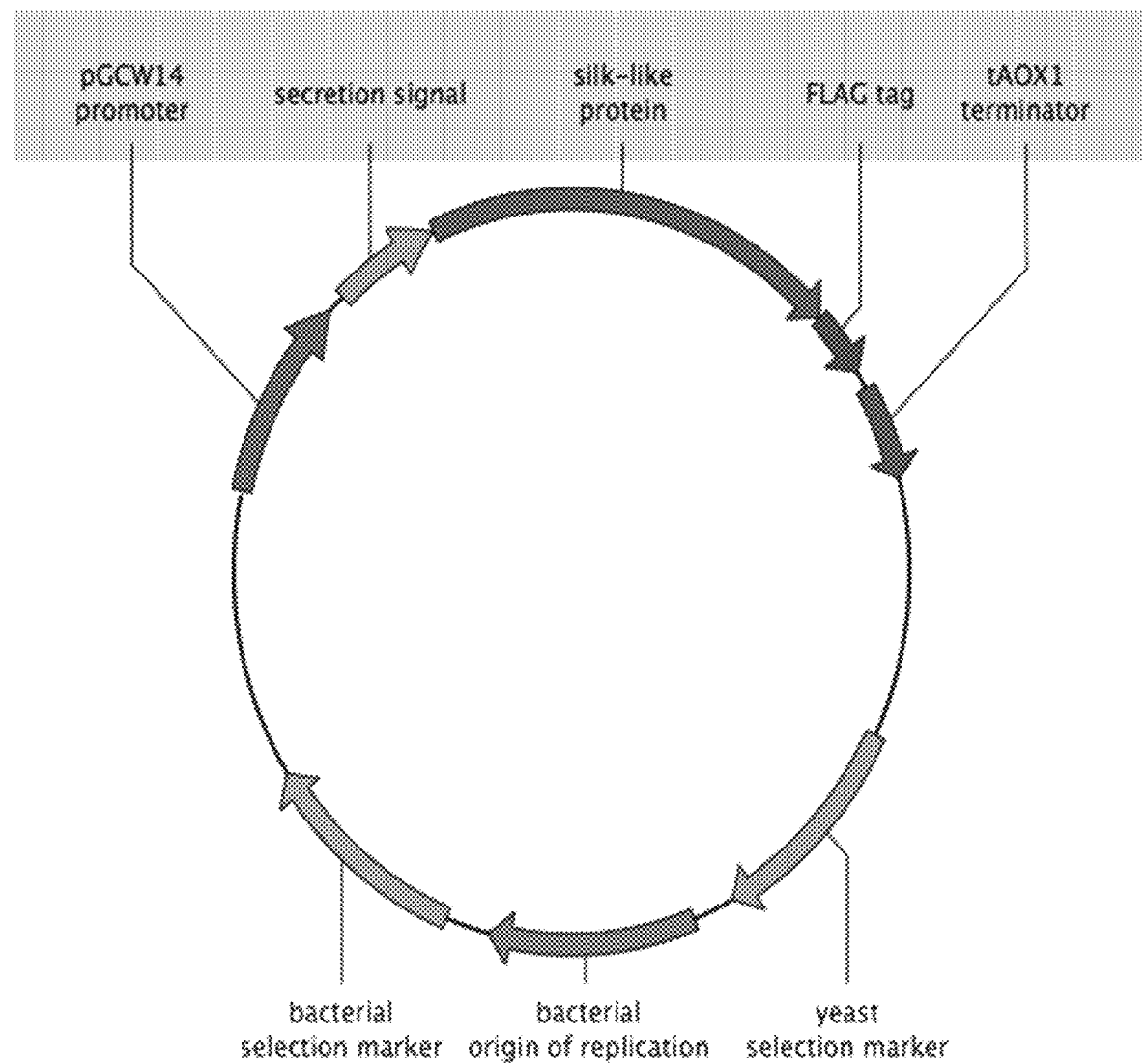
FIG. 5 is a plasmid map of a vector comprising an open reading frame (ORF) for expressing a silk-like polypeptide comprising a secretion signal and a FLAG tag. The ORF is operably linked to a pGCW14 promoter and a tAOX1 terminator. The vector also comprises selection markers to select successfully transformed cells.

In some embodiments, the silk polypeptide nucleotide coding sequence can be operatively linked to an alpha mating factor nucleotide coding sequence. In some embodiments, the silk polypeptide nucleotide coding sequence can be operatively linked to another endogenous or heterologous secretion signal coding sequence. In some embodiments, the silk polypeptide nucleotide coding sequence can be operatively linked to a 3X FLAG nucleotide coding sequence. In some embodiments, the silk polypeptide nucleotide coding sequence is operatively linked to other affinity tags such as 6-8 His residues (SEQ ID NO: 107). An example of a vector for delivering a silk polypeptide nucleotide coding sequence to a host cell is shown in FIG. 5, which depicts a plasmid map of a vector comprising an open reading frame (ORF) for expressing a silk-like polypeptide comprising a secretion signal and a FLAG tag. The ORF is operably linked to a pGCW14 promoter and a tAOX1 terminator. The vector also comprises selection markers to select successfully transformed cells.

In some embodiments, the silk polypeptide comprises a full length spider silk polypeptide. In some embodiments, the full length spider silk polypeptide is Major ampullate spidron 1 (MaSp1) or Major ampullate spidroin 2 (MaSp2).

Silk-Like Polypeptides

In some embodiments, the *P. pastoris* strains disclosed herein have been modified to express a silk-like polypeptide. Methods of manufacturing preferred embodiments of silk-like polypeptides are provided in WO 2015/042164, especially at Paragraphs 114-134, incorporated herein by reference. Disclosed therein are synthetic proteinaceous copolymers based on recombinant spider silk protein fragment sequences derived from MaSp2, such as from the species *Argiope bruennichi*. Silk-like polypeptides are described that include two to twenty repeat units, in which a molecular weight of each repeat unit is greater than about 20 kDa. Within each repeat unit of the copolymer are more than about 60 amino acid residues that are organized into a number of "quasi-repeat units." In some embodiments, the repeat unit of a polypeptide described in this disclosure has at least 95% sequence identity to a MaSp2 dragline silk protein sequence.

In some embodiments, each "repeat unit" of a silk-like polypeptide comprises from two to twenty "quasi-repeat" units (i.e., $n_3$ is from 2 to 20). Quasi-repeats do not have to be exact repeats. Each repeat can be made up of concatenated quasi-repeats. Equation 1 shows the composition of a repeat unit according the present disclosure and that incorporated by reference from WO 2015/042164. Each silk-like polypeptide can have one or more repeat units as defined by Equation 1.

(Equation 1)
(SEQ ID NO: 13)
$\{\text{GGY-[\textbf{GPG}-X}_1]_{n1}\text{-\textbf{GPS}-(A)}_{n2}\}_{n3}$.

The variable compositional element $X_1$ (termed a "motif") is according to any one of the following amino acid sequences shown in Equation 2 and $X_1$ varies randomly within each quasi-repeat unit.

(Equation 2)

$X_1 =$ SGGQQ (SEQ ID NO: 14)

or

GAGQQ (SEQ ID NO: 15)

or

GQGPY (SEQ ID NO: 16)

or

AGQQ (SEQ ID NO: 17)

or

SQ

Referring again to Equation 1, the compositional element of a quasi-repeat unit represented by "GGY-[GPG-$X_1]_{n1}$-GPS" (SEQ ID NO: 18) in Equation 1 is referred to a "first region." A quasi-repeat unit is formed, in part by repeating from 4 to 8 times the first region within the quasi-repeat unit. That is, the value of $n_1$ indicates the number of first region units that are repeated within a single quasi-repeat unit, the value of $n_1$ being any one of 4, 5, 6, 7 or 8. The compositional element represented by "(A)$_{n2}$" (SEQ ID NO: 19) (i.e., a polyA sequence) is referred to as a "second region" and is formed by repeating within each quasi-repeat unit the amino acid sequence "A" $n_2$ times (SEQ ID NO: 19). That is, the value of $n_2$ indicates the number of second region units that are repeated within a single quasi-repeat unit, the value of $n_2$ being any one of 6, 7, 8, 9, 10, 11, 12, 13, 14, 15, 16, 17, 18, 19, or 20. In some embodiments, the repeat unit of a polypeptide of this disclosure has at least 95% sequence identity to a sequence containing quasi-repeats described by Equations 1 and 2. In some embodiments, the repeat unit of a polypeptide of this disclosure has at least 80%, or at least 90%, or at least 95%, or at least 99% sequence identity to a sequence containing quasi-repeats described by Equations 1 and 2.

In additional embodiments, 3 "long" quasi repeats are followed by 3 "short" quasi-repeat units. Short quasi-repeat units are those in which $n_1=4$ or 5. Long quasi-repeat units are defined as those in which $n_1=6$, 7 or 8. In some embodiments, all of the short quasi-repeats have the same $X_1$ motifs in the same positions within each quasi-repeat unit of a repeat unit. In some embodiments, no more than 3 quasi-repeat units out of 6 share the same $X^1$ motifs.

In additional embodiments, a repeat unit is composed of quasi-repeat units that do not use the same $X_1$ more than two occurrences in a row within a repeat unit. In additional embodiments, a repeat unit is composed of quasi-repeat units where at least 1, 2, 3, 4, 5, 6, 7, 8, 9, 10, 11, 12, 13, 14, 15, 16, 17, 18, 19 or 20 of the quasi-repeats do not use the same $X_1$ more than 2 times in a single quasi-repeat unit of the repeat unit.

Thus, in some embodiments, provided herein are strains of yeast that recombinantly express silk-like polypeptides with a reduced degradation to increase the amount of full-length polypeptides present in the isolated product from a cell culture. In some embodiments, the strain expressing a silk-like polypeptide is a *P. pastoris* strain comprises a PAS_chr4_0584 knock-out and a PAS_chr3_1157 knock-out. In some embodiments, the strain expressing a silk-like polypeptide is a *P. pastoris* strain comprising an sec72 knock-out and/or an overexpressed SSH1 translocon complex.

TABLE 5

| | | 18B vector | |
|---|---|---|---|
| Description | SEQ ID NO: | 5' to 3' Sequence | |

| | | | |
|---|---|---|---|
| 18B silk-lik3 polypeptide encoding sequence | 20 | ggtggttacg gtccaggcgc tggtcaacaa ggtccaggaa gtggtggtca acaaggacct   60<br>ggcggtcaag gaccctacgg tagtggccaa caaggtccag gtggagcagg acagcagggt  120<br>ccggagaggcc aaggaccta cggaccaggt gctgctgctg ccgccgctgc cgctgccgga  180<br>ggttacggtc caggagccgg acaacagggt ccaggtggag ctggacaaca aggtccagga  240<br>tcacaaggtc ctggtggaca aggtccatac ggtcctggtg ctggtcaaca gggaccaggt  300<br>agtcaaggac ctggttcagg tggtcagcag gtccaggag acagggtcc ttacggccct  360<br>tctgccgctg cagcagcagc cgctgccgca ggaggatacg gacctggtgc tggacaacga  420<br>tctcaaggac caggaggaca aggtcctat ggacctggcg ctggccaaca aggacctggt  480<br>tctcagggtc caggttcagg aggccaacaa ggcccaggag gtcaaggacc atacggacca  540<br>tccgctgcgg cagctgcagc tgctgcaggt ggatatggcc caggagccgg acaacagggt  600<br>cctggttcac aaggtccagg atctggtggt caacagggac caggcggcca gggaccttat  660<br>ggtccaggag ccgctgcagc agcagcagct gttggaggtt acggccctgg tgccggtcaa  720<br>caaggcccag gatctcaggg tcctggatct ggaggacaac aaggtcctgg aggtcagggt  780<br>ccatacggac cttcagcagc agctgctgct gcagccgctg gtggttatgg acctggtgct  840<br>ggtcaacaag gaccgggttc tcagggtccg ggttcaggag gtcagcaggg ccctggtgga  900<br>caaggacctt atggacctag tgcggctgca gcagctgccg ccgcaggtgg ttacggtcca  960<br>ggcgctggtc aacaaggtcc aggaagtggt ggtcaacaag gacctggcgg tcaaggaccc 1020<br>tacggtagtg gccaacaagg tccaggtgga gcaggacagc agggtccagg aggccaagga 1080<br>ccttacggac caggtgctgc tgctgccgcc gctgccgctg ccggaggtta cggtccagga 1140<br>gccggacaac agggtccagg tggagctgga caacaaggtc caggatcaca aggtcctggt 1200<br>ggacaaggtc catacggtcc tggtgctggt caacagggac caggtagtca aggacctggt 1260<br>tcaggtggtc agcagggtcc aggaggacag ggtccttacg gcccttctgc cgctgcagca 1320<br>gcagccgctg ccgcaggagg atacggacct ggtgctggac aacgatctca aggaccagga 1380<br>ggacaaggtc cttatggacc tggcgctggc caacaaggac ctggttctca gggtccaggt 1440<br>tcaggaggcc aacaagggcc caggaggtcaa ggaccatacg gaccatccgc tgcggcagct 1500<br>gcagctgctg caggtggata tggccccagga gccggacaac agggtcctgg ttcacaaggt 1560<br>ccaggatctg gtggtcaaca gggaccagc ggccaggac cttatggtcc aggagccgct 1620<br>gcagcagcag cagctgttgg aggttacggc cctggtgccg gtcaacaagg cccaggatct 1680<br>cagggtcctg gatctggagg acaacaaggt cctggaggtc agggtccata cggaccttca 1740<br>gcagcagctg ctgctgcagc cgctggtggt tatggacctg gtgctggtca acaaggaccg 1800<br>ggttctcagg gtccgggttc aggaggtcag cagggccctg gtggacaagg accttatgga 1860<br>cctagtgcgg ctgcagcagc tgccgccgca ggtggttacg gtccaggcgc tggtcaacaa 1920<br>ggtccaggaa gtggtggtca acaaggacct ggcggtcaag gaccctacgg tagtggccaa 1980<br>caaggtccag gtggagcagg acagcagggt ccggagaggcc aaggaccta cggaccaggt 2040<br>gctgctgctg ccgccgctgc cgctgccgga ggttacggtc caggagccgg acaacagggt 2100<br>ccaggtggag ctggacaaca aggtccagga tcacaaggtc ctggtggaca aggtccatac 2160<br>ggtcctggtg ctggtcaaca gggaccaggt agtcaaggac ctggttcagg tggtcagcag 2220<br>gtccaggag acagggtcc ttacggcct tctgccgctg cagcagcagc cgctgccgca 2280<br>ggaggatacg gacctggtgc tggacaacga tctcaaggac caggaggaca aggtccttat 2340<br>ggacctggcg ctggccaaca aggacctggt tctcagggtc caggttcagg aggccaacaa 2400<br>ggcccaggag gtcaaggacc atacggacca tccgctgcgg cagctgcagc tgctgcaggt 2460<br>ggatatggcc caggagccgg acaacagggt cctggttcac aaggtccagg atctggtggt 2520<br>caacagggac caggcggcca gggaccttat ggtccaggag ccgctgcagc agcagcagct 2580<br>gttggaggtt acggccctgg tgccggtcaa caaggcccag gatctcaggg tcctggatct 2640<br>ggaggacaac aaggtcctgg aggtcagggt ccatacggac cttcagcagc agctgctgct 2700<br>gcagccgctg gtggttatgg acctggtgct ggtcaacaag gaccgggttc tcagggtccg 2760<br>ggttcaggag gtcagcaggg ccctggtgga caaggacctt atggacctag tgcggctgca 2820<br>gcagctgccg ccgca 2835 |
| 18B polypeptide sequence | 21 | GGYGPGAGQQGPGSGGQQGPGGQGPYGSGQQGPGGAGQQGPGGQGPYGPGAAAAAAAAGGYGPGAGQQG<br>PGGAGQQGPGSQGPGGQGPYGPGAGQQGPGSQGPGSGGQQGPGGQGPYGPSAAAAAAAAGGYGPGAGQR<br>SQGPGGQGPYGPGAGQQGPGSQGPGSGGQQGPGGQGPYGPSAAAAAAAAGGYGPGAGQQGPGSQGPGSGG<br>QQGPGGQGPYGPGAAAAAAAAVGGYGPGAGQQGPGSQGPGSGGQQGPGGQGPYGPSAAAAAAAAGGYGPGA<br>GQQGPGSQGPGSGGQQGPGGQGPYGPSAAAAAAAAGGYGPGAGQQGPGSGGQQGPGGQGPYGSGQQGPGG<br>AGQQGPGGQGPYGPGAAAAAAAAGGYGPGAGQQGPGGAGQQGPGSQGPGGQGPYGPGAGQQGPGSQGPG<br>SGGQQGPGGQGPYGPSAAAAAAAAGGYGPGAGQRSQGPGGQGPYGPGAGQQGPGSQGPGSGGQQGPGGQ<br>GPYGPSAAAAAAAAGGYGPGAGQQGPGSQGPGSGGQQGPGGQGPYGPGAAAAAAAAVGGYGPGAGQQGPGS<br>QGPGSGGQQGPGGQGPYGPSAAAAAAAAGGYGPGAGQQGPGSQGPGSGGQQGPGGQGPYGPSAAAAAAAA<br>GGYGPGAGQQGPGSGGQQGPGGQGPYGSGQQGPGGAGQQGPGGQGPYGPGAAAAAAAAGGYGPGAGQQG<br>PGGAGQQGPGSQGPGGQGPYGPGAGQQGPGSQGPGSGGQQGPGGQGPYGPSAAAAAAAAGGYGPGAGQR<br>SQGPGGQGPYGPGAGQQGPGSQGPGSGGQQGPGGQGPYGPSAAAAAAAAGGYGPGAGQQGPGSQGPGSGG<br>QQGPGGQGPYGPGAAAAAAAAVGGYGPGAGQQGPGSQGPGSGGQQGPGGQGPYGPSAAAAAAAAGGYGPGA<br>GQQGPGSQGPGSGGQQGPGGQGPYGPSAAAAAAAA |
| Repeat sequence of a silk-like polypeptide | 22 | GGYGPGAGQQGPGSGGQQGPGGQGPYGSGQQGPGGAGQQGPGGQGPYGPGAAAAAAAAGGYGPGAGQQG<br>PGGAGQQGPGSQGPGGQGPYGPGAGQQGPGSQGPGSGGQQGPGGQGPYGPSAAAAAAAAGGYGPGAGQR<br>SQGPGGQGPYGPGAGQQGPGSQGPGSGGQQGPGGQGPYGPSAAAAAAAAGGYGPGAGQQGPGSQGPGSGG<br>QQGPGGQGPYGPGAAAAAAAAVGGYGPGAGQQGPGSQGPGSGGQQGPGGQGPYGPSAAAAAAAAGGYGPGA<br>GQQGPGSQGPGSGGQQGPGGQGPYGPSAAAAAAAA |

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pa.: Mack Publishing Company, 1990); Carey and Sundberg Advanced Organic Chemistry 3rd Ed. (Plenum Press) Vols A and B (1992).

Example 1: Production of Recombinant Yeast Expressing 18B

Strains of *P. pastoris* were modified to recombinantly express 18B silk-like polypeptides as follows:

First, we transformed a strain of *P. pastoris* to abrogate KU70 function to facilitate further editing and engineering. A HIS+ derivative of *Pichia pastoris* (*Komagataella phaffii*) strain GS115 (NRRL Y15851) was electroporated with a DNA cassette consisting of homology arms flanking a zeocin resistance marker and targeting the KU70 locus. Sequences are provided in Table 12. Transformants were plated on YPD agar plates supplemented with zeocin. This resulted in abrogation of KU70 function.

Then, we modified this strain to express a recombinant gene encoding a silk-like polypeptide. A HIS+ derivative of *Pichia pastoris* (*Komagataella phaffii*) strain GS115 (NRRL Y15851) was transformed with a recombinant vector (SEQ ID NO: 20) to cause expression and secretion of a silk-like polypeptide ("18B") (SEQ ID NO: 21). Transformation was accomplished by electroporation as described in PMID 15679083, incorporated by reference herein.

Each vector includes an 18B expression cassette with the polynucleotide sequence encoding the silk-like protein in the recombinant vectors flanked by a promoter (pGCW14) and a terminator (tAOX1 pA signal). The recombinant vectors further comprised dominant resistance markers for selection of bacterial and yeast transformants, and a bacterial origin of replication. The first recombinant vector included targeting regions that directed integration of the 18B polynucleotide sequences immediately 3' of the AOX2 loci in the *Pichia pastoris* genome. The resistance marker in the first vector conferred resistance to G418 (aka geneticin). The second recombinant vector included targeting regions that directed integration of the 18B polynucleotide sequences immediately 3' of the TEF1 loci in the *Pichia pastoris* genome. The resistance marker in the second vector conferred resistance to Hygromycin B.

Example 2: Production of Recombinant ΔSec72 Strain

Cells modified to express 18B were transformed with a vector comprising a DNA cassette with 5' and 3' homology arms targeting sec72 (SEQ ID NO: 1). The homology arms flank a yeast selection marker, as shown in the plasmid map in FIG. 2, which knocks out the sec72 gene when inserted into the sec72 gene. Transformants were plated on YPD agar plates supplemented with yeast selection medium, and incubated for 48 hours at 30° C.

Example 3: Production of Recombinant ΔSec72 Strain Overexpressing an SSH1 Translocon Complex

*P. pastoris* (Δsec72) cells modified to express 18B (SEQ ID NO: 21) were transformed with a vector for overexpression of the SSH1 translocon complex. A plasmid map of the vector is shown in FIG. 3. The vector comprises open reading frames for SSH1 (SEQ ID NO: 3), SSS1 (SEQ ID NO: 5), and SBH2 (SEQ ID NO: 7). Each open reading frame is operatively linked to a promoter and a terminator.

Transformants were plated on YPD agar plates supplemented with yeast selection medium, and incubated at 48 hours at 30° C.

Example 4: Production of Protease Double Knock-Out Strain

Figure 4A:
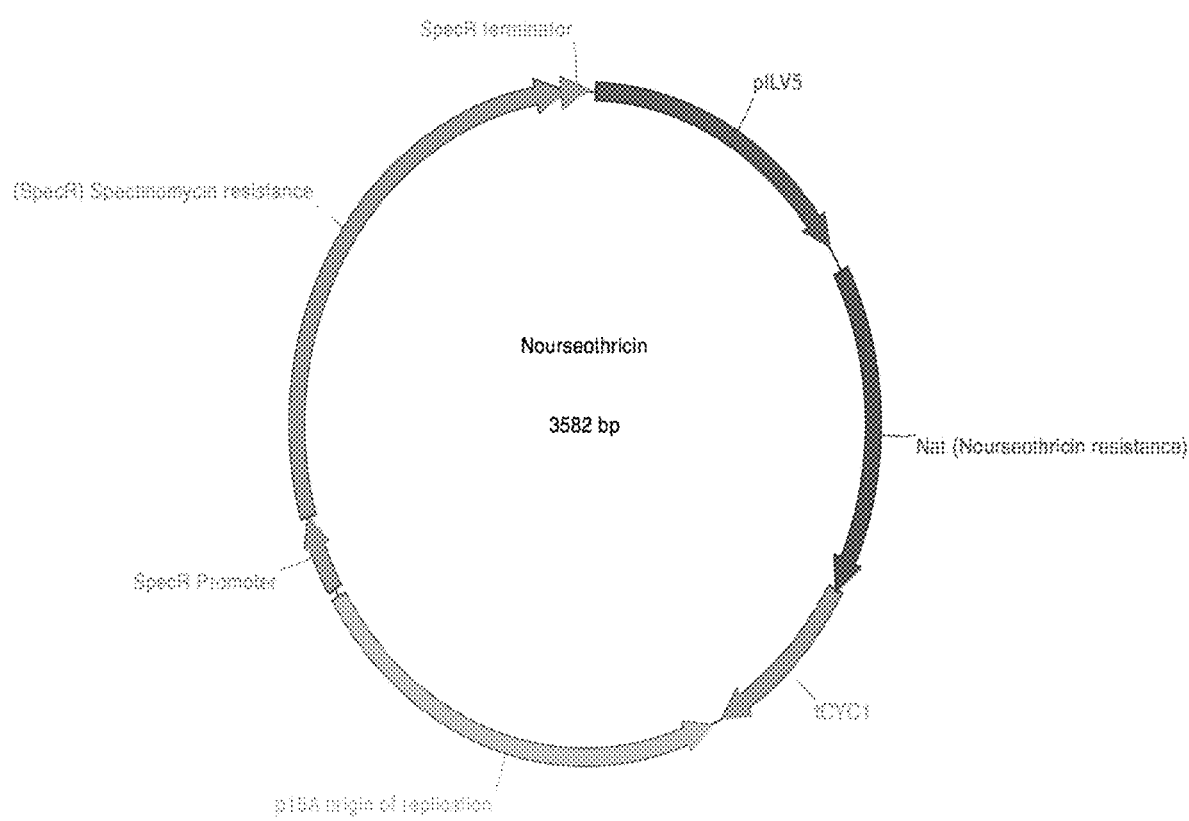
FIG. 4A is a plasmid map of a vector comprising a nourseothricin marker used with homology arms for targeted protease gene deletion.
Figure 4B:
FIG. 4B and FIG. 4C are cassettes for protease knockout with homology arms targeting the desired protease gene flanking a nourseothricin resistance marker.
Figure 4C:

To generate ΔΔprotease strains (i.e., double protease knock-out), a selected yeast strain was transformed with vector comprising a DNA cassette with 1150 bp homology arms flanking a nourseothricin resistance marker. A plasmid map comprising the nourseothricin resistance marker is shown in FIG. 4A, and sequences provided in Table 13. Homology arms used for each target were amplified by the primers provided in Table 8, and inserted into the nourseothricin resistance plasmid. Homology arms were inserted into the nourseothricin plasmid to generate cassettes comprising a nourseothricin resistance marker flanded by 3' and 5' homology arms to the target protease as shown in FIG. 4B and FIG. 4C. In FIG. 4B, the resistance cassette (Nour Resistance Cassette) is shown flanked by homology arms (HA1 and HA2). In FIG. 4C, details of the nourseothricin marker are shown, including the promoter from ILV5 gene from *Saccharomyces cerevisiae* (pILV5), the Nourseothricin acetyltransferase gene from *Streptomyces noursei* (nat), and the polyA signal from CYC1 gene from *Saccharomyces cerevisiae*.

A vector with homology arms targeting YPS1-1 (SEQ ID NO: 77) was used to transform modified yeast strains. Transformants were plated on YPD agar plates supplemented with nourseothricin, and incubated for 48 hours at 30° C.

TABLE 6

Proteases targeted for deletion in *P. pastoris* strain.

| Protease Gene Symbol | Protease ORF Sequence (SEQ ID NO:) | Protease polypeptide sequence (SEQ ID NO:) |
| --- | --- | --- |
| PAS_chr4_0584 (YPS1-1) | 9 | 10 |
| PAS_chr3_1157 (YPS1-2) | 11 | 12 |

To generate double knockouts, nourseothricin resistance was eliminated from the single protease knock-out strains produced above. A vector with homology arms targeting YPS1-2 (SEQ ID NO: 80) was used to transform the single protease knock-out strains. Transformants were plated on YPD agar plates supplemented with nourseothricin, and incubated for 48 hours at 30° C.

Example 5: ΔSec72 Improves MFα-18B Secretion Across Integration Copy Numbers

*Pichia pastoris* strains modified to express two, four, or six copies of 18B (Ab MaSp2 79 kDa) comprising the MFα1(sc) pre-pro leader sequence were prepared using techniques described in Example 1.

Δsec72 strains of each of the above were prepared using techniques described in Example 2. Δsec72 and WT strains for each of the 2×, 4×, and 6× 18B expressing strains were prepared. Secretion of MFα-18B from WT and Δsec72 strains (i.e., SEC72 KO strains) from each of the 2×, 4× and 6× 18B expressing strains was measured by ELISA, with the results shown in FIG. 6.

Figure 6:
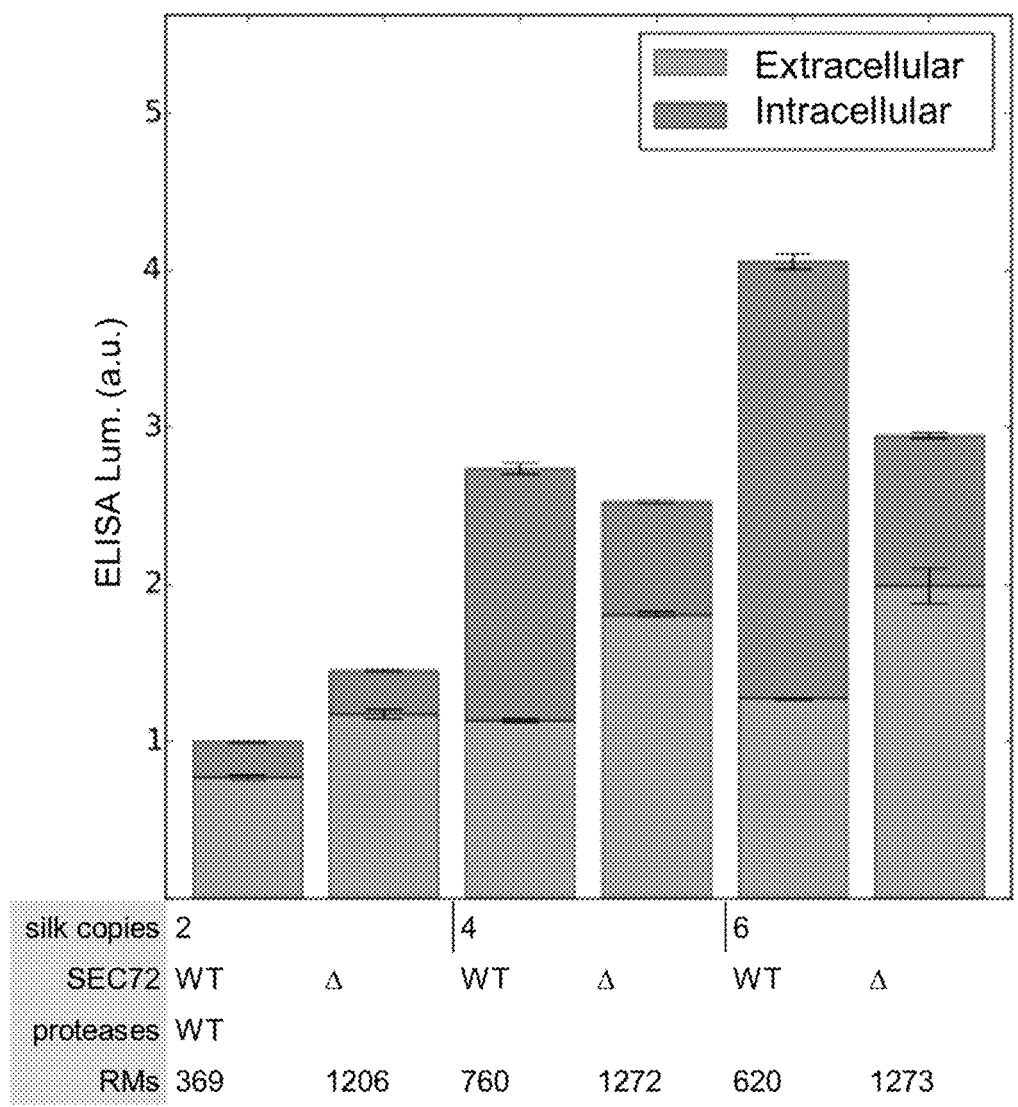
FIG. 6 shows secretion of recombinant 18B silk-like polypeptide expressed by wild-type (WT) and Δsec72 (Δ) strains expressing 2×, 4×, or 6× copies of 18B, as measured by an enzyme-linked immunosorbent assay (i.e., ELISA).

Referring to FIG. 6, "silk copies" are the number of expression cassettes for 18B (Ab MaSp2 79 kDa) using the MFα1(sc) pre-pro leader sequence in each strain. The 18B is C-terminally tagged with a 3×FLAG epitope for ELISA detection. Error bars show standard error of the mean among n≥4 biological replicates. The results show that deletion of the sec72 gene improves MFα-18B secretion across integration copy numbers (i.e., 2×, 4×, and 6× silk copies).

Example 6: ΔSec72 Improves Secretion from Non-MFα Signals

Figure 7:
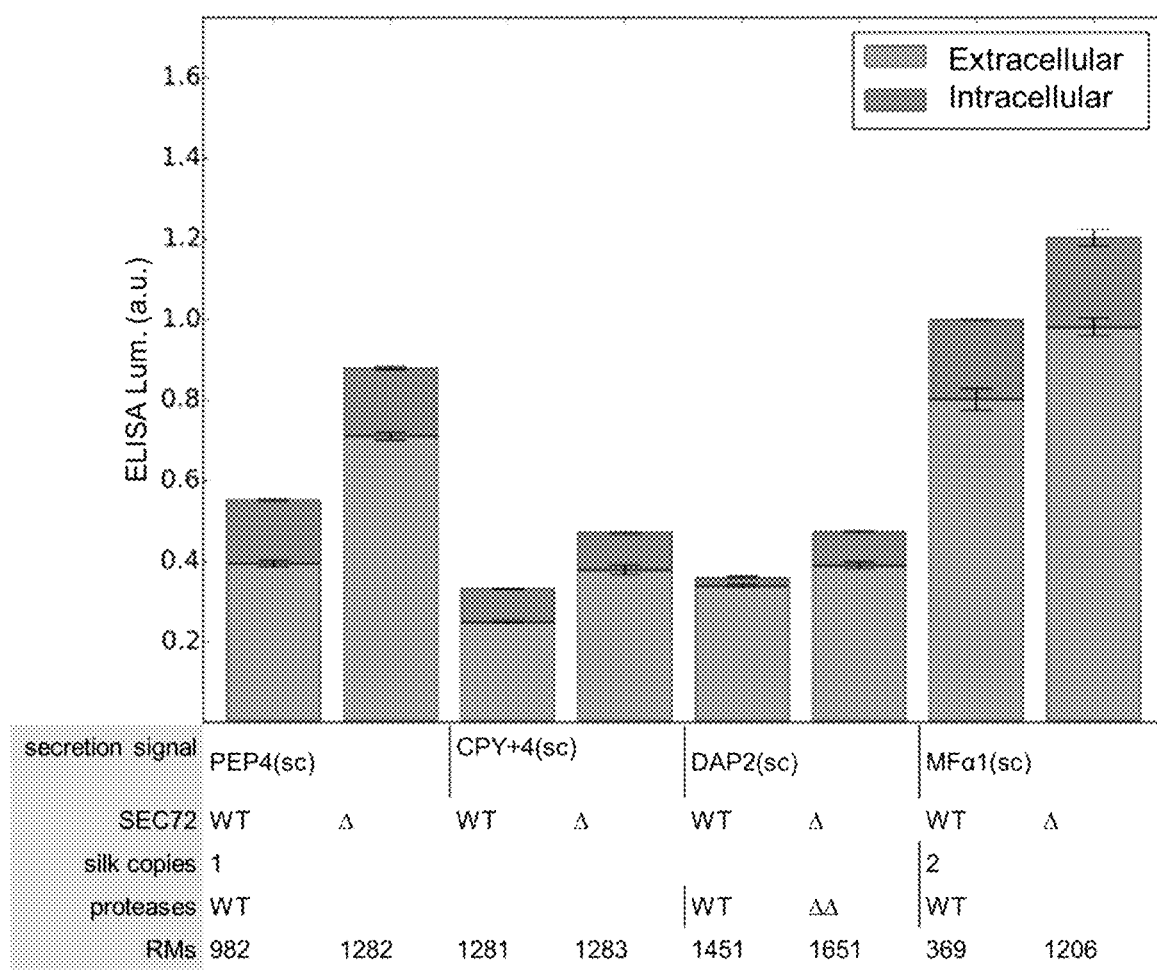
FIG. 7 shows shows secretion of recombinant protein comprising PEP4(sc), CPY+4(sc), DAP2(sc), or MFα1 (sc) signal peptides as expressed by wild-type (WT) and Δsec72 (Δ) strains and measured by ELISA. (sc) indicates the signal peptide derives from *S. cerevisiae*.

*P. pastoris* strains were modified according to Example 1 to express 4 different silk polypeptides each comprising a different secretion signal: PEP4(sc), CPY+4(sc), DAP2(sc), and MFα1(sc). Each complete leader sequence is a hybrid composed of the indicated signal peptide with the MFα1 (sc) propeptide (*S. cerevisiae* ortholog systematic name: YPL187W). (sc) indicates the signal peptide derives from *S. cerevisiae*. Strains recombinantly expressing polypeptides with PEP4(sc), CPY+4(sc), and DAP2(sc) each comprise a single expression cassette (i.e., 1 silk copy). Strains recombinantly expressing MFα1 (sc) comprise 2 expression cassettes (i.e., 2 silk copies). Δsec72 strains of each of the above were prepared using techniques described in Example 2 to compare secretion from WT and Δsec72 strains. For the Δsec72strain comprising DAP2(sc), the strain was additionally modified to knockout YPS1-1 and YPS1-2 proteases, as described in Example 4. Secretion of polypeptides with each secretion signal from WT and Δsec72 strains was measured by ELISA, with the results shown in FIG. 7.

The results indicate that the deletion of the sec72 gene improves secretion for polypeptides comprising non-MFα1 (sc) signal peptides. Error bars show standard error of the mean among n≥4 biological replicates.

TABLE 7A

MFα1(sc) propeptide sequence

| | Sequence | SEQ ID NO: |
| --- | --- | --- |
| MFα1(sc) propeptide Nucleotide Encoding Sequence (5' to 3') | gctccagtcaacactacaacagaagatga aacggcacaaattccggctgaagctgtca tcggttactcagatttagaagggatttc gatgttgctgttttgccattttccaacag cacaaataacgggttattgtttataaata ctactattgccagcattgctgctaaagaa gaaggggtatctctcgagaaaagagaggc tgaa | 105 |
| MFα1(sc) propeptide Polypeptide Sequence | APVNTTTEDETAQIPAEAVIGYSDLEGDF DVAVLPFSNSTNNGLLFINTTIASIAAKE EGVSLEKREAE | 106 |

TABLE 7B

Silk Secretion Signals

| Secretion Signal | Sequence | SEQ ID NO: |
|---|---|---|
| PEP4 Nucleotide Encoding Sequence (5' to 3') | atgttcagcttgaaagcattattgccatt ggccttgttgttggtcagcgccaaccaag ttgctgca | 83 |
| PEP4 Polypeptide Sequence | MFSLKALLPLALLLVSANQVAA | 84 |
| PRC1, mutant (i.e., CPY + 4) Nucleotide Encoding Sequence (5' to 3') | atgaaagcattcctgttgttactactttt actaggcctgtccactacactcgctaagg ca | 85 |
| PRC1, mutant (i.e., CPY + 4) Polypeptide Sequence | MKAFLLLLLLLGLSTTLAKA | 86 |
| DAP2 Nucleotide Encoding Sequence (5' to 3') | atggaaggtggcgaagaagaagttgagcg cattcctgatgaacttttcgatacaaaaa agaagcatttgttagataagctcataagg gtcggaataatccttgtactcctgatatg gggcactgttttgttgctaaaaagtatt | 87 |
| DAP2 Polypeptide Sequence | MEGGEEEVERIPDELFDTKKKHLLDKLIR VGIILVLLIWGTVLLLKSI | 88 |
| MF(alpha) 1, variant Nucleotide Encoding Sequence (5' to 3') | atgagatttccttcaattttttactgctgt tttattcgcagcatcctccgcattagct | 89 |
| MF(alpha) 1, variant Polypeptide Sequence | MRFPSIFTAVLFAASSALA | 90 |

Example 7: ΔSec72 Improves Secretion of Longer Silks and Distinct Silk Sequences

*P. pastoris* strains were modified according to Example 1 to express long silk polypeptides *Argioppe bruennichi* (Ab) MaSp2 (106 kDa) (SEQ ID NO: 43), *Latrodectus hesperus* (Lh) MaSp1 (55 kDa) (SEQ ID NO: 44). Ab MaSp2 106 kDa (aka 24B) is a longer concatemer of Ab MaSp2 79 kDa (18B). Lh MaSp1 55 kDa is distinct sequence from another class of spidroins.

Figure 8:
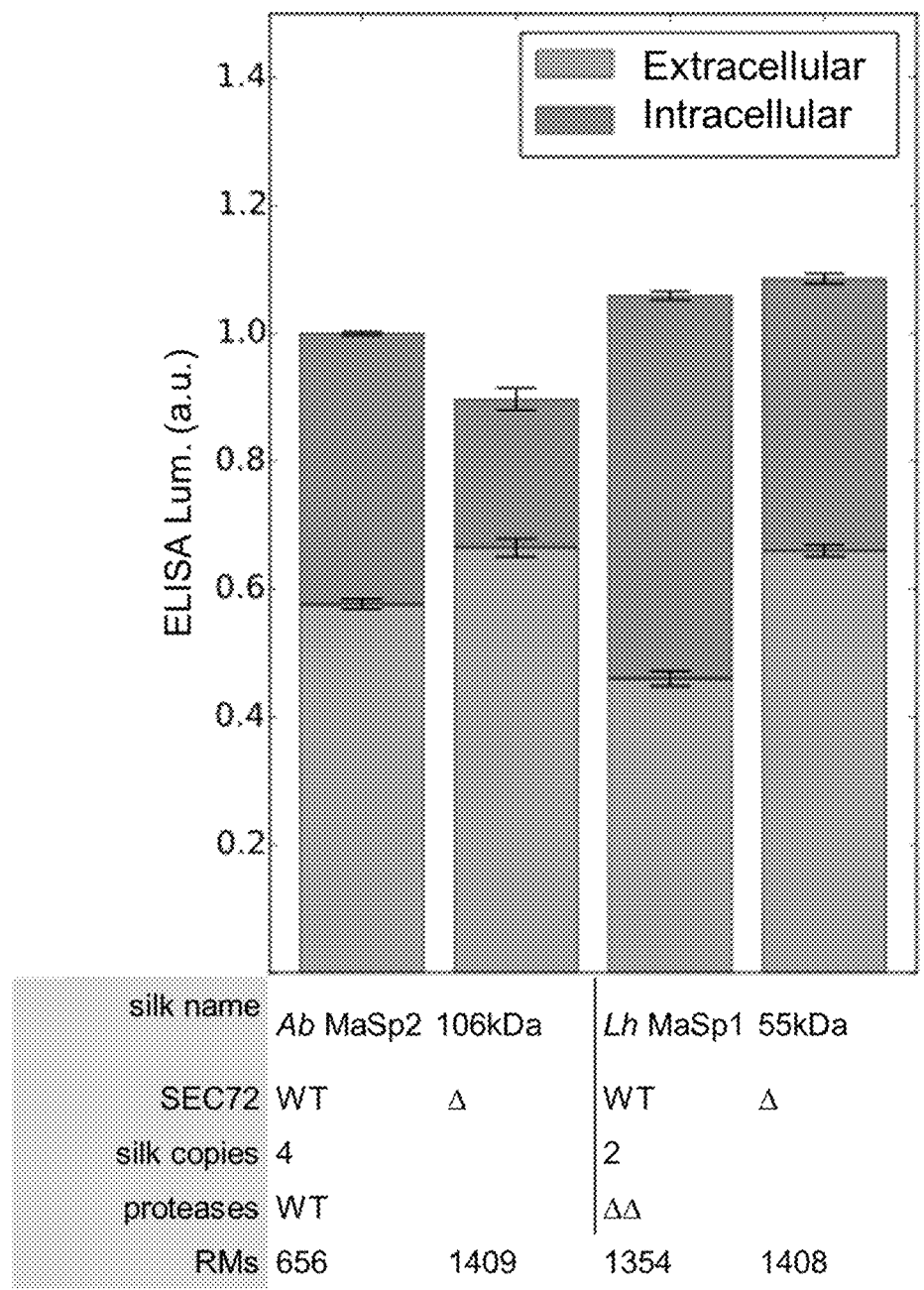
FIG. 8 shows secretion of long silk polypeptides *Argiope bruennichi* Major ampullate spidron 2 (i.e., Ab MaSp2) (106 kDa), and *Latrodectus hesperus* Major ampullate spidron 1 (i.e., Lh MaSp1 (55 kDa)) as expressed by wild-type (WT) and Δsec72 (Δ) strains and measured by ELISA.

Δsec72 strains of each were prepared using techniques described in Example 2 to compare secretion from WT and Δsec72 strains. The strains comprising Lh MaSp1 (55 kDa) were additionally modified to knockout YPS1-1 and YPS1-2 proteases, as described in Example 4. Secretion of the long silk polypeptides from WT and Δsec72 strains was measured by ELISA, with the results shown in FIG. 8. Error bars show standard error of the mean among n≥4 biological replicates.

*Argioppe bruennichi* MaSp2 protein amino acid sequence (SEQ ID NO: 43):
MNWSIRLALLGFVVLSTQTVFAVGQAATPWENSQLAEDFINSFLRFIAQS
GAFSPNQLDDMSSIGDTLKTAIEKMAQSRKSSKSKLQALNMAFASSMAEI
AVAEQGGLSLEAKTNAIANALASAFLETTGFVNQQFVSEIKSLIYMIAQA
SSNEISGSAAAAGGGSGGGGGSGQGGYGQGASASASAAAAYGSAPQGAGG
PAPQGPSQQGPVSQGPYGPGAAAAAAAAGGYGPGAGQQGPGSQGPGSGGQ
QGPGSQGPGSGGQQGPGGQGPYGPSAAAAAAAAGGYGPGAGQQGPGSQG
PGSGGQQGPGGQGPYGPGAAAAAAVGGYGPGAGQQGPGSQGPGSGGQQG
PGGQGPYGPSAAAAAAAAGGYGPGAGQQGPGSQGPGSGGQQGPGGQGPYG
PSAAAAAAAAGGYGPGAGQQGPGSGGQQGPGGQGPYGSGQQGPGGAGQQG
PGGQGPYGPGAAAAAAAAGGYGPGAGQQGPGGAGQQGPGSQGPGGQGPY
GPGAGQQGPGSQGPGSGGQQGPGGQGPYGPSAAAAAAAAGGYGPGAGQQG
PGSQGPGSGGQQGPGSQGPGSGGQQGPGGQGPYGPSAAAAAAAAGGYGPG
AGQQGPGSQGPGSGGQQGPGGQGPYGPGAAAAAAVGGYGPGAGQQGPGS
QGPGSGGQQGPGGQGPYGPSAAAAAAAGGYGPGAGQQGPGSQGPGSGGQ
QGPGGQGPYGPSAAAAAAAAGGYGPGAGQQGPGSGGQQGPGGQGPYGSGQ
QGPGGAGQQGPGGQGPYGPGAAAAAAAAGGYGPGAGQQGPGGAGQQGPG
SQGPGGQGPYGPGAGQQGPGSQGPGSGGQQGPGGQGPYGPSAAAAAAAA
GGYGPGAGQRSQGPGGQGPYGPGAGQQGPGSQGPGSGGQQGPGGQGPYGP
SAAAAAAAGPGAGRQGPGSQGPGSGGQQGPGGQGPYGPSAAAAAAAGP
GARRQGPGSQGPGSGGQQGPGGQGPYGSGQQGPGGAGQQGPGGQGPYGPG
AAAAAAAAGGYGPGAGQQGPGGAGQQGPGSQGPGGQGPYGPGAGQQGPG
SQGPGSGGQQGPGGQGPYGPSAAAAAAAAGGYGPGAGQQGPGSQGPGSGG
QQGPGGQGPYGPGAAAAAAVGGYGPGAGQQGPGSQGPGSGGQQGPGGQG
PYGPSAAAAAAAAGGYGPGAGQQGPGSQGPGSGGQQGPGGQGPYGPSAAA
AAAAAGGYGPGAGQQGPGSGGQQGPGGQGPYGSGQQGPGGAGQQGPGGQG
PYGPGAAAAAAAGGYGPGAGQQGPGGAGQQGPEGPGSQGPGSGGQQGP
GGQGPYGPGAAAAAAVGGYGPGAGQQGPGSQGPGSGGQQGPGGQGPYGP
SAAAAAAAGGYGPGAGQQGPGSQGPGSGGQQGPGGQGPYGPSAAAAAAA
AGGYGPGAGQQGPGSGGQQGPGGQGPYGSGQQGPGGAGQQGPGGQGPYGP
GAAAAAAAGGYGPGAGQQGPGGAGQQGPGSQGPGGQGPYGPGAGQQGP
GSQGPGSGGQQGPGGQGPYGPSAAAAAAAAGGYGPGAGQQGPGSQGPGSG
GQQGPGSQGPGSGGQQGPGGQGPYGPSAAAAAAAAGGYGPGAGQQGPGS
QGPGSGGQQGPGGQGPYGPGAAAAAAVGGYGPGAGQQGPGSQGPGSGGQ
QGPGGQGPYGPSAAAAAAAGGYGPGAGQQGPGSGGQQGPGGQGP
YGPSAAAAAAAGGYGPGAGQQGPGSGGQQGPGGQGPYGSGQQGPGGAGQ
QGPGGQGPYGPGAAAAAAAGGYGPGAGQQGPGGAGQQGPGSQGPGGQG
PYGPGAGQQGPGSQGPGSGGQQGPGGQGPYGPSAAAAAAAAGGYGPGAGQ
QGPGSQGPGSGGQQGPGGQGPYGPSAAAAAAAGGYGPGAGQQGPGSGGQ
QGPGGQGPYGSGQQGPGGAGQQGPGGQGPYGGYGPGAGQQGPGSQGPGS
GGQQGPGGQGPYGPSAAAAAAAGPGARRQGPGSQGPGSGGQQGPGGQGP -continued YGSGQQGPGGAGQQGPGGQGPYGPGAAAAAAAAAGGYGPGAGQQGPGGAG
QQGPGSQGPGGQGPYGPGAGQQGPGSQGPGSGGQQGPGGQGPYGPSAAAA
AAAAAGGYGPGAGQQGPGSQGPGSGGQQGPGGQGPYGPGAAAAAAVGGY
GPGAGQQGPGSQGPGSGGQQGPGGQGPYGPSAAAAAAAAAGGYGPGAGQQG
PGSQGPGSGGQQGPGGQGPYGPSAAAAAAAAGGYGPGAGQQGPGSGGQQG
PGGQGPYGSGQQGPGGAGQQGPGGQGPYGPGAAAAAAAAAGGYGPGAGQQ
GPGGAGQQGPGSQGPGGQGPYGPGAGQQGPGSQGPGSGGQQGPGGQGPYG
PSAAAAAAAAGPGAGRQGPGSQGPGSGGQQGPGGQGPYGPSAAAAAAAAG
PGARRQGPGSQGPGSGGQQGPGGQGPYGSGQQGPGGAGQQGPGGQGPYGP
GAAAAAAAAAGGYGPGAGQQGPGGAGQQGPGSQGPGGQGPYGPGAGQQGP
GSQGPGSGGQQGPGSQGPYGPSAAAAAAAAGGYGPGAGQQGPGSQGPGSG
GQQGPGGQGPYGPSAAAAAAAAGGYGPGAGQQGPGSGGQQGPGGQGPYGS
GQQGPGGAGQQGPGGQGPYGPGAAAAAAAAAGGYGPGAGQQGPGSQGPGS
GGQQGPGSQGPGSGGQGPGGQGPYGPSAAAAAAAAAGGYGPGAGQQGPG
SQGPGSGGQQGPGGQGPYGPGAAAAAAVGGYGPGAGQQGPGSQGPGSGG
QQGPGGQGPYGPSAAAAAAAAGGYGPGAGQQGPGSQGPGSGGQQGPGGQG
PYGPSAAAAAAAAGGYGPGAGQQGPGSGGQQGPGGQGPYGSGQQGPGGAG
QQGPGGQGPYGPGAAAAAAAAAGGYGPGAGQQGPGGAGQQGPGSQGPGGQ
GPYGPGAGQQGPGSQGPGSGGQQGPGGQGPYGPSAAAAAAAAGGYGPGAG
QQGPGSQGPGSGGQQGPGGQGPYGPGAAAAAAVGGYGPGAGQQGPGSQG
PGSGGQQGPGGQGPYGPSAAAAAAAAGGYGPGAGQQGPGSQGPGSGGQQG
PGGQGPYGPSAAAAAAAAGGYGPGAGQQGPGSGGQQGPGGQGPYGSGQQG
PGGAGQQGPGGQGPYGPGAAAAAAAAAGGYGPGAGQQGPGGAGQQGPGSQ
GPGGQGPYGPGAGQQGPGSQGPGSGGQQGPGGQGPYGPSAAAAAAAAGGY
GPGAGQQGPGSQGPGSGGQQGPGGQGPYGPSAAAAAAAAGGYGPGAGQQG
PSSQAPVASAAASRLSSPQASARVSSAVSTLVSSGPTSPAALSNAISSVV
SQVSASNPGLSGCDVLVQALLEIVSALVHILGSSSIGQINYAASSQYAQM
VGNSVAQALG Latrodectus hesperus MaSp1 protein amino acid
sequence (SEQ ID NO: 44):
MTWSTRLALSFLFVLCTQSLYALAQANTPWSSKANADAFINSFISAASNT
GSFSQDQMEDMSLIGNTLMAAMDNMGGRITPSKLQALDMAFASSVAEIAA
SEGGDLGVTTNAIADALTSAFYQTTGVVNSRFISEIRSLIGMFAQASAND
VYASAGSSGGGGYGASSASAASASAAAPSGVAYQAPAQAQISFTLRGQQP
VSYGQGGAGPGGAGAAAAAAAAAGGAGQGGQGGYGQGGYGQGGAGQGGSG
AAAAAAAAAGGTGQGGAGQGGAGAAAAAAAAAGGAGQGGQGGYGQGGYGQ
GGTGQGGAGAAAAAAAAGGAGQGGQGGYGQGGYGQGGYGQGGSGAAAAAA
AAGGAGQGGQGGYGQGGYGQGGAGQGGAGAAAAAAAAAGGAGQGGYGRG
GAGQGGAAAAAAAGAGQGGYGQGAGQGGSGAAAAAAAAGGAGQGGQG
GYGQGGYGQGGSGAAAAAAAAGGAGQGGQGGYGQGGYGQGGAGQGGAGAA
AAAAAGGAGQGGQGGYGQGGYGQGGAGQGGAGAAAAAAAAAGGAGQGGQG GYGQGGYGQGGAGQGGAGAAAAAAAAGGAGQGGQGGYGQGGYGQGGAGQG
GAAAAAAAAAGGAGQGGYGRGGAGQGGAAAAAGAGQGGYGGQGAGQGGAG
AAAAAAAAGGAGQGGQGGYGRGGYGQGGAGQGGAGAAAAAAAAAGGAGQGG
QGGYGQGGYGQGGAGQGGAAAAAAAAGGAGQGGYGRGGAGQGGAAAAAAA
AAGAGQGGYGGQGAGQGGAGAAAAAAAAGGAGQGGQGDYGRGGYGQGGAG
QGGAGAAAAAAAAGGAGQGGQGGYGQGGYGQGGAGQGGAAAASAAAAGG
AGQGGYGRGGAGQGGAAAAAGAGQGGYGGQGAGQGGAGAAAAAAAAAGGAG
QGGQGGYGRGGYGQGGAGQGGAGAAAAATAAGGAGQGGQGGYGQGGYGQG
GAGQGGAAAAAAAAGGAGQGGYGRGGAGQGGAAAAAAAAAGAGQGGYGG
QGAGQGGAGAAAAAAAAGGAGQGGQGGYGRGGYGQGGAGQGGAGAAAAAAAA
GGAGQGGQGGYGQGGYGQGGAGQGGAAAAAAAAAGGAGQGGYGRGGAGQG
GAAAAAGAGQGGYGGQGAGQGGAGAAAAASRGAGQGGQGGYGRGGYGQGG
AGQGGAGAAAAAAAAAGGAGQGGQGGYGQGGYGQGGAGQGGAAAAAAAGG
AGQGGYGRGGAGQGGAAAAAGAGQGGYGGQGAGQGGAGAAAAAAAAGGAG
QGGQGGYGRGGYGQGGAGQGGAGAAAAAAAAAGGAGQGGQGGYGQGGYGQG
GAGQGGAAAAAAAAGGAGQGGYGRGGAGQGGAAAAAAAAAGSGQGGYGG
QGAGQGGAGAAAAAAAAGGAGQGGQGGYGRGGYGQGGAGQGGAGAAAAAA
AAGGAGQGGQGGYGQGGYGQGGAGQGGAAAAAAAAAGGAGQGGYGRGGA
GQGGAAAAAGAGQGGYGGQGAGQGGAGAAAAAAAAAGGAGQGGQGGYGRGG
YGQGGAGQGGAGTAAAAAAAGGAGQGGQGGYGQGGYGQGGAGQGGAAAAA
AAAAGGAGQGGYGRGGAGQGGAAAAAAAAGAGQGGYGGQGAGQGGAGAA
AAAAAGGAGQGGQGGYGRGGYGQGGAGQGGAGAAAAAAAAAGGASQGGQG
GYGQGDYGQGGAGQGGAAAAAAAAGGAGQGGYGRGGAGQGGAAAAAGAGQ
GGYGGQGAGQGGAGAAAAAAAGGAGRGGQGGYGRGGYGQGGAGQGGAGA
AAAAAAGGAGQGGQGGYGQGGYGQGGVGQGGAAAAAAAAAGGAGQGGYG
RGGAGQGGAAAAAAAGAGQGGYGGQGAGQGGAGAAAAAAAAGGAGQGG
QGGYGRGGYGQGGAGQGGAAAAAAAGGAGQGGQGGYGQGGYGQGGYG
QGGAGQGGAAAAAAAAGGAGQGGYGRGGAGQGGAAAAAGAGQGGYGGQGA
GQGGAGAAAAAAAAGGAGQGGQGGYGQGGYGQGGAGQGGAAAAAAAAAG
AGQGGQGGYGQGGYGQGGAGQGGAAAAAAAAAGSGQGGYGGQGAGQGGAG
AAAAAAAAAGGAGQGGQGGYGQGGYGQGGYGQGGAGQGGAAAAAAAAAG
GAGQGGYGRGGAGQGGAAAAAGAGQGGYGGQGAGQGGAAAAAAAAAGAGAGAG
AAAAAAGGAGQGGYGRGGYGQGGAGQGGAAAAAAAAAGGAGQGG
QGGYGQGGNGQGGAGQGGAAAAAAGGAGQGGYGRGGAGQGGAAAAAA
AAGAGQGGYGGQGAGQGGAAAAAAAAAGGAGQGGQGGYGRGGYGQGGAG
QGGAAAAAAAGGASQGGQGGYGQGDYGQGGAGQGGAAAAAAAAAGGAG
QGGYGRGGAGQGGAAAAAGAGQGGYGGQGAGQGGAGAAAAAAAAAGGAGRG
GQGGYGRGGYGQGGAGQGGAGAAAAAAAAGGAGQGGQGGYGQGGYGQGGA
GQGGAAAAAAAAGGAGQGGYGRGGAGQGGAAAAAGAGQGGYGGQGAGQG
GAGAAAAAAAAGGAGRGGQGGYGRGGYGQGGAGQGGAGAAAAAAAAGGAG -continued

QGGQGGYGQGGYGQGGAGQGGAAAAAAAAVGGAGQGGYGRGGAGQGGAAA

AAAAAAGSQGGYGGQGAGQGGAGAAAAAAAAGGAGQGGQGGYGGGGYG

QGGAGQGGAGAAAAAAAAGGAGQGGQGGYGQGGYGQGGAGQGGAAAAAAA

AAGGAGQGGYGRGGAGQGGAAAATGAGQGGYGGQGAGQGGAGAAAAAAAA

GGAGQGGQGGYGRGGYGQGGAGQGGAGAAAAAAAAGGAGQGGQGGYGQGG

YGQGGAGQGGAAAAAAAAGGAGQGGYGRGGAGQGGAAAAAAAAAGAGQGG

YGGQGAGQGGAGAAAAAAAAGGAGQGGQGGYGRGGYGQGGAGQGGAGAAA

AGGAGQGGQGGYGQGGYGQGGAGQGGAAAAAAAAAAGGAGQGGYGGYGQQ

GGAGAAAAAASGPGQIYYGPQSVAAPAAAAASALAAPATSARISSHASAL

LSNGPTNPASISNVISNAVSQISSSNPGASACDVLVQALLELVTALLTII

GSSNIGSVNYDSSGQYAQVVTQSVQNAFA

Example 8: Secretion Improves with SEC72 Deletion, but Neither Knockdown Nor Overexpression

*P. pastoris* strains were modified according to Example 1 to comprise 4 copies of DNA cassettes comprising recombinant genes expressing 18B silk-like polypeptide. Δsec72 strains were prepared using techniques described in Example 2. The strains were additionally modified to knockout YPS1-1 and YPS1-2 proteases, as described in Example 4.

From this strain, a strain overexpressing sec72 was prepared by transforming with a vector comprising a recombinant sec72 gene operably linked to a THI11 promoter (pTHI11). pTHI11 is de-repressed in minimal media that lacks the vitamin thiamine. From prior RNAseq and promoter fusion studies, pTHI11 is among the strongest promoters in block and tank minimal media, which lack thiamine.

Additionally, from the *P. pastoris* strain modified to express 4 copies of recombinant genes expressing 18B silk-like polypeptide, instead of knocking out sec72, expression of SEC72 was knocked down using DAmP (decreased abundance by mRNA perturbation), a transcriptional knockdown strategy that disrupts the 3' UTR of a gene with a marker cassette.

Figure 9A:
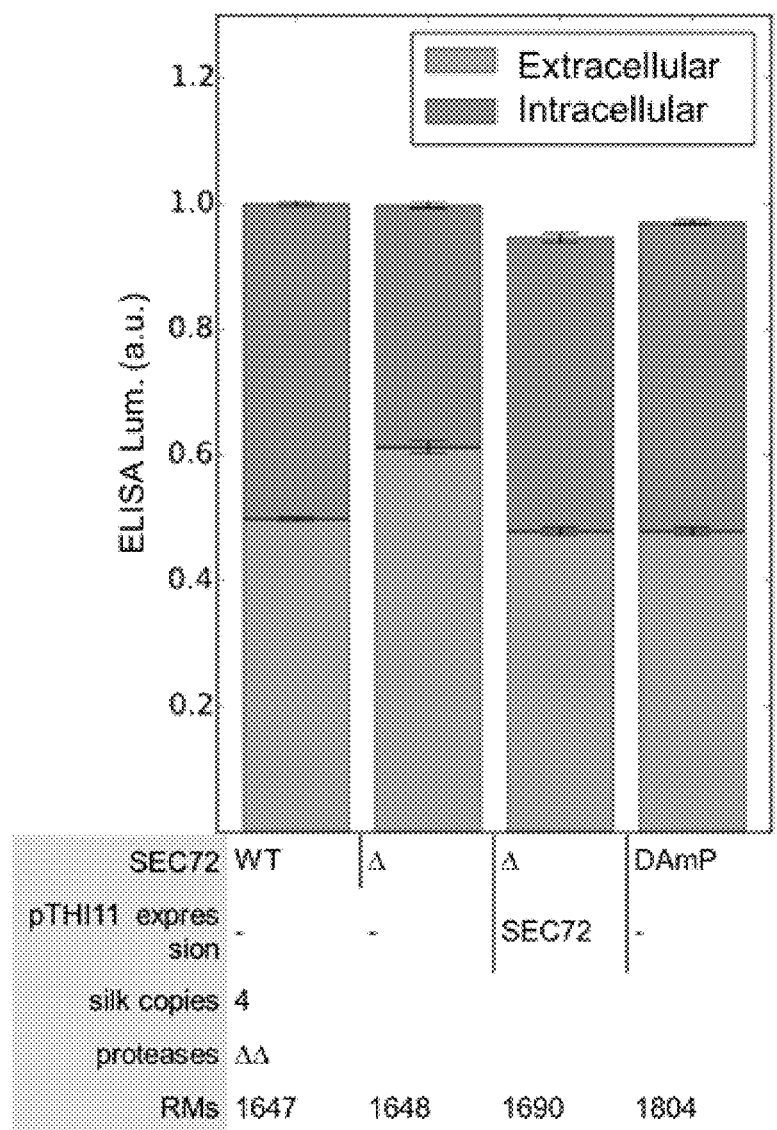
FIG. 9A shows secretion of of recombinant 18B silk-like polypeptide expressed by wild-type (WT), Δsec72 (Δ) strains, strains overexpressing sec72 under the control of pTHI11, and strains where SEC72 was knocked down by DAmP (Decreased Abundance by mRNA Perturbation), as measured by ELISA.

Secretion of the 18B silk-like polypeptides from WT, Δsec72, Δsec72 with recombinantly overexpressed sec72 (operably linked to pTHI11), and sec72 knockdown strains was measured by ELISA, with the results shown in FIG. 9A.

The Δsec7 2 phenotype reverts upon complementation with an inducible allele of sec72. Similarly, the knockdown of SEC72 did not measurably affect silk secretion as compared to WT. Thus, secretion improves with sec72 deletion, but not with knockdown nor overexpression of sec72.

Example 9: Other Disruptions to SEC63 Complex Stoichiometry do not Affect Silk Secretion

*P. pastoris* strains were modified according to Example 1 to comprise 4 copies of DNA cassettes comprising recombinant genes expressing 18B silk-like polypeptide. Δsec72 strains were prepared using techniques described in Example 2.

Figure 9B:
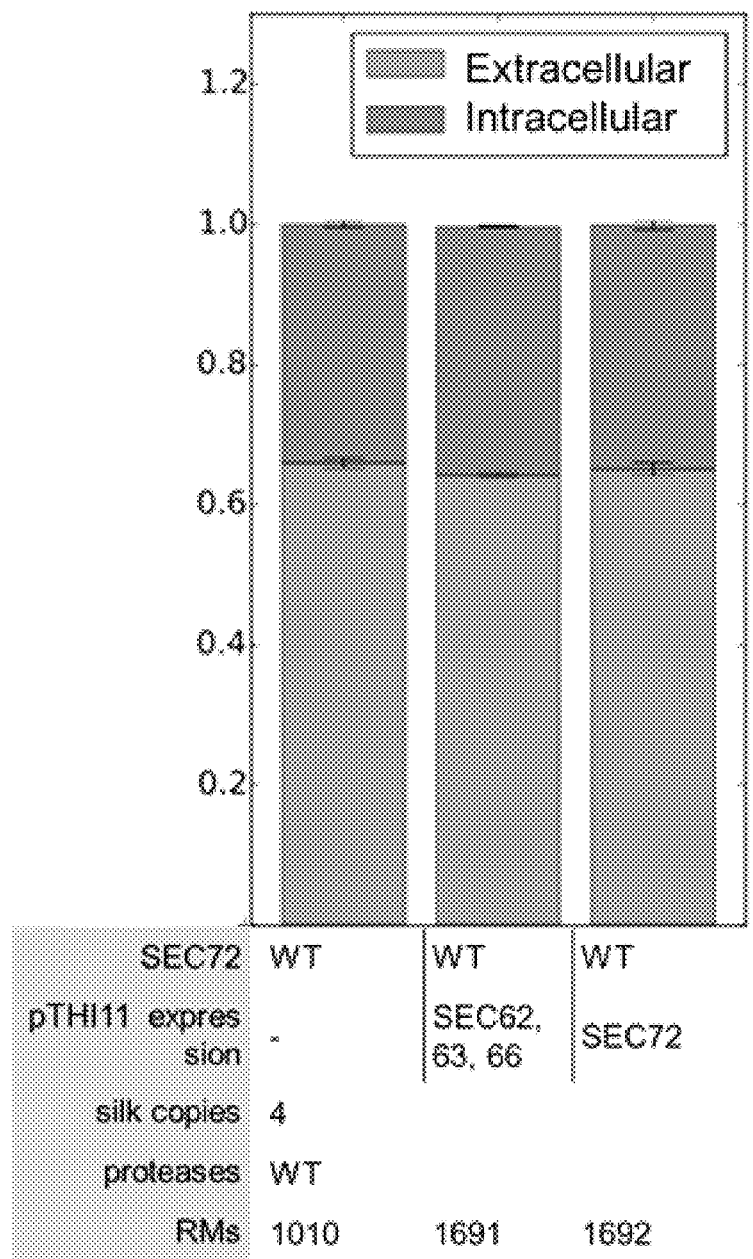
FIG. 9B shows secretion of of recombinant 18B silk-like polypeptide expressed by wild-type (WT), strains overexpressing non-SEC72 proteins from the SEC63 complex (i.e., sec62, sec63 and sec66) and strains overexpressing sec72, as measured by ELISA.

To test whether the Δsec72 phenotype is a direct effect of removal of SEC72 or an indirect effect of disrupting the SEC63 complex stoichiometry, pTHI11 was used to overexpress the 3 non-SEC72 complex members (SEC62, SEC63, and SEC66) simultaneously (by transforming the strain with a vector comprising 3 concatenated expression cassettes with sec62, sec63, and sec66). In addition, pTHI11 was used to overexpress SEC72. Secretion of 18B was measured from each strain and compared with Δsec72 strains using ELISA, with the results shown in FIG. 9B.

Neither stoichiometric change (overexpression of SEC62, SEC63, and SEC66, or overexpression of SEC72) measurably affected silk secretion. Error bars show standard error of the mean among n≥3 biological replicates.

Example 10: RTqPCR Shows Transcriptional Adaptation to ΔSec72, Including Translocon Levels Δsec72 strains were prepared using techniques described in Example 2. mRNA was isolated after growth and RTqPCR was performed on selected markers to analyze transcriptional adaptation to Δsec72.

Figure 10A:
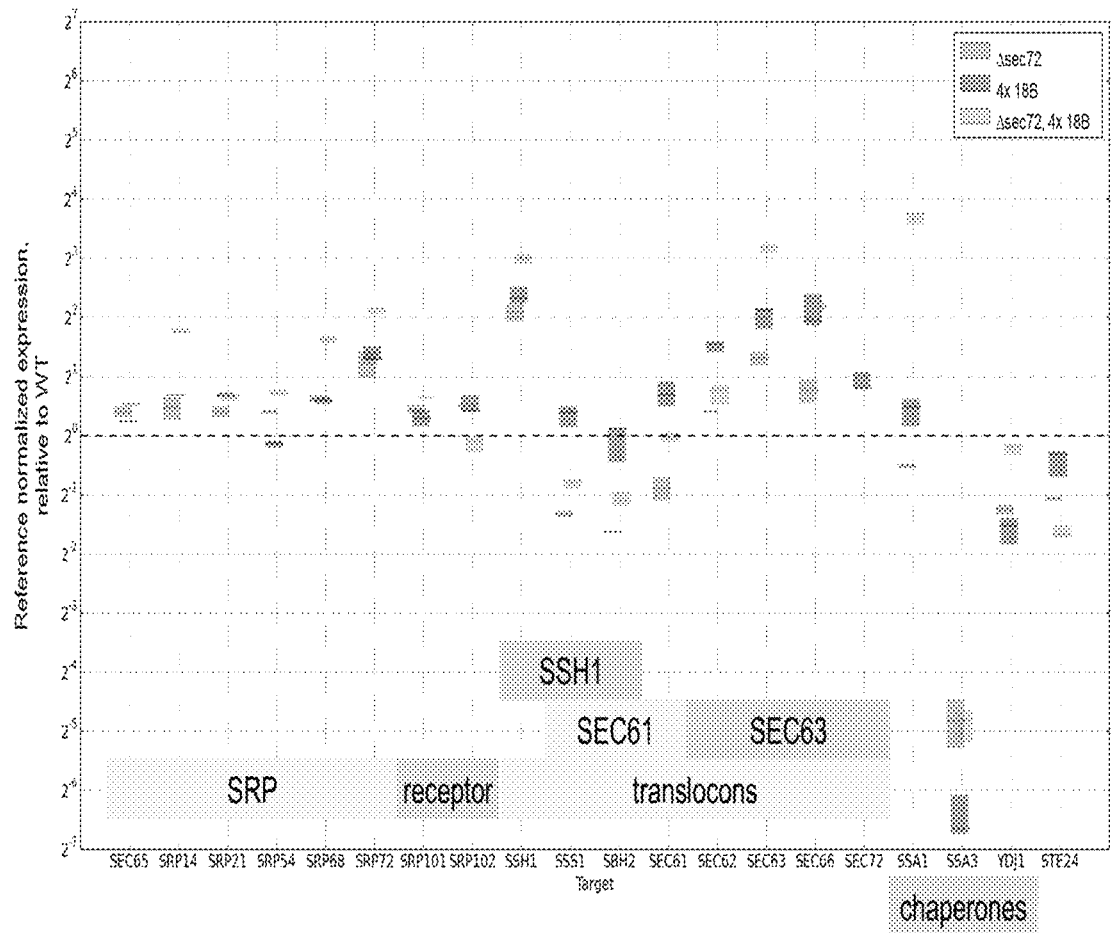
FIG. 10A shows reference-normalized expression in Δsec72 strains as a fold-change from the WT strain. Shading indicates range and center bar represents median among n=3 biological replicates (except n=2 for Δsec72).

Reference normalized expression (ALG9 or ACT1) as a fold change from the "WT" strain RMs71 in minimal media is shown in FIG. 10A. Shading indicates range and center bar represents median among n=3 biological replicates (except n=2 for Δsec72). SSH1 transcript levels increase 4-8 fold across all 3 perturbations. Δsec72 leads to a 2-4 fold reduction in SEC61 translocon component expression.

Figure 10B:
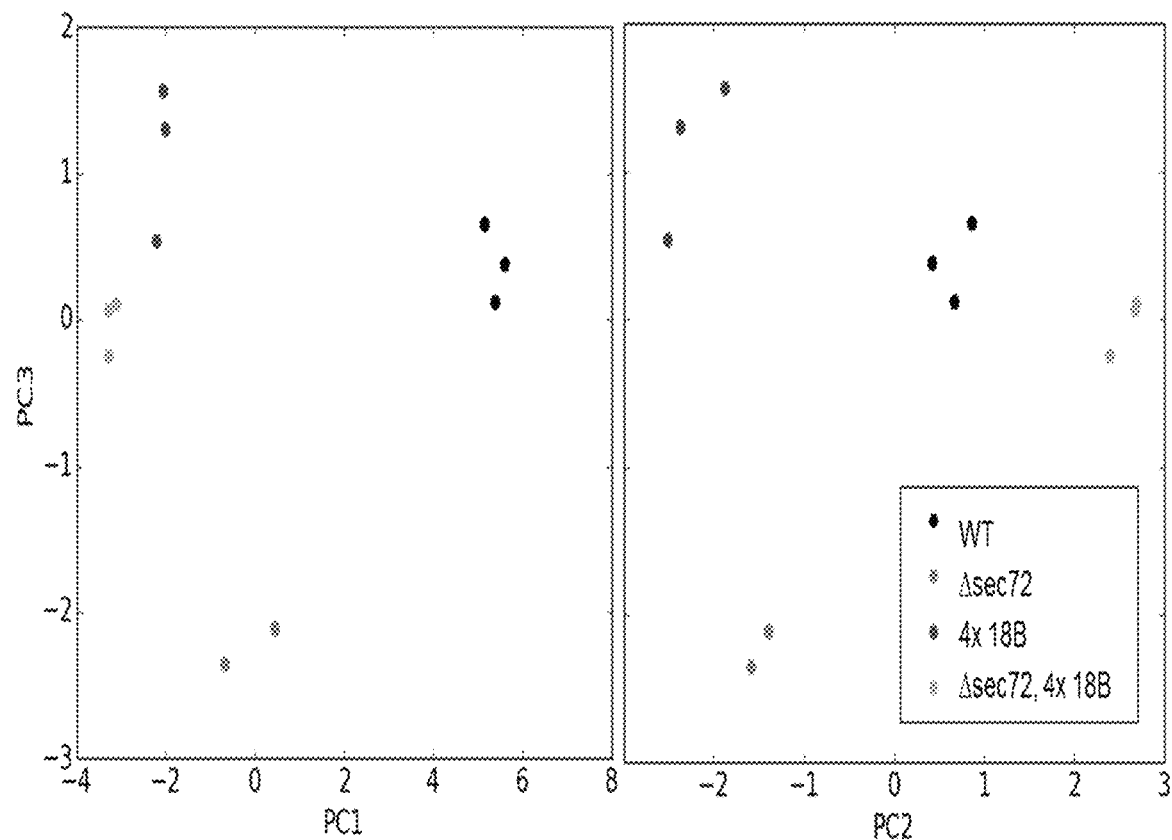
FIG. 10B shows a projection of centered, log-scaled, reference normalized expression data onto principal component space, left=PC1 vs. 3, right=PC2 vs. 3. Replicates are colored by strain genotype, showing low within-genotype variance compared variance across genotypes.

FIG. 10B shows a projection of centered, log-scaled, reference normalized expression data onto principal component space, left=PC1 vs. 3, right=PC2 vs. 3. Replicates are colored by strain genotype, showing low within-genotype variance compared variance across genotypes. Examining the loading coefficients revealed that most variation along PC1 is driven by strong SSA3 repression and along PC3 by SEC61 translocon complex repression. These 3 PCs reconstruct 99% of the variance from the original 20 dimensions.

Example 11: Overexpression of SSH1 Improves Growth Rate of the ΔSec72 Silk Secretion Strain Though SSH1 also functions in ER translocation, it is distinct from SEC61 in its dispensability for *S. cerevisiae* growth and lack of interaction with the SEC63 complex. SSH1 may show translocation substrate preferences, but they broadly overlap with those of SEC61.

To test whether overexpression of SSH1 could aid growth of Δsec72 strains, *P. pastoris* Δ*sec72* strains were prepared using techniques described in Example 2. The regulatory and coding sequences for the SEC61 and SSH1 complexes (SSS1, SBH2, and one of SEC61 or SSH1) were assembled by PCR onto an integrating plasmid. The resulting integration duplicates the gene copy number of one of the SEC61 or SSH1 complexes. *P. pastoris* (Δsec72) cells were transformed with a vector for overexpression of the SSH1 translocon complex as described in Example 3. Similarly, *P. pastoris* (Δsec72) cells were transformed with a vector for overexpression of SEC61. Selected strains (as indicated by "ΔΔ" in FIG. 11) were additionally modified to knockout YPS1-1 and YPS1-2 proteases, as described in Example 4.

Figure 11:
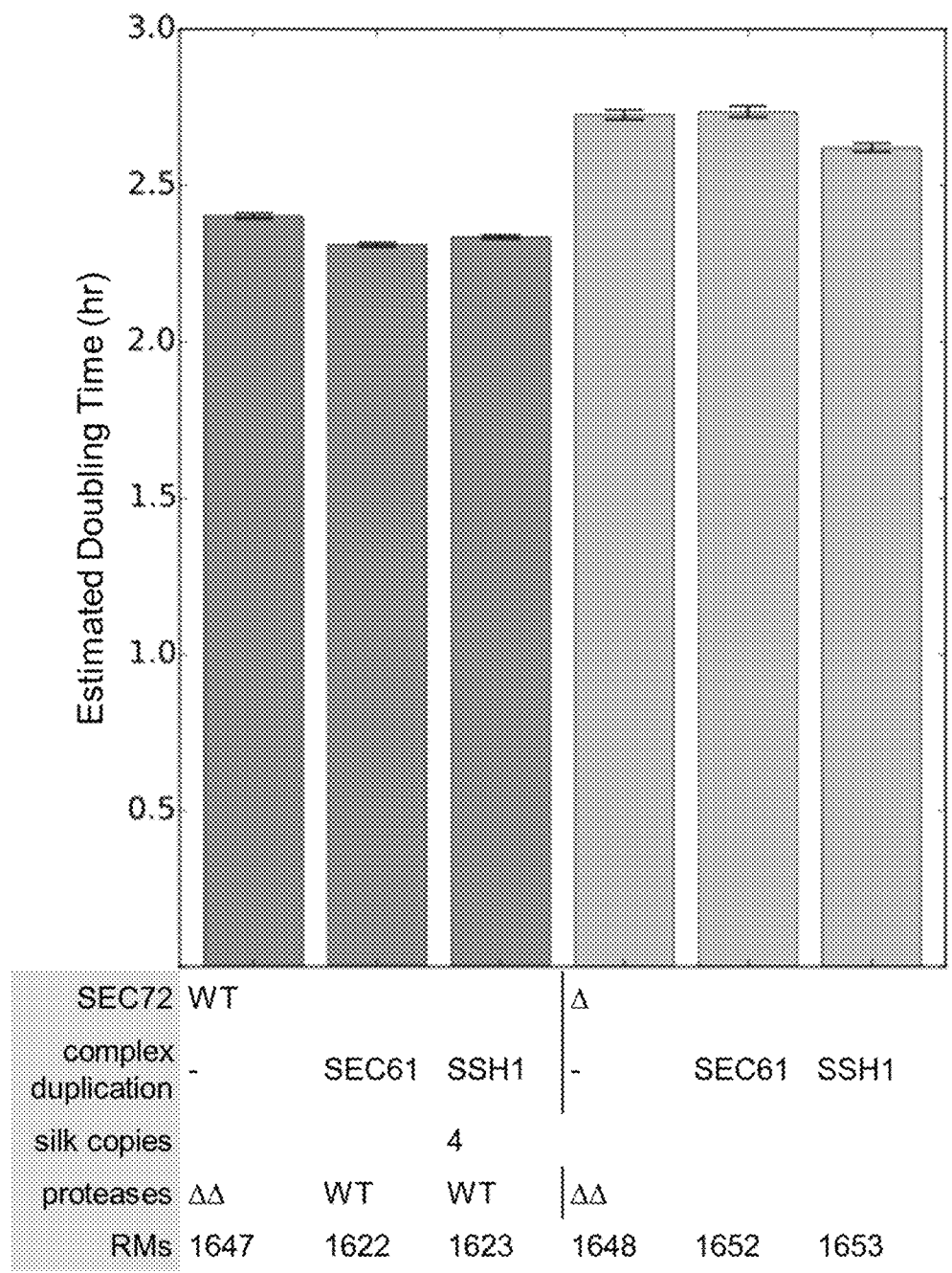
FIG. 11 shows growth rates observed for WT and Δsec72 strains, and comparison of each with growth rates for strains modified to overexpress the SSH1 translocon complex or SEC61.

Pre-cultures in YPD were diluted 1:1600 into minimal media (RMm17). OD600 was recorded over 6 timepoints spanning 8 hours of exponential growth beginning 19 hours after dilution. A linear model fit log(OD600) vs. time to estimate doubling rate and the standard error of the slope among n=6 biological replicates. The measured growth for each strain is shown in FIG. 11. Doubling times are shown as the reciprocal of doubling rate. Error bars are asymmetrical due to the reciprocal transformation of the estimates.

SEC61 and SSH1 duplication promote faster doubling of the SEC72 silk production strain (FIG. 11, left). This effect may be due to decreasing the load of intracellularly accumulated silk. However, Δsec72 leads to a significant growth defect, which is partially restored by duplication of SSH1 but not SEC61 (FIG. 11, right).

Example 12: SSH1 Duplication Improves Fermentation Performance of ΔSec72 Strain

*P. pastoris* strains were modified according to Example 1 to comprise 4 copies or 6 copies of DNA cassettes comprising recombinant genes expressing 18B silk-like polypeptide. Δsec72 strains were prepared from recombinant cells expressing 4 copies of the DNA cassette using techniques described in Example 2. Some of the resulting *P. pastoris* (Δsec72) cells were also transformed with a vector for overexpression of the SSH1 translocon complex as described in Example 3. Secretion of 18B from each strain was measured using ELISA, with the results shown in FIG. 12A and FIG. 12B.

Figure 12A:
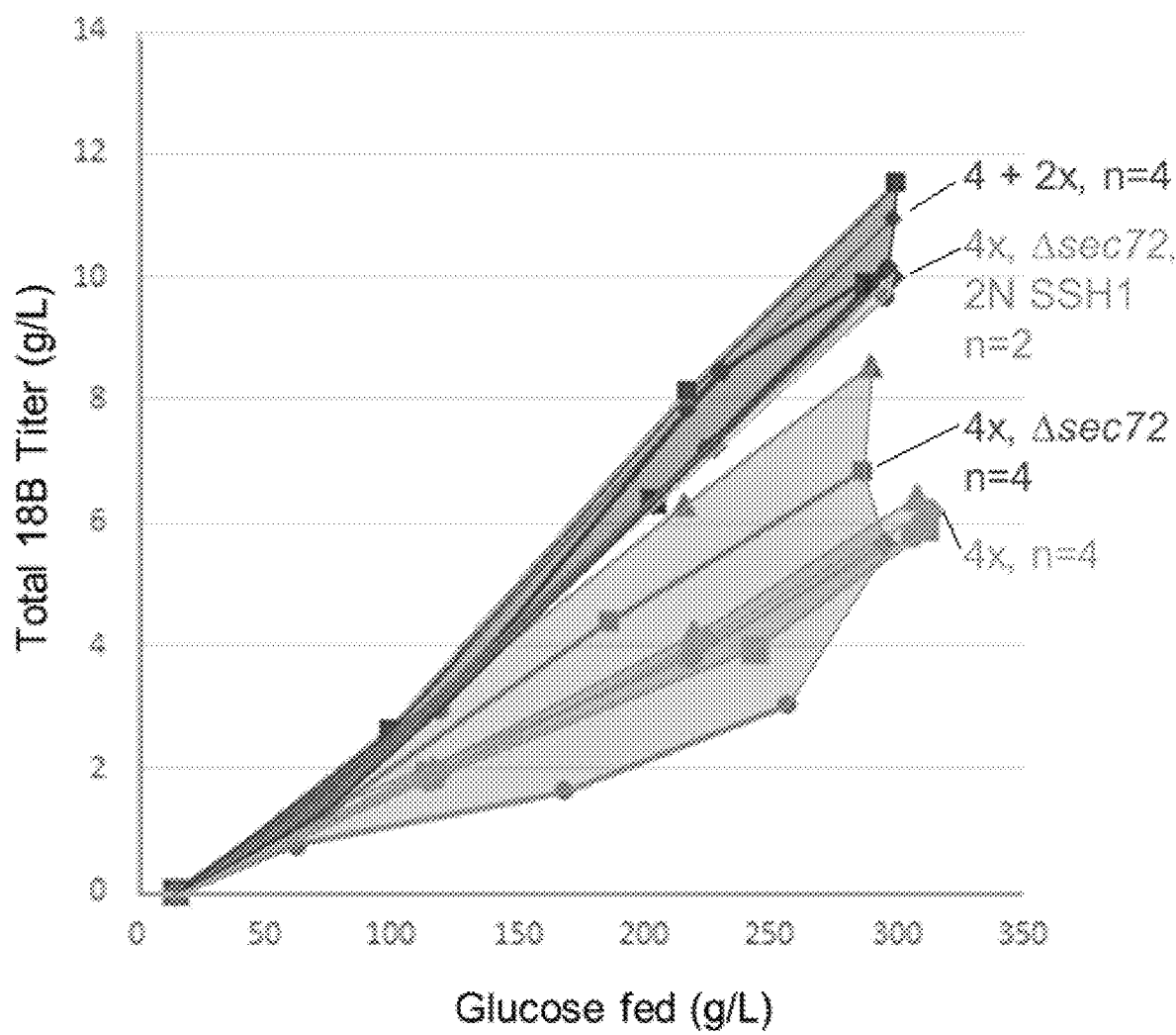
FIG. 12A shows the production of 18B as a function of glucose (yield) for wild-type (WT) strains expressing 4 (4×) or 6 (4+2×) copies of 18B, as compared to a Δsec72 strain (4×, Δsec72) and a Δsec72 strain overexpressing the SSH1 translocon complex (4×, Δsec72, 2N SSH1).

In FIG. 12A, each trajectory represents an independent batch-fed fermentation. Marked points are samples taken for analytes including the concentration of secreted silk protein in the broth ("18B titer", y-axis). The x-axis is cumulative glucose fed, since the feed program is time-varying. Shading depicts the range of all runs of the same strain. The Δsec72 deletion strain shows highly variable performance. When SSH1 is duplicated in this strain ("2N SSH1"), performance improves and variability decreases. The Δsec72 2N SSH1 strain with only 4 silk expression cassettes secretes approaches the range of a reference strain with 6 silk expression cassettes.

Figure 12B:
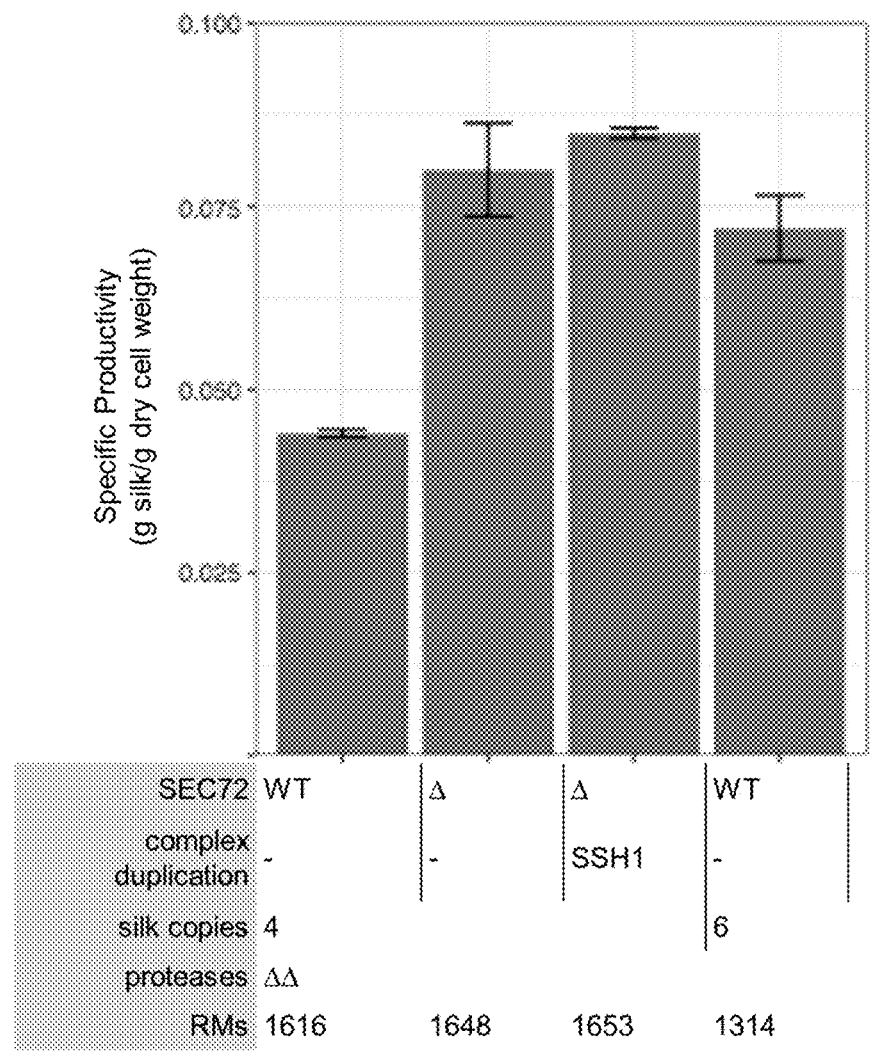
FIG. 12B shows the specific productivity (product-per biomass) of each strain.

Specific productivity (the ratio of product to biomass) was measured for each strain culture and shown in FIG. 12B. Δsec72 backgrounds grow more slowly and generate less biomass, elevating their metrics above that of the higher-expressing, highest-titer strain. Due to high variability in the Δsec72 strain, summarized data show only the top n=2 runs. Error bars are standard error of the mean.

Other Embodiments

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

SEQUENCES

TABLE 8

Forward (F) and Reverse (R) Primers for 5' and 3' homology arms (HA) targeting protease ORF

| Description | SEQ ID NO: | 5' to 3' Sequence |
| --- | --- | --- |
| KO_PAS_chr4_0584 5' HA F | 45 | TACTACAGGCTGGCTGTTCC |
| KO_PAS_chr4_0584 5' HA R | 46 | CTCACTTAATCTTCTGTACTCTGAAGAAGTCCAACTGTTGAACGCC |
| KO_PAS_chr4_0584 3' HA F | 47 | AGAAGTTGATTGAGACTTTCAACGAGGGTCCCCTTCAGCTACCTTT |
| KO_PAS_chr4_0584 3' HA R | 48 | TCCCTGCTAAGCCCTAATCG |
| KO_PAS_chr3_1157 5' HA F | 49 | CTCTGATTGCACGAGAAGGC |
| KO_PAS_chr3_1157 5' HA R | 50 | CTCACTTAATCTTCTGTACTCTGAAGTGAAAGGCGATTGGAGTTGC |
| KO_PAS_chr3_1157 3' HA F | 51 | AGAAGTTGATTGAGACTTTCAACGAGCTGGCTCTGCTTCTGGTACT |
| KO_PAS_chr3_1157 3' HA R | 52 | GATGTTGAGGCGGGCATAAG |

TABLE 9

Forward and reverse primers for amplifying modified sequences

| Description | SEQ ID NO: | Sequence (5' to 3') |
| --- | --- | --- |
| KO_PAS_chr4_0584 Verification F | 53 | ACTTGTCAGGACGATACGGA |
| KO_PAS_chr4_0584 Verification R | 54 | CCGGTCTCCCTGGAAATAGA |
| KO_PAS_chr3_1157 Verification F | 55 | AGTTGTCCGTCATTAGCCCT |
| KO_PAS_chr3_1157 Verification R | 56 | TGTTCCCTTTCGGCTAGACA |

TABLE 10 sec72 KO vector

| Description | SEQ ID NO: | Sequence (5' to 3') |
| --- | --- | --- |
| SEC72 KO full plasmid | 91 | ggcgcgccgtttaaaccctccaccagccatataccactacaacaccacagaagagaaagagctcatatcatccgtcatgagagagtac cagcacagaaatacagtcaagtaaaactagtatgcaagcattacgtaataatagcaactttatgacaaatcattccatttttttccac tggagcgtgcactgcgtaaatcattctctttggaaggcaagggaagaacaacaaaattttcctccgttatacaaacattgaatcat gtctactgaacccacttttaaattggtccttgtcggtgatggtggtaccggtaaagtaagtgcaaattatttgatgagtcggataatg ttttccgccccttagttcccctcatgattactaacaattcatagaccaccttcgttaagagacaccttactggagagttccgtaagaa gtacattgctactttgggagtcgaagttcatcccttgtcattccacactaactgtggtcctatcacattcaacgtttgggacactgct ggacaagagaagtttggtggactgagagatggttattacattaacggtgactgtggtatcatcatgttcgacgttacatcgagaatta cttacaagaacgttccaaactggcaccgtgacttggtcagagtgtgtgagaacattccaattgtgcttttgtggtaacaaggttgatgt caaggaaagaaaggtcaaggctaagaccatcacttcccacagaaagaagaacttgcaatactttgacatttctgccaagtccaactac aactttgagaagccattcttgtggttagctagaaagttgtctggtgagccccaattagagttcgttgctgctcccgacttgcaagccc cagagggttcaaattgatgccgatttaataaagaagtacgagcaagagaacgccgaggctgccgtatgccattgcctgatgaagatga tgccgacttgtaagcttttacttacagtacattgagaaccatacatagggcacgtatcgtaagtttagttgtttgctgatgtaagcta gtttgtttctgtagtgtttcgaggtcgcagagggatctctctagcttagacaaaaaaaaaaggttgacacgttgatacactctctg tttcatccgatctttcacctacgagtcccactcctcttcagagtacagaagattaagtgagagaattctaccgttcgtatagcataca ttatacgaagttatttcagtaatgtcttgtttctttttgttgcagtggtgagccattttgacttcgtgaaagtttcttttagaatagttg tttccagaggccaaacattccaccccgtagtaaaagtgcaagcgtaggaagtccaagactggcataaatcaggtataagtgtcgagcact ggcaggtgatcttctgaaagtttctactagcagataagatccagtagtcatgcatatggcaacaatgtaccgtgtggatctaagaacg cgtcctactaaccttcgcattcgttggtccagtttgttgttatcgatcaacgtgacaaggttgtcgattccgcgtaagcatgcatacc caaggacgcctgttgcaattccaagtgagcagttccaacaatctttgtaatattagagcacttcattgtgttgcgcttgaaagtaaa atgcgaacaaattaagagataatctcgaaaccgcgacttcaaacgccaatatgatgtgcggcacacaataagcgttcatatccgctgg gtgactttctcgctttaaaaaattatccgaaaaattttttgacggctagctcagtcctaggtacgctagcattaaagaggagaaatg gctaaactgacctctgctgttccggttctgaccgctcgtgacgttgctggtgctgttgagttctggaccgaccgtctgggtttctctc gtgacttcgttgaggacgacttcgctggtgttgttcgtgacgacgttacctgtcatctctgctgttcaggaccaggttgttccgga caacaccctggcttggtttcgtggtctggacgaacttgtacgctgaatggtctgaagttgtttctaccaacttccgtgacgct tctggtccggctcatgaccgaaatcggtgaacgccgtggggtcgtgagttcgctctgcgtgacccggctggtaactgcgttcacttcg ttgctgaagaacaggactaacacgtccgacggcggcccacgggtcccaggcctcggagatccgtcccccttttcctttgtcgatatca tgtaattagttatgtcacgcttacattcacgccctcccccacatccgctctaaccgaaaaggaaggagttagacaacctgaagtcta ggtccctatttattttttttatagttatgttagtattaagaacgttatttatattcaaattttctttttttctgtacagacgcgtg tacgcatgtaacattatactgaaaaccttgcttgagaaggttttgggacgctcgaaggctttaattgcaagctataacttcgtatag catacattataccttgttatgcggccgcagatctaacatccaaagacgaaaggttgaatgaaaccttttgccatccgacatccacag gagagttatagagctgctatgcgtgtaaaaatagtttaaatcttcgtaaagtatgttagtccatgtaatttgctatgaatcgatacgc taatctggatgctgaacggatgcttactggcatgcattattcattacccatctaagctgcgccacaacccagtaaattgcagtgaggg aagcttccctgtaaccgtcctgtccctttagggaccatcgatccccaacgatcaaatcgcgatacatctatccaactgtcccttttccat ctatctatgcaaggtaatgacagactctgttaactctgatgattctgatctggaaatcatagaggtgactgagcctactccaaaagtg gaccttttggcccccaatccagcatttaattttactgcccccataagcaacagtaacggcacaactccaataaggagaaaacttgatg accaatccaactccaattcttttgccagactggaatcgttacaggaatcatcagtgaaaccaagctagtacgttcaatagtagtag gttcatccccaagccgaccaattttccaataatcagaataatgaacttgataacaacaatggattcgccgactggatttctaagtcc caacctgaatttcccttttccacttaatgatggaccaaaaaagtccagcaatcaacctacaaactcaaattttgaagagatcatcgatt taactgaagtatatcgagataaatacatctgtccccgcatctacatcatcttctacccagttccctccagcacacagaatcagagcca tcatatagccaacaacaacacagcacaagatgcgcatatcttccaagggaaacgacctctccaatcatattcagatgatgaagacgaa gatttgcaaattgtaggatccaatattgttcagcagcctctaggaattatgccaggaacttcaacgcccctgcaaacatactccatt ttgacggttcaaaccagaatgaacaagccagatggctggacttgcggataaaagatttgttagataatcttcaacaatcttcgagttca tgctcagtcgaatattatggagatcaataggttcatttccactttggggcatttaaacagagaagtttaaaccctgcagggcgctcgg tcgttcggctgcggcgagcggtatcagctcactcaaaggcggtaatacggttatccacagaatcaggggataacgcaggaaagaacat gtgagcaaaaggccagcaaaaggccaggaaccgtaaaaaggccgcgttgctggcgtttttccataggctccgcccccctgacgagcat cacaaaaatcgacgctcaagtcagaggtggcgaaacccgacaggactataaagataccaggcgtttccccctggaagctccctcgtgc gctctcctgttccgaccctgccgcttaccggatacctgtccgcctttctcccttcgggaagcgtggcgctttctcatagctcacgctg taggtatctcagttcggtgtaggtcgttcgctccaagctgggctgtgtgcacgaaccccccgttcagcccgaccgctgcgccttatcc ggtaactatcgtcttgagtccaacccggtaagacacgacttatcgccactggcagcagccactggtaacaggattagcagagcgaggt atgtaggcggtgctacagagttcttgaagtggtggcctaactacggctacactagaagaacagtatttggtatctgcgctctgctgaa gccagttaccttcggaaaaagagttggtagctcttgatccggcaaacaaaccaccgctggtagcggtggtttttttgtttgcaagcag cagattacgcgcagaaaaaaaggatctcaagaagatcctttgatcttttctacggggtctgacgctcagtggaacgaaaactcacgtt aagggattttggtcatgagattatcaaaaaggatcttcacctagatccttttaaattaaaaatgaagttttaaatcaatctaaagtat atatgagtaaacttggtctgacagttaccaatgcttaatcagtgaggcacctatctcagcgatctgtctatttcgttcatccatagtt gcctgactccccgtcgtgtagataactacgatacgggagggcttaccatctggccccagtgctgcaatgataccgcgagacccacgct caccggctccagatttatcagcaataaaccagccagccggaagggccgagcgcagaagtggtcctgcaactttatccgcctccatcca gtctattaattgttgccgggaagctagagtaagtagttcgccagttaatagtttgcgcaacgttgttgccattgctacaggcatcgtg gtgtcacgctcgtcgtttggtatggcttcattcagctccggttcccaacgatcaaggcgagttacatgatcccccatgttgtgcaaaa aagcggttagctccttcggtcctccgatcgttgtcagaagtaagttggccgcagtgttatcactcatggttatggcagcactgcataa ttctcttactgtcatgccatccgtaagatgcttttctgtgactggtgagtactcaaccaagtcattctgagaatagtgtatgcggcga ccgagttgctcttgcccggcgtcaatacgggataataccgcgccacatagcagaactttaaaagtgctcatcattggaaaacgttctt cggggcgaaaactctcaaggatcttaccgctgttgagatccagttcgatgtaacccactcgtgcacccaactgatcttcagcatcttt tactttcaccagcgtttctgggtgagcaaaaacaggaaggcaaaatgccgcaaaaaagggaataagggcgacacggaaatgttgaata ctcatactcttcctttttcaatattattgaagcatttatcagggttattgtctcatgagcggatacatatttgaatgtatttagaaaa ataaacaaataggggttccgcgcacatttccccgaaaagtgccacct |
| SEC72 5' homology arm | 92 | aaaccctccaccagccatataccactacaacaccacagaagagaaagagctcatatcatccgtcatgagagagtaccagcacagaaat acagtcaagtaaaactagtatgcaagcattacgtaataatagcaactttatgacaaatcattccatttttttccactggagcgtgcac tgctaaatcattctctttggaaggcaagggaagaacaacaaaattttcctccgttatacaaacattgaatcatgtctactgaacc cacttttaaattggtccttgtcggtgatggtggtaccggtaaagtaagtgcaaattatttgatgagtcggataatgttttccgcccct tagttcccctcatgattactaacaattcatagaccaccttcgttaagagacaccttactggagagttccgtaagaagtacattgctac tttgggagtcgaagttcatcccttgtcattccacactaactgtggtcctatcacattcaacgtttgggacactgctggacaagagaag tttggtggactgagagatggttattacattaacggtgactgtggtatcatcatgttcgacgttacatcgagaattacttacaagaacg ttccaaactggcaccgtgacttggtcagagtgtgtgagaacattccaattgtgcttttgtggtaacaaggttgatgtcaaggaaagaaa |

TABLE 10-continued sec72 KO vector

| Description | SEQ ID NO: | Sequence (5' to 3') |
|---|---|---|
| | | ggtcaaggctaagaccatcacttttccacagaaagaagaacttgcaatactttgacatttctgccaagtccaactacaactttgagaag<br>ccattcttgtggttagctagaaagttgtctggtgagccccaattagagttcgttgctgctcccgacttgcaagccccagaggttcaaa<br>ttgatgccgatttaataaagaagtacgagcaagagaacgccgaggctgccgctatgccattgcctgatgaagatgatgccgacttgta<br>agcttttacttacagtacattgagaaccatacatagggcacgtatcgtaagtttagttgtttgctgatgtaagctagtttgtttctgt<br>agtgtttcgaggtcgcagagggatctctctagccttagacaaaaaaaaaaaggttgacacgttgatacactctctgtttcatccgatc<br>tttcacctacgag |
| SEC72 5' homology arm | 93 | ggagagttatagagctgctatgcgtgtaaaaatagtttaaatcttcgtaaagtatgttagtccatgtaatttgctatgaatcgatacg<br>ctaatctggatgctgaacggatgcttactggcatgcattattcattacccatctaagctgcgccacaacccagtaaattgcagtgagg<br>gaagcttccctgtaaccgtcctgtcccttagggaccatcgatccccaacgatcaaatcgcgatacatctatcaactgtccctttcca<br>tctatctatgcaaggtaatgacaagctctgttaactctgatgattctgatctggaaatcatagaggtgactgagcctactccaaaagt<br>ggaccttttggcccccaatccagcatttaattttactgcccccataagcaacagtaacggcacaactccaataaggagaaaacttgat<br>gaccaatccaactccaattcttttgccagactggaatcgttacggaatcatcagtgaaaccacaagctagtacgttcaatagtagta<br>ggttcatccccaagccgaccaatttttccaataatcagaataatgaacttgataacaacaatggattcgccgactggatttctaagtc<br>ccaacctgaatttcccttcacttaatgatggaccaaaaagtccagcaatcaacctacaaactcaaattttgaagagatcatcgat<br>ttaactgaagatatcgagatataaatacatctgtccccgcatctacatcatcttctaccccagttccctccagcacacagaatcagagcc<br>atcatatagccaacaacaacacagcacaagatgcgcatatcttccaagggaaacgacctctccaatcatattcagatgatgaagacga<br>agatttgcaaattgtaggatccaatattgttcagcagcctctaggaattatgccaggaacttttcaacgcccctgcaaacatactccat<br>tttgacggttcaaaccagaatgaacaagccagatggctggacttgcggataaaagatttgttagataatcttcacaatcttcgagttc<br>atgctcagtcgaatattatggagatcaataggttcatttccacttgggggcatttaaacagagaagttt |
| Yeast selection marker (Sh ble) for SEC72 KO (nucleotide sequence) | 94 | ttcagtaatgtcttgtttcttttgttgcagtggtgagccattttgacttcgtgaaagtttctttagaatagttgtttccagaggccaa<br>acattccaccgtagtaaagtgcaagcgtaggaagtccaagactggcataaatcaggtataagtgtcgagcactggcaggtgatcttc<br>tgaaagttctactagcagataagatccagtagtcatgcatatgtggcaacaatgtaccgtgtggatctaagaacgcgtcctactaacct<br>tcgcattcgttggtccagtttgttgttatcgatcaacgtgacaaggttgtcgattccgcgtaagcatgcatacccaaggacgcctgtt<br>gcaattccaagtgagccagttccaacaatctttgtaatattagagcacttcattgtgttgcgcttgaaagtaaaatgcgaacaaatta<br>agagataatctcgaaaccgcgacttcaaacgccaatatgatgtgcggcacacaataagcgttcatatccgctgggtgactttctcgct<br>ttaaaaaattatccgaaaaaatttttgacggctagctcagtcctaggtacgctagcattaaagaggagaaaatggctaaactgacctc<br>tgctgttccggttctgaccgctcgtgacgtgctggtgctgttgagttctggaccgaccgtctgggttctctcgtgacttcgttgag<br>gacgacttcgctggtgttgttcgtgacgacgttacccgttcatctctgctgttcaggaccaggttgttccggacaacaccctggctt<br>gggtttgggttcgtggtctggacgaactgtacgctgaatggtctgaagttgtttctaccaacttccgtgacgcttctggtccggctat<br>gaccgaaatcggtgaacagccgtggggtcgtgagttcgctctgcgtgaccggcgtgatcctggtgcttgctggacgaagaacag<br>gactaacacgtccgacggcggcccacgggccccaggcctcggagatccgtccccctttcctttgtcgatatcatgtaattagttatg<br>tcacgcttacattcacgccctccccccacatccgctctaaccgaaaaggaaggagttagacaacctgaagtctaggtccctatttatt<br>ttttatagttatgttagtattaagaacgttatttatatttcaaattttctttttttctgtacagacgcgtgtacgcatgtaacat<br>tatactgaaaaccttgcttgagaaggttttgggacgctcgaaggctttaatttgcaagct |
| Yeast selection marker (Sh ble) for SEC72 KO (protein sequence) | 95 | MAKLTSAVPVLTARDVAGAVEFWTDRLGFSRDFVEDDFAGVVRDDVTLFISAVQDQVVPDNTLAWVWVRGLDELYAEWSEVVSTNFRD<br>ASGPAMTEIGEQPWGREFALRDPAGNCVHFVAEEQD |

TABLE 11

SSH1 Complex Overexpression vector

| Description | SEQ ID NO: | Sequence (5' to 3') |
|---|---|---|
| Full Plasmid | 96 | ccagccaggacagaaatgcctcgacttcgctgctgcccaaggttgccgggtgacgcacaccgtggaaacggatgaaggcacgaacc<br>cagtggacataagcctgttcggttcgtaagctgtaatgcaagtagcgtatgcgctcacgcaactggtccagaaccttgaccgaacg<br>cagcggtggtaacggcgcagtggcggttttcatggcttgttatgactgttttttgggggtacagtctatgcctcggcatccaagc<br>agcaagcgcgttacgccgtgggtcgatgtttgatgttatggagcagcaacgatgttacgcagcagggcagtcgccctaaaacaaag<br>ttaaacatcatgagggaagcggtggtgatcgccgaagtatcgactcaactatcagaggtagttggcgtcatcgagcgccatctcgaacc<br>gacgttgctggccgtacatttgtacggctccgcagtggatggcggcctgaagcacacagtgatattgatttgcggttacggtga<br>ccgtaaggcttgatgaaacaacgcggcgagctttgatcaacgaccttttggaaacttcggcttcccctggagagagcgagattctc<br>cgcgctgtagaagtcaccattgttgtgcacgacgacatcattccgtggcgttatccagctaagctcggaactgcaatttggagaatg<br>gcagcgcaatacattcttgcaggtatcttcgagccagccacgatcgacattggctgtatctggctcattgctgacaaaagcaagagaac<br>atagcgttgccttggaggtccagcggcggaggaactccttgatccggttcctgaacaggactctatttgaggcgctaaatgaaacc<br>ttaacgctatggaactcgccgcccgactgggctggtgatgagcgaaatgtagtgcttacgttgtcccgcatttggtacagcgcagt<br>aaccggcaaaatcgcgccgaaggatgtcgctgccgactgggcaatggagcgcctgccgggcccagtatcagcccgtcatacttgaag<br>ctagacaggcttatcttggacaagaagaagatcgcttggcctcgcgcgcagatcagttggaagaattgtccactacgtgaaggc<br>gagatcaccaaggtagtcggcaaataacattactcgcatccattctccaggctgtctcgtctcgtctccaactttctgccgccaatc<br>tccttccattcaatttctctacaacaaggcaggcttcgtccgttgatgtgaagtttgcaaaagccaaaccacgaaaaacaccatt<br>gtcaaaatggtagttgaaggcataaggcaaaggcaagctaaactttgtcataacgtctaaaagttgctctttttttatggcaaaag<br>ggatgttctttatcacaatagcagtgggaatgacatcttcatcatcattcgtatcatcaataccatcgagttctgaatccaaaggt |

TABLE 11-continued

SSH1 Complex Overexpression vector

| Description | SEQ ID NO: | Sequence (5' to 3') |
|---|---|---|
| | | ttctgttgttgggataaggcatcagattctttgagcaggtcgtccttggcgtcctcctctagatgaaatttgccatcgttaggagg<br>tgagtattgggaaacgttgacttgttgctcaatccaaggatcaacgttgaccatcggattgccgttctgaggagacagccaggcat<br>tataccgtggttgaccggcgtttacgcgcagaggattgttgctggtgttgttgacagaagacgcatacccagacgctgcggatgac<br>atcgacgaaattgaagggcgacgttgcatacccatttgttgctgatccaagaaacttggtgtttcagtcaattgtctcaggtccat<br>attgatcaatgtgttcaactgtttcaatctggttccggagggtggctattacgacaagctgtggctactatctaagtgggagaagt<br>aacggaacacattgatgagacacaggaattacagggcgtgcatccaccaataacaattagtcgagatttcaaccaattacgtaagc<br>gctcaaccctttttttcgaacacgtatcgagcaaagtccaggtgaaaccttcatccattatatccaaagtcgaccgaagctttaaca<br>acatccataatggtaagtgtccagtttgatgagtgcagaatggttccaagttttagaccagttactaatatttaaagtctacagca<br>attccaggaggacagagaacgttagctaaaagaagagcagcaaacttggataagaaacaggatgaaccaacctccgccagatctgc<br>cggtgctggaggttcttcgtctaccatgctaaagttgtacacagacgaggcccaaggtttgaaagttgatcctttaattgttcttg<br>ttcttgctgttggtttcattttcagtgtcattggtttgcacgttgttgctaagctgacaggaaagttgatcaactaagacctatat<br>ttaaacaggttttcatcatatctgtactatatttacaagtccactgcgtttaggtatatactaaagacattcaagaagcacatccac<br>aacttgtgcaagtcctgtcaaatgtactagatgcttttcagaacatcctgcggtttgaggagattcctgaatttcccagtcccaag<br>tctttctcttgtagaggtctttgagttcttgtgaatgctgaattgggggttcttacctcaatttctattagtgggaaatgctttccc<br>acaattatttgcaatgggatcccggcaacttacttttgcttcaacttatgtcccatactgaacttccgtcacggttgtcaacttg<br>aacgtcgaatgagctcagtatttcggtgacagtgtctagattctttttacttgatgtttattcgaaagtagcgtgatttgatatg<br>gtgcgataatttgtggccagggctgggagttcgtagacggaaacaaacgcagaatccaagcagacaagtggagagtggacaaattc<br>ttgatgttaattcgtaagatccttaacaaatctttagcaaaactgaaaagtgaagactacgatagggatttacttgaaaaatatat<br>tcaagttttgtcagaataccactccatattaacgatattattgtccctagaactattacgtaccacttgtgtgatatttatactg<br>atgagttggaaaaggttatgtttagtgggcttcctggatttgaagaagaagaagattacgaggaagaagatgaagtctcggctcct<br>atcgaaaaaaaaaccagagatactgataattcagacgatgaggcctctgataccgatccagaaacgagtgacgaagaagacgaagg<br>tgagaatactgaaaacgagtcagaagaggaaccgatcaaactctctgcggaagaagaaacggctctgtggaaaacaaagatggaga<br>ttatccatgaaactcctactcgacaaattactctcaccttttgtctcattgaagaaagatacctcaaataaaccattaaaattgaaa<br>atccaagaagcagttcttgctgatccaagactcggcaaatggaaagttaaatcgtaccgaaagcctaaaccaaaaccaaaaccctct<br>tcaggtgctacagaaacagtttatacgaacagatcaaatataaaaagggtaaagcagtcacaggtgaagacgacgatgaactcaaag<br>acgaagacgaagatgacgatgacgaggtcatctcggagagtgaagctgataactctgatgaagaagaagatgaagaatggaatggc<br>tttggaactatctagaatacatatgtaaaaccatatcaggcaataacaatttctcgctattttgcatcccaacacctcgaccgacg<br>tgttcagttcgaccctttacctacagtgtcttttaactcccatttggatctcctaaataacctacacaaatgtcccaaaaagtcacc<br>gacgtccctctggaatttgttaaggaaggttccaaattcatctctaaatgtactaaaccctctcagaaggagtacttaaagatagt<br>aagagctgttggagttgggttttttaatgatgggcgtggttggttacgttgtcaagctcattcatattccaatcagatatttgattg<br>tttaaaagtttaggtttgaatacaatgtgtatgcttaattatattcacttcgtttcattgattttttgctatccctgttgtgcgtta<br>atcatctctatcgtgatcctctcaagttgcacctcaaatagaagacaacttatggaggtgtactacccaatatcagtcttgacgtt<br>tctagtttcgttgtatgctgcataccaatttcagttcttccgtagtgttttgagcataggctgtttacccgtcttctttacactc<br>tgatatgagcaccttatcaaacctcttatcacagctgaaaggagaaggcggtggtggttcttctggtcagaatcggcccagaactg<br>tggatcctgctgttgcaagattgaaagcagaaggaagatggaaagagagaagcaagctcttaaagaggctcagcaagcccaggaa<br>gctcgggaaaggcgaagaattagtcatgctacccaagctgtttgagaccaaccagtaaagctcccagcactgaaggtcctcaatc<br>gcactggaaacatcaaggtcgatgaccgcactaacagaaggagctaaactattcgaaaaggagattccttacattacagaattaga<br>gggtgatgtcgaaggaatgaaattcattatcaagggcgagggtactggtgacgctactaccggtacgattaaagcaaagtacatct<br>gtacaacaggtgaccttcctgttccgtgggctactctggtgagcactttgtcttatggagttcaatgttttgctaaatacccttcg<br>cacattaaagactttttcaaaagtgcaatgcctgagggctatactcaggagagacaatatcttcttcgaaggagatggtgtgtataa<br>gactagggctatggtcacgtatgaaagaggatccatctacaatagagtaactttaactggtgaaaacttcaaaaaggacggtcaca<br>tccttagaaagaatgttgcctttcaatgcccaccatccatcttgtacattttgccagacacagttaacaatggtatcagagttgag<br>tttaaccaagcttatgacatagagggtgtcaccgaaaagttggttacaaaatgttcacagatgaatcgtcccctggcaggatcagc<br>tgccgtccatatcccacgttaccatcatatcacttatcatacaaagctgtccaaagatcgatgagagaagggatcacatgtgtt<br>tggttgaagtggtaaaggccgtggatttggatacttaccaatgactgacctcctgccagcaatagtaagacaacacgcaaagtctc<br>tgaacgggtctttgagctgtctgtgtcatcaaacatatcttcatctgtagttgtattgttttctttatcactaggagtccatcct<br>tctggatggctgtcttgcacttatttagccactccaaaaatgccgggtctgggagatgaccgcagcaccattgacaccatatcaga<br>gagtatcgagactcctctggtttccagtcttgcatgggaatttcataaatgtctcctatcttaccttgttccatcagtgtttgtag<br>ttccaccctcatctggtcgacaaatggtttaactgttccaataaatcaacctatcacaaacttttatgcagaaaatctcttgtca<br>cgcggccaataccggcaccaaagtctataccatatttgattttgtcaggatcgttagagaaacgactctttaacttcttaaaaag<br>gtcatcgatccaacaacatctgcttttggaaccgaagttgtctcaccgtacccacccaaaactccgtcgacagatgctgggacgct<br>gttccagtatttcagggcatcgtcatagttgatcaaactgtccacctgtttagggtcatcccattatgttctgtcattgtggtaa<br>aaatgggatacagtgatatatttgaagggaatggttataagagcctacctgagaaataaaattattatgcgccatccgacatccag<br>aaaaattgatgaaagattggctattgttgacggttcttgatcccaaaaaaaaaaaaaaacaagaaatgctgccgtcctagttttgc<br>ttcaaagaatggtttcgtgctatgccattcccaacccaaagagctgtcccatcccattaagttgtgctgactgattatgttgcaca<br>atccagtgtcgtgattacctccaacatcgcacgcgaatttcgccatggctgggaaacccaaattcttcggtcgtccatcaaactct<br>gaagtcatttcaacaccaaactcaacagctatcataaaaaatatggcgggtttgcgttttttagacattgcaagaccattttgtca<br>gctggatcccggaagttgaacttccttatgaaaactgggggttcgatgaaaagctgatttactcattcttcactgctgccatctat<br>ttgattctgtccctgcctatatacggtgtcaaatcctctgaagtcgtgaccccagttcccatttgcgttctgccttagggagtga<br>gaagggaacattgctggagcttgggttactgcctgtgattacttcggcatttatcttgcagttgttggctggttggaaagttttca<br>agtaaacttttgatctggttagtgacagaaatattgttccaaacttttgcaaaagatcacttcagtcgttatcagcatcgtatatgct<br>gttcttctcacattttgtgactacttttactccaggtgtgtccactgataacgtcttgtggtcccaattctgatcatcttacagat<br>agtggtggtcaactcttggttactctactcgttgaagtcattgacaaggattacggattttcttcaggagctctattgttgcttg<br>cggtttattccgccaccaacttcgttttttggcacgattggtcttagcaccgtcaacacctccagatcgaacgaatctattggtgct<br>ctgatcaattattccgcaatttgagctctcaaacattggtgttgccatatatgactccttcttcagagtaaaccttcctaactt<br>gactcaatttttatctgggaattgccattattttgtgttttgtctgttcttgaataatgcaagatacgaagtaccaattaagccaaaca<br>aggttcgtgccatggcctcagcttacccaatcaagctactttcaatggttctttgccacttctgtacacgtggactgtgctgtac<br>aacttgaacttattggtttctttgtcttcaagcttaccaacttttctcttttagggaacttcaaagtggacccattcggcaacaa<br>ctactacgaaattacatctggactgctgctatttattgacctacttttcaacgctgaagctggacttttacccaagttgctaagc<br>catttgttttcattgccttctatgttggtgttagcacttttcttttgctagatcgtggtccaacattaacgggtcgtcaggcaaggac<br>attgccaagttttttcaaggctcaaggaatctcattgttaggaaaaagagatgcctctgtgtctaaagagtttaacaccctagttcc<br>tgttgcttctgcctctggagctttcctattgtcttttccagttgccgtcgctgagttattgggtggctctggtgttccaacctcta<br>tcggaatcggtcttttgagtggtttggctattttggaaactgttttgcaagaatggcaacagtctgagggtgcctcacagttctcc<br>caatacttccagacttcttaggtttagaaatccttgaagactatccagacattcacccgcacctcaatttaccttctacatacatc |

TABLE 11-continued

SSH1 Complex Overexpression vector

| Description | SEQ ID NO: | Sequence (5' to 3') |
|---|---|---|
| | | acatattctatagaggagagttccattgctcgtactgaaccccacaccactcttctttatacc ctacaaactcttcgtccaactca<br>atggcgtcattcgtgtcggtatagacaataatggtaccccagtccatttcaaagttgtcttttt cgatatccatgattaatttggg<br>cattatttgaagttcgaactgttttcctggcacttagctttgatgatcgtttgatatatttcatcc ttggagttatacagtagtg<br>gctttcctcccaggtggtatcgtaaaacctgggaaggattgtgctcaagagccaactcccttt acaacctcactcaagtccgttag<br>agggcgcgccgcacatgaagctgtacatggaaggcacggtgaataaccaccacttcaaatgcaccagcgagggtgagggtaaaccg<br>tatgaaggcacccaaacgatgcgtatcaaagttgttgagggtggcccgttgccgtttgcgttcgacatttt agcgacgagctttat<br>gtatggctctcgtacgtttatcaagtacccgaagggtattccggacttttttcaaacaatcttttccagagggtttcacctgggagc<br>gcgtgactcgctacgaagatggcggcgtcgtgaccgcaacgcaggatacctccctggaagatggctgcctggtctaccacgttcag<br>gtccgtggtgtcaatttcccgagcaatggtccggttatgcagaagaaaaccctgggttgggaaccgaacaccgagatgttgtatcc<br>tgcagatggtggcctggaaggtcgcagcgacatggcattgaaactggtcggtggcggccatctgagctgtagcttcgtgaccacgt<br>atcgttcgaagaaaacggtcggtaacatcaaaatgccggcttatccgcggttgaccaccgtctggtgcgcattaaagaagccgac<br>aaagagacttacgtggagcaacatgaagtagccgttgcgaaatttgctggtttgggcggtggtatggacgaactgtacagttcctt<br>atcatctggcgaatcggacccacaagagcactgggttccgttttacattccaggaagagtttcagtaatgtcttgtttctttgtt<br>gcagtggtgagccattttgacttcgtgaaagtttctttagaatagttgtttccagaggccaaacattccacccgtagtaaagtgca<br>agcgtaggaagaccaagactggcataaatcaggtataagtgtcgagcactgtcgagggtgatcttctgaaagtttctactagcagata<br>agatccagtagtcatgcatatggcaacaatgtaccgtgtggatctaagaacgcgtcctactaaccttcgcattcgttggtccagtt<br>tgttgttatcgatcaacgtgacaaggttgtcgattccgcgtaagcatgcataccccaaggacgcctgttgcaattccaagtgagcca<br>gttccaacaatctttgtaatattagagcacttcattgtgttgcgcttgaaagtaaaatgcgaacaaattaagagataatctcgaaa<br>ccgcgacttcaaacgccaatatgatgtgcggcacacaataagcgttcatatccgctgggtgacttttctcgcttttaaaaaattatcc<br>gaaaaaattttttgacggctagctcagtcctaggtacgcgctagcattaaagaggagaaaatgactactcttgatgacacagcctacag<br>atataggacatcagttccgggtgacgcagaggctatcgaagccttggacggttcattcactactgatacggtgtttagagtcaccg<br>ctacaggtgatggcttcaccttgagagaggttcctgtagacccaccccttaacgaaagtttttccctgatgacgaatcggatgacgag<br>tctgatgctggtgaggacggtgaccctgattccagaacatttgtcgcatacggagatgatggtgacctggctggctttgttgtggt<br>gtcctacagcggatggaatcgtagactcacagttgaggacattcgaagttgcacctgaacatcgtggtcacggtgttggtcgtgcac<br>tgatggggactggcaacagagtttgctagagaaagaggagccggacatttgtggttagaagtgaccaatgtcaacgtctcctgctatt<br>cacgcatataggcgaatgggtttcactttgtgcggtcttgatactgcttttgtatgacgaactgcttctgatggtgaacaagctct<br>ttacatgagtatgccatgtccatagcacgtccgacggcggccccacgggtcccaggcctcggagatccgtccccctttttcctttgtc<br>gatatcatgtaattagttatgtcacgcttacattcacgccctccccccacatccgctctaaccgaaaaggaaggagttagacaacc<br>tgaagtctaggtccctatttatttttttatagttatgttagtattaagaacgttatttatattcaaattttctttttttttctgt<br>acagacgcgtgtacgcatgtaacattatactgaaaaccttgcttgagaaggttttgggacgctcgaaggctttaatttgcaagctc<br>cgaataacttcgtatagcatacattataccttgttattacagcggccgcaaatattttatctgattaataagatgatcttcttgag<br>atcgttttggtctgcgtaatctcttgctctgaaaacgaaaaaaccgccttgcagggcggttttcgaaggttctctgagctacc<br>aactcttttgaaccgaggtaactggcttggaggagcgcagtcaccaaaacttgtcctttcagtttagccttaaccggcgcatgactt<br>caagactaactcctctaaatcaattaccagtggctgctgccagtggtgcttttgcatgtctttccgggttggactcaagacgatag<br>ttaccggataaggcgcagcggtcggactgaacggggggttcgtgcatacagtccagcttggagcgaactgcctacccgaactgag<br>tgtcaggcgtggaatgagacaaacgcggcataacgcggatgacaccggtaaacaggcaggaacaggagcgcacgagg<br>gagccgccaggggggaaacgcctggtatctttatagtcctgtcgggtttcgccaccactgatttgagcgtcagatttcgtgatgctt<br>gtcagggggcggagcctatggaaaaacggctttgccgcggccctctcacttccctgttaagtatcttcctggcatcttccaggaa<br>atctccgcccgttcgtaagccatttccgctcgccgcagtcgaacgaccgagcgtagcgagtcagtgagcgaggaagcggaatata<br>tcctgtatcacatattctgctgacgcaccggtgcagccttttttctcctgccacatgaagcacttcactgacaccctcatcagtgc<br>caacatagtaagccagtatacactccgctagcgctgatgtccggcggtgcgacgtc |
| SBH2 Promoter | 97 | caactttctgccgccaatctcctttccattcaaattctctacaacaaggcaggcttcgtccgttgatgtgaagtttgcaaaagcca<br>aaccacgaaaaacaccattgctcaaaatggtagttgaaggcataaggcaaagcaagctaaacttttgtcataacgtctaaaagttgc<br>tcttttttttatggcaaaagggatgttctttatcacaatagcagtgggaatgacatcttcatcatcattcgtatcatcaataccatc<br>gagttctgaatccaaaggtttctgttgttgggataaggcatcagattctttgagcaggtcgtccttggcgtcctcctctagatgaa<br>atttgccatcgttaggaggtgagtattgggaaacgttgacttgttgctcaatccaaggatcaacgttgaccatcggattgccgttc<br>tgaggagacagccaggcattataccgtggttgaccggcgtttacgcgcagaggattgttgctggtgttgttgacagaagacgcata<br>cccgacgctgcggatgacatcgacgaaatttgaagggcgacgttgcataccccattttgttgctgatccaagaaacttggtgtttcag<br>tcaattgtctcaggtccatattgatcaatgtgttcaactgttttcaatctggttccggagggtggctattacgacaagctgtggcta<br>ctatctaagtgggagaagtaacgaaacacattgatgagacacaggaattacagggcgtgcatccaccaataacaattagtcgagat<br>ttcaaccaattacgtaagcgctcaaccccttttttcgaacacgtatcgagcaaagtccaggtgaaaaccttcatccattatatccaaa<br>gtcgaccgaagctttaacaacatccata |
| SSS1 Promoter | 98 | agacaagtggagagtggacaaattcttgatgttaattcgtaagatccttaacaaatctttagcaaaactgaaaagtgaagactacg<br>atagggatttacttgaaaaatatattcaagttttgtcagaatacccactccatattaacgatattattgtccctagaactattacg<br>taccacttgtgtgatatttatactgatgagtgggaaaggttatgtttagtgggcttcgtggatttgaagaagaagaagattacga<br>ggaagaagtgaagctctcggctcctatcgaaaaaaaaaccagagatactgataattcagacgatgaggcctctgataccgatccag<br>aaacgagtgacgaagaagacgaaggtgagaatactgaaaacgagtcagaagaggaaccgatcaaactctctgcggaagaagaaacg<br>gctctgtgaaaacaaagatggagattatccatgaaactcctatcgacaaattactctcacccttttgtctcattgaagaaagatac<br>ctcaaataaaccattaaaattgaaaatccaagaagcgaatttctgctgatccaagactccggccaaatggaaagttaaatcgtaccgaa<br>agcctaaaccaaaaccaaaaccctcttcaggtgctacagaaactgttatcgaacagatcaaatataaaaagggtaaagcagtcaca<br>ggtgaagcgacgatgaactcaaagacgaagacgaagatgacgatgacgaggtcatctcggagagtgaagctgataactctgatga<br>agaagaagatgaagaatggaatggctttggaactatctagaatacatatgtaaaaccatatcaggcaataacaatttctcgctatt<br>ttgcatcccaacacctcgaccgacgtgttcagttcgaccctttacctacagtgtcttttaactcccatttggatctcctaaataacc<br>tacacaa |
| SSH1 Promoter | 99 | tctgaacgggtctttgagctgtctgtgtcatcaaacatatcttcatctgtagttgtattgttttcttttatcactaggagtccatc<br>cttctggatgctgctctgcacttatttagccactccaaaaatgccgggtctgggagatgaccgcagcaccattgacaccatatca<br>gagagtatcgagactcctctggtttccagtcttgcatgggaatttcataaatgtctcctatcttaccttgttccatcagtgtttgt<br>agttccaccctcatctggtcgacaaatggtttaactggttccaataaatcaacctttatcacaaactttatgcagaaaatctcttgt<br>cacgcggccaataccggcaccaaagtctataccatatttgatttgtcaggatcgttagagaaacgactctttaactttcttaaaa<br>aggtcatcgatccaacaacatctgcttttggaaccgaagttgtctcaccgtacccacccaaaactccgtcgacagatgctgggacg<br>ctgttccagtatttcagggcatcgtcatagttgatcaaactgtccacctgtttagggtcatcccattatgttctgtcattgtggt |

TABLE 11-continued

SSH1 Complex Overexpression vector

| Description | SEQ ID NO: | Sequence (5' to 3') |
|---|---|---|
| | | aaaaatgggatacagtgatatattgaaggggaatggttataagagcctacctgagaaataaaattattatgcgccatccgacatcc agaaaaattgatgaaagattggctattgttgacggttcttgatcccaaaaaaaaaaaaaaacaagaaatgctgccgtcctagtttt gcttcaaagaatggtttcgtgctatgccattcccaacccaaagagctgtcccatcccattaagttgtgctgactgattatgttgca caatccagtgtcgtgattacctccaacatcgcacgcgaatttcgccatggctgggaaacccaaattcttcggtcgtccatcaaact ctgaagtcatttcaacaccaaactcaacagctatcatagaaaaat |
| SBH2 Terminator | 100 | gacctatatttaaacaggtttcatcatatctgtactatatttacaagtccactgcgtttaggtatatactaaagacattcaagaag cacatccacaacttgtgcaagtcctgtcaaatgtactagatgcttttcagaacatcctgcggtttgaggagattcctgaatttccc agtcccaagtctttctcttgtagaggtctttgagttcttgtgaatgctgaattggggttcttacctcaatttctattagtgggaaa tgctttcccacaattatttgcaatgggatcccggcaactttactttgcttcaacttatgtcccatactgaactttcgtcacggtt gtcaacttgaacgtcgaatgagctcagtatttcggtgacagtgtctagattcttttttacttgatgttttattcgaaagtagcgtga tttgatatggtgcgataatttgtggccagg |
| SSS1 Terminator | 101 | aagtttaggtttgaatacaatgtgtatgcttaattatattcacttcgtttcattgattttttgctatccctgttgtgcgttaatcat ctctatcgtgatcctctcaagttgcacctcaaatagaagacaacttatggaggtgtactacccaatatcagtcttgacgtttctag tttcgttgtatgctgcataccaatttcagttcttccgtagtgttttgagcataggctgtttacccgtcttctttacactctgata tgagcacccttatcaaacctcttatcacagctgaaaggagaaggcggtggtggtcttctggtcagaatcggcccagaactgtggat cctgctgttgcaagattgaaagcagaaaggaagatggaaagagagaagcaagctcttaaagaggctcagcaagcccaggaagctcg ggaaaggcgaagaattagtcatgctacccagataggtttgagaccaaccagtaaagctccca |
| SSH1 Terminator | 102 | gtttagaaatccttgaagactatccagacattcaccgcacctcaatttaccttctacatacatcacatattctatagaggagagt tccattgctcgtactgaaccccacaccactcttctttatacccctacaaactcttcgtccaactcaatgcgtcattcgtgtcggta tagacaataatggtacccagtccatttcaaagttgtcttttttcgatatccatgattaatttgggcattatttgaagttcgaactg ttttcctggcactttagctttgatgatcgtttgatatatttcatccttggagttatacagtagtggctttcctcccaggtggtatc gtaaaacctgggaaggattgtgctcaa |
| Yeast Selection Marker (Nat) for SSH1 overexpression genes (Nucleotide) | 103 | ttcagtaatgtcttgtttctttttgttgcagtggtgagccatttttgacttcgtgaaagtttcttttagaatagttgtttccagaggcc aaacattccaccgtagtaaagtgcaagcgtaggaagaccaagactggcataaatcaggtataagtgtcgagcactggcaggtgat cttctgaaagtttctactagcagataagatccagtagtcatgcatatggcaacaatgtaccgtgtggatctaagaacgcgtcctac taaccttcgcattcgttggtccagtttgttgttatcgatcaacgtgacaaggttgtcgattccgcgtaagcatgcatacccaagga cgcctgttgcaattccaagtgagccagttccaacaatctttgtaatattagagcactcattgtgttgcgcttgaaagtaaaatgc gaacaaattaagagataatctcgaaaccgcgacttcaaacgccaatatgatgtgcggcacacaataagcgttcatatccgctgggt gactttctcgctttaaaaaattatccgaaaaaatttttgacggctagctcagtcctaggtacgctagcattaaagaggagaaatg actactcttgatgacacagcctacagatataggacatcagttccgggtgacgcagaggctatcgaagccttggacggttcattcac tactgatcggtgtttagagtcaccgctacaggtgatggcttcaccttgagagaggttcctgtagacccaccccttaacgaaagttt tccctgatgacgaatcggatgacgatctgatgctggtgaggacggtgaccctgattccagaacattttgtcgcatacggagatgat ggtgacctggctggctttgttgtggtgtcctacagcggatggaatcgtagactcacagttgaggacatcgaagttgcacctgaaca tcgtggtcacggtgttggtcgtgcactgatgggactggcaacagagtttgctagagaaagaggagccggacatttgtggttagaag tgaccaatgtcaacgctcctgctattcacgcatataggcgaatgggtttcactttgtgcggtcttgatactgctttgtatgacgga actgcttctgatggtgaacaagctcttacatgagtatgccatgtccatagcacgtccgacggcggcccagggtcccaggcctcg gagatccgtcccccttttcctttgtcgatatcatgtaattagttatgtcacgcttacattcacgcctcccccacatccgctcta accgaaaaggaaggagttagacaacctgaagtctaggtccctatttatttttttatagttatgttagtattaagaacgttatttat atttcaaatttttctttttttttctgtacagacgcgtgtacgcatgtaacattatactgaaaaccttgcttgagaaggttttgggac gctcgaaggctttaatttgcaagct |
| Y Yeast Selection Marker (Nat) for SSH1 overexpression genes (Amino Acid) | 104 | MTTLDDTAYRYRTSVPGDAEAIEALDGSFTTDTVFRVTATGDGFTLREVPVDPPLTKVFPDDESDDESDAGEDGDPDSRTFVAYGD DGDLAGFVVVSYSGWNRRLTVEDIEVAPEHRGHGVGRALMGLATEFARERGAGHLWLEVTNVNAPAIHAYRRMGFTLCGLDTALYD GTASDGEQALYMSMPCP |

TABLE 12

Zeocin Cassette with HA arms for KU70 deletion in P. pastoris

| Description | SEQ ID NO: | 5' to 3' Sequence |
|---|---|---|
| Plasmid sequence | 57 | ggagttgaatcacatcttactggatagcgagcttttgacgaagtgaaaatttctaattttaaacaagaggaagggtca aaaacggagatatcttatacttggaaaaagagatgacaatcagtgatttcatcaattttgtatctagttggccttctgtg ttttcgtggaagcagcaacgaggaaaggagggtatcctagatgattttacaacgaactgaacgactgctttgaggggg taacatgaaagtaatatggaactccgtcctagtatttgccaggaggaagcaaaggggttgtataggctttagtacttatag aggaaacgggggttacgtgcaagcgcgcatgcctgagctttgaggggggggactttcacatctcttcttctcacacttagc cctaacacagagaataataaaaagcattgcaagatgagtgttgtcagcaagcaatacgacatccacgaaggcattatctt tgtaattgaattgaccccgggagcttcacgcgccggcttcagaaggggaaatctcagctccagatcatcttagagaatgtca |

TABLE 12-continued

Zeocin Cassette with HA arms for KU70 deletion in *P. pastoris*

| Description | SEQ ID NO: | 5' to 3' Sequence |
|---|---|---|
| | | gtgaggttatttctgagctaatcattaccttgcccggtacaggaatagggtgttaccttattaattacgacggtggtcaa |
| | | aacgacgaaatttaccccatttttgagttacaagaccgtgaatttggaaatgatgaaacaattgtaccaagtcttggagga |
| | | ccatgtaagtgggcttaatcctctcgagaagcaatcccaattgaacacagtaaaccgttatcagccactctgttctttc |
| | | acttaaggtctcttttttacatggcgaagactcataagcgtactggaagacattacaacttgaaaaagattttcttgttc |
| | | actaataacgataaaccttacaatggaaactctcagctgagagttccctgaagaaaaccctggctgattacaatgacgt |
| | | agacattactttgattccgtttcttctgaacaagccttcaggtgtcaagtttgacaagacggaatactcagaaattttgt |
| | | tctatgataaagatgcttgttcgatgtcaattgaggagatccgccaacgaatttctagacataaggagatcaagcgggtt |
| | | tacttcacctgtccttttgaaaatcgcaaataacttgtgcatttctgtgaaaggttattctatgttttatcatgaaactcc |
| | | aaggaagatcaaatttgtcgtcaatgagggttcaactttcaaagatgtggagacaaaatctcagtttgtcgatccaacat |
| | | ccggaaaagagttttccagtgaacagctgatcaaagcatatcctctaggtgccgatgcttacattcctttaaactcagag |
| | | caagtcaaaacaataaatcgatttaatgatatcatcaatatccctcttttggaaattctaggtttcagggatatatctaa |
| | | ttggttgccacagtatcagtttggcaaagcatcgttttatccctaataactatggtgattttacacattcgcagagaa |
| | | catttagttgtcttcagtaatgtcttgtttcttttgttgcagtggtgagccatttgacttcgtgaaagtttctttagaa |
| | | tagttgtttccagaggccaaacattccaccgtagtaaagtgcaagcgtaggaagaccaagactggcataaatcaggtat |
| | | aagtgtcgagcactggcaggtgatcttctgaaagtttctactagcagataagatccagtagtcatgcatatggcaacaat |
| | | gtaccgtgtggatctaagaacgcgtcctactaaccttcgcattcgttggtccagtttgttgttatcgatcaacgtgacaa |
| | | ggttgtcgattccgcgtaagcatgcatacccaaggacgcctgttgcaattccaagtgagccagttccaacaatctttgta |
| | | atattagagcacttcattgtgttgcgcttgaaagtaaaatgcgaacaaattaagagataatctcgaaaccgcgacttcaa |
| | | acgccaatatgatgtgcggcacacataagcgttcatatccgctgggtgactttctcgctttaaaaaattatccgaaaaa |
| | | attttttgacggctagctcagtcctaggtacgctagcattaaagagggagaaaatggctaaactgacctctgctgttccggt |
| | | tctgaccgctcgtgacgttgctggtgctgttgagttctggaccgaccgtctgggtttctctcgtgacttcgttgaagacg |
| | | acttcgctggtgttgttcgtgacgacgttaccctgttcatctctgctgttcaggaccaggttgttccggacaacaccctg |
| | | gcttgggtttgggttcgtggtctggacgaactgtacgctgaatggtctgaagttgtttctaccaacttccgtgacgcttc |
| | | tggtccggctatgaccgaaatcggtgaacagccgtgggtcgtgagttcgctctgcgtgaccggctggtaactgcgttc |
| | | acttcgttgctgaagaacaggactaacacgtccgacggcggcccacgggtcccaggcctcggagatccgtcccccttttc |
| | | ctttgtcgatatcatgtaattagttatgtcacgcttacattcacgccctccccccacatccgctctaaccgaaaaggaag |
| | | gagttagacaacctgaagtctaggtccctatttattttttatagttatgttagtattaagaacgttatttatattcaa |
| | | atttttcttttttctgtacagacgcgtgtacgcatgtaacattatactgaaaaccttgcttgagaaggttttgggacg |
| | | ctcgaaggctttaatttgcaagctgtattagtttcacttttcagcaacctggtcggaaagatccacatcaagaatggata |
| | | ccaaccccaagagtatgaaaatccttccctacaatggcacttcaaaatgttacgtgacgattaccttcaattggaacacg |
| | | atatcgacatcagtgacccccttgagaaacaaagtacataaacagcctcgatgagacaaaaaccaagatcatgaaacta |
| | | cgggactatgtcaaggaaactgccgatgatgacgacccttcacggcttgccaacactctcaaagagctcaaccaagagct |
| | | gaacaaaatttccaactttgatatcatcgccaataagaagccaaagacccccacgacagtagaccctgttcctactgatg |
| | | atgacatcatcaacgcctggaaggcaggaactctgaacggtttcaaggtggatcaattacgaaaatacgtaaggtcacga |
| | | aacaactttctggagacggcctccaaaaaggcagatctcatcgccaacattgacaagtacttcagcagaagttcaaaga |
| | | gactaaggcctgattcgtgttccttacttttttcctcgcaagcgtgttttttcctaccacattgcctatgttgtaatgcaa |
| | | tgcagatgctggcccagttttttgacgattctcgaaaattggcattttcgtcgatgccattggccaaactgaaaattcaag |
| | | acaaaatagattggattttatctgcaacgtcttccacctacacaaccactctacaaacttcagacaaacatgtttataaa |
| | | agcagctactagatccaaaatgacaagttcgttattctctactacgtttgttgtggcatttggattggtggctagcaaca |
| | | acctcttgccatgtcctgttgaccactctatgaaacaacgagactccgcaagaattgaacactctcaaagagctcaaccaagagct |
| | | actagaaagttgaactcttccgcttaagtcaaataaaactactgacacagatgatgcacagaaacaacggatcacgctct |
| | | tgactgattagtcccgtcatttttggttctcattttcttcacagtcacctatcaatgtatgatcacctggaaggatttccc |
| | | tacgatacttcaaatcttttacttgataatattactcattatggctcaggaatgcagactgcctgattcaagacgctgct |
| | | cttcttatttaacacttgtacactaacccatggaagcgagggaaggggaataaccatctctctggtaataaatcggtctt |
| | | tatttatgcatagaaaaggaatctattatatttcgttcatttggcactctgctaactgtagattaacgggtctcgtaaat |
| | | tcaaaatcttcttccgatcaaaccggggtgaaatattacttctcgtgcatagctaattttcaaataaccgtcctaaaatg |
| | | aacggtcatttacctggactctcttgccaaatgggcaacaaaacataaagctgatcagaacgtaactagtctctcggaat |
| | | ccat |
| HA F | 58 | ggagttgaatcacatcttactg |
| KU70 HA 1 | 59 | gacaactaaatgttctctgcgaatgtgtaaaatcaccatagttattaggggataaaaacgatgctttgccaaactgatac |
| | | tgtggcaaccaattagatatatccctgaaacctagaatttccaaagagggatattgatgatatcattaaatcgatttat |
| | | tgttttgacttgctctgagtttaaaggaatgtaagcatcggcacctagaggatatgctttgatcagctgttcactggaaa |
| | | actcttttccggatgttggatcgacaaactgagattttgtctccacatctttgaagttgaaccctcattgacgacaaat |
| | | ttgatcttccttggagtttcatgataaaacatagaataaccttcacagaaatgcacaagttatttgcgattttcaaagg |
| | | acaggtgaagtaaacccgcttgatctccttatgtctagaaattcgttggcggatctcctcaattgacatcgaacaagcat |
| | | ctttatcatagaacaaaatttctgagtattccgtcttgtcaaacttgacacctgaaggcttgttcagaagaaacggaatc |
| | | aaagtaatgtctacgtcattgtaatcagccaggggttttcttcaagggaactctcagctgagagtttccattgtaaggttt |
| | | atcgttattagtgaacaagaaatcttttttcaagttgtaatgtcttccagtacgcttatgagtcttcgccatgtaaaaaa |
| | | gagaccttaagtgaaagaacagagtggctgataacggtttactgtgttcaattgggaattgcttctcgagaggattaagc |
| | | ccacttacatggtcctccaagacttggtacaattgtttcatcatttccaaattcaggtcttgtaactcaaaaatggggta |
| | | aatttcgtcgtttttgaccaccgtcgtaattaataaggtaacaccctattcctgtaccgggcaaggtaatgattagctcag |
| | | aaataacctcactgacattctctaagatgatctggagctgagatttcccttctgaagccggcgcgtgaagctccggggtc |
| | | aattcaattacaaagataatgccttcgtggatgtcgtattgcttgctgacaacactcat |
| KU70 HA 2 | 60 | tcaggccttagtctcttttgaacttctgctgaaagtacttgtcaatgttggcgatgagatctgccttttttggaggccgtct |
| | | ccagaaagttgtttcgtgaccttacgtattttcgtaattgatccaccttgaaaccgttcagagttcctgccttccaggcg |
| | | ttgatgatgtcatcatcagtaggaacaggggtctactgtcgtgggggtcttttggcttcttattggcgatgatatcaaagtt |
| | | ggaaattttgttcagctcttggttgagctctttgagagtgttggcaagccgtgaaggggtcgtcatcatcggcagtttcct |
| | | tgacatagtcccgtagtttcatgatcttggttttttgtctcatcgaggctgtttatgtactttttgtttctcaaggggtca |
| | | ctgatgtcgatatcgtgttccaattgaaggtaatcgtcacgtaacattttgaagtgccattgtagggaaggattttcata |
| | | ctcttggggttggtatccattcttgatgtggatctttccgaccaggttgctgaaaagtgaaactaatac |

TABLE 12-continued

Zeocin Cassette with HA arms for KU70 deletion in P. pastoris

| Description | SEQ ID NO: | 5' to 3' Sequence |
|---|---|---|
| pILV5 | 61 | ttcagtaatgtcttgtttcttttgttgcagtggtgagccattttgacttcgtgaaagtttctttagaatagttgtttcca<br>gaggccaaacattccaccgtagtaaagtgcaagcgtaggaagaccaagactggcataaatcaggtataagtgtcgagca<br>ctggcaggtgatcttctgaaagtttctactagcagataagatccagtagtcatgcatatggcaacaatgtaccgtgtgga<br>tctaagaacgcgtcctactaaccttcgcattcgttggtccagtttgttgttatcgatcaacgtgacaaggttgtcgattc<br>cgcgtaagcatgcatacccaaggacgcctgttgcaattccaagtgagccagttccaacaatctttgtaatattagagcac<br>ttcattgtgttgcgcttgaaagtaaaatgcgaacaaattaagagataatctcgaaaccgcgacttcaaacgccaatatga<br>tgtgcggcacacaataagcgttcatatccgctgggtgactttctcgctttaaaaaattatccgaaaaaattt |
| RM2734;<br>testR | 62 | cagaggccaaacattccacc |
| pproRBS | 63 | ttaaagaggagaaa |
| Sh ble<br>(codon<br>optimized) | 64 | atggctaaactgaccctctgctgttccggttctgaccgctcgtgacgttgctggtgctgttgagttctggaccgaccgtct<br>gggtttctctcgtgacttcgttgaagacgatcgctggtgttgttcgtgacgacgttaccctgttcatctctgctgttc<br>aggaccaggttgttccggacaacaccctggcttgggtttgggttcgtgctggacgaactgtacgctgaatggtctgaa<br>gttgtttctaccaacttccgtgacgcttctggtccggctatgaccgaaatcggtgaacagccgtggggtcgtgagttcgc<br>tctgcgtgacccggctggtaactgcgttcacttcgttgctgaagaacaggactaa |
| CYC1<br>terminator | 65 | cacgtccgacggcgggcccacgggtcccaggcctcggagatccgtccccctttttcctttgtcgatatcatgtaattagtta<br>tgtcacgcttacattcacgcctccccccacatccgctctaaccgaaaaggaaggagttagacaacctgaagtctaggtc<br>cctatttatttttttatagttatgttagtattaagaacgttatttatatttcaaattttctttttttctgtacagacg<br>cgtgtacgcatgtaacattatactgaaaacctgcttgagaaggttttgggacgctcgaaggctttaatttgcaagct |
| Rm3386;<br>F test<br>oligo | 66 | aggagttagacaacctgaag |
| HA R | 67 | gtaactagtctctcggaatccat |

TABLE 13

Template Nourseothricin Cassette for protease deletion in P. pastoris

| Description | SEQ ID NO: | 5' to 3' Sequence |
|---|---|---|
| Plasmid<br>sequence | 68 | cttcagagtacagaagattaagtgagagaattctaccgttcgtatagcatacattatacgaagttatttcagtaatgtct<br>tgtttcttttgttgcagtggtgagccattttgacttcgtgaaagtttctttagaatagttgtttccagaggccaaacatt<br>ccaccgtagtaaagtgcaagcgtaggaagaccaagactggcataaatcaggtataagtgtcgagcactggcaggtgatc<br>ttctgaaagtttctactagcagataagatccagtagtcatgcatatggcaacaatgtaccgtgtggatctaagaacgcgt<br>cctactaaccttcgcattcgttggtccagtttgttgttatcgatcaacgtgacaaggttgtcgattccgcgtaagcatgc<br>atacccaaggacgcctgttgcaattccaagtgagccagttccaacaatctttgtaatattagagcacttcattgtgttgc<br>gcttgaaagtaaaatgcgaacaaattaagagataatctcgaaaccgcgacttcaaacgccaatatgatgtgcggcacaca<br>ataagcgttcatatccgctgggtgactttctcgctttaaaaaattatccgaaaaaattttgacggctagctcagtccta<br>ggtacgctagcattaaagaggagaaaatgactactcttgatgacacagcctacagatataggacatcagttccgggtgac<br>gcagaggctatcgaagccttggacggtgttcattcactactgatacggtgtttagagtcaccgctacaggtgatggcttcac<br>cttgagagaggttcctgtagacccaccccttaacgaaagttttccctgatgacgaatcggatgacgagtctgatgctggtg<br>aggacggtgaccctgattccagaacatttgtcgcatacggagatgatggtgacctggctggctttgttgtggtgtcctac<br>agcggatggaatcgtagactcacagttgaggacatcgaagttgcacctgaacatcgtggtcacggtgttggtcgtgcact<br>gatgggactggcaacagaagtttgctagagaaaaggagccggacatttgtggttagaagtgaccaatgtcaacgctcctg<br>ctattcacgcatataggcgaatgggtttcacttttgtgcggtcttgatactgctttgtatgacggaacttgcttctgatgt<br>gaacaagctctttacatgagtatgccatgtccatagcacgtccgacggcgggcccacgggtcccaggcctcggagatccgt<br>ccccctttttcctttgtcgatatcatgtaattagttatgtcacgcttacattcacgcctccccccacatccgctctaacc<br>gaaaaggaaggagttagacaacctgaagtctaggtccctatttatttttttatagttatgttagtattaagaacgttatt<br>tatatttcaaattttctttttttctgtacagacgcgtgtacgcatgtaacattatactgaaaacctgcttgagaagg<br>ttttgggacgctcgaaggctttaatttgcaagctataacttcgtatagcatacattatacctttgttatgcggccgcaaga<br>agttgattgagactttcaacgag |
| AOX1 pA<br>terminator | 69 | cttcagagtacagaagattaagtgaga |
| Lox71 F | 70 | taccgttcgtatagcatacattatacgaagttat |
| pILV5 | 71 | ttcagtaatgtcttgtttcttttgttgcagtggtgagccattttgacttcgtgaaagtttctttagaatagttgtttcca<br>gaggccaaacattccaccgtagtaaagtgcaagcgtaggaagaccaagactggcataaatcaggtataagtgtcgagca<br>ctggcaggtgatcttctgaaagtttctactagcagataagatccagtagtcatgcatatggcaacaatgtaccgtgtgga<br>tctaagaacgcgtcctactaaccttcgcattcgttggtccagtttgttgttatcgatcaacgtgacaaggttgtcgattc |

TABLE 13-continued

Template Nourseothricin Cassette for protease deletion in P. pastoris

| Description | SEQ ID NO: | 5' to 3' Sequence |
|---|---|---|
| | | cgcgtaagcatgcatacccaaggacgcctgttgcaattccaagtgagccagttccaacaatctttgtaatattagagcac<br>ttcattgtgttgcgcttgaaagtaaaatgcgaacaaattaagagataatctcgaaaccgcgacttcaaacgccaatatga<br>tgtgcggcacacaataagcgttcatatccgctgggtgactttctcgctttaaaaaattatccgaaaaaattt |
| pproRBS | 72 | ttaaagaggagaaa |
| nat<br>(Nourseothricin<br>resistance) | 73 | atgactactcttgatgacacagcctacagatataggacatcagttccgggtgacgcagaggctatcgaagccttggacgg<br>ttcattcactactgatacggtgtttagagtcaccgctacaggtgatggcttcaccttgagagaggttcctgtagaccac<br>ccttaacgaaagttttccctgatgacgaatcggatgacgagtctgatgctggtgaggacggtgaccctgattccagaaca<br>tttgtcgcatacggagatgatggtgacctggctggctttgttgtggtgtcctacagcggatggaatcgtagactcacagt<br>tgaggacatcgaagttgcacctgaacatcgtggtcacggtgttggtcgtgcactgatgggactggcaacagagtttgcta<br>gagaaagaggagccggacatttgtggttagaagtgaccaatgtcaacgctcctgctattcacgcatataggcgaatgggt<br>ttcactttgtgcggtcttgatactgctttgtatgacggaactgcttctgatggtgaacaagctctttacatgagtatgcc<br>atgtccatag |
| CYC1<br>terminator | 74 | cacgtccgacggcggcccacgggtcccaggcctcggagatccgtcccccttttccttttgtcgatatcatgtaattagtta<br>tgtcacgcttacattcacgccctccccccacatccgctctaaccgaaaaggaaggagttagacaacctgaagtctaggtc<br>cctatttattttttatagttatgttagtattaagaacgttatttatatttcaaattttctttttttctgtacagacg<br>cgtgtacgcatgtaacattatactgaaaaccttgcttgagaaggttttgggacgctcgaaggctttaatttgcaagct |
| LoxKR3 F | 75 | ataacttcgtatagcatacattatacccttgttat |
| HSP82 | 76 | gcggccgcaagaagttgattgagactttcaacgag |

TABLE 14

Exemplary nourseothricin cassettes with HA arms for YPS1-1 and YPS1-2 protease deletion in P. pastoris

| Description | SEQ ID NO: | 5' to 3' Sequence |
|---|---|---|
| Nourseothricin<br>cassette with<br>homology arms<br>targeting<br>PAS_chr4_0584<br>(YPS1-1) | 77 | tactacaggctggctgttcctcgcatggtgtttaatgtcctgactgggttttcgtttatcggtattaccggagccaccttg<br>actgtaagggaacgatactggactaagagagtaatgcgaaaggcaacagcgtttctggcgaacctaatcaatgacggttac<br>gagtttactactcctaaagccagtctctatttttgctagagcgagtcaacgcttacttaaagggcagggacctaattatgac<br>atcgattttgacgagcaggaggcgttcattaaagaaatggaggagttgaggacctctggtggatatgagaacagatactca<br>tattcaggaacgcgatgaaacacccagaagatccgggttgcctgtttcttcccattgctttaaataaatggcacttttgatgtg<br>ctagactgcctgaggatatacggtactcaggaagatctggaatctaaattattaagtgttcagcaattggtgttacaatgt<br>tgcatgaagcacagtggcatgactccagacatggtctttgcaacggaagtagctcagaagccgaccttcgaagacgacata<br>gtttgtgatgatattgacgcttatgcccaggggggtgattgtctagattattgttacacgccaagcaattactccagaact<br>ttagaaattcatggcaagattgctaccttacaacgagagctggggctatgctataatattctcggaattttggaccgttt<br>tccgattaaggttttagctccattgcgccaaccccgctctccagactcctcgttatccagcattcagcatggacaggt<br>tcaaaaaaataaaatttcttgatatgggtccacttcaaacatgcgcctacctgtaggaaaaaaaagagaacataaatgc<br>cgcgaacagaaaacgtaatgtactgttctatatataaactgttcagatcaatcataaattctcagtttcaaactttccgct<br>cagccagatttattcgtaaagaacgcatcattggctctatgttgaaggatcagttcttcttgttatgggttgctttgataggcg<br>agcgtaccggtttccggcgtgatggcagctcctagcgagtccgggcataacacggttgaaaaacgagatgccaaaaacgtt<br>gttggcgttcaacagttggacttcttcagagtacagaagattaagtgagagaattctaccgttcgtatagcatacattata<br>cgaagttatttcagtaatgtcttgtttcttttgttgcagtggtgagccattttgacttcgtgaaagtttctttagaatagt<br>tgtttccagaggccaaacattccacccgtagtaaagtgcaagcgtaggaagaccaagactggcataaatcaggtataagtg<br>tcgagcactggcaggtgatcttctgaaagtttctactagcagataagatccagtagtcatgcatatggcaacaatgtaccg<br>tgtggatctaagaacgcgtcctactaaccttcgcattcgttggtccagtttgttgttatcgatcaacgtgacaaggttgtc<br>gattccgcgtaagcatgcatacccaaggacgcctgttgcaattccaagtgagccagttccaacaatctttgtaatattaga<br>gcacttcattgtgttgcgcttgaaagtaaaatgcgaacaaattaagagataatctcgaaaccgcgacttcaaacgccaata<br>tgatgtgcggcacacaataagcgttcatatccgctgggtgactttctcgctttaaaaaattatccgaaaaattttgacg<br>gctagctcagtcctaggtacgctagcattaaagaggagaaaatgactactcttgatgacacagcctacagatataggacat<br>cagttccgggtgacgcagaggctatcgaagccttggacggttcattcactactgatacggtgtttagagtcaccgctacag<br>gtgatggcttcaccttgagagaggttcctgtagaccacccttaacgaaagttttccctgatgacgaatcggatgacgagt<br>ctgatgctggtgaggacggtgaccctgattccagaacatttgtcgcatacggagatgatggtgacctggctggctttgttg<br>tggtgtcctacagcggatggaatcgtagactcacagttgaggacatcgaagttgcacctgaacatcgtggtcacggtgttg<br>gtcgtgcactgatgggactggcaacagagtttgctagagaaagaggagccggacatttgtggttagaagtgaccaatgtca<br>acgctcctgctattcacgcatataggcgaatgggtttcactttgtgcggtcttgatactgctttgtatgacggaactgctt<br>ctgatggtgaacaagctctttacatgagtatgccatgtccatagtccgacggcggcccacgggtcccaggcctcgga<br>gatccgtcccccttttccttttgtcgatatcatgtaattagttatgtcacgcttacattcacgccctccccccacatccgct<br>ctaaccgaaaaggaaggagttagacaacctgaagtctaggtccctatttatttttatagttatgttagtattaagaacg<br>ttatttatatttcaaattttctttttttctgtacagacgcgtgtacgcatgtaacattatactgaaaaccttgcttgag<br>aaggttttgggacgctcgaaggctttaatttgcaagctataacttcgtatagcatacattatacccttgttatgcgccgca<br>agaagttgattgagactttcaacgagggtccccttcagctaccttttctctgtttggtagttattctcggcgtgtata<br>gtatagtataaaagggcctacattggataggcttcaacattcctcaataaacaaacatccaacatcgcgcattccgcattt<br>cgcatttcacatttcgcgcctgccttcctttaggttcttgaatcatcatcaatcgtcgccgtctacatcagagcaggact<br>tatctttgccttccccaaaaattgccactccgtcaaatagattcttttgaatccttgactatttttgcctaaatagggtttt |

TABLE 14-continued

Exemplary nourseothricin cassettes with HA arms for YPS1-1 and YPS1-2 protease deletion in *P. pastoris*

| Description | SEQ ID NO: | 5' to 3' Sequence |
|---|---|---|
| | | tgttagttttttcttcaaagcccaaaagaaactctatttagattcatccagaaacaatcttttttctcaccccatttcgaagt gccgtggagcacagacataaaaagatgactaccgttcaacctacagggccagacaggctcaccctgccgcatattctactg gaattcaacgatggctcctcgcagcatgcagtgatcgagctaagcatgaacgaggggattaatatatccacccatgagtgg aatccatccactaatgagcaatcgccacgggaagagagagcaccaccccaacaatccaatccatcgcatcatccagaatca tcgaacatagctactcaaagtcccgctcaggaaaccgagactcagcccggcattccaggactagataggcctgcctttgat acctcggcaacggggtcgtcagaacaggttgacccagtacagggaaggatcctggatgatatttataggccaatcattaagg acttccgaagaagacgataccgaatcccgccagagaccacgagaccagaagaacattatgatcaccgtgaattacttgtac gcagacgacacaaattccagaagtgctaatacaaacaaccagacgcccaataacacttctagaacttccgacagtgaacgt gtgggctccttatcgttgcacgttccggatctaccagataatgccgacgattactatatcgatgtactcattaaactaacc acaagcattgccctcagcgtcatcacgtccatgatcaagaaacgattagggcttagcaggga |
| PAS_chr4_0584 Homology Arm 1 | 78 | tactacaggctggctgttcctcgcatggtgtttaatgtcctgactgggttttcgtttatcggtattaccggagccaccttg actgtaagggaacgatactggactaagagagtaatgcgaaaggcaacagcgtttctggcgaacctaatcaatgacggttac gagtttactactcctaaagccagtcttatttttgctagagcagctcaacgcttacttaaagggcagggacctaattatgac atcgattttgacgagcaggaggcgttcattaaagaaatggaggagttgaggacctctggtggatatgagaacagatactca tattcaggaaccgatgaaacacccagagatccgggttgcctgtttcttcccattgctttaaataaatggcactttgatgtg ctagactgcctgaggatatacggtactcaggaagatctggaatctaaattattaagtgttcagcaattggtgttacaatgt tgcatgaagcacagtggcatgactccagacatggtctttgcaacggaagtagctcagaagccgaccttcgaagacgacata gtttgtgatgatattgacgcttatgcccaggggggtgattgtctagattattgttacacgccaagcaattactccagaact ttagaaattcatggcaagattgctaccttacaacgagagctggggctatgctataatattctcggaattttggaccgtttt tccgattaaggttttagctccattgcgccaaccccgctctccagactccttcgttatccagcattcagcatggacaggt tcaaaaaataaaatttcttgatatgggtccacttcaaacatgcgcctacctgtaggaaaaaaaaagagaacataaatatgc cgcgaacagaaaacgtaatgtactgttctatataaaactgttcagatcaatcataaattctcagtttcaaactttccgct cagccagattttattcgtaaagaacgcatcattggctctatgttgaaggatcagttcttgttatggggtgctttgatagcg agcgtaccggtttccggcgtgatggcagctcctagcgagtccgggcataacacggttgaaaaacgagatgccaaaaacgtt gttggcgttcaacagttggactt |
| PAS_chr4_0584 Homology Arm 2 | 79 | ggtccccttcagctaccttttctctctgtttggtagttattctcggcgtgtgtatagtatagtataaaagggcctacattgg ataggcttcaacattcctcaataaacaaacatccaacatcgcgcattccgcatttcgcatttcacatttcgcgcctgcctt cctttaggtctttgaatcatcatcaatcgtcgccgtctacatcagagcaggactatctttgccttccccaaaaattgcc actccgtcaatagattcttttgaatccttgactattttttgcctaaataggttttttgttagttttcttcaaagcccaaaa gaaactctatttagattcatccagaaacaatcttttttctcaccccatttcgaagtgccgtggagcacagacataaaaagat gactaccgttcaacctacagggccagacaggctcaccctgccgcatattctactggaattcaacgatggctcctcgcagca tgcagtgatcgagctaagcatgaacgaggggattaatatatccacccatgagtggaatccatccactaatgagcaatcgcc acgggaagagagagcaccaccccaacaatccaatccatcgcatcatccagaatcatcgaacatagctactcaaagtcccgc tcaggaaaccgagactcagcccggcattccaggactagataggcctgcctttgatacctcggcaacggggtcgtcagaaca ggttgacccagtacagggaaggatcctggatgatatttataggccaatcattaaggacttccgaagaagacgataccgaatc ccgccagagaccacgagaccagaagaacattatgatcaccgtgaattacttgtacgcagacgacacaaattccagaagtgc taatacaaacaaccagacgcccaataacacttctagaacttccgacagtgaacgtgtgggctccttatcgttgcacgttcc ggatctaccagataatgccgacgattactatatcgatgtactcattaaactaaccacaagcattgccctcagcgtcatcac gtccatgatcaagaaacgattagggcttagcaggga |
| Nourseothricin cassette with homology arms targeting PAS_chr3_1157 (YPS1-2) | 80 | gccttctcgtgcaatcagagctgttgaaagagagaagagggcacacggaagctgctgttcaattgtgtgaattgaccggat tacaacctgctggagtgataggagagctggttcgtgacgaggacggctctatgatgcgattagacgactgtgttcagtttg gtctccgccacaacgtaaaaattatcaaccttgaccagatcattgaatacatggattccaagaacagctagatacgatgga taggaatacagagatatcatgattgaggaacgtaagagcttttttcgaaagtgtgagtttgtggtgagggccaggcggtggg gaggtggtggggagcctccttggtcgaattgtagatatagtaagcaagacacaagagcgcgcgaagtcttcaacgaggcggc gttgggtcttgtacgcaacgtaatgactacacagttgagctttgtcgcgaaccgctcgacattttgatcatgcatactatgt tgagacaccatctcgtactattgcggcaaccagtcgtaaatttgactaattaaagctgatgaaggatgcagggcgtcgtca atttttttgattgattgcatttaatttgtttgagccattcaaggctgaatgcccggcaccctagacccttcttgtgagtacta taaaccccgcaggcagggtacccttggccttctgcgagactaccagtcataacgtatatccacaatgtactagtaatagccc cggaaaactctaatcccacagaacgtctaacgcctcatctgccctactggccatggccatgccccccctta cgtgatcattttcacttactcccgcctaagcttcgcccacatgcctgcgtttgccaagatttactgacgagtttggtttac tcatcctctatttataactactagactttcaccattcttcaccaccctcgtgccaatgatcatcaaccacttggtattgac agccctcagcattgcactagcaagtgcgcaactccaatcgcctttcacttcagagtacagaagattaagtgagagaattct accgttcgtatagcatacattatacgaagttatttcagtaatgtcttgttttcttttgttgcagtggtgagccattttgact tcgtgaaagttctcttagaatagttgtttccagaggccaaacattccacccgtagtaaagtgcaagcgtaggaagaccaag actggcataaatcaggtataagtgtcgagcactggcaggtgatcttctgaaagtttctactagcagataagatccagtagt catgcatatggcaacaatgtaccgtgtggatctaagaacgcgtcctactaaccttcgcattcgttggtccagtttgttgtt atcgatcaacgtgacaaggttgtcgattccgcgtaagcatgcataccaaggacgcctgttgcaattccaagtgagccagt tccaacaatctttgtaatattagacacttcattgtgttgcgcttgaaagtaaaatgcgaacaaattaagagataatctcg aaaccgcgacttcaaacgccaatatgatgtgcggcacacaataagcgttcatatccgctgggtgactttctcgctttaaaa aattatccgaaaaattttttgacggctagctcagtcctaggtacgctagcattaaagaggagaaaatgactactcttgatg acacagcctacagataggacatcagttccgggtgaccgcagaggctatcgaagccttggacggttcattcactactgata cggtgtttagagtcaccgctacaggtgatgcttcacctgagagaggttcctgtagacccaccctttaacgaaagttttcc ctgatgacgaatcggatgacgagtctgatgctgtggaggacggtgaccctgattccagaacatttgtcgcatacggagatg atggtgacctggctggctttgttgtggtgtcctacagcggatggaatcgtagactcacagttgaggacatcgaagttgcac ctgaacatcgtcacggtgttggtcgtgcacttggacaggtgcaacagagttttgctagagaaagaggagccgacatt tgtggttagaagtgaccaatgtcaacgctcctgctattcacgcatataggcgaatgggtttcactttgtgcggtcttgata ctgctttgatgacggaactgcttctgatgtgaacaagctcttttacatgagtatgccatgtccatagcacgtccgacggc ggcccacgggtcccaggcctcggagatccgtccccctttttcctttgtcgatatcatgtaattagttatgtcacgcttacat tcacgcctccccccacatccgctctaaccgaaaaggaaggagttagacaacctgaagtctaggtccctatttatttttttt atagttatgttagtattaagaacgttatttatatttcaaattttttctttttttttctgtacagacgcgtgtacgcatgtaac |

TABLE 14-continued

Exemplary nourseothricin cassettes with HA arms for YPS1-1 and YPS1-2 protease deletion in *P. pastoris*

| Description | SEQ ID NO: | 5' to 3' Sequence |
|---|---|---|
| | | attatactgaaaaccttgcttgagaaggttttgggacgctcgaaggctttaatttgcaagctataacttcgtatagcatac attataccttgttatgcggccgcaagaagttgattgagactttcaacgagctggctctgcttctggtacttcttcaggtgc atcttctgctactcaaaatgacgaaacatccactgatcttggagctccagctgcatctttaagtgcaacgccatgtctttt tgccatcttgctgctcatgttgtagtagacttttttttttcactgagttttatgtactactgattacattgtgtaggtgta atgatgtgcactataatactaatatagtcaaaatgctacagaggaaagtgcaggttgcctgtggtggttttttcttattagc accctctgaacactcttttacctctaacatcctcagccatgctaatcgcgcataaaataaatcttcgaactttttttccattt tatgctcataaagcttccttactgtcaccttatcaaaagagcttttgccactaaagtagtcacacccagaattgctcccga atatcgtccaacaatgctaggatctgtgaaagtttgacaaataatttgaaaccttgagcttgaagcttcctgaagttaa tatccaaggctccttccagaaagtaacccagtggacctttgagaaactacatcactcaagaacttagtaaaatttctgg agttgacaaagaattgattttcccagccttggaatggggtaccacactggaaaagggtgatcttttgatcccagttcctcg tctgagaataaagggtgctaatcctaaagatttagccgaacaatgggctgctgcattcccaaagggtggatatcttaaaga cgttattgcgcaaggacctttcttgcagttcttttttaacacatcggttctgtacaagttggtgatatctgatgctctgga gagaggcgatgactttggtgcacttcctctaggaaagggacaaaaagttatagtggagttttcttctcaaatattgccaa acctttccacgctggccatcttagaagtacaatcatcggtggttttatttccaatctgtatgaaaagctgggtcatgaagt tatgaggatgaatatttgggagactggggaaaacaatttggtgttcttgcagtaggatttgagcgttacggtgatgaggc aaaattaaagactgatccaatcaaccatttgtttgaggtctatgttaaaatcaaccaagatattaaggctcaatcagagtc tactgaggagattgcagaagggcaatcattagatgaccaggcaagagcttttttcaagaaaatggaaaatggcgacgaatc ggctgtaagcttgtggaaaagattccgtgagttatccattgagaagtacattgatacttatgcccgcctcaacatc |
| PAS_chr3_1157 Homology Arm 1 | 81 | gccttctcgtgcaatcagagctgttgaaagagagaagagggcacacggaagctgctgttcaattgtgtgaattgaccggat tacaacctgctggagtgataggagagctggttcgtgacgaggacggctctatgatgcgattagacgactgtgttcagtttg gtctccgccacaacgtaaaaattatcaaccttgaccagatcattgaatacatggattccaagaacagctagatacgatgga taggaatacagagatatcatgattgaggaacgtaagagcttttttcgaaagtgtgagtttgtggtgagggccaggcggtggg gaggtggtggggagcctccttggtcgaatgtagatatagtaagcaagacacaagagcgcgcgaagtcttcaacgaggcggc gtttgggtcttgtacgcaacgtaatgactacacagttgagcttgtcgcgaaccggtcgacattttgatcatgcatactatgt tgagacaccatctcgtactattgcggcaaccagctgtaaatttgactaattaaagctgatgaaggatgcagggcgtcgtca attttttgattgattgcatttaattgtttgagccattcaaggctgaatgcccggcaccctagaccccttcttgtgatacta taaaccccgcaggcagggtacccttggcctctgcgagactaccagtcataacgtatatccacaatgtactagtaatagccc cggaaaactctaatcccacagaacgtctaacgcctcctatgtcatcgatacccattcgcactactgccatggcccccctta cgtgatcatttcacttactcccgcctaagcttcgcccacatgcctgcgttttgccaagatttactgacgagtttggtttac tcatcctctatttataactactagactttcaccattcttcaccaccctcgtgccaatgatcatcaaccacttggtattgac agccctcagcattgcactagcaagtgcgcaactccaatcgcctttca |
| PAS_chr3_1157 Homology Arm 2 | 82 | ctggctctgcttctggtacttcttcaggtgcatcttctgctactcaaaatgacgaaacatccactgatcttggagctccag ctgcatctttaagtgcaacgccatgtctttttgccatcttgctgctcatgttgtagtagactttttttttcactgagttttt tatgtactactgattacattgtgtaggtgtaatgatgtgcactataatactaatagtcaaaatgctacagaggaaagtg caggttgcctgtggtggttttttcttattagcaccctctgaacactcttttacctctaacatcctcagccatgctaatcgcgc ataaaataaatcttcgaacttttttccatttttatgctcataaagcttccttactgtcaccttatcaaaagagcttttgcca ctaaagtagtcacacccagaattgctcccgaatatcgtccaacaatgctaggatctgtgaaagtttgacaaataatttga acaccttgagcttgaagcttcctgaagttaatatccaaggctccttccagaaagtaacccagtggaccttttgagaaact acatcactcaagaacttagtaaaatttctggagttgacaaagaattgattttcccagccttggaatggggtaccacactgg aaaaagggtgatcttttgatcccagttcctcgtctgagaataaagggtgctaatcctaaagatttagccgaacaatgggctg ctgcattcccaaagggtggatatcttaaagacgttattgcgcaaggacctttcttgcagttcttttttaacacatcggttc tgtacaagttggtgatatctgatgctctggagagaggcgatgactttggtgcacttcctctaggaaagggacaaaaagtta tagtggagttttcttctcaaatattgccaaacctttccacgctggccatcttagaagtacaatcatcggtggttttatttt ccaatctgtatgaaagctgggtcatgaagttatgaggatgaatatttgggagactggggaaaacaatttggtgttcttg cagtaggatttgagcgttacggtgatgaggcaaaattaaagactgatccaatcaaccatttgtttgaggtctatgttaaaa tcaaccaagatattaaggctcaatcagagtctactgaggagattgcagaagggcaatcattagatgaccaggcaagagctt ttttcaagaaaatggaaaatggcgacgaatcggctgtaagcttgtggaaaagattccgtgagttatccattgagaagtaca ttgatacttatgcccgcctcaacatc |

TABLE 15

Information on genes and sequences disclosed herein

| S. cerevisiae ortholog standard name | S. cerevisiae ortholog systematic name | P. pastoris (K. phaffii) gene ID | P. pastoris (K. phaffii) ORF coordinates (strand) | Open Reading Frame (ORF) SEQ ID NO: | Peptide SEQ ID NO: |
|---|---|---|---|---|---|
| SEC72 | YLR292C | PAS_chr2-1_0448 | chr2: 827202-827789(−) | 1 | 2 |
| SBH2 | YER019C-A | PAS_chr2-2_0210 | chr2: 1994927-1995252(+) | 7 | 8 |
| SSS1 | YDR086C | PAS_chr1-1_0023 | chr1: 580942-581136(+) | 5 | 6 |
| SSH1 | YBR283C | PAS_chr1-4_0629 | chr1: 2584924-2586363(−) | 3 | 4 |
| PEP4 | YPL154C | n/a | n/a | 83 | 84 |
| PRC1, mutant | YMR297W | n/a | n/a | 85 | 86 |

TABLE 15-continued

Information on genes and sequences disclosed herein

| S. cerevisiae ortholog standard name | S. cerevisiae ortholog systematic name | P. pastoris (K. phaffii) gene ID | P. pastoris (K. phaffii) ORF coordinates (strand) | Open Reading Frame (ORF) SEQ ID NO: | Peptide SEQ ID NO: |
|---|---|---|---|---|---|
| DAP2 | YHR028C | n/a | n/a | 87 | 88 |
| MF(alpha)1, variant | YPL187W | n/a | n/a | 89 | 90 |

TABLE 16

Information on promoters and terminators for the SSH1 complex genes

| S. cerevisiae ortholog standard name | S. cerevisiae ortholog systematic name | Promoter/ Terminator | P. pastoris (K. phaffii) ORF coordinates (strand) | Nucleotide Sequence SEQ ID NO: |
|---|---|---|---|---|
| SBH2 | YER019C-A | Promoter | chr2: 1994039-1994926(+) | 97 |
| SBH2 | YER019C-A | Terminator | chr2: 1995253-1995712(+) | 100 |
| SSS1 | YDR086C | Promoter | chr1: 579989-580941(+) | 98 |
| SSS1 | YDR086C | Terminator | chr1: 581137-581628(+) | 101 |
| SSH1 | YBR283C | Promoter | chr1: 2586364-2587353(−) | 99 |
| SSH1 | YBR283C | Terminator | chr1: 2584553-2584923(−) | 102 |

The invention claimed is:

1. A *Pichia pastoris* microorganism, in which the activity of a SEC72 protein comprising a polypeptide sequence of SEQ ID NO: 2 has been eliminated, and wherein said microorganism expresses a recombinant silk-like protein comprising a secretion signal peptide derived from yeast and selected from a PEP4 signal sequence, a CPY+4 signal sequence, a DAP2 signal sequence, and a MFα1 signal sequence.

2. The microorganism of claim 1, wherein said SEC72 protein is encoded by an sec72 gene comprising SEQ ID NO: 1, and wherein said sec72 gene has been deleted.

3. The microorganism of claim 1, further comprising a recombinantly expressed translocon complex.

4. The microorganism of claim 3, wherein said recombinantly expressed translocon complex is a recombinantly expressed SSH1 translocon complex.

5. The microorganism of claim 4, wherein said SSH1 translocon complex comprises a first polypeptide sequence at least 95% identical to SEQ ID NO: 4, a second polypeptide sequence at least 95% identical to SEQ ID NO: 6, and a third polypeptide sequence at least 95% identical to SEQ ID NO: 8.

6. A cell culture comprising a microorganism of claim 4, wherein said cell culture has an improved strain growth rate and fermentation performance under standard cell culture conditions as compared to a cell culture that does not comprise a recombinantly expressed SSH1 translocon complex.

7. A cell culture comprising a microorganism of claim 4, wherein said cell culture has an improved yield or specific productivity of said recombinant protein under standard cell culture conditions as compared to a cell culture of an otherwise identical microorgansims that comprises a functional sec72 gene and does not comprise a recombinantly expressed SSH1 translocon complex.

8. A method of producing a recombinant protein, comprising: culturing the microorganism of claim 4 in a culture medium under conditions suitable for expression of the recombinantly expressed protein; and isolating the recombinant protein from the microorganism or the culture medium.

9. The method of claim 8, wherein said recombinant protein is secreted from said microorganism, and wherein isolating said recombinant protein comprises collecting a culture medium comprising said secreted recombinant protein.

10. The method of claim 8, wherein said microorganism has an increased yield or specific productivity of said recombinant protein as compared to an otherwise identical microorganism not comprising said recombinantly expressed SSH1 translocon complex, and wherein said sec72 gene is not deleted.

11. The microorganism of claim 3, wherein said translocon complex is expressed from a recombinant SSH1 gene, a recombinant SSS1 gene, and a recombinant SBH2 gene.

12. The microorganism of claim 11, wherein said SSH1 gene comprises a polynucleotide sequence at least 95% identical to SEQ ID NO: 3, wherein said SSS1 gene comprises a polynucleotide sequence at least 95% identical to SEQ ID NO: 5, or wherein said SBH2 gene comprises a polynucleotide sequence at least 95% identical to SEQ ID NO: 7.

13. The microorganism of claim 3 wherein said translocon complex comprises an SSH1 protein, an SSS1 protein, and an SBH2 protein.

14. The microorganism of claim 13, wherein said SSH1 protein comprises a polypeptide sequence at least 95% identical to SEQ ID NO: 4, wherein said SSS1 protein comprises a polypeptide sequence at least 95% identical to SEQ ID NO: 6, or wherein said SBH2 protein comprises a polypeptide sequence at least 95% identical to SEQ ID NO: 8.

15. The microorganism of claim 1, wherein the activity of a YPS1-1 protease and a YPS1-2 protease has been attenuated or eliminated.

16. The microorganism of claim 15, wherein said YPS1-1 protease comprises a polypeptide sequence at least 95% identical to SEQ ID NO: 10, or wherein said YPS1-2 protease comprises a polypeptide sequence at least 95% identical to SEQ ID NO: 12.

17. The microorganism of claim 1, wherein said secretion signal peptide is selected from the group consisting of: SEQ ID NO: 84, SEQ ID NO: 86, SEQ ID NO: 88, and SEQ ID NO: 90.

18. A cell culture comprising a microorganism of claim 1.

19. The microorganism of claim 1, wherein said secretion signal peptide is endogenous to *P. pastoris*.

20. The microorganism of claim 1, wherein said secretion signal peptide is heterologous to *P. pastoris*.

21. The microorganism of claim 1, wherein said secretion signal is derived from *S. cerevisiae*.

22. A method of modifying a *Pichia pastoris* microorganism to improve the secretion of a recombinantly expressed protein, sad method comprising knocking out a gene encoding an SEC72 protein, and wherein sad microorganism expresses a recombinant silk-like protein comprising a secretion signal peptide derived from yeast and selected from a PEP4 signal sequence, a CPY+4 signal sequence, a DAP2 signal sequence, and a MFa1 signal sequence.

23. The method of claim 22, further comprising transforming said *Pichia pastoris* with a vector comprising genes encoding a recombinantly expressed SSH1 translocon complex.

* * * * *

UNITED STATES PATENT AND TRADEMARK OFFICE
CERTIFICATE OF CORRECTION

| | | |
|---|---|---|
| PATENT NO. | : 11,634,729 B2 | Page 1 of 1 |
| APPLICATION NO. | : 16/415605 | |
| DATED | : April 25, 2023 | |
| INVENTOR(S) | : Thomas Stevens | |

It is certified that error appears in the above-identified patent and that said Letters Patent is hereby corrected as shown below:

In the Claims

At Column 247, Line 26, "an" should be -- a --.

At Column 247, Line 50, "microorgansims" should be -- microorganism --.

At Column 248, Line 61, "sad" should be -- said --.

At Column 248, Line 62, "sad" should be -- said --.

At Column 248, Line 66, "MFa1" should be -- MFα1 --.

Signed and Sealed this
Twenty-third Day of April, 2024

*Katherine Kelly Vidal*

Katherine Kelly Vidal
*Director of the United States Patent and Trademark Office*

SEQUENCE LISTING

```
<160> NUMBER OF SEQ ID NOS: 107

<210> SEQ ID NO 1
<211> LENGTH: 588
<212> TYPE: DNA
<213> ORGANISM: Pichia pastoris

<400> SEQUENCE: 1
atgctaccat tttcgtacga cgtgagctca aagaaactga aagtcacagg tgactacgca        60
gacttagaat atgacataca gcagctgaac accttgagcg gagagatcct ggccaataaa       120
gcagatgttc cttctccacc aagtaaggag tcgtttgaca agaaattgtc ccacatggct       180
cagaaattac acgagtcggc tgtatccaac ataaagacag gcaagtatcc tgaggctatc       240
aaattgttga cgacgggtct tgaaatggtt aacagaaggc ccaagtacga gagttttcag       300
atgacgttga gtgaaatgac gatctttatt gtcactagag ctgacgctta catgatgaat       360
ggagactttg aagggcatt caatgatgca gatttactgg taacgctcct gccatccatt       420
ccagataatt acattagaag aggggtagcc cttttcaaga tggggagata cgttgatgca       480 aaaacaatt tgagagagg actttcattt gacccagata atgcaaaatt gaagaaggag       540
ttagattttg tgctgaagaa gatcgacgag gagaatggag agttatag                   588

<210> SEQ ID NO 2
<211> LENGTH: 195
<212> TYPE: PRT
<213> ORGANISM: Pichia pastoris

<400> SEQUENCE: 2

Met Leu Pro Phe Ser Tyr Asp Val Ser Lys Lys Leu Lys Val Thr
1               5                   10                  15

Gly Asp Tyr Ala Asp Leu Glu Tyr Asp Ile Gln Gln Leu Asn Thr Leu
            20                  25                  30

Ser Gly Glu Ile Leu Ala Asn Lys Ala Asp Val Pro Ser Pro Pro Ser
```

```
                35                  40                  45
Lys Glu Ser Phe Asp Lys Lys Leu Ser His Met Ala Gln Lys Leu His
 50                  55                  60

Glu Ser Ala Val Ser Asn Ile Lys Thr Gly Lys Tyr Pro Glu Ala Ile
 65                  70                  75                  80

Lys Leu Leu Thr Thr Gly Leu Glu Met Val Asn Arg Arg Pro Lys Tyr
                 85                  90                  95

Glu Ser Phe Gln Met Thr Leu Ser Glu Met Thr Ile Phe Ile Val Thr
                100                 105                 110

Arg Ala Asp Ala Tyr Met Met Asn Gly Asp Phe Glu Gly Ala Phe Asn
            115                 120                 125

Asp Ala Asp Leu Leu Val Thr Leu Leu Pro Ser Ile Pro Asp Asn Tyr
        130                 135                 140

Ile Arg Arg Gly Val Ala Leu Phe Lys Met Gly Arg Tyr Val Asp Ala
145                 150                 155                 160

Lys Asn Asn Phe Glu Arg Gly Leu Ser Phe Asp Pro Asp Asn Ala Lys
                165                 170                 175

Leu Lys Lys Glu Leu Asp Phe Val Leu Lys Lys Ile Asp Glu Glu Asn
            180                 185                 190

Gly Glu Leu
        195
```

<210> SEQ ID NO 3
<211> LENGTH: 1440
<212> TYPE: DNA
<213> ORGANISM: Pichia pastoris

<400> SEQUENCE: 3

```
atggcggggt gcgttttttt agacattgca agaccatttg tcagctggat cccggaagtt      60
gaacttcctt atgaaaactg ggggttcgat gaaaagctga tttactcatt tttcactgct     120
gccatctatt tgattctgtc cctgcctata tacggtgtca atcctctga agtcgtggac      180 ccagttcccc atttgcgttc tgccttaggg agtgagaagg gaacattgct ggagcttggg     240
ttactgcctg tgattacttc ggcatttatc ttgcagttgt tggctggttg aaaagttttc     300 aaagtaaaact ttgatctggt tagtgacaga atattgttcc aaactttgca aaagatcact    360
tcagtcgtta tcagcatcgt atatgctgtt cttctcacat tttgtgacta ctttactcca     420
ggtgtgtcca ctgataacgt cttgtggtcc caatttctga tcatcttaca gatagtggtg     480
gtcaacttct tggttactct actcgttgaa gtcattgaca aggattacgg attttcttca     540
ggagctctat tgttgcttgc ggtttattcc gccaccaact tcgtttttgg cacgattggt     600
cttagcaccg tcaacacctc cagatcgaac gaatctattg gtgctctgat tcaattattc     660
cgcaatttga gctctaaacc aattggtgtt gccatatatg actccttctt cagagtaaac     720
cttcctaact tgactcaatt ttatctgggg attgccatta tttgtgtttg tctgttcttg     780
aataatgcaa gatacgaagt accaattaag ccaaacaagg ttcgtgccat ggcctcagct     840
tacccaatca agctactttt caatggttct ttgccacttc tgtacacgtg gactgtgctg     900
tacaacttga accttattgg tttctttgtc ttcaagctta ccaactttc tcttttaggg     960 aacttcaaag tggacccatt cggcaacaac tactacgaaa ttacatctgg actgctgtat    1020
ttattgactc ctactttcaa cgctgaagct ggacttttac ccaatgttgc taagccattt    1080
gttttcattg ccttctatgt tggtgttagc actttctttg ctagatcgtg gtccaacatt    1140
aacgggtcgt caggcaagga cattgccaag ttttcaagg ctcaaggaat ctcattgtta     1200
```

```
ggaaaaagag atgcctctgt gtctaaagag tttaacaccc tagttcctgt tgcttctgcc    1260
tctggagctt tcctattgtc ttttccagtt gccgtcgctg agttattggg tggctctggt    1320
gttccaacct ctatcggaat cggtcttttg agtggtttgg ctattttgga aactgttttg    1380
caagaatggc aacagtctgg aggtgcctca cagttctccc aatacttcca gacttcttag    1440

<210> SEQ ID NO 4
<211> LENGTH: 479
<212> TYPE: PRT
<213> ORGANISM: Pichia pastoris

<400> SEQUENCE: 4
```

Met Ala Gly Leu Arg Phe Leu Asp Ile Ala Arg Pro Phe Val Ser Trp
1               5                   10                  15

Ile Pro Glu Val Glu Leu Pro Tyr Glu Asn Trp Gly Phe Asp Glu Lys
            20                  25                  30

Leu Ile Tyr Ser Phe Phe Thr Ala Ala Ile Tyr Leu Ile Leu Ser Leu
        35                  40                  45

Pro Ile Tyr Gly Val Lys Ser Ser Glu Val Val Asp Pro Val Pro His
    50                  55                  60

Leu Arg Ser Ala Leu Gly Ser Glu Lys Gly Thr Leu Leu Glu Leu Gly
65                  70                  75                  80

Leu Leu Pro Val Ile Thr Ser Ala Phe Ile Leu Gln Leu Leu Ala Gly
                85                  90                  95

Trp Lys Val Phe Lys Val Asn Phe Asp Leu Val Ser Asp Arg Ile Leu
            100                 105                 110

Phe Gln Thr Leu Gln Lys Ile Thr Ser Val Val Ile Ser Ile Val Tyr
        115                 120                 125

Ala Val Leu Leu Thr Phe Cys Asp Tyr Phe Thr Pro Gly Val Ser Thr
    130                 135                 140

Asp Asn Val Leu Trp Ser Gln Phe Leu Ile Ile Leu Gln Ile Val Val
145                 150                 155                 160

Val Asn Phe Leu Val Thr Leu Leu Val Glu Val Ile Asp Lys Asp Tyr
                165                 170                 175

Gly Phe Ser Ser Gly Ala Leu Leu Leu Leu Ala Val Tyr Ser Ala Thr
            180                 185                 190

Asn Phe Val Phe Gly Thr Ile Gly Leu Ser Thr Val Asn Thr Ser Arg
        195                 200                 205

Ser Asn Glu Ser Ile Gly Ala Leu Ile Gln Leu Phe Arg Asn Leu Ser
    210                 215                 220

Ser Lys Pro Ile Gly Val Ala Ile Tyr Asp Ser Phe Phe Arg Val Asn
225                 230                 235                 240

Leu Pro Asn Leu Thr Gln Phe Tyr Leu Gly Ile Ala Ile Ile Cys Val
                245                 250                 255

Cys Leu Phe Leu Asn Asn Ala Arg Tyr Glu Val Pro Ile Lys Pro Asn
            260                 265                 270

Lys Val Arg Ala Met Ala Ser Ala Tyr Pro Ile Lys Leu Leu Phe Asn
        275                 280                 285

Gly Ser Leu Pro Leu Leu Tyr Thr Trp Thr Val Leu Tyr Asn Leu Asn
    290                 295                 300

Leu Ile Gly Phe Phe Val Phe Lys Leu Thr Asn Phe Ser Leu Leu Gly
305                 310                 315                 320

Asn Phe Lys Val Asp Pro Phe Gly Asn Asn Tyr Tyr Glu Ile Thr Ser
                325                 330                 335

```
Gly Leu Leu Tyr Leu Leu Thr Pro Thr Phe Asn Ala Glu Ala Gly Leu
            340                 345                 350

Leu Pro Asn Val Ala Lys Pro Phe Val Phe Ile Ala Phe Tyr Val Gly
            355                 360                 365

Val Ser Thr Phe Phe Ala Arg Ser Trp Ser Asn Ile Asn Gly Ser Ser
            370                 375                 380

Gly Lys Asp Ile Ala Lys Phe Phe Lys Ala Gln Gly Ile Ser Leu Leu
385                 390                 395                 400

Gly Lys Arg Asp Ala Ser Val Ser Lys Glu Phe Asn Thr Leu Val Pro
                405                 410                 415

Val Ala Ser Ala Ser Gly Ala Phe Leu Leu Ser Phe Pro Val Ala Val
                420                 425                 430

Ala Glu Leu Leu Gly Gly Ser Gly Val Pro Thr Ser Ile Gly Ile Gly
                435                 440                 445

Leu Leu Ser Gly Leu Ala Ile Leu Glu Thr Val Leu Gln Glu Trp Gln
            450                 455                 460

Gln Ser Gly Gly Ala Ser Gln Phe Ser Gln Tyr Phe Gln Thr Ser
465                 470                 475
```

<210> SEQ ID NO 5
<211> LENGTH: 195
<212> TYPE: DNA
<213> ORGANISM: Pichia pastoris

<400> SEQUENCE: 5

```
atgtcccaaa aagtcaccga cgtccctctg gaatttgtta aggaaggttc caaattcatc      60
tctaaatgta ctaaaccctc tcagaaggag tacttaaaga tagtaagagc tgttggagtt     120 gggttttaa tgatgggcgt ggttggttac gttgtcaagc tcattcatat tccaatcaga     180
tatttgattg tttaa                                                      195
```

<210> SEQ ID NO 6
<211> LENGTH: 64
<212> TYPE: PRT
<213> ORGANISM: Pichia pastoris

<400> SEQUENCE: 6

```
Met Ser Gln Lys Val Thr Asp Val Pro Leu Glu Phe Val Lys Glu Gly
1               5                   10                  15

Ser Lys Phe Ile Ser Lys Cys Thr Lys Pro Ser Gln Lys Glu Tyr Leu
            20                  25                  30

Lys Ile Val Arg Ala Val Gly Val Gly Phe Leu Met Met Gly Val Val
            35                  40                  45

Gly Tyr Val Val Lys Leu Ile His Ile Pro Ile Arg Tyr Leu Ile Val
        50                  55                  60
```

<210> SEQ ID NO 7
<211> LENGTH: 326
<212> TYPE: DNA
<213> ORGANISM: Pichia pastoris

<400> SEQUENCE: 7

```
atggtaagtg tccagtttga tgagtgcaga atggttccaa gttttagacc agttactaat      60
atttaaagtc tacagcaatt ccaggaggac agagaacgtt agctaaaaga gagcagcaa     120 acttggataa gaaacaggat gaaccaacct ccgccagatc tgccggtgct ggaggttctt    180
cgtctaccat gctaaagttg tacacagacg aggcccaagg tttgaaagtt gatcctttaa    240
```

```
ttgttcttgt tcttgctgtt ggtttcattt tcagtgtcat tggtttgcac gttgttgcta    300
agctgacagg aaagttgatc aactaa                                         326

<210> SEQ ID NO 8
<211> LENGTH: 86
<212> TYPE: PRT
<213> ORGANISM: Pichia pastoris

<400> SEQUENCE: 8

Met Ser Thr Ala Ile Pro Gly Gly Gln Arg Thr Leu Ala Lys Arg Arg
1               5                   10                  15

Ala Ala Asn Leu Asp Lys Lys Gln Asp Glu Pro Thr Ser Ala Arg Ser
            20                  25                  30

Ala Gly Ala Gly Gly Ser Ser Ser Thr Met Leu Lys Leu Tyr Thr Asp
        35                  40                  45

Glu Ala Gln Gly Leu Lys Val Asp Pro Leu Ile Val Leu Val Leu Ala
    50                  55                  60

Val Gly Phe Ile Phe Ser Val Ile Gly Leu His Val Val Ala Lys Leu
65                  70                  75                  80

Thr Gly Lys Leu Ile Asn
                85

<210> SEQ ID NO 9
<211> LENGTH: 1800
<212> TYPE: DNA
<213> ORGANISM: Pichia pastoris

<400> SEQUENCE: 9
atgttgaagg atcagttctt gttatgggtt gctttgatag cgagcgtacc ggtttccggc     60
gtgatggcag ctcctagcga gtccgggcat aacacggttg aaaaacgaga tgccaaaaac    120
gttgttggcg ttcaacagtt ggacttcagc gttctgaggg gtgattcctt cgaaagtgcc    180
tcttcagaga acgtgcctcg gcttgtgagg agagatgaca cgctagaagc tgagctaatc    240
aaccagcaat cattctactt gtcacgactg aaagttggat cacatcaagc ggatattgga    300
atcctagtgg acacaggatc ctctgattta tgggtaatgg actcggtaaa cccatactgc    360
agtagccgtt cccgcgtgaa gagagatata cacgatgaga agatcgccga atgggatccc    420
atcaatctca agaaaaatga aacttctcag aataaaaatt tttgggattg gctcgttgga    480
actagcacta gttctccttc caccgccacg gcaactggta gtggtagtgg tagtggtagt    540
ggtagtggta gtggtagtgc tgccacagcc gtatcggtaa gttctgcaca ggcaacattg    600
gattgctcta cgtatggaac gtttgatcac gctgattcct cgacgttcca tgacaataat    660
acagactttt tcatctcata cgctgatacc acttttgctt caggaatctg ggttatgac    720 gacgtcatta tcgacggcat agaggtgaaa gaactttcct tcgccgttgc agacatgacc    780
aattcctcta ttggtgtgtt aggtattgga ctgaaaggcc tagaatccac atatgctagt    840
gcatcttcgg tcagtgaaat gtatcagtat gacaatttgc cagccaagat ggtcaccgat    900
gggttgatca acaaaaatgc atactccttg tacttgaact ccaaggacgc ctcaagtggt    960
tccatcctct ttgaggtgt ggatcatgaa aaatattcgg acaattgtt gacagttcca    1020 gtcatcaaca cactcgcttc agtggttac agagaggcaa ttcgtttaca aattacttta   1080
aatggaatag atgtgaaaaa gggttctgac cagggaactc ttttacaagg agatttgct   1140 gcattattgg actctggagc tacgctaacg tatgctcctt cttctgtttt aaattcaatt  1200
```

```
ggccggaacc tgggcggctc ctatgattcg tcaagacaag cttataccat tcgttgtgtt   1260
tctgcatcag ataccacttc tctggtattc aattttgggg gtgctacagt ggaagtttcc   1320
ctgtacgatc tacagattgc aacatattac accgggggaa gtgccacgca atgtcttatt   1380
ggaatattca gctctggaag tgatgagttt gtgctcggtg ataccttctt gaggtcagcc   1440
tacgtggttt acgatcttga tgggcttgaa gtgtcgcttg cccaagccaa cttcaacgaa   1500
accgattctg atgttgaggc tattacctcc agtgtaccct ccgctactcg tgcatccgga   1560
tacagttcta catggtctgg ttctgccagc ggtacagttt acacttcggt tcagatggaa   1620
tccggtgctg cttccagctc caactcttct ggatcgaata tgggttcctc ttcctcatcg   1680
tcctcttcat cgtcctcgac ttccagtgga gacgaagaag gagggagctc cgccaacagg   1740
gtccccttca gctacctttc tctctgtttg gtagttattc tcggcgtgtg tatagtatag   1800
```

<210> SEQ ID NO 10
<211> LENGTH: 599
<212> TYPE: PRT
<213> ORGANISM: Pichia pastoris

<400> SEQUENCE: 10

```
Met Leu Lys Asp Gln Phe Leu Leu Trp Val Ala Leu Ile Ala Ser Val
1               5                   10                  15

Pro Val Ser Gly Val Met Ala Ala Pro Ser Glu Ser Gly His Asn Thr
            20                  25                  30

Val Glu Lys Arg Asp Ala Lys Asn Val Val Gly Val Gln Gln Leu Asp
        35                  40                  45

Phe Ser Val Leu Arg Gly Asp Ser Phe Glu Ser Ala Ser Ser Glu Asn
    50                  55                  60

Val Pro Arg Leu Val Arg Arg Asp Asp Thr Leu Glu Ala Glu Leu Ile
65                  70                  75                  80

Asn Gln Gln Ser Phe Tyr Leu Ser Arg Leu Lys Val Gly Ser His Gln
                85                  90                  95

Ala Asp Ile Gly Ile Leu Val Asp Thr Gly Ser Ser Asp Leu Trp Val
            100                 105                 110

Met Asp Ser Val Asn Pro Tyr Cys Ser Ser Arg Ser Arg Val Lys Arg
        115                 120                 125

Asp Ile His Asp Glu Lys Ile Ala Glu Trp Asp Pro Ile Asn Leu Lys
    130                 135                 140

Lys Asn Glu Thr Ser Gln Asn Lys Asn Phe Trp Asp Trp Leu Val Gly
145                 150                 155                 160

Thr Ser Thr Ser Ser Pro Ser Thr Ala Thr Ala Thr Gly Ser Gly Ser
                165                 170                 175

Gly Ser Gly Ser Gly Ser Gly Ser Gly Ser Ala Ala Thr Ala Val Ser
            180                 185                 190

Val Ser Ser Ala Gln Ala Thr Leu Asp Cys Ser Thr Tyr Gly Thr Phe
        195                 200                 205

Asp His Ala Asp Ser Ser Thr Phe His Asp Asn Thr Asp Phe Phe
    210                 215                 220

Ile Ser Tyr Ala Asp Thr Thr Phe Ala Ser Gly Ile Trp Gly Tyr Asp
225                 230                 235                 240

Asp Val Ile Ile Asp Gly Ile Glu Val Lys Glu Leu Ser Phe Ala Val
                245                 250                 255

Ala Asp Met Thr Asn Ser Ser Ile Gly Val Leu Gly Ile Gly Leu Lys
            260                 265                 270
```

Gly Leu Glu Ser Thr Tyr Ala Ser Ala Ser Val Ser Glu Met Tyr
            275                 280                 285

Gln Tyr Asp Asn Leu Pro Ala Lys Met Val Thr Asp Gly Leu Ile Asn
        290                 295                 300

Lys Asn Ala Tyr Ser Leu Tyr Leu Asn Ser Lys Asp Ala Ser Ser Gly
305                 310                 315                 320

Ser Ile Leu Phe Gly Val Asp His Glu Lys Tyr Ser Gly Gln Leu
                325                 330                 335

Leu Thr Val Pro Val Ile Asn Thr Leu Ala Ser Ser Gly Tyr Arg Glu
                340                 345                 350

Ala Ile Arg Leu Gln Ile Thr Leu Asn Gly Ile Asp Val Lys Lys Gly
            355                 360                 365

Ser Asp Gln Gly Thr Leu Leu Gln Gly Arg Phe Ala Ala Leu Leu Asp
370                 375                 380

Ser Gly Ala Thr Leu Thr Tyr Ala Pro Ser Ser Val Leu Asn Ser Ile
385                 390                 395                 400

Gly Arg Asn Leu Gly Gly Ser Tyr Asp Ser Ser Arg Gln Ala Tyr Thr
                405                 410                 415

Ile Arg Cys Val Ser Ala Ser Asp Thr Thr Ser Leu Val Phe Asn Phe
            420                 425                 430

Gly Gly Ala Thr Val Glu Val Ser Leu Tyr Asp Leu Gln Ile Ala Thr
        435                 440                 445

Tyr Tyr Thr Gly Gly Ser Ala Thr Gln Cys Leu Ile Gly Ile Phe Ser
        450                 455                 460

Ser Gly Ser Asp Glu Phe Val Leu Gly Asp Thr Phe Leu Arg Ser Ala
465                 470                 475                 480

Tyr Val Val Tyr Asp Leu Asp Gly Leu Glu Val Ser Leu Ala Gln Ala
                485                 490                 495

Asn Phe Asn Glu Thr Asp Ser Asp Val Glu Ala Ile Thr Ser Ser Val
                500                 505                 510

Pro Ser Ala Thr Arg Ala Ser Gly Tyr Ser Ser Thr Trp Ser Gly Ser
            515                 520                 525

Ala Ser Gly Thr Val Tyr Thr Ser Val Gln Met Glu Ser Gly Ala Ala
530                 535                 540

Ser Ser Ser Asn Ser Ser Gly Ser Asn Met Gly Ser Ser Ser Ser
545                 550                 555                 560

Ser Ser Ser Ser Ser Ser Thr Ser Ser Gly Asp Glu Gly Gly Ser
                565                 570                 575

Ser Ala Asn Arg Val Pro Phe Ser Tyr Leu Ser Leu Cys Leu Val Val
            580                 585                 590

Ile Leu Gly Val Cys Ile Val
        595

<210> SEQ ID NO 11
<211> LENGTH: 1781
<212> TYPE: DNA
<213> ORGANISM: Pichia pastoris

<400> SEQUENCE: 11
atgatcatca accacttggt attgacagcc ctcagcattg cactagcaag tgcgcaactc      60
caatcgcctt tcaaggctaa caagttgcca ttcaaaaagt ttatcattcc aacgacccaa     120
aggaccgttt aattaagaga gatgactacg agtccctcga cttgagacac atcggagtct     180
tgtacactgc agagatccaa attggatctg acgaaactga aattgaggtc attgtcgaca     240

```
ctggttctgc cgacttgtgg gtcatcgatt ccgacgctgc cgtctgtgag ttatcctacg    300
atgagattga ggccaatagc ttttcctcgg cttctgccaa attcatggac aagatagctc    360
ctccatcaca agagctcctg gatgggctga gtgagtttgg atttgctctc gatggtgaaa    420
tttctcaata cctagccgat aaatctggac gtgtttcgaa aagagaggaa atcaacaag    480 atttcaacat taaccgtgac gagcctgtgt gtgaacagtt tggttccttc gattctagtt    540
cttccgacac tttccaaagc aacaattcag cttttggtat tgcttacctt gatgaaacca    600
ctgctaacgg aacttgggtc agggacacag tccgcatcgg cgactttgcc atcagccaac    660
agagttttgc cttagtcaac atcacagata actacatggg aatcttgggt ctcggtcctg    720
ctacccaaca aaccaccaat agtaacccaa ttgcagcaaa cagatttact tatgatggtg    780
ttgtggattc attgcggtcc caaggattta tcaattcagc atcgtttttct gtttacttgt    840 ctccagatga agataacgag cacgacgaat tcagcgacgg agaaatttta tttggtgcta    900
ttgatagggc caagatagac gggccattta gacttttccc atatgtcaat ccttacaaac    960
cagtttaccc cgatcaatat acttcctacg ttacagtgtc cacaattgcg gtgtcttcgt    1020
cagatgaaac tctcattatt gaaagacgtc ctcgtttggc attaatcgat acaggtgcca    1080
ccttctccta tttgccaacc tacccattga ttcgtttagc gttttccatc catggaggct    1140
ttgaatatgt ttctcaattg ggactatttg tcattcgtac aagttctctg tctgttgcta    1200
gaaataaggt gattgagttc aagtttggtg aagacgttgt gatccaatcc ccagtttctg    1260
atcatctatt ggacgtctca ggcctttta ctgatggcca acaatactcc gcattaactg    1320
tacgtgaaag tcttgacgga cttttccattc taggtgatac attcatcaaa tcggcctact    1380
tattctttga caatgaaaac agccagctgg gtattggtca gatcaacgtc actgatgacg    1440
aggatattga ggtggtcggt gatttcacta ttgaacgaga cccagcctac tcctctactt    1500
ggtctagcga tttacctcat gaaacaccca ctagggcttt gagtactgct tcaggggag    1560 gccttggtac cggaataaac acggccacaa gtcgtgcaag ttctcgttcc acatctggct    1620
ctacttcacg aacttcttct acatctggct ctgcttctgg tacttcttca ggtgcatctt    1680
ctgctactca aaatgacgaa acatccactg atcttggagc tccagctgca tctttaagtg    1740
caacgccatg tcttttttgcc atcttgctgc tcatgttgta g                        1781
```

<210> SEQ ID NO 12
<211> LENGTH: 562
<212> TYPE: PRT
<213> ORGANISM: Pichia pastoris

<400> SEQUENCE: 12

```
Met Ile Ile Asn His Leu Val Leu Thr Ala Leu Ser Ile Ala Leu Ala
1               5                   10                  15

Asn Asp Tyr Glu Ser Leu Asp Leu Arg His Ile Gly Val Leu Tyr Thr
            20                  25                  30

Ala Glu Ile Gln Ile Gly Ser Asp Glu Thr Glu Ile Glu Val Ile Val
        35                  40                  45

Asp Thr Gly Ser Ala Asp Leu Trp Val Ile Asp Ser Asp Ala Ala Val
    50                  55                  60

Cys Glu Leu Ser Tyr Asp Gly Ile Glu Ala Asn Ser Phe Ser Ser Ala
65                  70                  75                  80

Ser Ala Lys Phe Met Asp Lys Ile Ala Pro Pro Ser Gln Glu Leu Leu
                85                  90                  95

Asp Gly Leu Ser Glu Phe Gly Phe Ala Leu Asp Gly Glu Ile Ser Gln
```

```
                    100                 105                 110
Tyr Leu Ala Asp Lys Ser Gly Arg Val Ser Lys Arg Glu Glu Asn Gln
            115                 120                 125
Gln Asp Phe Asn Ile Asn Arg Asp Glu Pro Val Cys Glu Gln Phe Gly
            130                 135                 140
Ser Phe Asp Ser Ser Ser Ser Asp Thr Phe Gln Ser Asn Asn Ser Ala
145                 150                 155                 160
Phe Gly Ile Ala Tyr Leu Asp Gly Thr Thr Ala Asn Gly Thr Trp Val
                165                 170                 175
Arg Asp Thr Val Arg Ile Gly Asp Phe Ala Ile Ser Gln Gln Ser Phe
            180                 185                 190
Ala Leu Val Asn Ile Thr Asp Asn Tyr Met Gly Ile Leu Gly Leu Gly
            195                 200                 205
Pro Ala Thr Gln Gln Thr Thr Asn Ser Asn Pro Ile Ala Ala Asn Arg
            210                 215                 220
Phe Thr Tyr Asp Gly Val Val Asp Ser Leu Arg Ser Gln Gly Phe Ile
225                 230                 235                 240
Asn Ser Ala Ser Phe Ser Val Tyr Leu Ser Pro Asp Glu Asp Asn Glu
                245                 250                 255
His Asp Glu Phe Ser Asp Gly Glu Ile Leu Phe Gly Ala Ile Asp Arg
            260                 265                 270
Ala Lys Ile Asp Gly Pro Phe Arg Leu Phe Pro Tyr Val Asn Pro Tyr
            275                 280                 285
Lys Pro Val Tyr Pro Asp Gln Tyr Thr Ser Tyr Val Thr Val Ser Thr
            290                 295                 300
Ile Ala Val Ser Ser Asp Glu Thr Leu Ile Ile Glu Arg Arg Pro
305                 310                 315                 320
Arg Leu Ala Leu Ile Asp Thr Gly Ala Thr Phe Ser Tyr Leu Pro Thr
                325                 330                 335
Tyr Pro Leu Ile Arg Leu Ala Phe Ser Ile His Gly Phe Glu Tyr
                340                 345                 350
Val Ser Gln Leu Gly Leu Phe Val Ile Arg Thr Ser Ser Leu Ser Val
            355                 360                 365
Ala Arg Asn Lys Val Ile Glu Phe Lys Phe Gly Glu Asp Val Val Ile
            370                 375                 380
Gln Ser Pro Val Ser Asp His Leu Leu Asp Val Ser Gly Leu Phe Thr
385                 390                 395                 400
Asp Gly Gln Gln Tyr Ser Ala Leu Thr Val Arg Glu Ser Leu Asp Gly
                405                 410                 415
Leu Ser Ile Leu Gly Asp Thr Phe Ile Lys Ser Ala Tyr Leu Phe Phe
                420                 425                 430
Asp Asn Glu Asn Ser Gln Leu Gly Ile Gly Gln Ile Asn Val Thr Asp
            435                 440                 445
Asp Glu Asp Ile Glu Val Val Gly Asp Phe Thr Ile Glu Arg Asp Pro
450                 455                 460
Ala Tyr Ser Ser Thr Trp Ser Ser Asp Leu Pro His Glu Thr Pro Thr
465                 470                 475                 480
Arg Ala Leu Ser Thr Ala Ser Gly Gly Leu Gly Thr Gly Ile Asn
                485                 490                 495
Thr Ala Thr Ser Arg Ala Ser Ser Arg Ser Thr Ser Gly Ser Thr Ser
            500                 505                 510
Arg Thr Ser Ser Thr Ser Gly Ser Ala Ser Gly Thr Ser Ser Gly Ala
            515                 520                 525
```

```
Ser Ser Ala Thr Gln Asn Asp Glu Thr Ser Thr Asp Leu Gly Ala Pro
        530                 535                 540

Ala Ala Ser Leu Ser Ala Thr Pro Cys Leu Phe Ala Ile Leu Leu Leu
545                 550                 555                 560

Met Leu

<210> SEQ ID NO 13
<211> LENGTH: 1800
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (7)..(11)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (15)..(19)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (23)..(27)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (31)..(35)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (39)..(43)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (47)..(51)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (55)..(59)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (63)..(67)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (4)..(67)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (71)..(90)
<223> OTHER INFORMATION: This region may encompass 6-20 residues
<220> FEATURE:
<221> NAME/KEY: MISC_FEATURE
<222> LOCATION: (97)..(101)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (105)..(109)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
```

```
<222> LOCATION: (113)..(117)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (121)..(125)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (129)..(133)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (137)..(141)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (145)..(149)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (153)..(157)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (94)..(157)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (161)..(180)
<223> OTHER INFORMATION: This region may encompass 6-20 residues
<220> FEATURE:
<221> NAME/KEY: MISC_FEATURE
<222> LOCATION: (187)..(191)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (195)..(199)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (203)..(207)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (211)..(215)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (219)..(223)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (227)..(231)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (235)..(239)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (243)..(247)
<223> OTHER INFORMATION: This region may encompass "SGGQQ," "GAGQQ,"
      "GQGPY," "AGQQ" or "SQ," wherein some positions may be absent
<220> FEATURE:
```

```
<221> NAME/KEY: MISC_FEATURE
<222> LOCATION: (184)..(247)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (251)..(270)
<223> OTHER INFORMATION: This region may encompass 6-20 residues
<220> FEATURE:
<221> NAME/KEY: MISC_FEATURE
<222> LOCATION: (277)..(281)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (285)..(289)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (293)..(297)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (301)..(305)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (309)..(313)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (317)..(321)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (325)..(329)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (333)..(337)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (274)..(337)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (341)..(360)
<223> OTHER INFORMATION: This region may encompass 6-20 residues
<220> FEATURE:
<221> NAME/KEY: MISC_FEATURE
<222> LOCATION: (367)..(371)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (375)..(379)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (383)..(387)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (391)..(395)
<223> OTHER INFORMATION: This region may encompass "SGGQQ," "GAGQQ,"
      "GQGPY," "AGQQ" or "SQ," wherein some positions may be absent
```

```
<220> FEATURE:
<221> NAME/KEY: MISC_FEATURE
<222> LOCATION: (399)..(403)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (407)..(411)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (415)..(419)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (423)..(427)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (364)..(427)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (431)..(450)
<223> OTHER INFORMATION: This region may encompass 6-20 residues
<220> FEATURE:
<221> NAME/KEY: MISC_FEATURE
<222> LOCATION: (457)..(461)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (465)..(469)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (473)..(477)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (481)..(485)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (489)..(493)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (497)..(501)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (505)..(509)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (513)..(517)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (454)..(517)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (521)..(540)
```

```
<223> OTHER INFORMATION: This region may encompass 6-20 residues
<220> FEATURE:
<221> NAME/KEY: MISC_FEATURE
<222> LOCATION: (547)..(551)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (555)..(559)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (563)..(567)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (571)..(575)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (579)..(583)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (587)..(591)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (595)..(599)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (603)..(607)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (544)..(607)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (611)..(630)
<223> OTHER INFORMATION: This region may encompass 6-20 residues
<220> FEATURE:
<221> NAME/KEY: MISC_FEATURE
<222> LOCATION: (637)..(641)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (645)..(649)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (653)..(657)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (661)..(665)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (669)..(673)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (677)..(681)
```

```
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (685)..(689)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (693)..(697)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (634)..(697)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (701)..(720)
<223> OTHER INFORMATION: This region may encompass 6-20 residues
<220> FEATURE:
<221> NAME/KEY: MISC_FEATURE
<222> LOCATION: (727)..(731)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (735)..(739)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (743)..(747)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (751)..(755)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (759)..(763)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (767)..(771)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (775)..(779)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (783)..(787)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (724)..(787)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (791)..(810)
<223> OTHER INFORMATION: This region may encompass 6-20 residues
<220> FEATURE:
<221> NAME/KEY: MISC_FEATURE
<222> LOCATION: (817)..(821)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
```

```
<222> LOCATION: (825)..(829)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (833)..(837)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (841)..(845)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (849)..(853)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (857)..(861)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (865)..(869)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (873)..(877)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (814)..(877)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (881)..(900)
<223> OTHER INFORMATION: This region may encompass 6-20 residues
<220> FEATURE:
<221> NAME/KEY: MISC_FEATURE
<222> LOCATION: (907)..(911)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (915)..(919)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (923)..(927)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (931)..(935)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (939)..(943)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (947)..(951)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (955)..(959)
<223> OTHER INFORMATION: This region may encompass "SGGQQ," "GAGQQ,"
      "GQGPY," "AGQQ" or "SQ," wherein some positions may be absent
<220> FEATURE:
```

```
<221> NAME/KEY: MISC_FEATURE
<222> LOCATION: (963)..(967)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (904)..(967)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (971)..(990)
<223> OTHER INFORMATION: This region may encompass 6-20 residues
<220> FEATURE:
<221> NAME/KEY: MISC_FEATURE
<222> LOCATION: (997)..(1001)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1005)..(1009)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1013)..(1017)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1021)..(1025)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1029)..(1033)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1037)..(1041)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1045)..(1049)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1053)..(1057)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (994)..(1057)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1061)..(1080)
<223> OTHER INFORMATION: This region may encompass 6-20 residues
<220> FEATURE:
<221> NAME/KEY: MISC_FEATURE
<222> LOCATION: (1087)..(1091)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1095)..(1099)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1103)..(1107)
<223> OTHER INFORMATION: This region may encompass "SGGQQ," "GAGQQ,"
      "GQGPY," "AGQQ" or "SQ," wherein some positions may be absent
```

```
<220> FEATURE:
<221> NAME/KEY: MISC_FEATURE
<222> LOCATION: (1111)..(1115)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1119)..(1123)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1127)..(1131)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1135)..(1139)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1143)..(1147)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1084)..(1147)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1151)..(1170)
<223> OTHER INFORMATION: This region may encompass 6-20 residues
<220> FEATURE:
<221> NAME/KEY: MISC_FEATURE
<222> LOCATION: (1177)..(1181)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1185)..(1189)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1193)..(1197)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1201)..(1205)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1209)..(1213)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1217)..(1221)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1225)..(1229)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1233)..(1237)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1174)..(1237)
<223> OTHER INFORMATION: This region may encompass 4-8 repeating
```

```
        "GPG-X1" repeating units, wherein X1 is "SGGQQ," "GAGQQ,"
        "GQGPY," "AGQQ" or "SQ," and some positions may be absent
<220> FEATURE:
<221> NAME/KEY: MISC_FEATURE
<222> LOCATION: (1241)..(1260)
<223> OTHER INFORMATION: This region may encompass 6-20 residues
<220> FEATURE:
<221> NAME/KEY: MISC_FEATURE
<222> LOCATION: (1267)..(1271)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (1275)..(1279)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (1283)..(1287)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (1291)..(1295)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (1299)..(1303)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (1307)..(1311)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (1315)..(1319)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (1323)..(1327)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (1264)..(1327)
<223> OTHER INFORMATION: This region may encompass 4-8 repeating
        "GPG-X1" repeating units, wherein X1 is "SGGQQ," "GAGQQ,"
        "GQGPY," "AGQQ" or "SQ," and some positions may be absent
<220> FEATURE:
<221> NAME/KEY: MISC_FEATURE
<222> LOCATION: (1331)..(1350)
<223> OTHER INFORMATION: This region may encompass 6-20 residues
<220> FEATURE:
<221> NAME/KEY: MISC_FEATURE
<222> LOCATION: (1357)..(1361)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (1365)..(1369)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (1373)..(1377)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (1381)..(1385)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (1389)..(1393)
```

```
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1397)..(1401)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1405)..(1409)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1413)..(1417)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1354)..(1417)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1421)..(1440)
<223> OTHER INFORMATION: This region may encompass 6-20 residues
<220> FEATURE:
<221> NAME/KEY: MISC_FEATURE
<222> LOCATION: (1447)..(1451)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1455)..(1459)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1463)..(1467)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1471)..(1475)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1479)..(1483)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1487)..(1491)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1495)..(1499)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1503)..(1507)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1444)..(1507)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1511)..(1530)
<223> OTHER INFORMATION: This region may encompass 6-20 residues
<220> FEATURE:
<221> NAME/KEY: MISC_FEATURE
```

```
<222> LOCATION: (1537)..(1541)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1545)..(1549)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1553)..(1557)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1561)..(1565)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1569)..(1573)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1577)..(1581)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1585)..(1589)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1593)..(1597)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1534)..(1597)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1601)..(1620)
<223> OTHER INFORMATION: This region may encompass 6-20 residues
<220> FEATURE:
<221> NAME/KEY: MISC_FEATURE
<222> LOCATION: (1627)..(1631)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1635)..(1639)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1643)..(1647)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1651)..(1655)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1659)..(1663)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1667)..(1671)
<223> OTHER INFORMATION: This region may encompass "SGGQQ," "GAGQQ,"
      "GQGPY," "AGQQ" or "SQ," wherein some positions may be absent
<220> FEATURE:
```

```
<221> NAME/KEY: MISC_FEATURE
<222> LOCATION: (1675)..(1679)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1683)..(1687)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1624)..(1687)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1691)..(1710)
<223> OTHER INFORMATION: This region may encompass 6-20 residues
<220> FEATURE:
<221> NAME/KEY: MISC_FEATURE
<222> LOCATION: (1717)..(1721)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1725)..(1729)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1733)..(1737)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1741)..(1745)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1749)..(1753)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1757)..(1761)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1765)..(1769)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1773)..(1777)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1714)..(1777)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1781)..(1800)
<223> OTHER INFORMATION: This region may encompass 6-20 residues
<220> FEATURE:
<221> NAME/KEY: MISC_FEATURE
<222> LOCATION: (1)..(1800)
<223> OTHER INFORMATION: This sequence may encompass 2-20
      "GGY-[GPG-X1]n1-GPS-(A)n2" repeating units, wherein X1 is "SGGQQ,"
      "GAGQQ," "GQGPY," "AGQQ" or "SQ," n1 is 4-8 and n2 is 6-20 and
      some positions may be absent

<400> SEQUENCE: 13
```

```
Gly Gly Tyr Gly Pro Gly Xaa Xaa Xaa Xaa Gly Pro Gly Xaa Xaa
1               5                   10                  15

Xaa Xaa Xaa Gly Pro Gly Xaa Xaa Xaa Xaa Gly Pro Gly Xaa Xaa
            20                  25                  30

Xaa Xaa Xaa Gly Pro Gly Xaa Xaa Xaa Xaa Gly Pro Gly Xaa Xaa
            35                  40                  45

Xaa Xaa Xaa Gly Pro Gly Xaa Xaa Xaa Xaa Gly Pro Gly Xaa Xaa
            50                  55                  60

Xaa Xaa Xaa Gly Pro Ser Ala Ala Ala Ala Ala Ala Ala Ala Ala
65                  70                  75                  80

Ala Ala Ala Ala Ala Ala Ala Ala Ala Gly Gly Tyr Gly Pro Gly
            85                  90                  95

Xaa Xaa Xaa Xaa Xaa Gly Pro Gly Xaa Xaa Xaa Xaa Gly Pro Gly
            100                 105                 110

Xaa Xaa Xaa Xaa Xaa Gly Pro Gly Xaa Xaa Xaa Xaa Gly Pro Gly
            115                 120                 125

Xaa Xaa Xaa Xaa Xaa Gly Pro Gly Xaa Xaa Xaa Xaa Gly Pro Gly
            130                 135                 140

Xaa Xaa Xaa Xaa Xaa Gly Pro Gly Xaa Xaa Xaa Xaa Gly Pro Ser
145                 150                 155                 160

Ala Ala Ala Ala Ala Ala Ala Ala Ala Ala Ala Ala Ala Ala Ala
            165                 170                 175

Ala Ala Ala Ala Gly Gly Tyr Gly Pro Gly Xaa Xaa Xaa Xaa Gly
            180                 185                 190

Pro Gly Xaa Xaa Xaa Xaa Xaa Gly Pro Gly Xaa Xaa Xaa Xaa Gly
        195                 200                 205

Pro Gly Xaa Xaa Xaa Xaa Xaa Gly Pro Gly Xaa Xaa Xaa Xaa Gly
        210                 215                 220

Pro Gly Xaa Xaa Xaa Xaa Xaa Gly Pro Gly Xaa Xaa Xaa Xaa Gly
225             230                 235                 240

Pro Gly Xaa Xaa Xaa Xaa Xaa Gly Pro Ser Ala Ala Ala Ala Ala
        245                 250                 255

Ala Ala Ala Ala Ala Ala Ala Ala Ala Ala Ala Ala Ala Gly Gly
            260                 265                 270

Tyr Gly Pro Gly Xaa Xaa Xaa Xaa Xaa Gly Pro Gly Xaa Xaa Xaa
        275                 280                 285

Xaa Gly Pro Gly Xaa Xaa Xaa Xaa Xaa Gly Pro Gly Xaa Xaa Xaa
        290                 295                 300

Xaa Gly Pro Gly Xaa Xaa Xaa Xaa Xaa Gly Pro Gly Xaa Xaa Xaa
305             310                 315                 320

Xaa Gly Pro Gly Xaa Xaa Xaa Xaa Xaa Gly Pro Gly Xaa Xaa Xaa
            325                 330                 335

Xaa Gly Pro Ser Ala Ala Ala Ala Ala Ala Ala Ala Ala Ala Ala
            340                 345                 350

Ala Ala Ala Ala Ala Ala Ala Gly Gly Tyr Gly Pro Gly Xaa Xaa
            355                 360                 365

Xaa Xaa Xaa Gly Pro Gly Xaa Xaa Xaa Xaa Gly Pro Gly Xaa Xaa
            370                 375                 380

Xaa Xaa Xaa Gly Pro Gly Xaa Xaa Xaa Xaa Gly Pro Gly Xaa Xaa
385                 390                 395                 400

Xaa Xaa Xaa Gly Pro Gly Xaa Xaa Xaa Xaa Gly Pro Gly Xaa Xaa
            405                 410                 415

Xaa Xaa Xaa Gly Pro Gly Xaa Xaa Xaa Xaa Xaa Gly Pro Ser Ala Ala
```

```
            420             425             430
Ala Ala Ala Ala Ala Ala Ala Ala Ala Ala Ala Ala Ala
        435             440             445
Ala Ala Gly Gly Tyr Gly Pro Gly Xaa Xaa Xaa Xaa Xaa Gly Pro Gly
    450             455             460
Xaa Xaa Xaa Xaa Xaa Gly Pro Gly Xaa Xaa Xaa Xaa Xaa Gly Pro Gly
465             470             475             480
Xaa Xaa Xaa Xaa Xaa Gly Pro Gly Xaa Xaa Xaa Xaa Xaa Gly Pro Gly
            485             490             495
Xaa Xaa Xaa Xaa Xaa Gly Pro Gly Xaa Xaa Xaa Xaa Xaa Gly Pro Gly
        500             505             510
Xaa Xaa Xaa Xaa Xaa Gly Pro Ser Ala Ala Ala Ala Ala Ala Ala
        515             520             525
Ala Ala Ala Ala Ala Ala Ala Ala Ala Ala Ala Gly Gly Tyr Gly
        530             535             540
Pro Gly Xaa Xaa Xaa Xaa Xaa Gly Pro Gly Xaa Xaa Xaa Xaa Xaa Gly
545             550             555             560
Pro Gly Xaa Xaa Xaa Xaa Xaa Gly Pro Gly Xaa Xaa Xaa Xaa Xaa Gly
            565             570             575
Pro Gly Xaa Xaa Xaa Xaa Xaa Gly Pro Gly Xaa Xaa Xaa Xaa Xaa Gly
        580             585             590
Pro Gly Xaa Xaa Xaa Xaa Xaa Gly Pro Gly Xaa Xaa Xaa Xaa Xaa Gly
        595             600             605
Pro Ser Ala Ala Ala Ala Ala Ala Ala Ala Ala Ala Ala Ala Ala
        610             615             620
Ala Ala Ala Ala Ala Ala Gly Gly Tyr Gly Pro Gly Xaa Xaa Xaa Xaa
625             630             635             640
Xaa Gly Pro Gly Xaa Xaa Xaa Xaa Xaa Gly Pro Gly Xaa Xaa Xaa Xaa
            645             650             655
Xaa Gly Pro Gly Xaa Xaa Xaa Xaa Xaa Gly Pro Gly Xaa Xaa Xaa Xaa
        660             665             670
Xaa Gly Pro Gly Xaa Xaa Xaa Xaa Xaa Gly Pro Gly Xaa Xaa Xaa Xaa
        675             680             685
Xaa Gly Pro Gly Xaa Xaa Xaa Xaa Xaa Gly Pro Ser Ala Ala Ala Ala
        690             695             700
Ala Ala Ala Ala Ala Ala Ala Ala Ala Ala Ala Ala Ala Ala Ala
705             710             715             720
Gly Gly Tyr Gly Pro Gly Xaa Xaa Xaa Xaa Xaa Gly Pro Gly Xaa Xaa
            725             730             735
Xaa Xaa Xaa Gly Pro Gly Xaa Xaa Xaa Xaa Xaa Gly Pro Gly Xaa Xaa
        740             745             750
Xaa Xaa Xaa Gly Pro Gly Xaa Xaa Xaa Xaa Xaa Gly Pro Gly Xaa Xaa
        755             760             765
Xaa Xaa Xaa Gly Pro Gly Xaa Xaa Xaa Xaa Xaa Gly Pro Gly Xaa Xaa
        770             775             780
Xaa Xaa Xaa Gly Pro Ser Ala Ala Ala Ala Ala Ala Ala Ala Ala
785             790             795             800
Ala Ala Ala Ala Ala Ala Ala Ala Ala Gly Gly Tyr Gly Pro Gly
            805             810             815
Xaa Xaa Xaa Xaa Xaa Gly Pro Gly Xaa Xaa Xaa Xaa Xaa Gly Pro Gly
        820             825             830
Xaa Xaa Xaa Xaa Xaa Gly Pro Gly Xaa Xaa Xaa Xaa Xaa Gly Pro Gly
        835             840             845
```

Xaa Xaa Xaa Xaa Xaa Gly Pro Gly Xaa Xaa Xaa Xaa Xaa Gly Pro Gly
        850                 855                 860

Xaa Xaa Xaa Xaa Xaa Gly Pro Gly Xaa Xaa Xaa Xaa Xaa Gly Pro Ser
865                 870                 875                 880

Ala Ala Ala Ala Ala Ala Ala Ala Ala Ala Ala Ala Ala
                885                 890                 895

Ala Ala Ala Ala Gly Gly Tyr Gly Pro Gly Xaa Xaa Xaa Xaa Xaa Gly
        900                 905                 910

Pro Gly Xaa Xaa Xaa Xaa Xaa Gly Pro Gly Xaa Xaa Xaa Xaa Xaa Gly
        915                 920                 925

Pro Gly Xaa Xaa Xaa Xaa Xaa Gly Pro Gly Xaa Xaa Xaa Xaa Xaa Gly
        930                 935                 940

Pro Gly Xaa Xaa Xaa Xaa Xaa Gly Pro Gly Xaa Xaa Xaa Xaa Xaa Gly
945                 950                 955                 960

Pro Gly Xaa Xaa Xaa Xaa Xaa Gly Pro Ser Ala Ala Ala Ala Ala Ala
        965                 970                 975

Ala Ala Ala Ala Ala Ala Ala Ala Ala Ala Ala Ala Ala Gly Gly
        980                 985                 990

Tyr Gly Pro Gly Xaa Xaa Xaa Xaa Xaa Gly Pro Gly Xaa Xaa Xaa Xaa
        995                 1000                1005

Xaa Gly Pro Gly Xaa Xaa Xaa Xaa Xaa Gly Pro Gly Xaa Xaa Xaa
        1010                1015                1020

Xaa Xaa Gly Pro Gly Xaa Xaa Xaa Xaa Xaa Gly Pro Gly Xaa Xaa
        1025                1030                1035

Xaa Xaa Xaa Gly Pro Gly Xaa Xaa Xaa Xaa Xaa Gly Pro Gly Xaa
        1040                1045                1050

Xaa Xaa Xaa Xaa Gly Pro Ser Ala Ala Ala Ala Ala Ala Ala Ala
        1055                1060                1065

Ala Ala Ala Ala Ala Ala Ala Ala Ala Ala Ala Gly Gly Tyr
        1070                1075                1080

Gly Pro Gly Xaa Xaa Xaa Xaa Xaa Gly Pro Gly Xaa Xaa Xaa Xaa
        1085                1090                1095

Xaa Gly Pro Gly Xaa Xaa Xaa Xaa Xaa Gly Pro Gly Xaa Xaa Xaa
        1100                1105                1110

Xaa Xaa Gly Pro Gly Xaa Xaa Xaa Xaa Xaa Gly Pro Gly Xaa Xaa
        1115                1120                1125

Xaa Xaa Xaa Gly Pro Gly Xaa Xaa Xaa Xaa Xaa Gly Pro Gly Xaa
        1130                1135                1140

Xaa Xaa Xaa Xaa Gly Pro Ser Ala Ala Ala Ala Ala Ala Ala Ala
        1145                1150                1155

Ala Ala Ala Ala Ala Ala Ala Ala Ala Ala Ala Gly Gly Tyr
        1160                1165                1170

Gly Pro Gly Xaa Xaa Xaa Xaa Xaa Gly Pro Gly Xaa Xaa Xaa Xaa
        1175                1180                1185

Xaa Gly Pro Gly Xaa Xaa Xaa Xaa Xaa Gly Pro Gly Xaa Xaa Xaa
        1190                1195                1200

Xaa Xaa Gly Pro Gly Xaa Xaa Xaa Xaa Xaa Gly Pro Gly Xaa Xaa
        1205                1210                1215

Xaa Xaa Xaa Gly Pro Gly Xaa Xaa Xaa Xaa Xaa Gly Pro Gly Xaa
        1220                1225                1230

Xaa Xaa Xaa Xaa Gly Pro Ser Ala Ala Ala Ala Ala Ala Ala Ala
        1235                1240                1245

-continued

```
Ala Ala  Ala Ala Ala Ala Ala  Ala Ala Ala Ala  Gly Gly Tyr
    1250             1255                 1260

Gly Pro  Gly Xaa Xaa Xaa  Xaa Gly Pro Gly  Xaa Xaa Xaa Xaa
    1265             1270                 1275

Xaa Gly  Pro Gly Xaa Xaa  Xaa Xaa Gly Pro Gly  Xaa Xaa Xaa
    1280             1285                 1290

Xaa Xaa  Gly Pro Gly Xaa  Xaa Xaa Xaa Gly Pro  Gly Xaa Xaa
    1295             1300                 1305

Xaa Xaa  Xaa Gly Pro Gly  Xaa Xaa Xaa Xaa Gly  Pro Gly Xaa
    1310             1315                 1320

Xaa Xaa  Xaa Xaa Gly Pro Ser  Ala Ala Ala Ala  Ala Ala Ala
    1325             1330                 1335

Ala Ala  Ala Ala Ala Ala Ala  Ala Ala Ala Ala  Gly Gly Tyr
    1340             1345                 1350

Gly Pro  Gly Xaa Xaa Xaa  Xaa Gly Pro Gly  Xaa Xaa Xaa Xaa
    1355             1360                 1365

Xaa Gly  Pro Gly Xaa Xaa  Xaa Xaa Gly Pro Gly  Xaa Xaa Xaa
    1370             1375                 1380

Xaa Xaa  Gly Pro Gly Xaa  Xaa Xaa Xaa Gly Pro  Gly Xaa Xaa
    1385             1390                 1395

Xaa Xaa  Xaa Gly Pro Gly  Xaa Xaa Xaa Xaa Gly  Pro Gly Xaa
    1400             1405                 1410

Xaa Xaa  Xaa Xaa Gly Pro Ser  Ala Ala Ala Ala  Ala Ala Ala
    1415             1420                 1425

Ala Ala  Ala Ala Ala Ala Ala  Ala Ala Ala Ala  Gly Gly Tyr
    1430             1435                 1440

Gly Pro  Gly Xaa Xaa Xaa  Xaa Gly Pro Gly  Xaa Xaa Xaa Xaa
    1445             1450                 1455

Xaa Gly  Pro Gly Xaa Xaa  Xaa Xaa Gly Pro Gly  Xaa Xaa Xaa
    1460             1465                 1470

Xaa Xaa  Gly Pro Gly Xaa  Xaa Xaa Xaa Gly Pro  Gly Xaa Xaa
    1475             1480                 1485

Xaa Xaa  Xaa Gly Pro Gly  Xaa Xaa Xaa Xaa Gly  Pro Gly Xaa
    1490             1495                 1500

Xaa Xaa  Xaa Xaa Gly Pro Ser  Ala Ala Ala Ala  Ala Ala Ala
    1505             1510                 1515

Ala Ala  Ala Ala Ala Ala Ala  Ala Ala Ala Ala  Gly Gly Tyr
    1520             1525                 1530

Gly Pro  Gly Xaa Xaa Xaa  Xaa Gly Pro Gly  Xaa Xaa Xaa Xaa
    1535             1540                 1545

Xaa Gly  Pro Gly Xaa Xaa  Xaa Xaa Gly Pro Gly  Xaa Xaa Xaa
    1550             1555                 1560

Xaa Xaa  Gly Pro Gly Xaa  Xaa Xaa Xaa Gly Pro  Gly Xaa Xaa
    1565             1570                 1575

Xaa Xaa  Xaa Gly Pro Gly  Xaa Xaa Xaa Xaa Gly  Pro Gly Xaa
    1580             1585                 1590

Xaa Xaa  Xaa Xaa Gly Pro Ser  Ala Ala Ala Ala  Ala Ala Ala
    1595             1600                 1605

Ala Ala  Ala Ala Ala Ala Ala  Ala Ala Ala Ala  Gly Gly Tyr
    1610             1615                 1620

Gly Pro  Gly Xaa Xaa Xaa  Xaa Gly Pro Gly  Xaa Xaa Xaa Xaa
    1625             1630                 1635

Xaa Gly  Pro Gly Xaa Xaa Xaa  Xaa Xaa Gly Pro Gly  Xaa Xaa Xaa
```

```
                1640                1645                1650

Xaa Xaa Gly Pro Gly Xaa Xaa Xaa Xaa Xaa Gly Pro Gly Xaa Xaa
        1655                1660                1665

Xaa Xaa Xaa Gly Pro Gly Xaa Xaa Xaa Xaa Gly Pro Gly Xaa
        1670                1675                1680

Xaa Xaa Xaa Xaa Gly Pro Ser Ala Ala Ala Ala Ala Ala Ala
        1685                1690                1695

Ala Ala Ala Ala Ala Ala Ala Ala Ala Ala Ala Gly Gly Tyr
        1700                1705                1710

Gly Pro Gly Xaa Xaa Xaa Xaa Xaa Gly Pro Gly Xaa Xaa Xaa Xaa
        1715                1720                1725

Xaa Gly Pro Gly Xaa Xaa Xaa Xaa Xaa Gly Pro Gly Xaa Xaa Xaa
        1730                1735                1740

Xaa Xaa Gly Pro Gly Xaa Xaa Xaa Xaa Xaa Gly Pro Gly Xaa Xaa
        1745                1750                1755

Xaa Xaa Xaa Gly Pro Gly Xaa Xaa Xaa Xaa Gly Pro Gly Xaa
        1760                1765                1770

Xaa Xaa Xaa Xaa Gly Pro Ser Ala Ala Ala Ala Ala Ala Ala
        1775                1780                1785

Ala Ala Ala Ala Ala Ala Ala Ala Ala Ala Ala
        1790                1795                1800

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Gly Gly Gln Gln
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Ala Gly Gln Gln
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gln Gly Pro Tyr
1               5

<210> SEQ ID NO 17
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 17

Ala Gly Gln Gln
1

<210> SEQ ID NO 18
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (7)..(11)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (15)..(19)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (23)..(27)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (31)..(35)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (39)..(43)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (47)..(51)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (55)..(59)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (63)..(67)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (4)..(67)
<223> OTHER INFORMATION: This region may encompass 4-8 "GPG-X1"
      repeating units, wherein X1 is "SGGQQ," "GAGQQ," "GQGPY," "AGQQ"
      or "SQ," and some positions may be absent

<400> SEQUENCE: 18

Gly Gly Tyr Gly Pro Gly Xaa Xaa Xaa Xaa Xaa Gly Pro Gly Xaa Xaa
1               5                   10                  15

Xaa Xaa Xaa Gly Pro Gly Xaa Xaa Xaa Xaa Xaa Gly Pro Gly Xaa Xaa
            20                  25                  30

Xaa Xaa Xaa Gly Pro Gly Xaa Xaa Xaa Xaa Xaa Gly Pro Gly Xaa Xaa
        35                  40                  45

Xaa Xaa Xaa Gly Pro Gly Xaa Xaa Xaa Xaa Xaa Gly Pro Gly Xaa Xaa
    50                  55                  60

Xaa Xaa Xaa Gly Pro Ser
```

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (1)..(20)
<223> OTHER INFORMATION: This sequence may encompass 6-20 residues

<400> SEQUENCE: 19

Ala Ala Ala Ala Ala Ala Ala Ala Ala Ala Ala Ala Ala Ala Ala
1               5                   10                  15

Ala Ala Ala Ala
            20

<210> SEQ ID NO 20
<211> LENGTH: 2835
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

| | | |
|---|---|---|
| ggtggttacg gtccaggcgc tggtcaacaa ggtccaggaa gtggtggtca acaaggacct | 60 |
| ggcggtcaag gaccctacgg tagtggccaa caaggtccag gtggagcagg acagcagggt | 120 |
| ccgggaggcc aaggacctta cggaccaggt gctgctgctg ccgccgctgc cgctgccgga | 180 |
| ggttacggtc caggagccgg acaacagggt ccaggtggac tggacaacaa aggtccagga | 240 |
| tcacaaggtc ctggtggaca aggtccatac ggtcctggtg ctggtcaaca gggaccaggt | 300 |
| agtcaaggac ctggttcagg tggtcagcag ggtccaggag acagggtcc ttacggccct | 360 |
| tctgccgctg cagcagcagc cgctgccgca ggaggatacg gacctggtgc tggacaacga | 420 |
| tctcaaggac caggaggaca aggtccttat ggacctggcg ctggccaaca aggacctggt | 480 |
| tctcagggtc caggttcagg aggccaacaa ggcccaggag gtcaaggacc atacggacca | 540 |
| tccgctgcgg cagctgcagc tgctgcaggt ggatatggcc aggagccgg acaacagggt | 600 |
| cctggttcac aaggtccagg atctggtggt caacagggac caggcggcca gggaccttat | 660 |
| ggtccaggag ccgctgcagc agcagcagct gttggaggtt acggccctgg tgccggtcaa | 720 |
| caaggcccag gatctcaggg tcctggatct ggaggacaac aaggtcctgg aggtcagggt | 780 |
| ccatacggac cttcagcagc agctgctgct gcagccgctg gtggttatgg acctggtgct | 840 |
| ggtcaacaag gaccgggttc tcagggtccg ggttcaggag gtcagcaggg ccctggtgga | 900 |
| caaggacctt atggacctag tgcggctgca gcagctgccg ccgcaggtgg ttacggtcca | 960 |
| ggcgctggtc aacaaggtcc aggaagtggt ggtcaacaag gacctggcgg tcaaggaccc | 1020 |
| tacggtagtg gccaacaagg tccaggtgga gcaggacagc agggtccggg aggccaagga | 1080 |
| ccttacggac caggtgctgc tgctgccgcc gctgccgctg ccgagggtta cggtccagga | 1140 |
| gccggacaac agggtccagg tggagctgga caacaaggtc caggatcaca aggtcctggt | 1200 |
| ggacaaggtc catacggtcc tggtgctggt caacagggac caggtagtca aggacctggt | 1260 |
| tcaggtggtc agcagggtcc aggaggacag ggtccttacg gcccttctgc cgctgcagca | 1320 |
| gcagccgctg ccgcaggagg atacggacct ggtgctggac aacgatctca aggaccagga | 1380 |

```
ggacaaggtc cttatggacc tggcgctggc aacaaggac ctggttctca gggtccaggt     1440
tcaggaggcc aacaaggccc aggaggtcaa ggaccatacg gaccatccgc tgcggcagct     1500
gcagctgctg caggtggata tggcccagga gccggacaac agggtcctgg ttcacaaggt     1560
ccaggatctg gtggtcaaca gggaccaggc ggccaggac cttatggtcc aggagccgct     1620
gcagcagcag cagctgttgg aggttacggc cctggtgccg gtcaacaagg cccaggatct     1680
cagggtcctg gatctggagg acaacaaggt cctggaggtc agggtccata cggaccttca     1740
gcagcagctg ctgctgcagc cgctggtggt tatggacctg gtgctggtca acaaggaccg     1800
ggttctcagg gtccgggttc aggaggtcag cagggccctg gtggacaagg accttatgga     1860
cctagtgcgg ctgcagcagc tgccgccgca ggtggttacg gtccaggcgc tggtcaacaa     1920
ggtccaggaa gtggtggtca acaaggacct ggcggtcaag gaccctacgg tagtggccaa     1980
caaggtccag gtggagcagg acagcagggt ccgggaggcc aaggaccttta cggaccaggt     2040 gctgctgctg ccgccgctgc cgctgccgga ggttacggtc caggagccgg acaacagggt     2100
ccaggtggag ctggacaaca aggtccagga tcacaaggtc ctggtggaca aggtccatac     2160
ggtcctggtg ctggtcaaca gggaccaggt agtcaaggac ctggttcagg tggtcagcag     2220
ggtccaggag gacagggtcc ttacggccct tctgccgctg cagcagcagc cgctgccgca     2280
ggaggatacg gacctggtgc tggacaacga tctcaaggac aggaggaca aggtccttat     2340 ggacctggcg ctggccaaca aggacctggt tctcagggtc caggttcagg aggccaacaa     2400
ggcccaggag gtcaaggacc atacggacca tccgctgcgg cagctgcagc tgctgcaggt     2460
ggatatggcc caggagccgg acaacagggt cctggttcac aaggtccagg atctggtggt     2520
caacagggac caggcggcca gggaccttat ggtccaggag ccgctgcagc agcagcagct     2580
gttggaggtt acggccctgg tgccggtcaa caaggcccag gatctcaggg tcctggatct     2640
ggaggacaac aaggtcctgg aggtcagggt ccatacggac cttcagcagc agctgctgct     2700
gcagccgctg gtggttatgg acctggtgct ggtcaacaag gaccgggttc tcagggtccg     2760
ggttcaggag gtcagcaggg ccctggtgga caaggacctt atggacctag tgcggctgca     2820
gcagctgccg ccgca                                                      2835
```

<210> SEQ ID NO 21
<211> LENGTH: 945
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Gly Gly Tyr Gly Pro Gly Ala Gly Gln Gln Pro Gly Ser Gly Gly
1               5                   10                  15

Gln Gln Gly Pro Gly Gly Gln Gly Pro Tyr Gly Ser Gly Gln Gln Gly
            20                  25                  30

Pro Gly Gly Ala Gly Gln Gln Gly Pro Gly Gly Gln Gly Pro Tyr Gly
        35                  40                  45

Pro Gly Ala Ala Ala Ala Ala Ala Ala Ala Gly Gly Tyr Gly Pro
    50                  55                  60

Gly Ala Gly Gln Gln Gly Pro Gly Gly Ala Gly Gln Gln Gly Pro Gly
65                  70                  75                  80

Ser Gln Gly Pro Gly Gly Gln Gly Pro Tyr Gly Pro Gly Ala Gly Gln
                85                  90                  95
```

```
Gln Gly Pro Gly Ser Gln Gly Pro Gly Gly Gln Gln Gly Pro
            100                 105                 110
Gly Gly Gln Gly Pro Tyr Gly Pro Ser Ala Ala Ala Ala Ala
            115                 120                 125
Ala Ala Gly Gly Tyr Gly Pro Gly Ala Gly Arg Ser Gln Gly Pro
130             135                 140
Gly Gly Gln Gly Pro Tyr Gly Pro Gly Ala Gly Gln Gln Gly Pro
145                 150                 155                 160
Ser Gln Gly Pro Gly Ser Gly Gln Gln Gly Pro Gly Gly Gln Gly
                165                 170                 175
Pro Tyr Gly Pro Ser Ala Ala Ala Ala Ala Ala Ala Gly Gly Tyr
        180                 185                 190
Gly Pro Gly Ala Gly Gln Gln Gly Pro Gly Ser Gln Gly Pro Gly Ser
            195                 200                 205
Gly Gly Gln Gln Gly Pro Gly Gly Gln Gly Pro Tyr Gly Pro Gly Ala
            210                 215                 220
Ala Ala Ala Ala Ala Ala Val Gly Gly Tyr Gly Pro Gly Ala Gly Gln
225                 230                 235                 240
Gln Gly Pro Gly Ser Gln Gly Pro Gly Ser Gly Gly Gln Gln Gly Pro
            245                 250                 255
Gly Gly Gln Gly Pro Tyr Gly Pro Ser Ala Ala Ala Ala Ala Ala
            260                 265                 270
Ala Gly Gly Tyr Gly Pro Gly Ala Gly Gln Gln Gly Pro Gly Ser Gln
        275                 280                 285
Gly Pro Gly Ser Gly Gly Gln Gln Gly Pro Gly Gly Gln Gly Pro Tyr
290                 295                 300
Gly Pro Ser Ala Ala Ala Ala Ala Ala Ala Gly Gly Tyr Gly Pro
305                 310                 315                 320
Gly Ala Gly Gln Gln Gly Pro Gly Ser Gly Gly Gln Gln Gly Pro Gly
                325                 330                 335
Gly Gln Gly Pro Tyr Gly Ser Gly Gln Gln Gly Pro Gly Gly Ala Gly
            340                 345                 350
Gln Gln Gly Pro Gly Gly Gln Gly Pro Tyr Gly Pro Gly Ala Ala Ala
        355                 360                 365
Ala Ala Ala Ala Ala Ala Gly Gly Tyr Gly Pro Gly Ala Gly Gln Gln
370                 375                 380
Gly Pro Gly Gly Ala Gly Gln Gln Gly Pro Gly Ser Gln Gly Pro Gly
385                 390                 395                 400
Gly Gln Gly Pro Tyr Gly Pro Gly Ala Gly Gln Gln Gly Pro Gly Ser
                405                 410                 415
Gln Gly Pro Gly Ser Gly Gly Gln Gln Gly Pro Gly Gly Gln Gly Pro
            420                 425                 430
Tyr Gly Pro Ser Ala Ala Ala Ala Ala Ala Ala Gly Gly Tyr
        435                 440                 445
Gly Pro Gly Ala Gly Gln Arg Ser Gln Gly Pro Gly Gln Gly Pro
            450                 455                 460
Tyr Gly Pro Gly Ala Gly Gln Gln Gly Pro Gly Ser Gln Gly Pro Gly
465                 470                 475                 480
Ser Gly Gly Gln Gln Gly Pro Gly Gly Gln Gly Pro Tyr Gly Pro Ser
                485                 490                 495
Ala Ala Ala Ala Ala Ala Ala Gly Gly Tyr Gly Pro Gly Ala Gly
            500                 505                 510
```

```
Gln Gln Gly Pro Gly Ser Gln Gly Pro Ser Gly Gln Gln Gly
        515                 520                 525

Pro Gly Gly Gln Gly Pro Tyr Gly Pro Gly Ala Ala Ala Ala Ala
    530                 535                 540

Ala Val Gly Gly Tyr Gly Pro Gly Ala Gly Gln Gln Gly Pro Gly Ser
545                 550                 555                 560

Gln Gly Pro Gly Ser Gly Gln Gln Gly Pro Gly Gln Gly Pro
            565                 570                 575

Tyr Gly Pro Ser Ala Ala Ala Ala Ala Ala Gly Tyr Gly
                580                 585                 590

Pro Gly Ala Gly Gln Gln Gly Pro Gly Ser Gln Gly Pro Ser Gly
        595                 600                 605

Gly Gln Gln Gly Pro Gly Gly Gln Gly Pro Tyr Gly Pro Ser Ala Ala
    610                 615                 620

Ala Ala Ala Ala Ala Ala Gly Gly Tyr Gly Pro Gly Ala Gly Gln Gln
625                 630                 635                 640

Gly Pro Gly Ser Gly Gln Gln Gly Pro Gly Gly Gln Gly Pro Tyr
        645                 650                 655

Gly Ser Gly Gln Gln Gly Pro Gly Gly Ala Gly Gln Gln Gly Pro Gly
        660                 665                 670

Gly Gln Gly Pro Tyr Gly Pro Gly Ala Ala Ala Ala Ala Ala Ala
        675                 680                 685

Ala Gly Gly Tyr Gly Pro Gly Ala Gly Gln Gln Gly Pro Gly Gly Ala
        690                 695                 700

Gly Gln Gln Gly Pro Gly Ser Gln Gly Pro Gly Gly Gln Gly Pro Tyr
705                 710                 715                 720

Gly Pro Gly Ala Gly Gln Gln Gly Pro Gly Ser Gln Gly Pro Gly Ser
            725                 730                 735

Gly Gly Gln Gln Gly Pro Gly Gly Gln Gly Pro Tyr Gly Pro Ser Ala
                740                 745                 750

Ala Ala Ala Ala Ala Ala Ala Gly Gly Tyr Gly Pro Gly Ala Gly
        755                 760                 765

Gln Arg Ser Gln Gly Pro Gly Gly Gln Gly Pro Tyr Gly Pro Gly Ala
770                 775                 780

Gly Gln Gln Gly Pro Gly Ser Gln Gly Pro Gly Ser Gly Gly Gln Gln
785                 790                 795                 800

Gly Pro Gly Gly Gln Gly Pro Tyr Gly Pro Ser Ala Ala Ala Ala
            805                 810                 815

Ala Ala Ala Gly Gly Tyr Gly Pro Gly Ala Gly Gln Gln Gly Pro Gly
            820                 825                 830

Ser Gln Gly Pro Gly Ser Gly Gly Gln Gln Gly Pro Gly Gly Gln Gly
        835                 840                 845

Pro Tyr Gly Pro Gly Ala Ala Ala Ala Ala Ala Val Gly Gly Tyr
    850                 855                 860

Gly Pro Gly Ala Gly Gln Gln Gly Pro Gly Ser Gln Gly Pro Gly Ser
865                 870                 875                 880

Gly Gly Gln Gln Gly Pro Gly Gly Gln Gly Pro Tyr Gly Pro Ser Ala
            885                 890                 895

Ala Ala Ala Ala Ala Ala Gly Gly Tyr Gly Pro Gly Ala Gly Gln
            900                 905                 910

Gln Gly Pro Gly Ser Gln Gly Pro Gly Ser Gly Gly Gln Gln Gly Pro
        915                 920                 925

Gly Gly Gln Gly Pro Tyr Gly Pro Ser Ala Ala Ala Ala Ala Ala Ala
```

Ala
945

<210> SEQ ID NO 22
<211> LENGTH: 315
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gly Gly Tyr Gly Pro Gly Ala Gly Gln Gln Gly Pro Gly Ser Gly Gly
1               5                   10                  15

Gln Gln Gly Pro Gly Gly Gln Gly Pro Tyr Gly Ser Gly Gln Gln Gly
            20                  25                  30

Pro Gly Gly Ala Gly Gln Gln Gly Pro Gly Gly Gln Gly Pro Tyr Gly
        35                  40                  45

Pro Gly Ala Ala Ala Ala Ala Ala Ala Ala Gly Gly Tyr Gly Pro
    50                  55                  60

Gly Ala Gly Gln Gln Gly Pro Gly Gly Ala Gly Gln Gln Gly Pro Gly
65                  70                  75                  80

Ser Gln Gly Pro Gly Gly Gln Gly Pro Tyr Gly Pro Gly Ala Gly Gln
                85                  90                  95

Gln Gly Pro Gly Ser Gln Gly Pro Ser Gly Gly Gln Gln Gly Pro
            100                 105                 110

Gly Gly Gln Gly Pro Tyr Gly Pro Ser Ala Ala Ala Ala Ala Ala
            115                 120                 125

Ala Ala Gly Gly Tyr Gly Pro Gly Ala Gly Gln Arg Ser Gln Gly Pro
130                 135                 140

Gly Gly Gln Gly Pro Tyr Gly Pro Gly Ala Gly Gln Gln Gly Pro Gly
145                 150                 155                 160

Ser Gln Gly Pro Gly Ser Gly Gly Gln Gln Gly Pro Gly Gly Gln Gly
                165                 170                 175

Pro Tyr Gly Pro Ser Ala Ala Ala Ala Ala Ala Ala Gly Gly Tyr
            180                 185                 190

Gly Pro Gly Ala Gly Gln Gln Gly Pro Gly Ser Gln Gly Pro Gly Ser
        195                 200                 205

Gly Gly Gln Gln Gly Pro Gly Gly Gln Gly Pro Tyr Gly Pro Gly Ala
    210                 215                 220

Ala Ala Ala Ala Ala Ala Val Gly Gly Tyr Gly Pro Gly Ala Gly Gln
225                 230                 235                 240

Gln Gly Pro Gly Ser Gln Gly Pro Gly Ser Gly Gly Gln Gln Gly Pro
                245                 250                 255

Gly Gly Gln Gly Pro Tyr Gly Pro Ser Ala Ala Ala Ala Ala Ala
            260                 265                 270

Ala Gly Gly Tyr Gly Pro Gly Ala Gly Gln Gln Gly Pro Gly Ser Gln
        275                 280                 285

Gly Pro Gly Ser Gly Gly Gln Gln Gly Pro Gly Gly Gln Gly Pro Tyr
    290                 295                 300

Gly Pro Ser Ala Ala Ala Ala Ala Ala Ala
305                 310                 315

<210> SEQ ID NO 23
<211> LENGTH: 5

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Gly Ala Gly Gly
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Ser Gly Ala Gly
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gly Ser Gly Ala
1               5

<210> SEQ ID NO 26
<211> LENGTH: 181
<212> TYPE: PRT
<213> ORGANISM: Aliatypus gulosus

<400> SEQUENCE: 26

Gly Ala Ala Ser Ser Ser Ser Thr Ile Ile Thr Thr Lys Ser Ala Ser
1               5                   10                  15

Ala Ser Ala Ala Ala Asp Ala Ser Ala Ala Thr Ala Ser Ala Ala
            20                  25                  30

Ser Arg Ser Ser Ala Asn Ala Ala Ala Ser Ala Phe Ala Gln Ser Phe
        35                  40                  45

Ser Ser Ile Leu Leu Glu Ser Gly Tyr Phe Cys Ser Ile Phe Gly Ser
    50                  55                  60

Ser Ile Ser Ser Tyr Ala Ala Ile Ala Ser Ala Ala Ser Arg
65                  70                  75                  80

Ala Ala Ala Glu Ser Asn Gly Tyr Thr Thr His Ala Tyr Ala Cys Ala
                85                  90                  95

Lys Ala Val Ala Ser Ala Val Glu Arg Val Thr Ser Gly Ala Asp Ala
            100                 105                 110

Tyr Ala Tyr Ala Gln Ala Ile Ser Asp Ala Leu Ser His Ala Leu Leu
        115                 120                 125

Tyr Thr Gly Arg Leu Asn Thr Ala Asn Ala Asn Ser Leu Ala Ser Ala
    130                 135                 140

Phe Ala Tyr Ala Phe Ala Asn Ala Ala Gln Ala Ser Ala Ser Ser
145                 150                 155                 160

Ala Ser Ala Gly Ala Ala Ser Ala Ser Gly Ala Ala Ser Ala Ser Gly
                165                 170                 175
```

Ala Gly Ser Ala Ser
            180

<210> SEQ ID NO 27
<211> LENGTH: 126
<212> TYPE: PRT
<213> ORGANISM: Plectreurys tristis

<400> SEQUENCE: 27

Gly Ala Gly Ala Gly Ala Gly Ala Gly Ala Gly Ala Gly Ala
1               5                   10                  15

Gly Ser Gly Ala Ser Thr Ser Val Ser Thr Ser Ser Ser Gly Ser
            20                  25                  30

Gly Ala Gly Ala Gly Ala Gly Ser Gly Ala Gly Ser Gly Ala Gly Ala
            35                  40                  45

Gly Ser Gly Ala Gly Ala Gly Ala Gly Ala Gly Ala Gly Ala Gly
            50                  55                  60

Phe Gly Ser Gly Leu Gly Leu Gly Tyr Gly Val Gly Leu Ser Ser Ala
65                  70                  75                  80

Gln Ala Gln Ala Gln Ala Gln Ala Ala Ala Gln Ala Gln Ala Gln Ala
                85                  90                  95

Gln Ala Gln Ala Tyr Ala Ala Ala Gln Ala Gln Ala Gln Ala Gln Ala
            100                 105                 110

Gln Ala Gln Ala Ala Ala Ala Ala Ala Ala Ala Ala
            115                 120                 125

<210> SEQ ID NO 28
<211> LENGTH: 239
<212> TYPE: PRT
<213> ORGANISM: Plectreurys tristis

<400> SEQUENCE: 28

Gly Ala Ala Gln Lys Gln Pro Ser Gly Glu Ser Ser Val Ala Thr Ala
1               5                   10                  15

Ser Ala Ala Ala Thr Ser Val Thr Ser Gly Gly Ala Pro Val Gly Lys
            20                  25                  30

Pro Gly Val Pro Ala Pro Ile Phe Tyr Pro Gln Gly Pro Leu Gln Gln
            35                  40                  45

Gly Pro Ala Pro Gly Pro Ser Asn Val Gln Pro Gly Thr Ser Gln Gln
            50                  55                  60

Gly Pro Ile Gly Gly Val Gly Gly Ser Asn Ala Phe Ser Ser Ser Phe
65                  70                  75                  80

Ala Ser Ala Leu Ser Leu Asn Arg Gly Phe Thr Glu Val Ile Ser Ser
                85                  90                  95

Ala Ser Ala Thr Ala Val Ala Ser Ala Phe Gln Lys Gly Leu Ala Pro
            100                 105                 110

Tyr Gly Thr Ala Phe Ala Leu Ser Ala Ala Ser Ala Ala Ala Asp Ala
            115                 120                 125

Tyr Asn Ser Ile Gly Ser Gly Ala Asn Ala Phe Ala Tyr Ala Gln Ala
            130                 135                 140

Phe Ala Arg Val Leu Tyr Pro Leu Val Gln Gln Tyr Gly Leu Ser Ser
145                 150                 155                 160

Ser Ala Lys Ala Ser Ala Phe Ala Ser Ala Ile Ala Ser Ser Phe Ser
                165                 170                 175

Ser Gly Thr Ser Gly Gln Gly Pro Ser Ile Gly Gln Gln Gln Pro Pro
            180                 185                 190

```
Val Thr Ile Ser Ala Ala Ser Ala Gly Ala Ser Ala Ala
        195                 200                 205

Val Gly Gly Gln Val Gly Gln Gly Pro Tyr Gly Gln Gln Gln
210                 215                 220

Ser Thr Ala Ala Ser Ala Ser Ala Ala Ala Thr Ala Thr Ser
225                 230                 235
```

<210> SEQ ID NO 29
<211> LENGTH: 182
<212> TYPE: PRT
<213> ORGANISM: Araneus gemmoides

<400> SEQUENCE: 29

```
Gly Asn Val Gly Tyr Gln Leu Gly Leu Lys Val Ala Asn Ser Leu Gly
1               5                   10                  15

Leu Gly Asn Ala Gln Ala Leu Ala Ser Ser Leu Ser Gln Ala Val Ser
                20                  25                  30

Ala Val Gly Val Gly Ala Ser Ser Asn Ala Tyr Ala Asn Ala Val Ser
            35                  40                  45

Asn Ala Val Gly Gln Val Leu Ala Gly Gln Gly Ile Leu Asn Ala Ala
        50                  55                  60

Asn Ala Gly Ser Leu Ala Ser Ser Phe Ala Ser Ala Leu Ser Ser Ser
65                  70                  75                  80

Ala Ala Ser Val Ala Ser Gln Ser Ala Ser Gln Ser Ala Ala Ser
                85                  90                  95

Gln Ser Gln Ala Ala Ser Ala Phe Arg Gln Ala Ala Ser Gln Ser
            100                 105                 110

Ala Ser Gln Ser Asp Ser Arg Ala Gly Ser Gln Ser Ser Thr Lys Thr
        115                 120                 125

Thr Ser Thr Ser Thr Ser Gly Ser Gln Ala Asp Ser Arg Ser Ala Ser
130                 135                 140

Ser Ser Ala Ser Gln Ala Ser Ala Ser Ala Phe Ala Gln Gln Ser Ser
145                 150                 155                 160

Ala Ser Leu Ser Ser Ser Ser Phe Ser Ala Phe Ser Ser Ala
                165                 170                 175

Thr Ser Ile Ser Ala Val
            180
```

<210> SEQ ID NO 30
<211> LENGTH: 180
<212> TYPE: PRT
<213> ORGANISM: Argiope aurantia

<400> SEQUENCE: 30

```
Gly Ser Leu Ala Ser Ser Phe Ala Ser Ala Leu Ser Ala Ser Ala Ala
1               5                   10                  15

Ser Val Ala Ser Ser Ala Ala Gln Ala Ala Ser Gln Ser Gln Ala
                20                  25                  30

Ala Ala Ser Ala Phe Ser Arg Ala Ala Ser Gln Ser Ala Ser Gln Ser
            35                  40                  45

Ala Ala Arg Ser Gly Ala Gln Ser Ile Ser Thr Thr Thr Thr Thr Ser
        50                  55                  60

Thr Ala Gly Ser Gln Ala Ala Ser Gln Ser Ala Ser Ser Ala Ala Ser
65                  70                  75                  80

Gln Ala Ser Ala Ser Ser Phe Ala Arg Ala Ser Ser Ala Ser Leu Ala
                85                  90                  95
```

```
Ala Ser Ser Ser Phe Ser Ser Ala Phe Ser Ala Asn Ser Leu Ser
                100                 105                 110

Ala Leu Gly Asn Val Gly Tyr Gln Leu Gly Phe Asn Val Ala Asn Asn
            115                 120                 125

Leu Gly Ile Gly Asn Ala Ala Gly Leu Gly Asn Ala Leu Ser Gln Ala
        130                 135                 140

Val Ser Ser Val Gly Val Gly Ala Ser Ser Thr Tyr Ala Asn Ala
145                 150                 155                 160

Val Ser Asn Ala Val Gly Gln Phe Leu Ala Gly Gln Gly Ile Leu Asn
                165                 170                 175

Ala Ala Asn Ala
        180

<210> SEQ ID NO 31
<211> LENGTH: 199
<212> TYPE: PRT
<213> ORGANISM: Deinopis spinosa

<400> SEQUENCE: 31

Gly Ala Ser Ala Ser Ala Tyr Ala Ser Ala Ile Ser Asn Ala Val Gly
1               5                   10                  15

Pro Tyr Leu Tyr Gly Leu Gly Leu Phe Asn Gln Ala Asn Ala Ala Ser
            20                  25                  30

Phe Ala Ser Ser Phe Ala Ser Ala Val Ser Ser Ala Val Ala Ser Ala
        35                  40                  45

Ser Ala Ser Ala Ala Ser Ser Ala Tyr Ala Gln Ser Ala Ala Ala Gln
    50                  55                  60

Ala Gln Ala Ala Ser Ser Ala Phe Ser Gln Ala Ala Gln Ser Ala
65                  70                  75                  80

Ala Ala Ala Ser Ala Gly Ala Ser Ala Gly Ala Gly Ala Ser Ala Gly
                85                  90                  95

Ala Gly Ala Val Ala Gly Ala Gly Ala Val Ala Gly Ala Gly Ala Val
            100                 105                 110

Ala Gly Ala Ser Ala Ala Ala Ala Ser Gln Ala Ala Ala Ser Ser Ser
        115                 120                 125

Ala Ser Ala Val Ala Ser Ala Phe Ala Gln Ser Ala Ser Tyr Ala Leu
    130                 135                 140

Ala Ser Ser Ser Ala Phe Ala Asn Ala Phe Ala Ser Ala Thr Ser Ala
145                 150                 155                 160

Gly Tyr Leu Gly Ser Leu Ala Tyr Gln Leu Gly Leu Thr Thr Ala Tyr
                165                 170                 175

Asn Leu Gly Leu Ser Asn Ala Gln Ala Phe Ala Ser Thr Leu Ser Gln
            180                 185                 190

Ala Val Thr Gly Val Gly Leu
        195

<210> SEQ ID NO 32
<211> LENGTH: 171
<212> TYPE: PRT
<213> ORGANISM: Nephila clavipes

<400> SEQUENCE: 32

Gly Ala Thr Ala Ala Ser Tyr Gly Asn Ala Leu Ser Thr Ala Ala Ala
1               5                   10                  15

Gln Phe Phe Ala Thr Ala Gly Leu Leu Asn Ala Gly Asn Ala Ser Ala
            20                  25                  30
```

-continued

```
Leu Ala Ser Ser Phe Ala Arg Ala Phe Ser Ala Ser Ala Glu Ser Gln
            35                  40                  45

Ser Phe Ala Gln Ser Gln Ala Phe Gln Gln Ala Ser Ala Phe Gln Gln
 50                  55                  60

Ala Ala Ser Arg Ser Ala Ser Gln Ser Ala Ala Glu Ala Gly Ser Thr
 65                  70                  75                  80

Ser Ser Ser Thr Thr Thr Thr Thr Ser Ala Ala Arg Ser Gln Ala Ala
                 85                  90                  95

Ser Gln Ser Ala Ser Ser Ser Tyr Ser Ser Ala Phe Ala Gln Ala Ala
                100                 105                 110

Ser Ser Ser Leu Ala Thr Ser Ser Ala Leu Ser Arg Ala Phe Ser Ser
            115                 120                 125

Val Ser Ser Ala Ser Ala Ala Ser Ser Leu Ala Tyr Ser Ile Gly Leu
130                 135                 140

Ser Ala Ala Arg Ser Leu Gly Ile Ala Asp Ala Ala Gly Leu Ala Gly
145                 150                 155                 160

Val Leu Ala Arg Ala Ala Gly Ala Leu Gly Gln
                165                 170

<210> SEQ ID NO 33
<211> LENGTH: 268
<212> TYPE: PRT
<213> ORGANISM: Argiope trifasciata

<400> SEQUENCE: 33

Gly Gly Ala Pro Gly Gly Pro Gly Gly Ala Gly Pro Gly Gly Ala
 1               5                  10                  15

Gly Phe Gly Pro Gly Gly Ala Gly Phe Gly Pro Gly Gly Gly Ala
                20                  25                  30

Gly Phe Gly Pro Gly Gly Ala Ala Gly Pro Gly Gly Pro Gly Gly
            35                  40                  45

Pro Gly Gly Pro Gly Gly Ala Gly Gly Tyr Gly Pro Gly Ala Gly
 50                  55                  60

Gly Tyr Gly Pro Gly Gly Val Gly Pro Gly Gly Ala Gly Gly Tyr Gly
 65                  70                  75                  80

Pro Gly Gly Ala Gly Gly Tyr Gly Pro Gly Gly Ser Gly Pro Gly Gly
                 85                  90                  95

Ala Gly Pro Gly Gly Ala Gly Gly Glu Gly Pro Val Thr Val Asp Val
                100                 105                 110

Asp Val Thr Val Gly Pro Glu Gly Val Gly Gly Pro Gly Gly Ala
            115                 120                 125

Gly Pro Gly Gly Ala Gly Phe Gly Pro Gly Gly Ala Gly Phe Gly
130                 135                 140

Pro Gly Gly Ala Pro Gly Ala Pro Gly Gly Pro Gly Gly Pro Gly Gly
145                 150                 155                 160

Pro Gly Gly Pro Gly Gly Pro Gly Gly Val Gly Pro Gly Gly Ala Gly
                165                 170                 175

Gly Tyr Gly Pro Gly Gly Ala Gly Gly Val Gly Pro Ala Gly Thr Gly
                180                 185                 190

Gly Phe Gly Pro Gly Gly Ala Gly Gly Phe Gly Pro Gly Gly Ala Gly
                195                 200                 205

Gly Phe Gly Pro Gly Gly Ala Gly Gly Phe Gly Pro Ala Gly Ala Gly
                210                 215                 220

Gly Tyr Gly Pro Gly Gly Val Gly Pro Gly Gly Ala Gly Gly Phe Gly
```

-continued

```
            225                 230                 235                 240
Pro Gly Gly Val Gly Pro Gly Gly Ser Gly Pro Gly Gly Ala Gly Gly
                245                 250                 255
Glu Gly Pro Val Thr Val Asp Val Asp Val Ser Val
            260                 265

<210> SEQ ID NO 34
<211> LENGTH: 420
<212> TYPE: PRT
<213> ORGANISM: Nephila clavipes

<400> SEQUENCE: 34

Gly Val Ser Tyr Gly Pro Gly Gly Ala Gly Gly Pro Tyr Gly Pro Gly
1               5                   10                  15
Gly Pro Tyr Gly Pro Gly Gly Glu Gly Pro Gly Gly Ala Gly Gly Pro
                20                  25                  30
Tyr Gly Pro Gly Gly Val Gly Pro Gly Gly Ser Gly Pro Gly Gly Tyr
                35                  40                  45
Gly Pro Gly Gly Ala Gly Pro Gly Gly Tyr Gly Pro Gly Gly Ser Gly
            50                  55                  60
Pro Gly Gly Tyr Gly Pro Gly Ser Gly Pro Gly Gly Tyr Gly Pro
65                  70                  75                  80
Gly Gly Ser Gly Pro Gly Gly Tyr Gly Pro Gly Gly Ser Gly Pro Gly
                85                  90                  95
Gly Tyr Gly Pro Gly Gly Tyr Gly Pro Gly Gly Ser Gly Pro Gly Gly
                100                 105                 110
Ser Gly Pro Gly Gly Ser Gly Pro Gly Gly Tyr Gly Pro Gly Gly Thr
            115                 120                 125
Gly Pro Gly Gly Ser Gly Pro Gly Gly Tyr Gly Pro Gly Gly Ser Gly
            130                 135                 140
Pro Gly Gly Ser Gly Pro Gly Gly Tyr Gly Pro Gly Gly Ser Gly Pro
145                 150                 155                 160
Gly Gly Phe Gly Pro Gly Gly Ser Gly Pro Gly Gly Tyr Gly Pro Gly
                165                 170                 175
Gly Ser Gly Pro Gly Gly Ala Gly Pro Gly Gly Val Gly Pro Gly Gly
            180                 185                 190
Phe Gly Pro Gly Gly Ala Gly Pro Gly Gly Ala Ala Pro Gly Gly Ala
                195                 200                 205
Gly Pro Gly Gly Ala Gly Pro Gly Gly Ala Gly Pro Gly Gly Ala Gly
            210                 215                 220
Pro Gly Gly Ala Gly Pro Gly Gly Ala Gly Pro Gly Gly Ala Gly Gly
225                 230                 235                 240
Ala Gly Gly Ala Gly Ser Gly Gly Ala Gly Gly Ser Gly Gly Thr
                245                 250                 255
Thr Ile Ile Glu Asp Leu Asp Ile Thr Ile Asp Gly Ala Asp Gly Pro
                260                 265                 270
Ile Thr Ile Ser Glu Glu Leu Pro Ile Ser Gly Ala Gly Gly Ser Gly
            275                 280                 285
Pro Gly Gly Ala Gly Pro Gly Gly Val Gly Pro Gly Gly Ser Gly Pro
            290                 295                 300
Gly Gly Val Gly Pro Gly Gly Ser Gly Pro Gly Gly Val Gly Pro Gly
305                 310                 315                 320
Gly Ser Gly Pro Gly Gly Val Gly Pro Gly Gly Ala Gly Gly Pro Tyr
                325                 330                 335
```

```
Gly Pro Gly Gly Ser Gly Pro Gly Gly Ala Gly Ala Gly Gly Pro
            340                 345                 350

Gly Gly Ala Tyr Gly Pro Gly Gly Ser Tyr Gly Pro Gly Gly Ser Gly
        355                 360                 365

Gly Pro Gly Gly Ala Gly Gly Pro Tyr Gly Pro Gly Gly Glu Gly Pro
    370                 375                 380

Gly Gly Ala Gly Gly Pro Tyr Gly Pro Gly Gly Ala Gly Gly Pro Tyr
385                 390                 395                 400

Gly Pro Gly Gly Ala Gly Gly Pro Tyr Gly Pro Gly Gly Glu Gly Gly
            405                 410                 415

Pro Tyr Gly Pro
            420

<210> SEQ ID NO 35
<211> LENGTH: 376
<212> TYPE: PRT
<213> ORGANISM: Latrodectus hesperus

<400> SEQUENCE: 35

Gly Ile Asn Val Asp Ser Asp Ile Gly Ser Val Thr Ser Leu Ile Leu
1               5                   10                  15

Ser Gly Ser Thr Leu Gln Met Thr Ile Pro Ala Gly Gly Asp Asp Leu
            20                  25                  30

Ser Gly Gly Tyr Pro Gly Gly Phe Pro Ala Gly Ala Gln Pro Ser Gly
        35                  40                  45

Gly Ala Pro Val Asp Phe Gly Gly Pro Ser Ala Gly Gly Asp Val Ala
    50                  55                  60

Ala Lys Leu Ala Arg Ser Leu Ala Ser Thr Leu Ala Ser Ser Gly Val
65                  70                  75                  80

Phe Arg Ala Ala Phe Asn Ser Arg Val Ser Thr Pro Val Ala Val Gln
                85                  90                  95

Leu Thr Asp Ala Leu Val Gln Lys Ile Ala Ser Asn Leu Gly Leu Asp
            100                 105                 110

Tyr Ala Thr Ala Ser Lys Leu Arg Lys Ala Ser Gln Ala Val Ser Lys
        115                 120                 125

Val Arg Met Gly Ser Asp Thr Asn Ala Tyr Ala Leu Ala Ile Ser Ser
    130                 135                 140

Ala Leu Ala Glu Val Leu Ser Ser Ser Gly Lys Val Ala Asp Ala Asn
145                 150                 155                 160

Ile Asn Gln Ile Ala Pro Gln Leu Ala Ser Gly Ile Val Leu Gly Val
                165                 170                 175

Ser Thr Thr Ala Pro Gln Phe Gly Val Asp Leu Ser Ser Ile Asn Val
            180                 185                 190

Asn Leu Asp Ile Ser Asn Val Ala Arg Asn Met Gln Ala Ser Ile Gln
        195                 200                 205

Gly Gly Pro Ala Pro Ile Thr Ala Glu Gly Pro Asp Phe Gly Ala Gly
    210                 215                 220

Tyr Pro Gly Gly Ala Pro Thr Asp Leu Ser Gly Leu Asp Met Gly Ala
225                 230                 235                 240

Pro Ser Asp Gly Ser Arg Gly Gly Asp Ala Thr Ala Lys Leu Leu Gln
                245                 250                 255

Ala Leu Val Pro Ala Leu Leu Lys Ser Asp Val Phe Arg Ala Ile Tyr
            260                 265                 270

Lys Arg Gly Thr Arg Lys Gln Val Val Gln Tyr Val Thr Asn Ser Ala
        275                 280                 285
```

Leu Gln Gln Ala Ala Ser Ser Leu Gly Leu Asp Ala Ser Thr Ile Ser
        290                 295                 300

Gln Leu Gln Thr Lys Ala Thr Gln Ala Leu Ser Ser Val Ser Ala Asp
305                 310                 315                 320

Ser Asp Ser Thr Ala Tyr Ala Lys Ala Phe Gly Leu Ala Ile Ala Gln
                325                 330                 335

Val Leu Gly Thr Ser Gly Gln Val Asn Asp Ala Asn Val Asn Gln Ile
            340                 345                 350

Gly Ala Lys Leu Ala Thr Gly Ile Leu Arg Gly Ser Ser Ala Val Ala
        355                 360                 365

Pro Arg Leu Gly Ile Asp Leu Ser
    370                 375

<210> SEQ ID NO 36
<211> LENGTH: 200
<212> TYPE: PRT
<213> ORGANISM: Argiope trifasciata

<400> SEQUENCE: 36

Gly Ala Gly Tyr Thr Gly Pro Ser Gly Pro Ser Thr Gly Pro Ser Gly
1               5                   10                  15

Tyr Pro Gly Pro Leu Gly Gly Ala Pro Phe Gly Gln Ser Gly Phe
            20                  25                  30

Gly Gly Ser Ala Gly Pro Gln Gly Gly Phe Gly Ala Thr Gly Gly Ala
        35                  40                  45

Ser Ala Gly Leu Ile Ser Arg Val Ala Asn Ala Leu Ala Asn Thr Ser
    50                  55                  60

Thr Leu Arg Thr Val Leu Arg Thr Gly Val Ser Gln Gln Ile Ala Ser
65                  70                  75                  80

Ser Val Val Gln Arg Ala Ala Gln Ser Leu Ala Ser Thr Leu Gly Val
                85                  90                  95

Asp Gly Asn Asn Leu Ala Arg Phe Ala Val Gln Ala Val Ser Arg Leu
            100                 105                 110

Pro Ala Gly Ser Asp Thr Ser Ala Tyr Ala Gln Ala Phe Ser Ser Ala
        115                 120                 125

Leu Phe Asn Ala Gly Val Leu Asn Ala Ser Asn Ile Asp Thr Leu Gly
    130                 135                 140

Ser Arg Val Leu Ser Ala Leu Leu Asn Gly Val Ser Ser Ala Ala Gln
145                 150                 155                 160

Gly Leu Gly Ile Asn Val Asp Ser Gly Ser Val Gln Ser Asp Ile Ser
                165                 170                 175

Ser Ser Ser Ser Phe Leu Ser Thr Ser Ser Ser Ala Ser Tyr Ser
            180                 185                 190

Gln Ala Ser Ala Ser Ser Thr Ser
        195                 200

<210> SEQ ID NO 37
<211> LENGTH: 357
<212> TYPE: PRT
<213> ORGANISM: Uloborus diversus

<400> SEQUENCE: 37

Gly Ala Ser Ala Ala Asp Ile Ala Thr Ala Ile Ala Ala Ser Val Ala
1               5                   10                  15

Thr Ser Leu Gln Ser Asn Gly Val Leu Thr Ala Ser Asn Val Ser Gln
            20                  25                  30

```
Leu Ser Asn Gln Leu Ala Ser Tyr Val Ser Ser Gly Leu Ser Ser Thr
            35                  40                  45

Ala Ser Ser Leu Gly Ile Gln Leu Gly Ala Ser Leu Gly Ala Gly Phe
        50                  55                  60

Gly Ala Ser Ala Gly Leu Ser Ala Ser Thr Asp Ile Ser Ser Ser Val
65                  70                  75                  80

Glu Ala Thr Ser Ala Ser Thr Leu Ser Ser Ala Ser Ser Thr Ser
                85                  90                  95

Val Val Ser Ser Ile Asn Ala Gln Leu Val Pro Ala Leu Ala Gln Thr
                100                 105                 110

Ala Val Leu Asn Ala Ala Phe Ser Asn Ile Asn Thr Gln Asn Ala Ile
                115                 120                 125

Arg Ile Ala Glu Leu Leu Thr Gln Gln Val Gly Arg Gln Tyr Gly Leu
            130                 135                 140

Ser Gly Ser Asp Val Ala Thr Ala Ser Ser Gln Ile Arg Ser Ala Leu
145                 150                 155                 160

Tyr Ser Val Gln Gln Gly Ser Ala Ser Ser Ala Tyr Val Ser Ala Ile
                165                 170                 175

Val Gly Pro Leu Ile Thr Ala Leu Ser Ser Arg Gly Val Val Asn Ala
            180                 185                 190

Ser Asn Ser Ser Gln Ile Ala Ser Ser Leu Ala Thr Ala Ile Leu Gln
                195                 200                 205

Phe Thr Ala Asn Val Ala Pro Gln Phe Gly Ile Ser Ile Pro Thr Ser
            210                 215                 220

Ala Val Gln Ser Asp Leu Ser Thr Ile Ser Gln Ser Leu Thr Ala Ile
225                 230                 235                 240

Ser Ser Gln Thr Ser Ser Ser Val Asp Ser Ser Thr Ser Ala Phe Gly
                245                 250                 255

Gly Ile Ser Gly Pro Ser Gly Pro Ser Pro Tyr Gly Pro Gln Pro Ser
                260                 265                 270

Gly Pro Thr Phe Gly Pro Gly Pro Ser Leu Ser Gly Leu Thr Gly Phe
            275                 280                 285

Thr Ala Thr Phe Ala Ser Ser Phe Lys Ser Thr Leu Ala Ser Ser Thr
            290                 295                 300

Gln Phe Gln Leu Ile Ala Gln Ser Asn Leu Asp Val Gln Thr Arg Ser
305                 310                 315                 320

Ser Leu Ile Ser Lys Val Leu Ile Asn Ala Leu Ser Ser Leu Gly Ile
                325                 330                 335

Ser Ala Ser Val Ala Ser Ser Ile Ala Ala Ser Ser Ser Gln Ser Leu
                340                 345                 350

Leu Ser Val Ser Ala
            355

<210> SEQ ID NO 38
<211> LENGTH: 32
<212> TYPE: PRT
<213> ORGANISM: Euprosthenops australis

<400> SEQUENCE: 38

Gly Gly Gln Gly Gly Gln Gly Gln Gly Arg Tyr Gly Gln Gly Ala Gly
1               5                   10                  15

Ser Ser Ala Ala Ala Ala Ala Ala Ala Ala Ala Ala Ala Ala Ala Ala
                20                  25                  30
```

```
<210> SEQ ID NO 39
<211> LENGTH: 42
<212> TYPE: PRT
<213> ORGANISM: Tetragnatha kauaiensis

<400> SEQUENCE: 39

Gly Gly Leu Gly Gly Gln Gly Ala Gly Gln Gly Gly Gln Gln Gly
1               5                   10                  15

Ala Gly Gln Gly Gly Tyr Gly Ser Gly Leu Gly Gly Ala Gly Gln Gly
            20                  25                  30

Ala Ser Ala Ala Ala Ala Ala Ala Ala Ala
        35                  40

<210> SEQ ID NO 40
<211> LENGTH: 42
<212> TYPE: PRT
<213> ORGANISM: Argiope aurantia

<400> SEQUENCE: 40

Gly Gly Tyr Gly Pro Gly Ala Gly Gln Gln Gly Pro Gly Ser Gln Gly
1               5                   10                  15

Pro Gly Ser Gly Gly Gln Gln Gly Pro Gly Leu Gly Pro Tyr Gly
            20                  25                  30

Pro Ser Ala Ala Ala Ala Ala Ala Ala Ala
        35                  40

<210> SEQ ID NO 41
<211> LENGTH: 46
<212> TYPE: PRT
<213> ORGANISM: Deinopis spinosa

<400> SEQUENCE: 41

Gly Pro Gly Gly Tyr Gly Gly Pro Gly Gln Gln Gly Pro Gly Gln Gly
1               5                   10                  15

Gln Tyr Gly Pro Gly Thr Gly Gln Gln Gly Gly Gly Pro Ser Gly Gln
            20                  25                  30

Gln Gly Pro Ala Gly Ala Ala Ala Ala Ala Ala Ala Ala Ala
        35                  40                  45

<210> SEQ ID NO 42
<211> LENGTH: 42
<212> TYPE: PRT
<213> ORGANISM: Nephila clavata

<400> SEQUENCE: 42

Gly Pro Gly Gly Tyr Gly Leu Gly Gln Gln Gly Pro Gly Gln Gln Gly
1               5                   10                  15

Pro Gly Gln Gln Gly Pro Ala Gly Tyr Gly Pro Ser Gly Leu Ser Gly
            20                  25                  30

Pro Gly Gly Ala Ala Ala Ala Ala Ala Ala
        35                  40

<210> SEQ ID NO 43
<211> LENGTH: 3360
<212> TYPE: PRT
<213> ORGANISM: Argiope bruennichi

<400> SEQUENCE: 43

Met Asn Trp Ser Ile Arg Leu Ala Leu Leu Gly Phe Val Val Leu Ser
1               5                   10                  15

Thr Gln Thr Val Phe Ala Val Gly Gln Ala Ala Thr Pro Trp Glu Asn
```

```
                   20                  25                  30
Ser Gln Leu Ala Glu Asp Phe Ile Asn Ser Phe Leu Arg Phe Ile Ala
                35                  40                  45
Gln Ser Gly Ala Phe Ser Pro Asn Gln Leu Asp Asp Met Ser Ser Ile
                50                  55                  60
Gly Asp Thr Leu Lys Thr Ala Ile Glu Lys Met Ala Gln Ser Arg Lys
 65                  70                  75                  80
Ser Ser Lys Ser Lys Leu Gln Ala Leu Asn Met Ala Phe Ala Ser Ser
                85                  90                  95
Met Ala Glu Ile Ala Val Ala Glu Gln Gly Leu Ser Leu Glu Ala
                100                 105                 110
Lys Thr Asn Ala Ile Ala Asn Ala Leu Ala Ser Ala Phe Leu Glu Thr
                115                 120                 125
Thr Gly Phe Val Asn Gln Gln Phe Val Ser Glu Ile Lys Ser Leu Ile
                130                 135                 140
Tyr Met Ile Ala Gln Ala Ser Ser Asn Glu Ile Ser Gly Ser Ala Ala
145                 150                 155                 160
Ala Ala Gly Gly Gly Ser Gly Gly Gly Gly Ser Gly Gln Gly Gly
                165                 170                 175
Tyr Gly Gln Gly Ala Ser Ala Ser Ala Ser Ala Ala Ala Tyr Gly
                180                 185                 190
Ser Ala Pro Gln Gly Ala Gly Pro Ala Pro Gln Gly Pro Ser Gln
                195                 200                 205
Gln Gly Pro Val Ser Gln Gly Pro Tyr Gly Pro Gly Ala Ala Ala
                210                 215                 220
Ala Ala Ala Ala Gly Gly Tyr Gly Pro Gly Ala Gly Gln Gln Gly Pro
225                 230                 235                 240
Gly Ser Gln Gly Pro Gly Ser Gly Gly Gln Gln Gly Pro Gly Ser Gln
                245                 250                 255
Gly Pro Gly Ser Gly Gly Gln Gln Gly Pro Gly Gly Gln Gly Pro Tyr
                260                 265                 270
Gly Pro Ser Ala Ala Ala Ala Ala Ala Ala Gly Gly Tyr Gly
                275                 280                 285
Pro Gly Ala Gly Gln Gln Gly Pro Gly Ser Gln Gly Pro Gly Ser Gly
                290                 295                 300
Gly Gln Gln Gly Pro Gly Gln Gly Pro Tyr Gly Pro Gly Ala Ala
305                 310                 315                 320
Ala Ala Ala Ala Ala Val Gly Gly Tyr Gly Pro Gly Ala Gly Gln Gln
                325                 330                 335
Gly Pro Gly Ser Gln Gly Pro Gly Ser Gly Gly Gln Gln Gly Pro Gly
                340                 345                 350
Gly Gln Gly Pro Tyr Gly Pro Ser Ala Ala Ala Ala Ala Ala Ala
                355                 360                 365
Gly Gly Tyr Gly Pro Gly Ala Gly Gln Gln Pro Gly Ser Gln Gly
                370                 375                 380
Pro Gly Ser Gly Gly Gln Gln Gly Pro Gly Gly Gln Gly Pro Tyr Gly
385                 390                 395                 400
Pro Ser Ala Ala Ala Ala Ala Ala Ala Gly Gly Tyr Gly Pro Gly
                405                 410                 415
Ala Gly Gln Gln Gly Pro Gly Ser Gly Gly Gln Gln Gly Pro Gly Gly
                420                 425                 430
Gln Gly Pro Tyr Gly Ser Gly Gln Gln Gly Pro Gly Gly Ala Gly Gln
                435                 440                 445
```

-continued

Gln Gly Pro Gly Gly Gln Gly Pro Tyr Gly Pro Gly Ala Ala Ala
            450                 455                 460
Ala Ala Ala Ala Ala Gly Gly Tyr Gly Pro Gly Ala Gly Gln Gln Gly
465                 470                 475                 480
Pro Gly Gly Ala Gly Gln Gln Gly Pro Gly Ser Gln Gly Pro Gly Gly
                    485                 490                 495
Gln Gly Pro Tyr Gly Pro Gly Ala Gly Gln Gln Gly Pro Gly Ser Gln
                500                 505                 510
Gly Pro Gly Ser Gly Gly Gln Gln Gly Pro Gly Gly Gln Gly Pro Tyr
            515                 520                 525
Gly Pro Ser Ala Ala Ala Ala Ala Ala Ala Gly Gly Tyr Gly Pro
            530                 535                 540
Gly Ala Gly Gln Gln Gly Pro Gly Ser Gln Gly Pro Gly Ser Gly Gly
545                 550                 555                 560
Gln Gln Gly Pro Gly Ser Gln Gly Pro Gly Ser Gly Gly Gln Gln Gly
                    565                 570                 575
Pro Gly Gly Gln Gly Pro Tyr Gly Pro Ser Ala Ala Ala Ala Ala Ala
                580                 585                 590
Ala Ala Gly Gly Tyr Gly Pro Gly Ala Gly Gln Gln Gly Pro Gly Ser
            595                 600                 605
Gln Gly Pro Gly Ser Gly Gly Gln Gln Gly Pro Gly Gly Gln Gly Pro
            610                 615                 620
Tyr Gly Pro Gly Ala Ala Ala Ala Ala Ala Val Gly Gly Tyr Gly
625                 630                 635                 640
Pro Gly Ala Gly Gln Gln Gly Pro Gly Ser Gln Gly Pro Gly Ser Gly
                    645                 650                 655
Gly Gln Gln Gly Pro Gly Gly Gln Gly Pro Tyr Gly Pro Ser Ala Ala
                660                 665                 670
Ala Ala Ala Ala Ala Gly Gly Tyr Gly Pro Gly Ala Gly Gln Gln
            675                 680                 685
Gly Pro Gly Ser Gln Gly Pro Gly Ser Gly Gly Gln Gln Gly Pro Gly
            690                 695                 700
Gly Gln Gly Pro Tyr Gly Pro Ser Ala Ala Ala Ala Ala Ala Ala
705                 710                 715                 720
Gly Gly Tyr Gly Pro Gly Ala Gly Gln Gln Gly Pro Gly Ser Gly Gly
                    725                 730                 735
Gln Gln Gly Pro Gly Gly Gln Gly Pro Tyr Gly Ser Gly Gln Gln Gly
                740                 745                 750
Pro Gly Gly Ala Gly Gln Gln Gly Pro Gly Gly Gln Gly Pro Tyr Gly
            755                 760                 765
Pro Gly Ala Ala Ala Ala Ala Ala Ala Gly Gly Tyr Gly Pro
            770                 775                 780
Gly Ala Gly Gln Gln Gly Pro Gly Gly Ala Gly Gln Gln Gly Pro Gly
785                 790                 795                 800
Ser Gln Gly Pro Gly Gly Gln Gly Pro Tyr Gly Pro Gly Ala Gly Gln
                    805                 810                 815
Gln Gly Pro Gly Ser Gln Gly Pro Gly Ser Gly Gly Gln Gln Gly Pro
                820                 825                 830
Gly Gly Gln Gly Pro Tyr Gly Pro Ser Ala Ala Ala Ala Ala Ala
            835                 840                 845
Ala Ala Gly Gly Tyr Gly Pro Gly Ala Gly Gln Arg Ser Gln Gly Pro
850                 855                 860

```
Gly Gly Gln Gly Pro Tyr Gly Pro Gly Ala Gly Gln Gln Gly Pro Gly
865                 870                 875                 880

Ser Gln Gly Pro Gly Ser Gly Gln Gln Gly Pro Gly Gly Gln Gly
            885                 890                 895

Pro Tyr Gly Pro Ser Ala Ala Ala Ala Ala Ala Ala Gly Pro Gly
            900                 905                 910

Ala Gly Arg Gln Gly Pro Gly Ser Gln Gly Pro Gly Ser Gly Gly Gln
        915                 920                 925

Gln Gly Pro Gly Gly Gln Gly Pro Tyr Gly Pro Ser Ala Ala Ala
    930                 935                 940

Ala Ala Ala Ala Gly Pro Gly Ala Arg Arg Gln Gly Pro Gly Ser Gln
945                 950                 955                 960

Gly Pro Gly Ser Gly Gly Gln Gln Gly Pro Gly Gly Gln Gly Pro Tyr
            965                 970                 975

Gly Ser Gly Gln Gln Gly Pro Gly Gly Ala Gly Gln Gln Gly Pro Gly
            980                 985                 990

Gly Gln Gly Pro Tyr Gly Pro Gly Ala Ala Ala Ala Ala Ala Ala Ala
        995                 1000                1005

Ala Gly Gly Tyr Gly Pro Gly Ala Gly Gln Gln Gly Pro Gly Gly
    1010                1015                1020

Ala Gly Gln Gln Gly Pro Gly Ser Gln Gly Pro Gly Gly Gln Gly
    1025                1030                1035

Pro Tyr Gly Pro Gly Ala Gly Gln Gln Gly Pro Gly Ser Gln Gly
    1040                1045                1050

Pro Gly Ser Gly Gly Gln Gln Gly Pro Gly Gly Gln Gly Pro Tyr
    1055                1060                1065

Gly Pro Ser Ala Ala Ala Ala Ala Ala Ala Gly Gly Tyr Gly
    1070                1075                1080

Pro Gly Ala Gly Gln Gln Gly Pro Gly Ser Gln Gly Pro Gly Ser
    1085                1090                1095

Gly Gly Gln Gln Gly Pro Gly Gly Gln Gly Pro Tyr Gly Pro Gly
    1100                1105                1110

Ala Ala Ala Ala Ala Ala Ala Val Gly Gly Tyr Gly Pro Gly Ala
    1115                1120                1125

Gly Gln Gln Gly Pro Gly Ser Gln Gly Pro Gly Ser Gly Gly Gln
    1130                1135                1140

Gln Gly Pro Gly Gly Gln Gly Pro Tyr Gly Pro Ser Ala Ala Ala
    1145                1150                1155

Ala Ala Ala Ala Ala Gly Gly Tyr Gly Pro Gly Ala Gly Gln Gln
    1160                1165                1170

Gly Pro Gly Ser Gln Gly Pro Gly Ser Gly Gly Gln Gln Gly Pro
    1175                1180                1185

Gly Gly Gln Gly Pro Tyr Gly Pro Ser Ala Ala Ala Ala Ala Ala
    1190                1195                1200

Ala Ala Gly Gly Tyr Gly Pro Gly Ala Gly Gln Gln Gly Pro Gly
    1205                1210                1215

Ser Gly Gly Gln Gln Gly Pro Gly Gly Gln Gly Pro Tyr Gly Ser
    1220                1225                1230

Gly Gln Gln Gly Pro Gly Gly Ala Gly Gln Gln Gly Pro Gly Gly
    1235                1240                1245

Gln Gly Pro Tyr Gly Pro Gly Ala Ala Ala Ala Ala Ala Ala Ala
    1250                1255                1260

Ala Gly Gly Tyr Gly Pro Gly Ala Gly Gln Gln Gly Pro Gly Gly
```

```
                 1265                1270                1275

Ala Gly Gln Gln Gly Pro Glu Gly Pro Gly Ser Gln Gly Pro Gly
                 1280                1285                1290

Ser Gly Gly Gln Gln Gly Pro Gly Gly Gln Gly Pro Tyr Gly Pro
                 1295                1300                1305

Gly Ala Ala Ala Ala Ala Ala Val Gly Gly Tyr Gly Pro Gly
                 1310                1315                1320

Ala Gly Gln Gln Gly Pro Gly Ser Gln Gly Pro Gly Ser Gly Gly
                 1325                1330                1335

Gln Gln Gly Pro Gly Gly Gln Gly Pro Tyr Gly Pro Ser Ala Ala
                 1340                1345                1350

Ala Ala Ala Ala Ala Ala Gly Gly Tyr Gly Pro Gly Ala Gly Gln
                 1355                1360                1365

Gln Gly Pro Gly Ser Gln Gly Pro Gly Ser Gly Gly Gln Gln Gly
                 1370                1375                1380

Pro Gly Gly Gln Gly Pro Tyr Gly Pro Ser Ala Ala Ala Ala Ala
                 1385                1390                1395

Ala Ala Ala Gly Gly Tyr Gly Pro Gly Ala Gly Gln Gln Gly Pro
                 1400                1405                1410

Gly Ser Gly Gly Gln Gln Gly Pro Gly Gly Gln Gly Pro Tyr Gly
                 1415                1420                1425

Ser Gly Gln Gln Gly Pro Gly Gly Ala Gly Gln Gln Gly Pro Gly
                 1430                1435                1440

Gly Gln Gly Pro Tyr Gly Pro Gly Ala Ala Ala Ala Ala Ala Ala
                 1445                1450                1455

Ala Ala Gly Gly Tyr Gly Pro Gly Ala Gly Gln Gln Gly Pro Gly
                 1460                1465                1470

Gly Ala Gly Gln Gln Gly Pro Gly Ser Gln Gly Pro Gly Gly Gln
                 1475                1480                1485

Gly Pro Tyr Gly Pro Gly Ala Gly Gln Gln Gly Pro Gly Ser Gln
                 1490                1495                1500

Gly Pro Gly Ser Gly Gly Gln Gln Gly Pro Gly Gly Gln Gly Pro
                 1505                1510                1515

Tyr Gly Pro Ser Ala Ala Ala Ala Ala Ala Ala Gly Gly Tyr
                 1520                1525                1530

Gly Pro Gly Ala Gly Gln Gln Gly Pro Gly Ser Gln Gly Pro Gly
                 1535                1540                1545

Ser Gly Gly Gln Gln Gly Pro Gly Ser Gln Gly Pro Gly Ser Gly
                 1550                1555                1560

Gly Gln Gln Gly Pro Gly Gly Gln Gly Pro Tyr Gly Pro Ser Ala
                 1565                1570                1575

Ala Ala Ala Ala Ala Ala Ala Gly Gly Tyr Gly Pro Gly Ala
                 1580                1585                1590

Gly Gln Gln Gly Pro Gly Ser Gln Gly Pro Gly Ser Gly Gly Gln
                 1595                1600                1605

Gln Gly Pro Gly Gly Gln Gly Pro Tyr Gly Pro Gly Ala Ala Ala
                 1610                1615                1620

Ala Ala Ala Ala Val Gly Gly Tyr Gly Pro Gly Ala Gly Gln Gln
                 1625                1630                1635

Gly Pro Gly Ser Gln Gly Pro Gly Ser Gly Gly Gln Gln Gly Pro
                 1640                1645                1650

Gly Gly Gln Gly Pro Tyr Gly Pro Ser Ala Ala Ala Ala Ala Ala
                 1655                1660                1665
```

```
Ala Ala Gly Gly Tyr Gly Pro Gly Ala Gly Gln Gln Gly Pro Gly
    1670                1675                1680

Ser Gln Gly Pro Gly Ser Gly Gly Gln Gln Gly Pro Gly Gly Gln
    1685                1690                1695

Gly Pro Tyr Gly Pro Ser Ala Ala Ala Ala Ala Ala Ala Ala Gly
    1700                1705                1710

Gly Tyr Gly Pro Gly Ala Gly Gln Gln Gly Pro Gly Ser Gly Gly
    1715                1720                1725

Gln Gln Gly Pro Gly Gly Gln Gly Pro Tyr Gly Ser Gly Gln Gln
    1730                1735                1740

Gly Pro Gly Gly Ala Gly Gln Gln Gly Pro Gly Gly Gln Gly Pro
    1745                1750                1755

Tyr Gly Pro Gly Ala Ala Ala Ala Ala Ala Ala Ala Gly Gly
    1760                1765                1770

Tyr Gly Pro Gly Ala Gly Gln Gln Gly Pro Gly Gly Ala Gly Gln
    1775                1780                1785

Gln Gly Pro Gly Ser Gln Gly Pro Gly Gly Gln Gly Pro Tyr Gly
    1790                1795                1800

Pro Gly Ala Gly Gln Gln Gly Pro Gly Ser Gln Gly Pro Gly Ser
    1805                1810                1815

Gly Gly Gln Gln Gly Pro Gly Gly Gln Gly Pro Tyr Gly Pro Ser
    1820                1825                1830

Ala Ala Ala Ala Ala Ala Ala Gly Gly Tyr Gly Pro Gly Ala
    1835                1840                1845

Gly Gln Gln Gly Pro Gly Ser Gln Gly Pro Gly Ser Gly Gly Gln
    1850                1855                1860

Gln Gly Pro Gly Gly Gln Gly Pro Tyr Gly Pro Ser Ala Ala Ala
    1865                1870                1875

Ala Ala Ala Ala Ala Gly Gly Tyr Gly Pro Gly Ala Gly Gln Gln
    1880                1885                1890

Gly Pro Gly Ser Gly Gly Gln Gln Gly Pro Gly Gly Gln Gly Pro
    1895                1900                1905

Tyr Gly Ser Gly Gln Gln Gly Pro Gly Gly Ala Gly Gln Gln Gly
    1910                1915                1920

Pro Gly Gly Gln Gly Pro Tyr Gly Gly Gly Tyr Gly Pro Gly Ala
    1925                1930                1935

Gly Gln Gln Gly Pro Gly Ser Gln Gly Pro Gly Ser Gly Gly Gln
    1940                1945                1950

Gln Gly Pro Gly Gly Gln Gly Pro Tyr Gly Pro Ser Ala Ala Ala
    1955                1960                1965

Ala Ala Ala Ala Ala Gly Pro Gly Ala Arg Arg Gln Gly Pro Gly
    1970                1975                1980

Ser Gln Gly Pro Gly Ser Gly Gly Gln Gln Gly Pro Gly Gly Gln
    1985                1990                1995

Gly Pro Tyr Gly Ser Gly Gln Gln Gly Pro Gly Gly Ala Gly Gln
    2000                2005                2010

Gln Gly Pro Gly Gly Gln Gly Pro Tyr Gly Pro Gly Ala Ala Ala
    2015                2020                2025

Ala Ala Ala Ala Ala Ala Gly Gly Tyr Gly Pro Gly Ala Gly Gln
    2030                2035                2040

Gln Gly Pro Gly Gly Ala Gly Gln Gln Gly Pro Gly Ser Gln Gly
    2045                2050                2055
```

```
Pro Gly Gly Gln Gly Pro Tyr Gly Pro Gly Ala Gly Gln Gln Gly
    2060                2065                2070
Pro Gly Ser Gln Gly Pro Gly Ser Gly Gly Gln Gln Gly Pro Gly
    2075                2080                2085
Gly Gln Gly Pro Tyr Gly Pro Ser Ala Ala Ala Ala Ala Ala Ala
    2090                2095                2100
Ala Ala Gly Gly Tyr Gly Pro Gly Ala Gly Gln Gln Gly Pro Gly
    2105                2110                2115
Ser Gln Gly Pro Gly Ser Gly Gln Gln Gly Pro Gly Gly Gln
    2120                2125                2130
Gly Pro Tyr Gly Pro Gly Ala Ala Ala Ala Ala Ala Val Gly
    2135                2140                2145
Gly Tyr Gly Pro Gly Ala Gly Gln Gln Gly Pro Gly Ser Gln Gly
    2150                2155                2160
Pro Gly Ser Gly Gly Gln Gln Gly Pro Gly Gly Gln Gly Pro Tyr
    2165                2170                2175
Gly Pro Ser Ala Ala Ala Ala Ala Ala Ala Gly Gly Tyr Gly
    2180                2185                2190
Pro Gly Ala Gly Gln Gln Gly Pro Gly Ser Gln Gly Pro Gly Ser
    2195                2200                2205
Gly Gly Gln Gln Gly Pro Gly Gly Gln Gly Pro Tyr Gly Pro Ser
    2210                2215                2220
Ala Ala Ala Ala Ala Ala Ala Gly Gly Tyr Gly Pro Gly Ala
    2225                2230                2235
Gly Gln Gln Gly Pro Gly Ser Gly Gly Gln Gln Gly Pro Gly Gly
    2240                2245                2250
Gln Gly Pro Tyr Gly Ser Gly Gln Gln Gly Pro Gly Gly Ala Gly
    2255                2260                2265
Gln Gln Gly Pro Gly Gly Gln Gly Pro Tyr Gly Pro Gly Ala Ala
    2270                2275                2280
Ala Ala Ala Ala Ala Ala Gly Gly Tyr Gly Pro Gly Ala Gly
    2285                2290                2295
Gln Gln Gly Pro Gly Gly Ala Gly Gln Gln Gly Pro Gly Ser Gln
    2300                2305                2310
Gly Pro Gly Gly Gln Gly Pro Tyr Gly Pro Gly Ala Gly Gln Gln
    2315                2320                2325
Gly Pro Gly Ser Gln Gly Pro Gly Ser Gly Gly Gln Gly Pro
    2330                2335                2340
Gly Gly Gln Gly Pro Tyr Gly Pro Ser Ala Ala Ala Ala Ala
    2345                2350                2355
Ala Ala Gly Pro Gly Ala Gly Arg Gln Gly Pro Gly Ser Gln Gly
    2360                2365                2370
Pro Gly Ser Gly Gly Gln Gln Gly Pro Gly Gln Gly Pro Tyr
    2375                2380                2385
Gly Pro Ser Ala Ala Ala Ala Ala Ala Ala Gly Pro Gly Ala
    2390                2395                2400
Arg Arg Gln Gly Pro Gly Ser Gln Gly Pro Gly Ser Gly Gly Gln
    2405                2410                2415
Gln Gly Pro Gly Gly Gln Gly Pro Tyr Gly Ser Gly Gln Gln Gly
    2420                2425                2430
Pro Gly Gly Ala Gly Gln Gln Gly Pro Gly Gly Gln Gly Pro Tyr
    2435                2440                2445
Gly Pro Gly Ala Ala Ala Ala Ala Ala Ala Ala Gly Gly Tyr
```

-continued

```
            2450                2455                2460

Gly Pro Gly Ala Gly Gln Gln Gly Pro Gly Gly Ala Gly Gln Gln
            2465                2470                2475

Gly Pro Gly Ser Gln Gly Pro Gly Gly Gln Gly Pro Tyr Gly Pro
            2480                2485                2490

Gly Ala Gly Gln Gln Gly Pro Gly Ser Gln Gly Pro Gly Ser Gly
            2495                2500                2505

Gly Gln Gln Gly Pro Gly Ser Gln Gly Pro Tyr Gly Pro Ser Ala
            2510                2515                2520

Ala Ala Ala Ala Ala Ala Ala Gly Gly Tyr Gly Pro Gly Ala Gly
            2525                2530                2535

Gln Gln Gly Pro Gly Ser Gln Gly Pro Gly Ser Gly Gly Gln Gln
            2540                2545                2550

Gly Pro Gly Gly Gln Gly Pro Tyr Gly Pro Ser Ala Ala Ala Ala
            2555                2560                2565

Ala Ala Ala Ala Gly Gly Tyr Gly Pro Gly Ala Gly Gln Gln Gly
            2570                2575                2580

Pro Gly Ser Gly Gly Gln Gln Gly Pro Gly Gly Gln Gly Pro Tyr
            2585                2590                2595

Gly Ser Gly Gln Gln Gly Pro Gly Gly Ala Gly Gln Gln Gly Pro
            2600                2605                2610

Gly Gly Gln Gly Pro Tyr Gly Pro Gly Ala Ala Ala Ala Ala Ala
            2615                2620                2625

Ala Ala Ala Gly Gly Tyr Gly Pro Gly Ala Gly Gln Gln Gly Pro
            2630                2635                2640

Gly Ser Gln Gly Pro Gly Ser Gly Gly Gln Gln Gly Pro Gly Ser
            2645                2650                2655

Gln Gly Pro Gly Ser Gly Gly Gln Gln Gly Pro Gly Gly Gln Gly
            2660                2665                2670

Pro Tyr Gly Pro Ser Ala Ala Ala Ala Ala Ala Ala Ala Ala Gly
            2675                2680                2685

Gly Tyr Gly Pro Gly Ala Gly Gln Gln Gly Pro Gly Ser Gln Gly
            2690                2695                2700

Pro Gly Ser Gly Gly Gln Gln Gly Pro Gly Gly Gln Gly Pro Tyr
            2705                2710                2715

Gly Pro Gly Ala Ala Ala Ala Ala Ala Val Gly Gly Tyr Gly
            2720                2725                2730

Pro Gly Ala Gly Gln Gln Gly Pro Gly Ser Gln Gly Pro Gly Ser
            2735                2740                2745

Gly Gly Gln Gln Gly Pro Gly Gly Gln Gly Pro Tyr Gly Pro Ser
            2750                2755                2760

Ala Ala Ala Ala Ala Ala Ala Gly Gly Tyr Gly Pro Gly Ala
            2765                2770                2775

Gly Gln Gln Gly Pro Gly Ser Gln Gly Pro Gly Ser Gly Gly Gln
            2780                2785                2790

Gln Gly Pro Gly Gly Gln Gly Pro Tyr Gly Pro Ser Ala Ala Ala
            2795                2800                2805

Ala Ala Ala Ala Ala Gly Gly Tyr Gly Pro Gly Ala Gly Gln Gln
            2810                2815                2820

Gly Pro Gly Ser Gly Gly Gln Gln Gly Pro Gly Gly Gln Gly Pro
            2825                2830                2835

Tyr Gly Ser Gly Gln Gln Gly Pro Gly Gly Ala Gly Gln Gln Gly
            2840                2845                2850
```

-continued

Pro Gly Gly Gln Gly Pro Tyr Gly Pro Gly Ala Ala Ala Ala Ala
2855                     2860                2865

Ala Ala Ala Ala Gly Gly Tyr Gly Pro Gly Ala Gly Gln Gln Gly
2870                     2875                2880

Pro Gly Gly Ala Gly Gln Gln Gly Pro Gly Ser Gln Gly Pro Gly
2885                     2890                2895

Gly Gln Gly Pro Tyr Gly Pro Gly Ala Gly Gln Gln Gly Pro Gly
2900                     2905                2910

Ser Gln Gly Pro Gly Ser Gly Gly Gln Gln Gly Pro Gly Gly Gln
2915                     2920                2925

Gly Pro Tyr Gly Pro Ser Ala Ala Ala Ala Ala Ala Ala Ala Gly
2930                     2935                2940

Gly Tyr Gly Pro Gly Ala Gly Gln Gln Gly Pro Gly Ser Gln Gly
2945                     2950                2955

Pro Gly Ser Gly Gly Gln Gln Gly Pro Gly Gly Gln Gly Pro Tyr
2960                     2965                2970

Gly Pro Gly Ala Ala Ala Ala Ala Ala Ala Val Gly Gly Tyr Gly
2975                     2980                2985

Pro Gly Ala Gly Gln Gln Gly Pro Gly Ser Gln Gly Pro Gly Ser
2990                     2995                3000

Gly Gly Gln Gln Gly Pro Gly Gly Gln Gly Pro Tyr Gly Pro Ser
3005                     3010                3015

Ala Ala Ala Ala Ala Ala Ala Gly Gly Tyr Gly Pro Gly Ala
3020                     3025                3030

Gly Gln Gln Gly Pro Gly Ser Gln Gly Pro Gly Ser Gly Gly Gln
3035                     3040                3045

Gln Gly Pro Gly Gly Gln Gly Pro Tyr Gly Pro Ser Ala Ala Ala
3050                     3055                3060

Ala Ala Ala Ala Ala Gly Gly Tyr Gly Pro Gly Ala Gly Gln Gln
3065                     3070                3075

Gly Pro Gly Ser Gly Gly Gln Gln Gly Pro Gly Gly Gln Gly Pro
3080                     3085                3090

Tyr Gly Ser Gly Gln Gln Gly Pro Gly Gly Ala Gly Gln Gln Gly
3095                     3100                3105

Pro Gly Gly Gln Gly Pro Tyr Gly Pro Gly Ala Ala Ala Ala Ala
3110                     3115                3120

Ala Ala Ala Ala Gly Gly Tyr Gly Pro Gly Ala Gly Gln Gln Gly
3125                     3130                3135

Pro Gly Gly Ala Gly Gln Gln Gly Pro Gly Ser Gln Gly Pro Gly
3140                     3145                3150

Gly Gln Gly Pro Tyr Gly Pro Gly Ala Gly Gln Gln Gly Pro Gly
3155                     3160                3165

Ser Gln Gly Pro Gly Ser Gly Gly Gln Gln Gly Pro Gly Gly Gln
3170                     3175                3180

Gly Pro Tyr Gly Pro Ser Ala Ala Ala Ala Ala Ala Ala Ala Gly
3185                     3190                3195

Gly Tyr Gly Pro Gly Ala Gly Gln Gln Gly Pro Gly Ser Gln Gly
3200                     3205                3210

Pro Gly Ser Gly Gly Gln Gln Gly Pro Gly Gly Gln Gly Pro Tyr
3215                     3220                3225

Gly Pro Ser Ala Ala Ala Ala Ala Ala Ala Ala Gly Gly Tyr Gly
3230                     3235                3240

```
Pro Gly Ala Gly Gln Gln Gly Pro Ser Ser Gln Ala Pro Val Ala
    3245                3250                3255

Ser Ala Ala Ala Ser Arg Leu Ser Ser Pro Gln Ala Ser Ala Arg
3260                3265                3270

Val Ser Ser Ala Val Ser Thr Leu Val Ser Ser Gly Pro Thr Ser
3275                3280                3285

Pro Ala Ala Leu Ser Asn Ala Ile Ser Ser Val Val Ser Gln Val
    3290                3295                3300

Ser Ala Ser Asn Pro Gly Leu Ser Gly Cys Asp Val Leu Val Gln
3305                3310                3315

Ala Leu Leu Glu Ile Val Ser Ala Leu Val His Ile Leu Gly Ser
    3320                3325                3330

Ser Ser Ile Gly Gln Ile Asn Tyr Ala Ala Ser Ser Gln Tyr Ala
3335                3340                3345

Gln Met Val Gly Asn Ser Val Ala Gln Ala Leu Gly
    3350                3355                3360

<210> SEQ ID NO 44
<211> LENGTH: 3129
<212> TYPE: PRT
<213> ORGANISM: Latrodectus hesperus

<400> SEQUENCE: 44

Met Thr Trp Ser Thr Arg Leu Ala Leu Ser Phe Leu Phe Val Leu Cys
1               5                   10                  15

Thr Gln Ser Leu Tyr Ala Leu Ala Gln Ala Asn Thr Pro Trp Ser Ser
            20                  25                  30

Lys Ala Asn Ala Asp Ala Phe Ile Asn Ser Phe Ile Ser Ala Ala Ser
        35                  40                  45

Asn Thr Gly Ser Phe Ser Gln Asp Gln Met Glu Asp Met Ser Leu Ile
    50                  55                  60

Gly Asn Thr Leu Met Ala Ala Met Asp Asn Met Gly Gly Arg Ile Thr
65                  70                  75                  80

Pro Ser Lys Leu Gln Ala Leu Asp Met Ala Phe Ala Ser Ser Val Ala
                85                  90                  95

Glu Ile Ala Ala Ser Glu Gly Gly Asp Leu Gly Val Thr Thr Asn Ala
            100                 105                 110

Ile Ala Asp Ala Leu Thr Ser Ala Phe Tyr Gln Thr Thr Gly Val Val
        115                 120                 125

Asn Ser Arg Phe Ile Ser Glu Ile Arg Ser Leu Ile Gly Met Phe Ala
    130                 135                 140

Gln Ala Ser Ala Asn Asp Val Tyr Ala Ser Ala Gly Ser Ser Gly Gly
145                 150                 155                 160

Gly Gly Tyr Gly Ala Ser Ser Ala Ser Ala Ser Ala Ser Ala Ala
                165                 170                 175

Ala Pro Ser Gly Val Ala Tyr Gln Ala Pro Gln Ala Gln Ile Ser
            180                 185                 190

Phe Thr Leu Arg Gly Gln Gln Pro Val Ser Tyr Gly Gln Gly Gly Ala
    195                 200                 205

Gly Pro Gly Gly Ala Gly Ala Ala Ala Ala Ala Ala Ala Gly
    210                 215                 220

Gly Ala Gly Gln Gly Gly Gln Gly Gly Tyr Gly Gln Gly Gly Tyr Gly
225                 230                 235                 240

Gln Gly Gly Ala Gly Gln Gly Gly Ser Gly Ala Ala Ala Ala Ala Ala
                245                 250                 255
```

-continued

```
Ala Ala Ala Gly Gly Thr Gly Gln Gly Gly Ala Gly Gln Gly Gly Ala
            260                 265                 270
Gly Ala Ala Ala Ala Ala Ala Ala Ala Gly Gly Ala Gly Gln Gly
        275                 280                 285
Gly Gln Gly Gly Tyr Gly Gln Gly Gly Tyr Gly Gln Gly Gly Thr Gly
        290                 295                 300
Gln Gly Gly Ala Gly Ala Ala Ala Ala Ala Ala Ala Gly Gly Ala
305                 310                 315                 320
Gly Gln Gly Gly Gln Gly Gly Tyr Gly Gln Gly Gly Tyr Gly Gln Gly
                325                 330                 335
Gly Tyr Gly Gln Gly Gly Ser Gly Ala Ala Ala Ala Ala Ala Ala
            340                 345                 350
Ala Gly Gly Ala Gly Gln Gly Gly Gln Gly Gly Tyr Gly Gln Gly Gly
            355                 360                 365
Tyr Gly Gln Gly Gly Ala Gly Gln Gly Gly Ala Gly Ala Ala Ala Ala
    370                 375                 380
Ala Ala Ala Ala Ala Gly Gly Ala Gly Gln Gly Gly Tyr Gly Arg Gly
385                 390                 395                 400
Gly Ala Gly Gln Gly Gly Ala Ala Ala Ala Ala Ala Ala Ala Ala Gly
                405                 410                 415
Ala Gly Gln Gly Gly Tyr Gly Gly Gln Gly Ala Gly Gln Gly Gly Ser
            420                 425                 430
Gly Ala Ala Ala Ala Ala Ala Ala Gly Gly Ala Gly Gln Gly Gly
            435                 440                 445
Gln Gly Gly Tyr Gly Gln Gly Gly Tyr Gly Gln Gly Gly Ser Gly Ala
    450                 455                 460
Ala Ala Ala Ala Ala Ala Ala Gly Gly Ala Gly Gln Gly Gly Gln Gly
465                 470                 475                 480
Gly Tyr Gly Gln Gly Gly Tyr Gly Gln Gly Gly Ala Gly Gln Gly Gly
                485                 490                 495
Ala Gly Ala Ala Ala Ala Ala Ala Ala Gly Gly Ala Gly Gln Gly
            500                 505                 510
Gly Gln Gly Gly Tyr Gly Gln Gly Gly Tyr Gly Gln Gly Gly Ala Gly
        515                 520                 525
Gln Gly Gly Ala Gly Ala Ala Ala Ala Ala Ala Ala Ala Gly Gly Ala
530                 535                 540
Gly Gln Gly Gly Gln Gly Gly Tyr Gly Gln Gly Gly Tyr Gly Gln Gly
545                 550                 555                 560
Gly Ala Gly Gln Gly Gly Ala Gly Ala Ala Ala Ala Ala Ala Ala
            565                 570                 575
Gly Gly Ala Gly Gln Gly Gly Gln Gly Gly Tyr Gly Gln Gly Gly Tyr
            580                 585                 590
Gly Gln Gly Gly Ala Gly Gln Gly Gly Ala Ala Ala Ala Ala Ala
        595                 600                 605
Ala Ala Gly Gly Ala Gly Gln Gly Gly Tyr Gly Arg Gly Gly Ala Gly
    610                 615                 620
Gln Gly Gly Ala Ala Ala Ala Gly Ala Gly Gln Gly Gly Tyr Gly
625                 630                 635                 640
Gly Gln Gly Ala Gly Gln Gly Gly Ala Gly Ala Ala Ala Ala Ala
                645                 650                 655
Ala Ala Gly Gly Ala Gly Gln Gly Gly Gln Gly Gly Tyr Gly Arg Gly
            660                 665                 670
```

-continued

Gly Tyr Gly Gln Gly Gly Ala Gly Gln Gly Gly Ala Gly Ala Ala Ala
                675                 680                 685

Ala Ala Ala Ala Ala Gly Ala Gly Gln Gly Gly Gln Gly Gly Tyr
690                 695                 700

Gly Gln Gly Gly Tyr Gly Gln Gly Gly Ala Gly Gln Gly Gly Ala Ala
705                 710                 715                 720

Ala Ala Ala Ala Ala Gly Gly Ala Gly Gln Gly Gly Tyr Gly Arg
            725                 730                 735

Gly Gly Ala Gly Gln Gly Gly Ala Ala Ala Ala Ala Ala Ala
            740                 745                 750

Gly Ala Gly Gln Gly Gly Tyr Gly Gly Gln Gly Ala Gly Gln Gly Gly
            755                 760                 765

Ala Gly Ala Ala Ala Ala Ala Ala Ala Gly Gly Ala Gly Gln Gly
770                 775                 780

Gly Gln Gly Asp Tyr Gly Arg Gly Gly Tyr Gly Gln Gly Gly Ala Gly
785                 790                 795                 800

Gln Gly Gly Ala Gly Ala Ala Ala Ala Ala Ala Ala Gly Gly Ala
            805                 810                 815

Gly Gln Gly Gly Gln Gly Gly Tyr Gly Gln Gly Gly Tyr Gly Gln Gly
            820                 825                 830

Gly Ala Gly Gln Gly Gly Ala Ala Ala Ala Ser Ala Ala Ala
            835                 840                 845

Gly Gly Ala Gly Gln Gly Gly Tyr Gly Arg Gly Gly Ala Gly Gln Gly
            850                 855                 860

Gly Ala Ala Ala Ala Gly Ala Gly Gln Gly Gly Tyr Gly Gly Gln
865                 870                 875                 880

Gly Ala Gly Gln Gly Gly Ala Gly Ala Ala Ala Ala Ala Ala
            885                 890                 895

Gly Gly Ala Gly Gln Gly Gly Gln Gly Gly Tyr Gly Arg Gly Gly Tyr
            900                 905                 910

Gly Gln Gly Gly Ala Gly Gln Gly Gly Ala Gly Ala Ala Ala Ala
            915                 920                 925

Thr Ala Ala Gly Gly Ala Gly Gln Gly Gly Gln Gly Gly Tyr Gly Gln
930                 935                 940

Gly Gly Tyr Gly Gln Gly Gly Ala Gly Gln Gly Gly Ala Ala Ala Ala
945                 950                 955                 960

Ala Ala Ala Ala Ala Gly Gly Ala Gly Gln Gly Gly Tyr Gly Arg Gly
            965                 970                 975

Gly Ala Gly Gln Gly Gly Ala Ala Ala Ala Ala Ala Ala Gly
            980                 985                 990

Ala Gly Gln Gly Gly Tyr Gly Gly Gln Gly Ala Gly Gln Gly Gly Ala
            995                 1000                1005

Gly Ala Ala Ala Ala Ala Ala Gly Gly Ala Gly Gln Gly Gly Gln
            1010                1015                1020

Gly Gly Tyr Gly Arg Gly Gly Tyr Gly Gln Gly Gly Ala Gly Gln
            1025                1030                1035

Gly Gly Ala Gly Ala Ala Ala Ala Ala Ala Ala Gly Gly Ala
            1040                1045                1050

Gly Gln Gly Gly Gln Gly Gly Tyr Gly Gln Gly Gly Tyr Gly Gln
            1055                1060                1065

Gly Gly Ala Gly Gln Gly Gly Ala Ala Ala Ala Ala Ala Ala
            1070                1075                1080

Ala Gly Gly Ala Gly Gln Gly Gly Tyr Gly Arg Gly Gly Ala Gly

```
                1085                1090                1095
Gln Gly Gly Ala Ala Ala  Ala Gly Ala Gly Gln  Gly Gly Tyr
    1100                1105                1110

Gly Gly Gln Gly Ala Gly  Gln Gly Gly Ala Gly  Ala Ala Ala
    1115                1120                1125

Ala Ser Arg Gly Ala Gly  Gln Gly Gly Gln Gly  Tyr Gly Arg
    1130                1135                1140

Gly Gly Tyr Gly Gln Gly  Gly Ala Gly Gln Gly  Gly Ala Gly Ala
    1145                1150                1155

Ala Ala Ala Ala Ala Ala  Ala Gly Gly Ala Gly  Gln Gly Gly Gln
    1160                1165                1170

Gly Gly Tyr Gly Gln Gly  Gly Tyr Gln Gly Gly  Ala Gly Gln
    1175                1180                1185

Gly Gly Ala Ala Ala Ala  Ala Ala Ala Gly Gly  Ala Gly Gln
    1190                1195                1200

Gly Gly Tyr Gly Arg Gly  Gly Ala Gly Gln Gly  Gly Ala Ala Ala
    1205                1210                1215

Ala Ala Gly Ala Gly Gln  Gly Gly Tyr Gly Gly  Gln Gly Ala Gly
    1220                1225                1230

Gln Gly Gly Ala Gly Ala  Ala Ala Ala Ala Ala  Ala Gly Gly
    1235                1240                1245

Ala Gly Gln Gly Gly Gln  Gly Gly Tyr Gly Arg  Gly Gly Tyr Gly
    1250                1255                1260

Gln Gly Gly Ala Gly Gln  Gly Gly Ala Gly Ala  Ala Ala Ala
    1265                1270                1275

Ala Ala Ala Gly Gly Ala  Gly Gln Gly Gly Gln  Gly Gly Tyr Gly
    1280                1285                1290

Gln Gly Gly Tyr Gly Gln  Gly Gly Ala Gly Gln  Gly Gly Ala Ala
    1295                1300                1305

Ala Ala Ala Ala Ala Ala  Ala Gly Gly Ala Gly  Gln Gly Gly Tyr
    1310                1315                1320

Gly Arg Gly Gly Ala Gly  Gln Gly Gly Ala Ala  Ala Ala Ala Ala
    1325                1330                1335

Ala Ala Ala Gly Ser Gly  Gln Gly Gly Tyr Gly  Gly Gln Gly Ala
    1340                1345                1350

Gly Gln Gly Gly Ala Gly  Ala Ala Ala Ala Ala  Ala Ala Ala Gly
    1355                1360                1365

Gly Ala Gly Gln Gly Gly  Gln Gly Gly Tyr Gly  Arg Gly Gly Tyr
    1370                1375                1380

Gly Gln Gly Gly Ala Gly  Gln Gly Gly Ala Gly  Ala Ala Ala Ala
    1385                1390                1395

Ala Ala Ala Ala Gly Gly  Ala Gly Gln Gly Gly  Gln Gly Gly Tyr
    1400                1405                1410

Gly Gln Gly Gly Tyr Gly  Gln Gly Gly Ala Gly  Gln Gly Gly Ala
    1415                1420                1425

Ala Ala Ala Ala Ala Ala  Ala Ala Gly Gly Ala  Gly Gln Gly
    1430                1435                1440

Gly Tyr Gly Arg Gly Gly  Ala Gly Gln Gly Gly  Ala Ala Ala Ala
    1445                1450                1455

Ala Gly Ala Gly Gln Gly  Gly Tyr Gly Gly Gln  Gly Ala Gly Gln
    1460                1465                1470

Gly Gly Ala Gly Ala Ala  Ala Ala Ala Ala Ala  Ala Gly Gly Ala
    1475                1480                1485
```

-continued

Gly Gln Gly Gly Gln Gly Gly Tyr Gly Arg Gly Gly Tyr Gly Gln
    1490                1495                1500

Gly Gly Ala Gly Gln Gly Gly Ala Gly Thr Ala Ala Ala Ala Ala
    1505                1510                1515

Ala Ala Gly Gly Ala Gly Gln Gly Gly Gln Gly Gly Tyr Gly Gln
    1520                1525                1530

Gly Gly Tyr Gly Gln Gly Gly Ala Gly Gln Gly Gly Ala Ala Ala
    1535                1540                1545

Ala Ala Ala Ala Ala Ala Gly Gly Ala Gly Gln Gly Gly Tyr Gly
    1550                1555                1560

Arg Gly Gly Ala Gly Gln Gly Gly Ala Ala Ala Ala Ala Ala Ala
    1565                1570                1575

Ala Ala Gly Ala Gly Gln Gly Gly Tyr Gly Gly Gln Gly Ala Gly
    1580                1585                1590

Gln Gly Gly Ala Gly Ala Ala Ala Ala Ala Ala Ala Ala Gly Gly
    1595                1600                1605

Ala Gly Gln Gly Gly Gln Gly Gly Tyr Gly Arg Gly Gly Tyr Gly
    1610                1615                1620

Gln Gly Gly Ala Gly Gln Gly Gly Ala Gly Ala Ala Ala Ala Ala
    1625                1630                1635

Ala Ala Ala Gly Gly Ala Ser Gln Gly Gly Gln Gly Gly Tyr Gly
    1640                1645                1650

Gln Gly Asp Tyr Gly Gln Gly Gly Ala Gly Gln Gly Gly Ala Ala
    1655                1660                1665

Ala Ala Ala Ala Ala Ala Gly Gly Ala Gly Gln Gly Gly Tyr Gly
    1670                1675                1680

Arg Gly Gly Ala Gly Gln Gly Gly Ala Ala Ala Ala Ala Gly Ala
    1685                1690                1695

Gly Gln Gly Gly Tyr Gly Gly Gln Gly Ala Gly Gln Gly Gly Ala
    1700                1705                1710

Gly Ala Ala Ala Ala Ala Ala Ala Gly Gly Ala Gly Arg Gly
    1715                1720                1725

Gly Gln Gly Gly Tyr Gly Arg Gly Gly Tyr Gly Gln Gly Gly Ala
    1730                1735                1740

Gly Gln Gly Gly Ala Gly Ala Ala Ala Ala Ala Ala Ala Ala Gly
    1745                1750                1755

Gly Ala Gly Gln Gly Gly Gln Gly Gly Tyr Gly Gln Gly Gly Tyr
    1760                1765                1770

Gly Gln Gly Gly Thr Gly Gln Gly Gly Ala Ala Ala Ala Ala Ala
    1775                1780                1785

Ala Ala Ala Gly Gly Ala Gly Gln Gly Gly Tyr Gly Arg Gly Gly
    1790                1795                1800

Ala Gly Gln Gly Gly Ala Ala Ala Ala Ala Ala Ala Ala Ala Gly
    1805                1810                1815

Ala Gly Gln Gly Gly Tyr Gly Gly Gln Gly Ala Gly Gln Gly Gly
    1820                1825                1830

Ala Gly Ala Ala Ala Ala Ala Ala Ala Gly Gly Ala Gly Gln
    1835                1840                1845

Gly Gly Gln Gly Gly Tyr Gly Arg Gly Gly Tyr Gly Gln Gly Gly
    1850                1855                1860

Ala Gly Gln Gly Gly Ala Gly Ala Ala Ala Ala Ala Ala Ala
    1865                1870                1875

```
Gly Gly Ala Gly Gln Gly Gly Gln Gly Gly Tyr Gly Gln Gly Gly
    1880                1885                1890

Tyr Gly Gln Gly Gly Tyr Gly Gln Gly Gly Ala Gly Gln Gly Gly
    1895                1900                1905

Ala Ala Ala Ala Ala Ala Ala Ala Gly Gly Ala Gly Gln Gly Gly
    1910                1915                1920

Tyr Gly Arg Gly Gly Ala Gly Gln Gly Gly Ala Ala Ala Ala Ala
    1925                1930                1935

Gly Ala Gly Gln Gly Gly Tyr Gly Gln Gly Ala Gly Gln Gly
    1940                1945                1950

Gly Ala Gly Ala Ala Ala Ala Ala Ala Ala Gly Gly Ala Gly
    1955                1960                1965

Gln Gly Gly Gln Gly Gly Tyr Gly Arg Gly Gly Tyr Gly Gln Gly
    1970                1975                1980

Gly Ala Gly Gln Gly Gly Ala Gly Ala Ala Ala Ala Ala Ala
    1985                1990                1995

Ala Gly Gly Ala Gly Gln Gly Gln Gly Gly Tyr Gly Gln Gly
    2000                2005                2010

Gly Tyr Gly Gln Gly Gly Ala Gly Gln Gly Gly Ala Ala Ala
    2015                2020                2025

Ala Ala Ala Ala Ala Gly Gly Ala Gly Gln Gly Gly Tyr Gly Arg
    2030                2035                2040

Gly Gly Ala Gly Gln Gly Gly Ala Ala Ala Ala Ala Ala Ala
    2045                2050                2055

Ala Gly Ser Gly Gln Gly Gly Tyr Gly Gly Gln Gly Ala Gly Gln
    2060                2065                2070

Gly Gly Ala Gly Ala Ala Ala Ala Ala Ala Ala Gly Gly Ala
    2075                2080                2085

Gly Gln Gly Gly Gln Gly Gly Tyr Gly Arg Gly Gly Tyr Gly Gln
    2090                2095                2100

Gly Gly Ala Gly Gln Gly Gly Ala Gly Ala Ala Ala Ala Ala Ala
    2105                2110                2115

Ala Ala Gly Gly Ala Gly Gln Gly Gly Gln Gly Gly Tyr Gly Gln
    2120                2125                2130

Gly Gly Tyr Gly Gln Gly Gly Tyr Gly Gln Gly Gly Ala Gly Gln
    2135                2140                2145

Gly Gly Ala Ala Ala Ala Ala Ala Ala Ala Ala Gly Gly Ala
    2150                2155                2160

Gly Gln Gly Gly Tyr Gly Arg Gly Gly Ala Gly Gln Gly Gly Ala
    2165                2170                2175

Ala Ala Ala Ala Gly Ala Gly Gln Gly Gly Tyr Gly Gly Gln Gly
    2180                2185                2190

Ala Gly Gln Gly Gly Ala Gly Ala Ala Ala Ala Ala Ala Ala
    2195                2200                2205

Gly Gly Ala Gly Gln Gly Gly Gln Gly Gly Tyr Gly Arg Gly Gly
    2210                2215                2220

Tyr Gly Gln Gly Gly Ala Gly Gln Gly Gly Ala Gly Ala Ala Ala
    2225                2230                2235

Ala Ala Ala Ala Ala Gly Gly Ala Gly Gln Gly Gly Gln Gly Gly
    2240                2245                2250

Tyr Gly Gln Gly Gly Asn Gly Gln Gly Gly Ala Gly Gln Gly Gly
    2255                2260                2265

Ala Ala Ala Ala Ala Ala Ala Ala Gly Gly Ala Gly Gln Gly Gly
```

```
            2270                2275                2280

Tyr Gly Arg Gly Gly Ala Gly Gln Gly Gly Ala Ala  Ala Ala Ala
        2285                2290                2295

Ala Ala Ala Ala Gly Ala Gly Gln Gly Gly Tyr Gly  Gly Gln Gly
        2300                2305                2310

Ala Gly Gln Gly Gly Ala Gly Ala Ala Ala Ala  Ala Ala Ala
        2315                2320                2325

Gly Gly Ala Gly Gln Gly Gly Gln Gly Gly Tyr Gly  Arg Gly Gly
        2330                2335                2340

Tyr Gly Gln Gly Gly Ala Gly Gln Gly Gly Ala Gly  Ala Ala Ala
        2345                2350                2355

Ala Ala Ala Ala Ala Gly Gly Ala Ser Gln Gly Gly  Gln Gly Gly
        2360                2365                2370

Tyr Gly Gln Gly Asp Tyr Gly Gln Gly Gly Ala Gly  Gln Gly Gly
        2375                2380                2385

Ala Ala Ala Ala Ala Ala Ala Gly Gly Ala Gly  Gln Gly Gly
        2390                2395                2400

Tyr Gly Arg Gly Gly Ala Gly Gln Gly Gly Ala Ala  Ala Ala Ala
        2405                2410                2415

Gly Ala Gly Gln Gly Gly Tyr Gly Gly Gln Gly Ala  Gly Gln Gly
        2420                2425                2430

Gly Ala Gly Ala Ala Ala Ala Ala Ala Ala Gly  Gly Ala Gly
        2435                2440                2445

Arg Gly Gly Gln Gly Gly Tyr Gly Arg Gly Gly Tyr  Gly Gln Gly
        2450                2455                2460

Gly Ala Gly Gln Gly Gly Ala Gly Ala Ala Ala Ala  Ala Ala Ala
        2465                2470                2475

Ala Gly Gly Ala Gly Gln Gly Gly Gln Gly Gly Tyr  Gly Gln Gly
        2480                2485                2490

Gly Tyr Gly Gln Gly Gly Ala Gly Gln Gly Gly Ala  Ala Ala Ala
        2495                2500                2505

Ala Ala Ala Ala Ala Gly Gly Ala Gly Gln Gly Gly  Tyr Gly Arg
        2510                2515                2520

Gly Gly Ala Gly Gln Gly Gly Ala Ala Ala Ala  Gly Ala Gly
        2525                2530                2535

Gln Gly Gly Tyr Gly Gly Gln Gly Ala Gly Gln Gly  Gly Ala Gly
        2540                2545                2550

Ala Ala Ala Ala Ala Ala Ala Gly Gly Ala Gly  Arg Gly Gly
        2555                2560                2565

Gln Gly Gly Tyr Gly Arg Gly Gly Tyr Gly Gln Gly  Gly Ala Gly
        2570                2575                2580

Gln Gly Gly Ala Gly Ala Ala Ala Ala Ala Ala  Ala Gly Gly
        2585                2590                2595

Ala Gly Gln Gly Gly Gln Gly Gly Tyr Gly Gln Gly  Gly Tyr Gly
        2600                2605                2610

Gln Gly Gly Ala Gly Gln Gly Gly Ala Ala Ala Ala  Ala Ala Ala
        2615                2620                2625

Ala Val Gly Gly Ala Gly Gln Gly Gly Tyr Gly Arg  Gly Gly Ala
        2630                2635                2640

Gly Gln Gly Gly Ala Ala Ala Ala Ala Ala Ala  Ala Ala Gly
        2645                2650                2655

Ser Gly Gln Gly Gly Tyr Gly Gly Gln Gly Ala Gly  Gln Gly Gly
        2660                2665                2670
```

-continued

```
Ala Gly Ala Ala Ala Ala Ala Ala Ala Gly Gly Ala Gly Gln
    2675                2680                2685

Gly Gly Gln Gly Gly Tyr Gly Gly Gly Tyr Gly Gln Gly Gly
    2690                2695                2700

Ala Gly Gln Gly Gly Ala Gly Ala Ala Ala Ala Ala Ala Ala
    2705                2710                2715

Gly Gly Ala Gly Gln Gly Gly Gln Gly Gly Tyr Gly Gln Gly Gly
    2720                2725                2730

Tyr Gly Gln Gly Gly Ala Gly Gln Gly Gly Ala Ala Ala Ala Ala
    2735                2740                2745

Ala Ala Ala Ala Gly Gly Ala Gly Gln Gly Gly Tyr Gly Arg Gly
    2750                2755                2760

Gly Ala Gly Gln Gly Gly Ala Ala Ala Thr Gly Ala Gly Gln
    2765                2770                2775

Gly Gly Tyr Gly Gly Gln Gly Ala Gly Gln Gly Gly Ala Gly Ala
    2780                2785                2790

Ala Ala Ala Ala Ala Ala Gly Gly Ala Gly Gln Gly Gly Gln
    2795                2800                2805

Gly Gly Tyr Gly Arg Gly Gly Tyr Gly Gln Gly Gly Ala Gly Gln
    2810                2815                2820

Gly Gly Ala Gly Ala Ala Ala Ala Ala Ala Ala Gly Gly Ala
    2825                2830                2835

Gly Gln Gly Gly Gln Gly Gly Tyr Gly Gln Gly Gly Tyr Gly Gln
    2840                2845                2850

Gly Gly Ala Gly Gln Gly Gly Ala Ala Ala Ala Ala Ala Ala
    2855                2860                2865

Gly Gly Ala Gly Gln Gly Gly Tyr Gly Arg Gly Gly Ala Gly Gln
    2870                2875                2880

Gly Gly Ala Ala Ala Ala Ala Ala Ala Ala Gly Ala Gly Gln
    2885                2890                2895

Gly Gly Tyr Gly Gly Gln Gly Ala Gly Gln Gly Gly Ala Gly Ala
    2900                2905                2910

Ala Ala Ala Ala Ala Ala Gly Gly Ala Gly Gln Gly Gly Gln
    2915                2920                2925

Gly Gly Tyr Gly Arg Gly Gly Tyr Gly Gln Gly Gly Ala Gly Gln
    2930                2935                2940

Gly Gly Ala Gly Ala Ala Ala Gly Gly Ala Gly Gln Gly Gly
    2945                2950                2955

Gln Gly Gly Tyr Gly Gln Gly Gly Tyr Gly Gln Gly Gly Ala Gly
    2960                2965                2970

Gln Gly Gly Ala Ala Ala Ala Ala Ala Ala Ala Ala Gly Gly
    2975                2980                2985

Ala Gly Gln Gly Gly Tyr Gly Gly Tyr Gly Gln Gln Gly Gly Ala
    2990                2995                3000

Gly Ala Ala Ala Ala Ala Ser Gly Pro Gly Gln Ile Tyr Tyr
    3005                3010                3015

Gly Pro Gln Ser Val Ala Ala Pro Ala Ala Ala Ala Ser Ala
    3020                3025                3030

Leu Ala Ala Pro Ala Thr Ser Ala Arg Ile Ser Ser His Ala Ser
    3035                3040                3045

Ala Leu Leu Ser Asn Gly Pro Thr Asn Pro Ala Ser Ile Ser Asn
    3050                3055                3060
```

```
Val Ile Ser Asn Ala Val Ser Gln Ile Ser Ser Ser Asn Pro Gly
    3065                3070                3075

Ala Ser Ala Cys Asp Val Leu Val Gln Ala Leu Leu Glu Leu Val
    3080                3085                3090

Thr Ala Leu Leu Thr Ile Ile Gly Ser Ser Asn Ile Gly Ser Val
    3095                3100                3105

Asn Tyr Asp Ser Ser Gly Gln Tyr Ala Gln Val Val Thr Gln Ser
    3110                3115                3120

Val Gln Asn Ala Phe Ala
    3125

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tactacaggc tggctgttcc                                                    20

<210> SEQ ID NO 46
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ctcacttaat cttctgtact ctgaagaagt ccaactgttg aacgcc                       46

<210> SEQ ID NO 47
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
agaagttgat tgagactttc aacgagggtc cccttcagct acctttt                      46

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tccctgctaa gccctaatcg                                                    20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ctctgattgc acgagaaggc                                                    20
```

<210> SEQ ID NO 50
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ctcacttaat cttctgtact ctgaagtgaa aggcgattgg agttgc                          46

<210> SEQ ID NO 51
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
agaagttgat tgagactttc aacgagctgg ctctgcttct ggtact                          46

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gatgttgagg cgggcataag                                                       20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
acttgtcagg acgatacgga                                                       20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccggtctccc tggaaataga                                                       20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
agttgtccgt cattagccct                                                       20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
tgttcccttt cggctagaca                                              20

<210> SEQ ID NO 57
<211> LENGTH: 4324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 57

| | | | | | |
|---|---|---|---|---|---|
| ggagttgaat | cacatcttac | tggatagcga | gcttttgac | gaagtgaaaa | tttctaattt | 60 |
| taaacaagag | gaagggtca | aaaacggaga | tatcttatac | ttggaaaaag | agatgacaat | 120 |
| cagtgatttc | atcaattttg | tatctagttg | gccttctgtg | ttttcgtgga | agcagcaacg | 180 |
| aggaaaggag | ggtatcctag | atgattttta | caacgaactg | aacgactgct | tgaggggggg | 240 |
| taacatgaaa | gtaatatgga | actccgtcct | agtatttgcc | aggaggaagc | aaagggttgt | 300 |
| ataggcttta | gtacttatag | aggaaacggg | gttacgtgca | agcgcgcatg | cctgagcttt | 360 |
| gagggggggg | actttcacat | ctcttcttct | cacacttagc | cctaacacag | agaataataa | 420 |
| aaagcattgc | aagatgagtg | ttgtcagcaa | gcaatacgac | atccacgaag | gcattatctt | 480 |
| tgtaattgaa | ttgaccccgg | agcttcacgc | gccggcttca | gaagggaaat | ctcagctcca | 540 |
| gatcatctta | gagaatgtca | gtgaggttat | ttctgagcta | atcattacct | tgcccggtac | 600 |
| aggaataggg | tgttacctta | ttaattacga | cggtggtcaa | aacgacgaaa | tttacccat | 660 |
| ttttgagtta | caagacctga | atttggaaat | gatgaaacaa | ttgtaccaag | tcttggagga | 720 |
| ccatgtaagt | gggcttaatc | ctctcgagaa | gcaattccca | attgaacaca | gtaaaccgtt | 780 |
| atcagccact | ctgttctttc | acttaaggtc | tctttttac | atggcgaaga | ctcataagcg | 840 |
| tactggaaga | cattacaact | tgaaaaagat | tttcttgttc | actaataacg | ataaaccta | 900 |
| caatggaaac | tctcagctga | gagttccctt | gaagaaaacc | ctggctgatt | acaatgacgt | 960 |
| agacattact | ttgattccgt | tcttctgaa | caagccttca | ggtgtcaagt | ttgacaagac | 1020 |
| ggaatactca | gaaattttgt | tctatgataa | agatgcttgt | tcgatgtcaa | ttgaggagat | 1080 |
| ccgccaacga | atttctagac | ataaggagat | caagcgggtt | tacttcacct | gtcctttgaa | 1140 |
| aatcgcaaat | aacttgtgca | tttctgtgaa | aggttattct | atgttttatc | atgaaactcc | 1200 |
| aaggaagatc | aaatttgtcg | tcaatgaggg | ttcaacttc | aaagatgtgg | agacaaaatc | 1260 |
| tcagtttgtc | gatccaacat | ccggaaaaga | gttttccagt | gaacagctga | tcaaagcata | 1320 |
| tcctctaggt | gccgatgctt | acattccttt | aaactcagag | caagtcaaaa | caataaatcg | 1380 |
| atttaatgat | atcatcaata | tccctctctt | ggaaattcta | ggtttcaggg | atatatctaa | 1440 |
| ttggttgcca | cagtatcagt | ttggcaaagc | atcgttttta | tcccctaata | actatggtga | 1500 |
| ttttacacat | tcgcagagaa | catttagttg | tcttcagtaa | tgtcttgttt | cttttgttgc | 1560 |
| agtggtgagc | cattttgact | tcgtgaaagt | ttcttagaa | tagttgtttc | cagaggccaa | 1620 |
| acattccacc | cgtagtaaag | tgcaagcgta | ggaagaccaa | gactggcata | aatcaggtat | 1680 |

```
aagtgtcgag cactggcagg tgatcttctg aaagtttcta ctagcagata agatccagta    1740
gtcatgcata tggcaacaat gtaccgtgtg gatctaagaa cgcgtcctac taaccttcgc    1800
attcgttggt ccagtttgtt gttatcgatc aacgtgacaa ggttgtcgat tccgcgtaag    1860
catgcatacc caaggacgcc tgttgcaatt ccaagtgagc cagttccaac aatctttgta    1920
atattagagc acttcattgt gttgcgcttg aaagtaaaat gcgaacaaat taagagataa    1980
tctcgaaacc gcgacttcaa acgccaatat gatgtgcggc acacaataag cgttcatatc    2040
cgctgggtga ctttctcgct ttaaaaaatt atccgaaaaa attttttgacg gctagctcag    2100
tcctaggtac gctagcatta aagaggagaa aatggctaaa ctgacctctg ctgttccggt    2160
tctgaccgct cgtgacgttg ctggtgctgt tgagttctgg accgaccgtc tgggtttctc    2220
tcgtgacttc gttgaagacg acttcgctgg tgttgttcgt gacgacgtta ccctgttcat    2280
ctctgctgtt caggaccagg ttgttccgga caacaccctg gcttgggttt gggttcgtgg    2340
tctggacgaa ctgtacgctg aatggtctga agttgtttct accaacttcc gtgacgcttc    2400
tggtccggct atgaccgaaa tcggtgaaca gccgtggggt cgtgagttcg ctctgcgtga    2460
cccggctggt aactgcgttc acttcgttgc tgaagaacag gactaacacg tccgacggcg    2520
gcccacgggt cccaggcctc ggagatccgt ccccctttc ctttgtcgat atcatgtaat    2580
tagttatgtc acgcttacat tcacgccctc cccccacatc cgctctaacc gaaaaggaag    2640
gagttagaca acctgaagtc taggtcccta tttattttt tatagttatg ttagtattaa    2700
gaacgttatt tatatttcaa atttttcttt tttttctgta cagacgcgtg tacgcatgta    2760
acattatact gaaaaccttg cttgagaagg ttttgggacg ctcgaaggct ttaatttgca    2820
agctgtatta gttcactttt tcagcaacct ggtcggaaag atccacatca agaatggata    2880
ccaaccccaa gagtatgaaa tccttccct acaatggcac ttcaaaatgt tacgtgacga    2940
ttaccttcaa ttggaacacg atatcgacat cagtgacccc cttgagaaac aaaagtacat    3000
aaacagcctc gatgagacaa aaaccaagat catgaaacta cgggactatg tcaaggaaac    3060
tgccgatgat gacgacccct cacggcttgc caacactctc aaagagctca accaagagct    3120
gaacaaaatt tccaactttg atatcatcgc caataagaag ccaaagaccc ccacgacagt    3180
agaccctgtt cctactgatg atgacatcat caacgcctgg aaggcaggaa ctctgaacgg    3240
tttcaaggtg gatcaattac gaaaatacgt aaggtcacga acaactttc tggagacggc    3300
ctccaaaaag gcagatctca tcgccaacat tgacaagtac tttcagcaga gttcaaaga    3360
gactaaggcc tgattcgtgt tccttacttt ttcctcgcaa cgtgtttttt tcccaccaca    3420
ttgcctatgt tgtaatgcaa tgcagatgct ggcccagttt ttgacgattc tcgaaaattg    3480
gcattttcgt cgatgccatt ggccaaactg aaaattcaag acaaaataga ttggattta    3540
tctgcaacgt cttccaccta cacaaccact ctacaaactt cagacaaaca tgtttataaa    3600
agcagctact agatccaaaa tgacaagttc gttattctct actacgtttg ttgtggcatt    3660
tggattggtg gctagcaaca acctcttgcc atgtcctgtt gaccactcta tgaataacga    3720
gactccgcaa gaattgaaac cattgcaggc tgaatcttct actagaaagt tgaactcttc    3780
cgcttaagtc aaataaaact actgacacag atgatgcaca gaaacaacgg atcacgctct    3840
tgactgatta gtcccgtcat tttggttctc attttcttca cagtcaccta tcaatgtatg    3900
atcacctgga aggatttccc tacgatactt caaatctttt acttgataat attactcatt    3960
atggctcagg aatgcagact gcctgattca agacgctgct cttcttattt aacacttgta    4020
```

| cactaacccc atgaagcca gggaagggaa taaccatctc tctggtaata aatcggtctt | 4080 |
| tatttatgca tagaaaagga atctattata tttcgttcat ttggcactct gctaactgta | 4140 |
| gattaacggg tctcgtaaat tcaaaatctt cttccgatca aaccggggtg aaatattact | 4200 |
| tctcgtgcat agctaatttt caaataaccg tcctaaaatg aacggtcatt tacctggact | 4260 |
| ctcttgccaa atgggcaaca aaacataaag ctgatcagaa cgtaactagt ctctcggaat | 4320 |
| ccat | 4324 |

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 58

| ggagttgaat cacatcttac tg | 22 |

<210> SEQ ID NO 59
<211> LENGTH: 1099
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 59

| gacaactaaa tgttctctgc gaatgtgtaa aatcaccata gttattaggg gataaaaacg | 60 |
| atgctttgcc aaactgatac tgtggcaacc aattagatat atccctgaaa cctagaattt | 120 |
| ccaaagaggg gatattgatg atatcattaa atcgattat tgttttgact tgctctgagt | 180 |
| ttaaaggaat gtaagcatcg gcacctagag gatatgcttt gatcagctgt tcactggaaa | 240 |
| actcttttcc ggatgttgga tcgacaaact gagattttgt ctccacatct ttgaaagttg | 300 |
| aaccctcatt gacgacaaat ttgatcttcc ttggagtttc atgataaaac atagaataac | 360 |
| cttcacaga aatgcacaag ttatttgcga ttttcaaagg acaggtgaag taaacccgct | 420 |
| tgatctcctt atgtctagaa attcgttggc ggatctcctc aattgacatc gaacaagcat | 480 |
| ctttatcata gaacaaaatt tctgagtatt ccgtcttgtc aaacttgaca cctgaaggct | 540 |
| tgttcagaag aaacggaatc aaagtaatgt ctacgtcatt gtaatcagcc agggttttct | 600 |
| tcaagggaac tctcagctga gagtttccat tgtaaggttt atcgttatta gtgaacaaga | 660 |
| aaatcttttt caagttgtaa tgtcttccag tacgcttatg agtcttcgcc atgtaaaaaa | 720 |
| gagaccttaa gtgaaagaac agagtggctg ataacggttt actgtgttca attgggaatt | 780 |
| gcttctcgag aggattaagc ccacttacat ggtcctccaa gacttggtac aattgtttca | 840 |
| tcatttccaa attcaggtct tgtaactcaa aaatggggta aatttcgtcg ttttgaccac | 900 |
| cgtcgtaatt aataaggtaa caccctattc ctgtaccggg caaggtaatg attagctcag | 960 |
| aaataaccte actgacattc tctaagatga tctggagctg agatttccct tctgaagccg | 1020 |
| gcgcgtgaag ctccggggtc aattcaatta caaagataat gccttcgtgg atgtcgtatt | 1080 |
| gcttgctgac aacactcat | 1099 |

<210> SEQ ID NO 60
<211> LENGTH: 549
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 60
tcaggcctta gtctctttga acttctgctg aaagtacttg tcaatgttgg cgatgagatc      60
tgcctttttg gaggccgtct ccagaaagtt gtttcgtgac cttacgtatt ttcgtaattg     120
atccaccttg aaaccgttca gagttcctgc cttccaggcg ttgatgatgt catcatcagt     180
aggaacaggg tctactgtcg tgggggtctt tggcttctta ttggcgatga tatcaaagtt     240
ggaaattttg ttcagctctt ggttgagctc tttgagagtg ttggcaagcc gtgaagggtc     300
gtcatcatcg gcagtttcct tgacatagtc ccgtagtttc atgatcttgg ttttttgtctc    360 atcgaggctg tttatgtact tttgtttctc aaggggggtca ctgatgtcga tatcgtgttc    420
caattgaagg taatcgtcac gtaacatttt gaagtgccat tgtagggaag gattttcata    480
ctcttggggt tggtatccat tcttgatgtg gatctttccg accaggttgc tgaaaagtga    540
aactaatac                                                             549

<210> SEQ ID NO 61
<211> LENGTH: 552
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
ttcagtaatg tcttgtttct tttgttgcag tggtgagcca ttttgacttc gtgaaagttt      60
ctttagaata gttgtttcca gaggccaaac attccacccg tagtaaagtg caagcgtagg     120
aagaccaaga ctggcataaa tcaggtataa gtgtcgagca ctggcaggtg atcttctgaa     180
agtttctact agcagataag atccagtagt catgcatatg caacaatgt accgtgtgga     240 tctaagaacg cgtcctacta accttcgcat tcgttggtcc agtttgttgt tatcgatcaa     300
cgtgacaagg ttgtcgattc cgcgtaagca tgcatacca aggacgcctg ttgcaattcc      360
aagtgagcca gttccaacaa tctttgtaat attagagcac ttcattgtgt tgcgcttgaa     420
agtaaaatgc gaacaaatta agagataatc tcgaaaccgc gacttcaaac gccaatatga    480
tgtgcggcac acaataagcg ttcatatccg ctgggtgact ttctcgcttt aaaaaattat    540
ccgaaaaaat tt                                                        552

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
cagaggccaa acattccacc                                                  20

<210> SEQ ID NO 63
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 63
ttaaagagga gaaa                                                           14

<210> SEQ ID NO 64
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
atggctaaac tgacctctgc tgttccggtt ctgaccgctc gtgacgttgc tggtgctgtt          60
gagttctgga ccgaccgtct gggtttctct cgtgacttcg ttgaagacga cttcgctggt         120
gttgttcgtg acgacgttac cctgttcatc tctgctgttc aggaccaggt tgttccggac         180
aacaccctgg cttgggtttg ggttcgtggt ctggacgaac tgtacgctga atggtctgaa         240
gttgtttcta ccaacttccg tgacgcttct ggtccggcta tgaccgaaat cggtgaacag         300
ccgtggggtc gtgagttcgc tctgcgtgac ccggctggta actgcgttca cttcgttgct         360
gaagaacagg actaa                                                         375

<210> SEQ ID NO 65
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
cacgtccgac ggcggcccac gggtcccagg cctcggagat ccgtcccccc tttcctttgt          60
cgatatcatg taattagtta tgtcacgctt acattcacgc cctcccccca catccgctct         120
aaccgaaaag gaaggagtta gacaacctga agtctaggtc cctatttatt tttttatagt         180
tatgttagta ttaagaacgt tatttatatt tcaaattttt ctttttttc tgtacagacg          240 cgtgtacgca tgtaacatta tactgaaaac cttgcttgag aaggttttgg gacgctcgaa         300
ggctttaatt tgcaagct                                                      318

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
aggagttaga caacctgaag                                                     20

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gtaactagtc tctcggaatc cat                                                 23
```

<210> SEQ ID NO 68
<211> LENGTH: 1623
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68

| | |
|---|---|
| cttcagagta cagaagatta agtgagagaa ttctaccgtt cgtatagcat acattatacg | 60 |
| aagttatttc agtaatgtct tgtttctttt gttgcagtgg tgagccattt tgacttcgtg | 120 |
| aaagtttctt tagaatagtt gtttccagag gccaaacatt ccacccgtag taaagtgcaa | 180 |
| gcgtaggaag accaagactg gcataaatca ggtataagtg tcgagcactg gcaggtgatc | 240 |
| ttctgaaagt ttctactagc agataagatc cagtagtcat gcatatggca acaatgtacc | 300 |
| gtgtggatct aagaacgcgt cctactaacc ttcgcattcg ttggtccagt tgttgttat | 360 |
| cgatcaacgt gacaaggttg tcgattccgc gtaagcatgc atacccaagg acgcctgttg | 420 |
| caattccaag tgagccagtt ccaacaatct ttgtaatatt agagcacttc attgtgttgc | 480 |
| gcttgaaagt aaaatgcgaa caattaaga gataatctcg aaaccgcgac ttcaaacgcc | 540 |
| aatatgatgt gcggcacaca ataagcgttc atatccgctg ggtgactttc tcgctttaaa | 600 |
| aaattatccg aaaaaatttt tgacggctag ctcagtccta ggtacgctag cattaaagag | 660 |
| gagaaaatga ctactcttga tgacacagcc tacagatata ggcatcagt tccgggtgac | 720 |
| gcagaggcta tcgaagcctt ggacggttca ttcactactg atacggtgtt tagagtcacc | 780 |
| gctacaggtg atggcttcac cttgagagag gttcctgtag acccacccct aacgaaagtt | 840 |
| ttccctgatg acgaatcgga tgacgagtct gatgctggtg aggacggtga ccctgattcc | 900 |
| agaacatttg tcgcatacgg agatgatggt gacctggctg gctttgttgt ggtgtcctac | 960 |
| agcggatgga atcgtagact cacagttgag gacatcgaag ttgcacctga acatcgtggt | 1020 |
| cacggtgttg gtcgtgcact gatgggactg gcaacagagt ttgctagaga aagaggagcc | 1080 |
| ggacatttgt ggttagaagt gaccaatgtc aacgctcctg ctattcacgc atataggcga | 1140 |
| atgggtttca ctttgtgcgg tcttgatact gctttgtatg acggaactgc ttctgatggt | 1200 |
| gaacaagctc tttacatgag tatgccatgt ccatagcacg tccgacggcg gcccacgggt | 1260 |
| cccaggcctc ggagatccgt cccccttttc ctttgtcgat atcatgtaat tagttatgtc | 1320 |
| acgcttacat tcacgccctc cccccacatc cgctctaacc gaaaaggaag gagttagaca | 1380 |
| acctgaagtc taggtcccta tttatttttt tatagttatg ttagtattaa gaacgttatt | 1440 |
| tatatttcaa attttctttt tttttctgta cagacgcgtg tacgcatgta acattatact | 1500 |
| gaaaaccttg cttgagaagg ttttgggacg ctcgaaggct ttaatttgca agctataact | 1560 |
| tcgtatagca tacattatac cttgttatgc ggccgcaaga agttgattga gactttcaac | 1620 |
| gag | 1623 |

<210> SEQ ID NO 69
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69

| | |
|---|---|
| cttcagagta cagaagatta agtgaga | 27 |

<210> SEQ ID NO 70
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
taccgttcgt atagcataca ttatacgaag ttat                               34

<210> SEQ ID NO 71
<211> LENGTH: 552
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
ttcagtaatg tcttgtttct tttgttgcag tggtgagcca ttttgacttc gtgaaagttt    60
ctttagaata gttgtttcca gaggccaaac attccacccg tagtaaagtg caagcgtagg   120
aagaccaaga ctggcataaa tcaggtataa gtgtcgagca ctggcaggtg atcttctgaa   180
agtttctact agcagataag atccagtagt catgcatatg caacaatgt accgtgtgga    240 tctaagaacg cgtcctacta accttcgcat tcgttggtcc agtttgttgt tatcgatcaa   300
cgtgacaagg ttgtcgattc cgcgtaagca tgcataccca aggacgcctg ttgcaattcc   360
aagtgagcca gttccaacaa tctttgtaat attagagcac ttcattgtgt tgcgcttgaa   420
agtaaaatgc gaacaaatta agagataatc tcgaaaccgc gacttcaaac gccaatatga   480
tgtgcggcac acaataagcg ttcatatccg ctgggtgact ttctcgcttt aaaaaattat   540
ccgaaaaaat tt                                                       552

<210> SEQ ID NO 72
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ttaaagagga gaaa                                                     14

<210> SEQ ID NO 73
<211> LENGTH: 570
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
atgactactc ttgatgacac agcctacaga tataggacat cagttccggg tgacgcagag    60
gctatcgaag ccttggacgg ttcattcact actgatacgg tgtttagagt caccgctaca   120
ggtgatggct tcaccttgag agaggttcct gtagacccac ccttaacgaa agttttccct   180
gatgacgaat cggatgacga gtctgatgct ggtgaggacg gtgaccctga ttccagaaca   240
tttgtcgcat acggagatga tggtgacctg gctggctttg ttgtggtgtc ctacagcgga   300
tggaatcgta gactcacagt tgaggacatc gaagttgcac ctgaacatcg tggtcacggt   360

```
gttggtcgtg cactgatggg actggcaaca gagtttgcta gagaaagagg agccggacat    420
ttgtggttag aagtgaccaa tgtcaacgct cctgctattc acgcatatag gcgaatgggt    480
ttcactttgt gcggtcttga tactgctttg tatgacggaa ctgcttctga tggtgaacaa    540
gctctttaca tgagtatgcc atgtccatag                                    570
```

<210> SEQ ID NO 74
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

```
cacgtccgac ggcggcccac gggtcccagg cctcggagat ccgtccccct tttcctttgt     60
cgatatcatg taattagtta tgtcacgctt acattcacgc cctcccccca catccgctct    120
aaccgaaaag gaaggagtta gacaacctga agtctaggtc cctatttatt ttttttatagt    180 tatgttagta ttaagaacgt tatttatatt tcaaattttt cttttttttc tgtacagacg    240
cgtgtacgca tgtaacatta tactgaaaac cttgcttgag aaggttttgg gacgctcgaa    300
ggctttaatt tgcaagct                                                 318
```

<210> SEQ ID NO 75
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75

```
ataacttcgt atagcataca ttataccttg ttat                                34
```

<210> SEQ ID NO 76
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76

```
gcggccgcaa gaagttgatt gagactttca acgag                               35
```

<210> SEQ ID NO 77
<211> LENGTH: 3869
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

```
tactacaggc tggctgttcc tcgcatggtg tttaatgtcc tgactgggtt ttcgtttatc     60
ggtattaccg gagccacctt gactgtaagg gaacgatact ggactaagag agtaatgcga    120
aaggcaacag cgtttctggc gaacctaatc aatgacggtt acgagtttac tactcctaaa    180
gccagtctta ttttgctaga gcagtcaac gcttacttaa agggccaggg acctaattat     240
gacatcgatt ttgacgagca ggaggcgttc attaaagaaa tggaggagtt gaggacctct    300
```

```
ggtggatatg agaacagata ctcatattca ggaaccgatg aaacacccag agatccgggt    360
tgcctgtttc ttcccattgc tttaaataaa tggcactttg atgtgctaga ctgcctgagg    420
atatacggta ctcaggaaga tctggaatct aaattattaa gtgttcagca attggtgtta    480
caatgttgca tgaagcacag tggcatgact ccagacatgg tctttgcaac ggaagtagct    540
cagaagccga ccttcgaaga cgacatagtt tgtgatgata ttgacgctta tgcccagggg    600
ggtgattgtc tagattattg ttacacgcca agcaattact ccagaacttt agaaattcat    660
ggcaagattg ctaccttaca acgagagctg gggctatgct ataatattct cggaattttg    720
gaccgttttt ccgattaagg ttttttagctc cattgcgcca accccgctc tccagactcc    780 ttcgttatcc agcattcagc atggacaggt tcaaaaaata aaatttcttg atatgggtcc    840
acttcaaaca tgcgcctacc tgtaggaaaa aaaagagaa cataaatatg ccgcgaacag    900
aaaacgtaat gtactgttct atatataaac tgttcagatc aatcataaat tctcagtttc    960
aaactttccg ctcagccaga ttttattcgt aaagaacgca tcattggctc tatgttgaag    1020
gatcagttct tgttatgggt tgctttgata gcgagcgtac cggtttccgg cgtgatggca    1080
gctcctagcg agtccgggca taacacggtt gaaaacgag atgccaaaaa cgttgttggc    1140
gttcaacagt tggacttctt cagagtacag aagattaagt gagagaattc taccgttcgt    1200
atagcataca ttatacgaag ttatttcagt aatgtcttgt ttcttttgtt gcagtggtga    1260 gccatttga cttcgtgaaa gtttctttag aatagttgtt tccagaggcc aaacattcca    1320
cccgtagtaa agtgcaagcg taggaagacc aagactggca taaatcaggt ataagtgtcg    1380
agcactggca ggtgatcttc tgaaagtttc tactagcaga taagatccag tagtcatgca    1440
tatggcaaca atgtaccgtg tggatctaag aacgcgtcct actaaccttc gcattcgttg    1500
gtccagtttg ttgttatcga tcaacgtgac aaggttgtcg attccgcgta agcatgcata    1560
cccaaggacg cctgttgcaa ttccaagtga gccagttcca acaatctttg taatattaga    1620
gcacttcatt gtgttgcgct tgaaagtaaa atgcgaacaa attaagagat aatctcgaaa    1680
ccgcgacttc aaacgccaat atgatgtgcg gcacacaata agcgttcata tccgctgggt    1740
gactttctcg cttaaaaaaa ttatccgaaa aaattttga cggctagctc agtcctaggt    1800
acgctagcat aaagaggag aaaatgacta ctcttgatga cacagcctac agatatagga    1860
catcagttcc gggtgacgca gaggctatcg aagccttgga cggttcattc actactgata    1920
cggtgtttag agtcaccgct acaggtgatg gcttcacctt gagagaggtt cctgtagacc    1980 caccttaac gaaagttttc cctgatgacg aatcggatga cgagtctgat gctggtgagg    2040
acggtgaccc tgattccaga acatttgtcg catacggaga tgatggtgac ctggctggct    2100
ttgttgtggt gtcctacagc ggatggaatc gtagactcac agttgaggac atcgaagttg    2160
cacctgaaca tcgtggtcac ggtgttggtc gtgcactgat gggactggca acagagtttg    2220
ctagagaaag aggagccgga catttgtggt tagaagtgac caatgtcaac gctcctgcta    2280
ttcacgcata taggcgaatg ggtttcactt tgtgcggtct tgatactgct ttgtatgacg    2340
gaactgcttc tgatggtgaa caagctcttt acatgagtat gccatgtcca tagcacgtcc    2400
gacggcggcc cacgggtccc aggcctcgga gatccgtccc ccttttcctt tgtcgatatc    2460
atgtaattag ttatgtcacg cttacattca cgccctcccc ccacatccgc tctaaccgaa    2520
aaggaaggag ttagacaacc tgaagtctag gtccctattt attttttttat agttatgtta    2580 gtattaagaa cgttatttat atttcaaatt tttcttttttt ttctgtacag acgcgtgtac    2640
gcatgtaaca ttatactgaa aaccttgctt gagaaggttt tgggacgctc gaaggcttta    2700
```

-continued

```
atttgcaagc tataacttcg tatagcatac attataccct tgttatgcggc cgcaagaagt    2760 tgattgagac tttcaacgag ggtccccttc agctaccttt ctctctgttt ggtagttatt    2820
ctcggcgtgt gtatagtata gtataaaagg gcctacattg ataggcttc aacattcctc     2880 aataaacaaa catccaacat cgcgcattcc gcatttcgca tttcacattt cgcgcctgcc    2940
ttcctttagg ttctttgaat catcatcaat cgtcgccgtc tacatcagag caggacttat    3000 cttttgccttc cccaaaaatt gccactccgt caaatagatt cttttgaatc cttgactatt   3060
tttgcctaaa taggtttttg ttagttttc tcaaagccc aaaagaaact ctatttagat      3120
tcatccagaa acaatctttt tctcacccca tttcgaagtg ccgtggagca cagacataaa    3180
aagatgacta ccgttcaacc tacagggcca gacaggctca ccctgccgca tattctactg    3240
gaattcaacg atggctcctc gcagcatgca gtgatcgagc taagcatgaa cgagggggatt  3300 aatatatcca cccatgagtg gaatccatcc actaatgagc aatcgccacg ggaagagaga   3360
gcaccacccc aacaatccaa tccatcgcat catccagaat catcgaacat agctactcaa   3420
agtcccgctc aggaaaccga gactcagccc ggcattccag gactagatag gcctgccttt   3480
gatacctcgg caacggggtc gtcagaacag gttgacccag tacagggaag gatcctggat   3540
gatattatag gccaatcatt aaggacttcc gaagaagacg ataccgaatc ccgccagaga   3600
ccacgagacc agaagaacat tatgatcacc gtgaattact tgtacgcaga cgacacaaat   3660
tccagaagtg ctaatacaaa caaccagacg cccaataaca cttctagaac ttccgacagt   3720
gaacgtgtgg gctccttatc gttgcacgtt ccggatctac cagataatgc cgacgattac   3780
tatatcgatg tactcattaa actaaccaca agcattgccc tcagcgtcat cacgtccatg   3840
atcaagaaac gattagggct tagcaggga                                      3869
```

<210> SEQ ID NO 78
<211> LENGTH: 1157
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 78

```
tactacaggc tggctgttcc tcgcatggtg tttaatgtcc tgactgggtt ttcgtttatc      60
ggtattaccg gagccacctt gactgtaagg gaacgatact ggactaagag agtaatgcga    120
aaggcaacag cgtttctggc gaacctaatc aatgacggtt acgagtttac tactcctaaa    180
gccagtctta ttttgctaga gcgagtcaac gcttacttaa agggccaggg acctaattat    240
gacatcgatt ttgacgagca ggaggcgttc attaaagaaa tggaggagtt gaggacctct    300
ggtggatatg agaacagata ctcatattca ggaaccgatg aaacacccag agatccgggt    360
tgcctgtttc ttcccattgc tttaaataaa tggcactttg atgtgctaga ctgcctgagg    420
atatacggta ctcaggaaga tctggaatct aaattattaa gtgttcagca attggtgtta    480
caatgttgca tgaagcacag tggcatgact ccagacatgg tctttgcaac ggaagtagct    540
cagaagccga ccttcgaaga cgacatagtt tgtgatgata ttgacgctta tgcccagggg    600
ggtgattgtc tagattattg ttacacgcca agcaattact ccagaacttt agaaattcat    660
ggcaagattg ctaccttaca acgagagctg gggctatgct ataatattct cggaattttg    720
gaccgttttt ccgattaagg ttttagctc cattgcgcca accccgctc tccagactcc      780 ttcgttatcc agcattcagc atggacaggt tcaaaaaata aaatttcttg atatgggtcc    840
```

```
acttcaaaca tgcgcctacc tgtaggaaaa aaaaagagaa cataaatatg ccgcgaacag      900
aaaacgtaat gtactgttct atatataaac tgttcagatc aatcataaat tctcagtttc      960
aaactttccg ctcagccaga ttttattcgt aaagaacgca tcattggctc tatgttgaag     1020
gatcagttct tgttatgggt tgctttgata gcgagcgtac cggtttccgg cgtgatggca     1080
gctcctagcg agtccgggca taacacggtt gaaaaacgag atgccaaaaa cgttgttggc     1140
gttcaacagt tggactt                                                    1157
```

<210> SEQ ID NO 79
<211> LENGTH: 1089
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

```
ggtccccttc agctaccttt ctctctgttt ggtagttatt ctcggcgtgt gtatagtata       60
gtataaaagg gcctacattg gataggcttc aacattcctc aataaacaaa catccaacat      120
cgcgcattcc gcatttcgca tttcacattt cgcgcctgcc ttcctttagg ttctttgaat      180
catcatcaat cgtcgccgtc tacatcagag caggacttat ctttgccttc cccaaaaatt      240
gccactccgt caaatagatt cttttgaatc cttgactatt tttgcctaaa taggtttttg      300
ttagtttttc ttcaaagccc aaaagaaact ctatttagat tcatccagaa acaatctttt      360 tctcaccccca tttcgaagtg ccgtggagca cagacataaa aagatgacta ccgttcaacc     420
tacagggcca gacaggctca ccctgccgca tattctactg gaattcaacg atggctcctc     480
gcagcatgca gtgatcgagc taagcatgaa cgagggatt aatatatcca cccatgagtg      540
gaatccatcc actaatgagc aatcgccacg ggaagagaga gcaccacccc aacaatccaa     600
tccatcgcat catccagaat catcgaacat agctactcaa agtcccgctc aggaaaccga     660
gactcagccc ggcattccag gactagatag gcctgccttt gatacctcgg caacggggtc     720
gtcagaacag gttgacccag tacagggaag gatcctggat gatattatag gccaatcatt     780
aaggacttcc gaagaagacg ataccgaatc ccgccagaga ccacgagacc agaagaacat     840
tatgatcacc gtgaattact tgtacgcaga cgacacaaat tccagaagtg ctaatacaaa     900
caaccagacg cccaataaca cttctagaac ttccgacagt gaacgtgtgg gctccttatc     960
gttgcacgtt ccggatctac cagataatgc cgacgattac tatatcgatg tactcattaa    1020
actaaccaca agcattgccc tcagcgtcat cacgtccatg atcaagaaac gattagggct    1080
tagcaggga                                                            1089
```

<210> SEQ ID NO 80
<211> LENGTH: 3964
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80

```
gccttctcgt gcaatcagag ctgttgaaag agagaagagg gcacacggaa gctgctgttc       60
aattgtgtga attgaccgga ttacaacctg ctggagtgat aggagagctg gttcgtgacg      120
aggacggctc tatgatgcga ttagacgact gtgttcagtt tggtctccgc cacaacgtaa      180
```

```
aaattatcaa ccttgaccag atcattgaat acatggattc caagaacagc tagatacgat    240
ggataggaat acagagatat catgattgag aacgtaaga gcttttttcga aagtgtgagt    300 ttgtggtgag ggccaggcgg tggggaggtg gtggggagcc tccttggtcg aatgtagata    360
tagtaagcaa gacacaagag cgcgcgaagt cttcaacgag gcggcgttgg gtcttgtacg    420
caacgtaatg actacacagt tgagcttgtc gcgaaccggt cgacattttg atcatgcata    480
ctatgttgag acaccatctc gtactattgc ggcaaccagc tgtaaatttg actaattaaa    540
gctgatgaag gatgcagggc gtcgtcaatt ttttgattga ttgcatttaa ttgtttgagc    600
cattcaaggc tgaatgcccg gcaccctaga cccttcttgt gagtactata aacccgcagg    660
cagggtaccc ttggccttct gcgagactac cagtcataac gtatatccac aatgtactag    720
taatagcccc ggaaaactct aatcccacag aacgtctaac gcctcctatg tcatcgatac    780
ccattcgcac tactgccatg gccccccctta cgtgatcatt tcacttactc ccgcctaagc    840
ttcgcccaca tgcctgcgtt ttgccaagat ttactgacga gtttggttta ctcatcctct    900
atttataact actagacttt caccattctt caccaccctc gtgccaatga tcatcaacca    960
cttggtattg acagccctca gcattgcact agcaagtgcg caactccaat cgcctttcac   1020
ttcagagtac agaagattaa gtgagagaat tctaccgttc gtatagcata cattatacga   1080
agttatttca gtaatgtctt gtttctttttg ttgcagtggt gagccatttt gacttcgtga   1140
aagtttcttt agaatagttg tttccagagg ccaaacattc cacccgtagt aaagtgcaag   1200
cgtaggaaga ccaagactgg cataaatcag gtaagtgt cgagcactgg caggtgatct   1260
tctgaaagtt tctactagca gataagatcc agtagtcatg catatggcaa caatgtaccg   1320
tgtggatcta agaacgcgtc ctactaacct tcgcattcgt tggtccagtt tgttgttatc   1380
gatcaacgtg acaaggttgt cgattccgcg taagcatgca tacccaagga cgcctgttgc   1440
aattccaagt gagccagttc caacaatctt tgtaatatta gagcacttca ttgtgttgcg   1500
cttgaaagta aaatgcgaac aaattaagag ataatctcga aaccgcgact tcaaacgcca   1560
atatgatgtg cggcacacaa taagcgttca tatccgctgg gtgactttct cgctttaaaa   1620
aattatccga aaaattttt gacggctagc tcagtcctag gtacgctagc attaaagagg   1680
agaaaatgac tactcttgat gacacagcct acagatatag gacatcagtt ccgggtgacg   1740
cagaggctat cgaagccttg gacggttcat tcactactga tacggtgttt agagtcaccg   1800
ctacaggtga tggcttcacc ttgagagagg ttcctgtaga cccacccctta acgaaagttt   1860 tccctgatga cgaatcggat gacgagtctg atgctggtga ggacggtgac cctgattcca   1920
gaacatttgt cgcatacgga gatgatggtg acctggctgg cttttgttgtg gtgtcctaca   1980 gcggatggaa tcgtagactc acagttgagg acatcgaagt tgcacctgaa catcgtggtc   2040
acggtgttgg tcgtgcactg atgggactgg caacagagtt tgctagagaa agaggagccg   2100
gacatttgtg gttagaagtg accaatgtca acgctcctgc tattcacgca tataggcgaa   2160
tgggtttcac tttgtgcggt cttgatactg ctttgtatga cggaactgct tctgatggtg   2220
aacaagctct ttacatgagt atgccatgtc catagcacgt ccgacggcgg cccacgggtc   2280
ccaggcctcg gagatccgtc ccccttttcc tttgtcgata tcatgtaatt agttatgtca   2340
cgcttacatt cacgccctcc ccccacatcc gctctaaccg aaaaggaagg agttagacaa   2400
cctgaagtct aggtccctat ttattttttt atagttatgt tagtattaag aacgttattt   2460
atatttcaaa tttttctttt ttttctgtac agacgcgtgt acgcatgtaa cattatactg   2520
aaaaccttgc ttgagaaggt tttgggacgc tcgaaggctt taatttgcaa gctataactt   2580
```

```
cgtatagcat acattatacc ttgttatgcg gccgcaagaa gttgattgag actttcaacg    2640
agctggctct gcttctggta cttcttcagg tgcatcttct gctactcaaa atgacgaaac    2700
atccactgat cttggagctc cagctgcatc tttaagtgca acgccatgtc tttttgccat    2760
cttgctgctc atgttgtagt agactttttt tttcactgag tttttatgta ctactgatta    2820
cattgtgtag gtgtaatgat gtgcactata atactaatat agtcaaaatg ctacagagga    2880
aagtgcaggt tgcctgtggt ggttttttctt attagcaccc tctgaacact ctttacctct    2940
aacatcctca gccatgctaa tcgcgcataa aataaatctt cgaacttttt tccattttat    3000
gctcataaag cttccttact gtcaccttat caaaagagct tttgccacta aagtagtcac    3060
acccagaatt gctcccgaat atcgtccaac aatgctagga tctgtggaaa gtttgacaaa    3120
taatttgaac accttgagct tgaagcttcc tgaagttaat atccaaggct cctttccaga    3180
aagtaaccca gtggaccttt tgagaaacta catcactcaa gaacttagta aaatttctgg    3240
agttgacaaa gaattgattt tcccagcctt ggaatgggt accacactgg aaaaggtga    3300 tcttttgatc ccagttcctc gtctgagaat aaagggtgct aatcctaaag atttagccga    3360
acaatgggct gctgcattcc caaagggtgg atatcttaaa gacgttattg cgcaaggacc    3420
tttcttgcag ttcttttta acacatcggt tctgtacaag ttggtgatat ctgatgctct    3480
ggagagaggc gatgactttg gtgcacttcc tctaggaaag ggacaaaaag ttatagtgga    3540
gttttcttct ccaaatattg ccaaaccttt ccacgctggc catcttagaa gtacaatcat    3600
cggtggtttt atttccaatc tgtatgaaaa gctgggtcat gaagttatga ggatgaatta    3660
tttgggagac tggggaaaac aatttggtgt tcttgcagta ggatttgagc gttacggtga    3720
tgaggcaaaa ttaaagactg atccaatcaa ccatttgttt gaggtctatg ttaaaatcaa    3780
ccaagatatt aaggctcaat cagagtctac tgaggagatt gcagaagggc aatcattaga    3840
tgaccaggca agagcttttt tcaagaaaat ggaaaatggc gacgaatcgg ctgtaagctt    3900
gtggaaaaga ttccgtgagt tatccattga gaagtacatt gatacttatg cccgcctcaa    3960
catc                                                                 3964
```

<210> SEQ ID NO 81
<211> LENGTH: 1019
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

```
gccttctcgt gcaatcagag ctgttgaaag agagaagagg gcacacggaa gctgctgttc      60
aattgtgtga attgaccgga ttacaacctg ctggagtgat aggagagctg gttcgtgacg     120
aggacggctc tatgatgcga ttagacgact gtgttcagtt tggtctccgc cacaacgtaa     180
aaattatcaa ccttgaccag atcattgaat acatggattc caagaacagc tagatacgat     240
ggataggaat acagagatat catgattgag gaacgtaaga gcttttttcga aagtgtgagt     300 tgtggtgag ggccaggcgg tggggaggtg gtggggagcc tccttggtcg aatgtagata      360
tagtaagcaa gacacaagag cgcgcgaagt cttcaacgag gcggcgttgg gtcttgtacg     420
caacgtaatg actacacagt tgagcttgtc gcgaaccggt cgacattttg atcatgcata     480
ctatgttgag acaccatctc gtactattgc ggcaaccagc tgtaaatttg actaattaaa     540
gctgatgaag gatgcagggc gtcgtcaatt ttttgattga ttgcatttaa ttgtttgagc     600
```

-continued

```
cattcaaggc tgaatgcccg gcaccctaga cccttcttgt gagtactata aaccgcagg      660 cagggtaccc ttggccttct gcgagactac cagtcataac gtatatccac aatgtactag     720
taatagcccc ggaaaactct aatcccacag aacgtctaac gcctcctatg tcatcgatac     780
ccattcgcac tactgccatg gccccccttta cgtgatcatt tcacttactc ccgcctaagc    840
ttcgcccaca tgcctgcgtt ttgccaagat ttactgacga gtttggttta ctcatcctct    900
atttataact actagacttt caccattctt caccaccctc gtgccaatga tcatcaacca     960
cttggtattg acagccctca gcattgcact agcaagtgcg caactccaat cgcctttca    1019
```

<210> SEQ ID NO 82
<211> LENGTH: 1322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82

```
ctggctctgc ttctggtact tcttcaggtg catcttctgc tactcaaaat gacgaaacat      60
ccactgatct tggagctcca gctgcatctt taagtgcaac gccatgtctt tttgccatct     120
tgctgctcat gttgtagtag acttttttttt tcactgagtt tttatgtact actgattaca    180
ttgtgtaggt gtaatgatgt gcactataat actaatatag tcaaaatgct acagaggaaa    240
gtgcaggttg cctgtggtgg ttttttcttat tagcacccctc tgaacactct ttacctctaa    300
catcctcagc catgctaatc gcgcataaaa taaatcttcg aacttttttc cattttatgc    360
tcataaagct tccttactgt caccttatca aaagagcttt tgccactaaa gtagtcacac     420
ccagaattgc tcccgaatat cgtccaacaa tgctaggatc tgtggaaagt ttgacaaata    480
atttgaacac cttgagcttg aagcttcctg aagttaatat ccaaggctcc tttccagaaa    540
gtaacccagt ggacctttttg agaaaactaca tcactcaaga acttagtaaa atttctggag    600
ttgacaaaga attgattttc ccagccttgg aatggggtac cacactggaa aaaggtgatc    660
ttttgatccc agttcctcgt ctgagaataa agggtgctaa tcctaaagat ttagccgaac    720
aatgggctgc tgcattccca aagggtggat atcttaaaga cgttattgcg caaggacctt    780
tcttgcagtt ctttttttaac acatcggttc tgtacaagtt ggtgatatct gatgctctgg    840
agagaggcga tgactttggt gcacttcctc taggaaaggg acaaaaagtt atagtggagt    900
tttcttctcc aaatattgcc aaacctttcc acgctggcca tcttagaagt acaatcatcg    960
gtggttttat ttccaatctg tatgaaaagc tgggtcatga agttatgagg atgaattatt    1020
tgggagactg gggaaaacaa tttggtgttc ttgcagtagg atttgagcgt tacggtgatg    1080
aggcaaaatt aaagactgat ccaatcaacc atttgtttga ggtctatgtt aaaatcaacc    1140
aagatattaa ggctcaatca gagtctactg aggagattgc agaagggcaa tcattagatg    1200
accaggcaag agctttttttc aagaaaatgg aaaatggcga cgaatcggct gtaagcttgt    1260
ggaaaagatt ccgtgagtta tccattgaga agtacattga tacttatgcc cgcctcaaca    1320
tc                                                                   1322
```

<210> SEQ ID NO 83
<211> LENGTH: 66
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 83
atgttcagct tgaaagcatt attgccattg gccttgttgt tggtcagcgc caaccaagtt    60
gctgca    66

<210> SEQ ID NO 84
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Met Phe Ser Leu Lys Ala Leu Leu Pro Leu Ala Leu Leu Leu Val Ser
1               5                   10                  15

Ala Asn Gln Val Ala Ala
            20

<210> SEQ ID NO 85
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
atgaaagcat tcctgttgtt actacttttta ctaggcctgt ccactacact cgctaaggca    60

<210> SEQ ID NO 86
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Met Lys Ala Phe Leu Leu Leu Leu Leu Leu Gly Leu Ser Thr Thr
1               5                   10                  15

Leu Ala Lys Ala
            20

<210> SEQ ID NO 87
<211> LENGTH: 144
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
atggaaggtg gcgaagaaga agttgagcgc attcctgatg aacttttcga tacaaaaaag    60
aagcatttgt tagataagct cataagggtc ggaataatcc ttgtactcct gatatggggc   120
actgttttgt tgctaaaaag tatt   144

<210> SEQ ID NO 88
<211> LENGTH: 48
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 88

Met Glu Gly Gly Glu Glu Val Glu Arg Ile Pro Asp Glu Leu Phe
1               5                   10                  15

Asp Thr Lys Lys Lys His Leu Leu Asp Lys Leu Ile Arg Val Gly Ile
            20                  25                  30

Ile Leu Val Leu Leu Ile Trp Gly Thr Val Leu Leu Leu Lys Ser Ile
        35                  40                  45

<210> SEQ ID NO 89
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
atgagatttc cttcaatttt tactgctgtt ttattcgcag catcctccgc attagct        57

<210> SEQ ID NO 90
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Met Arg Phe Pro Ser Ile Phe Thr Ala Val Leu Phe Ala Ala Ser Ser
1               5                   10                  15

Ala Leu Ala

<210> SEQ ID NO 91
<211> LENGTH: 5679
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
ggcgcgccgt ttaaaccctc caccagccat ataccactac aacaccacag aagagaaaga     60
gctcatatca tccgtcatga gagagtacca gcacagaaat acagtcaagt aaaactagta    120
tgcaagcatt acgtaataat agcaacttta tgacaaatca ttccattttt ttccactgga    180
gcgtgcactg cgtaaatcat tctctttgga aggcaaggga agaacaacaa aattttttcct   240 tccgttatac aaacattgaa tcatgtctac tgaaccccact tttaaattgg tccttgtcgg   300
tgatggtggt accggtaaag taagtgcaaa ttatttgatg agtcggataa tgttttccgc    360
cccttagttc ccctcatgat tactaacaat tcatagacca ccttcgttaa gagacacctt    420
actggagagt tccgtaagaa gtacattgct actttgggag tcgaagttca tcccttgtca    480
ttccacacta actgtggtcc tatcacattc aacgtttggg acactgctgg acaagagaag    540
tttggtggac tgagagatgg ttattacatt aacggtgact gtggtatcat catgttcgac    600
gttacatcga gaattactta caagaacgtt ccaaactggc accgtgactt ggtcagagtg    660
tgtgagaaca ttccaattgt gctttgtggt aacaaggttg atgtcaagga agaaaaggtc    720
aaggctaaga ccatcacttt ccacagaaag aagaacttgc aatactttga catttctgcc    780

```
aagtccaact acaactttga gaagccattc ttgtggttag ctagaaagtt gtctggtgag    840
ccccaattag agttcgttgc tgctcccgac ttgcaagccc cagaggttca aattgatgcc    900
gatttaataa agaagtacga gcaagagaac gccgaggctg ccgctatgcc attgcctgat    960
gaagatgatg ccgacttgta agcttttact tacagtacat tgagaaccat acatagggca   1020
cgtatcgtaa gtttagttgt ttgctgatgt aagctagttt gtttctgtag tgtttcgagg   1080
tcgcagaggg atctctctag ccttagacaa aaaaaaaaag gttgacacgt tgatacactc   1140
tctgtttcat ccgatctttc acctacgagt cccactcctc ttcagagtac agaagattaa   1200
gtgagagaat tctaccgttc gtatagcata cattatacga agttatttca gtaatgtctt   1260
gtttcttttg ttgcagtggt gagccatttt gacttcgtga agtttctttt agaatagttg   1320
tttccagagg ccaaacattc caccgtagt aaagtgcaag cgtaggaagt ccaagactgg   1380
cataaatcag gtataagtgt cgagcactgg caggtgatct tctgaaagtt tctactagca   1440
gataagatcc agtagtcatg catatggcaa caatgtaccg tgtggatcta agaacgcgtc   1500
ctactaacct tcgcattcgt tggtccagtt tgttgttatc gatcaacgtg acaaggttgt   1560
cgattccgcg taagcatgca tacccaagga cgcctgttgc aattccaagt gagccagttc   1620
caacaatctt tgtaatatta gagcacttca ttgtgttgcg cttgaaagta aaatgcgaac   1680
aaattaagag ataatctcga aaccgcgact tcaaacgcca atatgatgtg cggcacacaa   1740
taagcgttca tatccgctgg gtgactttct cgctttaaaa aattatccga aaaattttt   1800 gacggctagc tcagtcctag gtacgctagc attaagagg agaaaatggc taaactgacc   1860
tctgctgttc cggttctgac cgctcgtgac gttgctggtg ctgttgagtt ctggaccgac   1920
cgtctgggtt tctctcgtga cttcgttgag gacgacttcg ctggtgttgt tcgtgacgac   1980
gttaccctgt tcatctctgc tgttcaggac caggttgttc cggacaacac cctggcttgg   2040
gtttgggttc gtggtctgga cgaactgtac gctgaatggt ctgaagttgt ttctaccaac   2100
ttccgtgacg cttctggtcc ggctatgacc gaaatcggtg aacagccgtg gggtcgtgag   2160
ttcgctctgc gtgacccggc tggtaactgc gttcacttcg ttgctgaaga acaggactaa   2220
cacgtccgac ggcggcccac gggtcccagg cctcggagat ccgtcccct tttcctttgt   2280 cgatatcatg taattagtta tgtcacgctt acattcacgc cctcccccca catccgctct   2340
aaccgaaaag gaaggagtta gacaacctga agtctaggtc cctatttatt tttttatagt   2400
tatgttagta ttaagaacgt tatttatatt tcaaattttt ctttttttc tgtacagacg   2460 cgtgtacgca tgtaacatta tactgaaaac cttgcttgag aaggttttgg gacgctcgaa   2520
ggctttaatt tgcaagctat aacttcgtat agcatacatt ataccttgtt atgcggccgc   2580
agatctaaca tccaaagacg aaaggttgaa tgaaaccttt ttgccatccg acatccacag   2640
gagagttata gagctgctat gcgtgtaaaa atagtttaaa tcttcgtaaa gtatgttagt   2700
ccatgtaatt tgctatgaat cgatacgcta atctggatgc tgaacggatg cttactggca   2760
tgcattattc attacccatc taagctgcgc cacaacccag taaattgcag tgagggaagc   2820
ttccctgtaa ccgtcctgtc cctttaggga ccatcgatcc caacgatca aatcgcgata   2880 catctatcaa ctgtcccttt ccatctatct atgcaaggta atgacagact ctgttaactc   2940
tgatgattct gatctggaaa tcatagaggt gactgagcct actccaaaag tggacctttt   3000
ggcccccaat ccagcattta atttactgc ccccataagc aacagtaacg gcacaactcc   3060
aataaggaga aaacttgatg accaatccaa ctccaattct tttgccagac tggaatcgtt   3120
acgggaatca tcagtgaaac cacaagctag tacgttcaat agtagtaggt tcatccccca   3180
```

-continued

```
agccgaccaa ttttccaata atcagaataa tgaacttgat aacaacaatg gattcgccga    3240
ctggatttct aagtcccaac ctgaatttcc ctttccactt aatgatggac caaaaaagtc    3300
cagcaatcaa cctacaaact caaattttga agagatcatc gatttaactg aagatatcga    3360
gataaataca tctgtccccg catctacatc atcttctacc ccagttccct ccagcacaca    3420
gaatcagagc catcatatag ccaacaacaa cacagcacaa gatgcgcata tcttccaagg    3480
gaaacgacct ctccaatcat attcagatga tgaagacgaa gatttgcaaa ttgtaggatc    3540
caatattgtt cagcagcctc taggaattat gccaggaact ttcaacgccc ctgcaaacat    3600
actccatttt gacggttcaa accagaatga acaagccaga tggctggact tgcggataaa    3660
agatttgtta gataatcttc acaatcttcg agttcatgct cagtcgaata ttatggagat    3720
caataggttc atttccactt tgggcatttt aaacagagaa gtttaaaccc tgcagggcgc    3780
tcggtcgttc ggctgcggcg agcggtatca gctcactcaa aggcggtaat acggttatcc    3840
acagaatcag gggataacgc aggaaagaac atgtgagcaa aaggccagca aaaggccagg    3900
aaccgtaaaa aggccgcgtt gctggcgttt ttccataggc tccgcccccc tgacgagcat    3960
cacaaaaatc gacgctcaag tcagaggtgg cgaaacccga caggactata agataccag    4020
gcgtttcccc ctggaagctc cctcgtgcgc tctcctgttc cgaccctgcc gcttaccgga    4080
tacctgtccg cctttctccc ttcgggaagc gtggcgcttt ctcatagctc acgctgtagg    4140
tatctcagtt cggtgtaggt cgttcgctcc aagctgggct gtgtgcacga accccccgtt    4200
cagcccgacc gctgcgcctt atccggtaac tatcgtcttg agtccaaccc ggtaagacac    4260
gacttatcgc cactggcagc agccactggt aacaggatta gcagagcgag gtatgtaggc    4320
ggtgctacag agttcttgaa gtggtggcct aactacggct acactagaag aacagtattt    4380
ggtatctgcg ctctgctgaa gccagttacc ttcggaaaaa gagttggtag ctcttgatcc    4440
ggcaaacaaa ccaccgctgg tagcggtggt ttttttgttt gcaagcagca gattacgcgc    4500
agaaaaaaag gatctcaaga agatcctttg atcttttcta cggggtctga cgctcagtgg    4560
aacgaaaact cacgttaagg gattttggtc atgagattat caaaaaggat cttcacctag    4620
atccttttaa attaaaaatg aagttttaaa tcaatctaaa gtatatatga gtaaacttgg    4680
tctgacagtt accaatgctt aatcagtgag gcacctatct cagcgatctg tctatttcgt    4740
tcatccatag ttgcctgact ccccgtcgtg tagataacta cgatacggga gggcttacca    4800
tctggcccca gtgctgcaat gataccgcgc gacccacgct caccggctcc agatttatca    4860
gcaataaacc agccagccgg aagggccgag cgcagaagtg gtcctgcaac tttatccgcc    4920
tccatccagt ctattaattg ttgccgggaa gctagagtaa gtagttcgcc agttaatagt    4980
ttgcgcaacg ttgttgccat tgctacaggc atcgtggtgt cacgctcgtc gtttggtatg    5040
gcttcattca gctccggttc ccaacgatca aggcgagtta catgatcccc catgttgtgc    5100
aaaaaagcgg ttagctcctt cggtcctccg atcgttgtca gaagtaagtt ggccgcagtg    5160
ttatcactca tggttatggc agcactgcat aattctctta ctgtcatgcc atccgtaaga    5220
tgcttttctg tgactggtga gtactcaacc aagtcattct gagaatagtg tatgcggcga    5280
ccgagttgct cttgcccggc gtcaatacgg gataataccg cgccacatag cagaacttta    5340
aaagtgctca tcattggaaa acgttcttcg gggcgaaaac tctcaaggat cttaccgctg    5400
ttgagatcca gttcgatgta acccactcgt gcacccaact gatcttcagc atcttttact    5460
ttcaccagcg tttctgggtg agcaaaaaca ggaaggcaaa atgccgcaaa aaagggaata    5520
```

```
agggcgacac ggaaatgttg aatactcata ctcttccttt ttcaatatta ttgaagcatt    5580
tatcagggtt attgtctcat gagcggatac atatttgaat gtatttagaa aaataaacaa    5640 atagggttc cgcgcacatt tccccgaaaa gtgccacct                            5679

<210> SEQ ID NO 92
<211> LENGTH: 1157
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
aaaccctcca ccagccatat accactacaa caccacagaa gagaaagagc tcatatcatc      60
cgtcatgaga gagtaccagc acagaaatac agtcaagtaa aactagtatg caagcattac     120
gtaataatag caactttatg acaaatcatt ccattttttt ccactggagc gtgcactgcg     180
taaatcattc tctttggaag gcaagggaag aacaacaaaa ttttttccttc cgttatacaa    240 acattgaatc atgtctactg aacccacttt taaattggtc cttgtcggtg atggtggtac     300
cggtaaagta agtgcaaatt atttgatgag tcggataatg ttttccgccc cttagttccc     360
ctcatgatta ctaacaattc atagaccacc ttcgttaaga gacaccttac tggagagttc     420
cgtaagaagt acattgctac tttgggagtc gaagttcatc ccttgtcatt ccacactaac     480
tgtggtccta tcacattcaa cgtttgggac actgctggac aagagaagtt tggtggactg     540
agagatggtt attacattaa cggtgactgt ggtatcatca tgttcgacgt tacatcgaga     600
attacttaca agaacgttcc aaactggcac cgtgacttgg tcagagtgtg tgagaacatt     660
ccaattgtgc tttgtggtaa caaggttgat gtcaaggaaa gaaaggtcaa ggctaagacc     720
atcactttcc acagaaagaa gaacttgcaa tactttgaca ttttctgccaa gtccaactac    780 aactttgaga gccattctt gtggttagct agaaagttgt ctggtgagcc ccaattagag      840
ttcgttgctg ctccccgactt gcaagcccca gaggttcaaa ttgatgccga tttaataaag    900
aagtacgagc aagagaacgc cgaggctgcc gctatgccat gcctgatga agatgatgcc      960 gacttgtaag cttttactta cagtacattg agaaccatac atagggcacg tatcgtaagt    1020
ttagttgttt gctgatgtaa gctagtttgt ttctgtagtg tttcgaggtc gcagagggat    1080
ctctctagcc ttagacaaaa aaaaaaggt tgacacgttg atacactctc tgtttcatcc     1140
gatctttcac ctacgag                                                   1157

<210> SEQ ID NO 93
<211> LENGTH: 1125
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
ggagagttat agagctgcta tgcgtgtaaa aatagtttaa atcttcgtaa agtatgttag      60
tccatgtaat ttgctatgaa tcgatacgct aatctggatg ctgaacggat gcttactggc    120
atgcattatt cattacccat ctaagctgcg ccacaaccca gtaaattgca gtgagggaag    180
cttccctgta accgtcctgt cccttttaggg accatcgatc cccaacgatc aaatcgcgat   240
acatctatca actgtcccctt tccatctatc tatgcaaggt aatgacagac tctgttaact   300
ctgatgattc tgatctggaa atcatagagg tgactgagcc tactccaaaa gtggaccttt   360
```

```
tggcccccaa tccagcattt aattttactg cccccataag caacagtaac ggcacaactc    420
caataaggag aaaacttgat gaccaatcca actccaattc ttttgccaga ctggaatcgt    480
tacgggaatc atcagtgaaa ccacaagcta gtacgttcaa tagtagtagg ttcatccccc    540
aagccgacca attttccaat aatcagaata atgaacttga taacaacaat ggattcgccg    600
actggatttc taagtcccaa cctgaatttc cctttccact taatgatgga ccaaaaagt    660 ccagcaatca acctacaaac tcaaattttg aagagatcat cgatttaact gaagatatcg    720
agataaatac atctgtcccc gcatctacat catcttctac cccagttccc tccagcacac    780
agaatcagag ccatcatata gccaacaaca acacagcaca agatgcgcat atcttccaag    840
ggaaacgacc tctccaatca tattcagatg atgaagacga agatttgcaa attgtaggat    900
ccaatattgt tcagcagcct ctaggaatta tgccaggaac tttcaacgcc cctgcaaaca    960
tactccattt tgacggttca aaccagaatg aacaagccag atggctggac ttgcggataa   1020
aagatttgtt agataatctt cacaatcttc gagttcatgc tcagtcgaat attatggaga   1080
tcaataggtt catttccact ttggggcatt taaacagaga agttt                   1125

<210> SEQ ID NO 94
<211> LENGTH: 1292
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
ttcagtaatg tcttgtttct tttgttgcag tggtgagcca ttttgacttc gtgaaagttt     60
ctttagaata gttgtttcca gaggccaaac attccacccg tagtaaagtg caagcgtagg    120
aagtccaaga ctggcataaa tcaggtataa gtgtcgagca ctggcaggtg atcttctgaa    180
agtttctact agcagataag atccagtagt catgcatatg caacaatgt accgtgtgga     240 tctaagaacg cgtcctacta accttcgcat tcgttggtcc agtttgttgt tatcgatcaa    300
cgtgacaagg ttgtcgattc cgcgtaagca tgcataccca aggacgcctg ttgcaattcc    360
aagtgagcca gttccaacaa tctttgtaat attagagcac ttcattgtgt tgcgcttgaa    420
agtaaaatgc gaacaaatta agagataatc tcgaaaccgc gacttcaaac gccaatatga    480
tgtgcggcac acaataagcg ttcatatccg ctgggtgact ttctcgcttt aaaaaattat    540
ccgaaaaaat ttttgacggc tagctcagtc ctaggtacgc tagcattaaa gaggagaaaa    600
tggctaaact gacctctgct gttccggttc tgaccgctcg tgacgttgct ggtgctgttg    660
agttctggac cgaccgtctg ggtttctctc gtgacttcgt tgaggacgac ttcgctggtg    720
ttgttcgtga cgacgttacc ctgttcatct ctgctgttca ggaccaggtt gttccggaca    780
acaccctggc ttgggtttgg ttcgtggtc tggacgaact gtacgctgaa tggtctgaag    840
ttgtttctac caacttccgt gacgcttctg gtccggctat gaccgaaatc ggtgaacagc    900
cgtggggtcg tgagttcgct ctgcgtgacc cggctggtaa ctgcgttcac ttcgttgctg    960
aagaacagga ctaacacgtc cgacggcggc ccacgggtcc caggcctcgg agatccgtcc   1020 ccctttcct ttgtcgatat catgtaatta gttatgtcac gcttacattc acgccctccc    1080
cccacatccg ctctaaccga aaaggaagga gttagacaac ctgaagtcta ggtccctatt   1140 tatttttta tagttatgtt agtattaaga acgttattta tatttcaaat ttttcttttt   1200
tttctgtaca gacgcgtgta cgcatgtaac attatactga aaaccttgct tgagaaggtt   1260
```
ttgggacgct cgaaggcttt aatttgcaag ct						1292

<210> SEQ ID NO 95
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Met Ala Lys Leu Thr Ser Ala Val Pro Val Leu Thr Ala Arg Asp Val
1               5                   10                  15

Ala Gly Ala Val Glu Phe Trp Thr Asp Arg Leu Gly Phe Ser Arg Asp
            20                  25                  30

Phe Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala
    50                  55                  60

Trp Val Trp Val Arg Gly Leu Asp Glu Leu Tyr Ala Glu Trp Ser Glu
65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
        115                 120

<210> SEQ ID NO 96
<211> LENGTH: 11322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
ccagccagga cagaaatgcc tcgacttcgc tgctgcccaa ggttgccggg tgacgcacac      60
cgtggaaacg gatgaaggca cgaacccagt ggacataagc ctgttcggtt cgtaagctgt     120
aatgcaagta gcgtatgcgc tcacgcaact ggtccgaaac cttgaccgaa cgcagcggtg     180
gtaacggcgc agtggcggtt ttcatggctt gttatgactg ttttttttggg gtacagtcta    240 tgcctcgggc atccaagcag caagcgcgtt acgccgtggg tcgatgtttg atgttatgga    300
gcagcaacga tgttacgcag cagggcagtc gccctaaaac aaagttaaac atcatgaggg    360
aagcggtgat cgccgaagta tcgactcaac tatcagaggg agttggcgtc atcgagcgcc    420
atctcgaacc gacgttgctg gccgtacatt tgtacggctc cgcagtggat ggcggcctga    480
agccacacag tgatattgat ttgctggtta cggtgaccgt aaggcttgat gaaacaacgc    540
ggcgagcttt gatcaacgac cttttggaaa cttcggcttc ccctggagag agcgagattc    600
tccgcgctgt agaagtcacc attgttgtgc acgacgacat cattccgtgg cgttatccag    660
ctaagcgcga actgcaattt ggagaatggc agcgcaatga cattcttgca ggtatcttcg    720
agccagccac gatcgacatt gatctggcta tcttgctgac aaaagcaaga gaacatagcg    780
ttgccttggt aggtccagcg gcggaggaac tctttgatcc ggttcctgaa caggatctat    840
ttgaggcgct aaatgaaacc ttaacgctat ggaactcgcc gcccgactgg gctggtgatg    900

```
agcgaaatgt agtgcttacg ttgtcccgca tttggtacag cgcagtaacc ggcaaaatcg    960
cgccgaagga tgtcgctgcc gactgggcaa tggagcgcct gccggcccag tatcagcccg   1020
tcatacttga agctagacag gcttatcttg acaagaaga agatcgcttg gcctcgcgcg   1080
cagatcagtt ggaagaattt gtccactacg tgaaaggcga gatcaccaag gtagtcggca   1140
aataacatta ctcgcatcca ttctcaggct gtctcgtctc gtctccaact ttctgccgcc   1200
aatctccttt ccattcaaat tctctacaac aaggcaggct tcgtccgttg atgtgaagtt   1260
tgcaaaagcc aaaccacgaa aaacaccatt gtcaaaatgg tagttgaagg cataaggcaa   1320
aggcaagcta aactttgtca taacgtctaa aagttgctct ttttttatgg caaaagggat   1380
gttctttatc acaatagcag tgggaatgac atcttcatca tcattcgtat catcaatacc   1440
atcgagttct gaatccaaag gtttctgttg ttgggataag gcatcagatt ctttgagcag   1500
gtcgtccttg gcgtcctcct ctagatgaaa tttgccatcg ttaggaggtg agtattggga   1560
aacgttgact tgttgctcaa tccaaggatc aacgttgacc atcggattgc cgttctgagg   1620
agacagccag gcattatacc gtggttgacc ggcgtttacg cgcagaggat tgttgctggt   1680
gttgttgaca agacgcat acccagacgc tgcgatgac atcgacgaaa ttgaagggcg   1740
acgttgcata cccatttgtt gctgatccaa gaaacttggt gtttcagtca attgtctcag   1800
gtccatattg atcaatgtgt tcaactgttt caatctggtt ccggagggtg gctattacga   1860
caagctgtgg ctactatcta agtgggagaa gtaacgaaac acattgatga gacacaggaa   1920
ttacagggcg tgcatccacc aataacaatt agtcgagatt caaccaatt acgtaagcgc   1980 tcaacccttt tttcgaacac gtatcgagca aagtccaggt gaaaccttca tccattatat   2040
ccaaagtcga ccgaagcttt aacaacatcc ataatggtaa gtgtccagtt tgatgagtgc   2100
agaatggttc caagttttag accagttact aatatttaaa gtctacagca attccaggag   2160
gacagagaac gttagctaaa agaagagcag caaacttgga taagaaacag gatgaaccaa   2220
cctccgccag atctgccggt gctggaggtt cttcgtctac catgctaaag ttgtacacag   2280
acgaggccca aggtttgaaa gttgatcctt taattgttct tgttcttgct gttggttttca   2340 ttttcagtgt cattggtttg cacgttgttg ctaagctgac aggaaagttg atcaactaag   2400
acctatattt aaacaggttt catcatatct gtactatatt tacaagtcca ctgcgtttag   2460
gtatatacta aagacattca agaagcacat ccacaacttg tgcaagtcct gtcaaatgta   2520
ctagatgctt ttcagaacat cctgcggttt gaggagattc ctgaatttcc cagtcccaag   2580
tctttctctt gtagaggtct ttgagttctt gtgaatgctg aattgggggtt cttacctcaa   2640 tttctattag tgggaaatgc tttcccacaa ttatttgcaa tgggatcccg gcaactttac   2700
tttgcttcaa cttatgtccc atactgaact ttccgtcacg gttgtcaact tgaacgtcga   2760
atgagctcag tatttcggtg acagtgtcta gattcttttt acttgatgtt ttattcgaaa   2820
gtagcgtgat ttgatatggt gcgataattt gtggccaggg ctgggagttc gtagacggaa   2880
acaaacgcag aatccaagca gacaagtgga gagtggacaa attcttgatg ttaattcgta   2940
agatccttaa caaatcttta gcaaaactga aaagtgaaga ctacgatagg gatttacttg   3000
aaaaatatat tcaagttttg tcagaatacc cactccatat taacgatatt attgtcccta   3060
gaactattac gtaccacttg tgtgatattt atactgatga gttggaaaag gttatgttta   3120
gtgggcttcc tggatttgaa gaagaagaag attacgagga agaagatgaa gtctcggctc   3180
ctatcgaaaa aaaaaccaga gatactgata attcagacga tgaggcctct gataccgatc   3240
cagaaacgag tgacgaagaa gacgaaggtg agaatactga aaacgagtca gaagaggaac   3300
```

```
cgatcaaaact ctctgcggaa gaagaaacgg ctctgtggaa aacaaagatg gagattatcc    3360
atgaaactcc tatcgacaaa ttactctcac cttttgtctc attgaagaaa gatacctcaa    3420
ataaaccatt aaaattgaaa atccaagaag cagttcttgc tgatccaaga ctcggcaaat    3480
ggaaagttaa atcgtaccga aagcctaaac caaaaccaaa acctcttcag gtgctacaga    3540
aacagttata cgaacagatc aaatataaaa agggtaaagc agtcacaggt gaagacgacg    3600
atgaactcaa agacgaagac gaagatgacg atgacgaggt catctcggag agtgaagctg    3660
ataactctga tgaagaagaa gatgaagaat ggaatggctt tggaactatc tagaatacat    3720
atgtaaaacc atatcaggca ataacaattt ctcgctattt tgcatcccaa cacctcgacc    3780
gacgtgttca gttcgaccct ttacctacag tgtctttaac tcccatttgg atctcctaaa    3840
taacctacac aaatgtccca aaaagtcacc gacgtccctc tggaatttgt taaggaaggt    3900
tccaaattca tctctaaatg tactaaaccc tctcagaagg agtacttaaa gatagtaaga    3960
gctgttggag ttgggttttt aatgatgggc gtggttggtt acgttgtcaa gctcattcat    4020
attccaatca gatatttgat tgtttaaaag tttaggtttg aatacaatgt gtatgcttaa    4080
ttatattcac ttcgtttcat tgattttgc tatccctgtt gtgcgttaat catctctatc    4140
gtgatcctct caagttgcac ctcaaataga agacaactta tggaggtgta ctacccaata    4200
tcagtcttga cgtttctagt ttcgttgtat gctgcatacc aatttcagtt cttccgtagt    4260
gttttgagca taggcttgtt tacccgtctt ctttacactc tgatatgagc accttatcaa    4320
acctcttatc acagctgaaa ggagaaggcg gtggtggttc ttctggtcag aatcggccca    4380
gaactgtgga tcctgctgtt gcaagattga aagcagaaag gaagatggaa agagagaagc    4440
aagctcttaa agaggctcag caagcccagg aagctcggga aaggcgaaga attagtcatg    4500
ctacccagat aggtttgaga ccaaccagta aagctcccag cactgaaggt cctcaatcgc    4560
actggaaaca tcaaggtcga tgaccgcact aacagaagga gctaaactat tcgaaaagga    4620
gattccttac attacagaat tagagggtga tgtcgaagga atgaaattca ttatcaaggg    4680
cgagggtact ggtgacgcta ctaccggtac gattaaagca aagtacatct gtacaacagg    4740
tgaccttcct gttccgtggg ctactctggt gagcactttg tcttatggag ttcaatgttt    4800
tgctaaatac ccttcgcaca ttaaagactt tttcaaaagt gcaatgcctg agggctatac    4860
tcaggagaga acaatatctt tcgaaggaga tggtgtgtat aagactaggg ctatggtcac    4920
gtatgaaaga ggatccatct acaatagagt aactttaact ggtgaaaact tcaaaaagga    4980
cggtcacatc cttagaaaga atgttgcctt tcaatgccca ccatccatct gtacattttt    5040
gccagacaca gttaacaatg gtatcagagt tgagtttaac caagcttatg acatagaggg    5100
tgtcaccgaa aagttggtta caaatgttc acagatgaat cgtcccctgg caggatcagc    5160
tgccgtccat atcccacgtt accatcatat cacttatcat accaagctgt ccaaagatcg    5220
tgatgagaga agggatcaca tgtgtttggt tgaagtggta aaggccgtgg atttggatac    5280
ttaccaatga ctgacctcct gccagcaata gtaagacaac acgcaaagtc tctgaacggg    5340
tctttgagct gtctgtgtca tcaaacatat cttcatctgt agttgtattg ttttcttta    5400 tcactaggag tccatccttc tggatggctg tcttgcactt atttagccac tccaaaaatg    5460
ccgggtctgg gagatgaccg cagcaccatt gacaccatat cagagagtat cgagactcct    5520 ctggttttcca gtcttgcatg ggaatttcat aaatgtctcc tatcttacct tgttccatca    5580
gtgtttgtag ttccacccctc atctggtcga caaatggttt aactggttcc aataaatcaa    5640
```

```
ccttatcaca aactttatgc agaaaatctc ttgtcacgcg gccaataccg gcaccaaagt    5700
ctataccata tttgattttg tcaggatcgt tagagaaacg actctttaac tttcttaaaa    5760
aggtcatcga tccaacaaca tctgcttttg gaaccgaagt tgtctcaccg tacccaccca    5820
aaactccgtc gacagatgct gggacgctgt tccagtattt cagggcatcg tcatagttga    5880
tcaaactgtc cacctgttta gggtcatccc cattatgttc tgtcattgtg gtaaaatgg     5940
gatacagtga tatattgaag gggaatggtt ataagagcct acctgagaaa taaaattatt    6000
atgcgccatc cgacatccag aaaaattgat gaaagattgg ctattgttga cggttcttga    6060
tcccaaaaaa aaaaaaaaac aagaaatgct gccgtcctag ttttgcttca agaatggtt     6120
tcgtgctatg ccattcccaa cccaaagagc tgtcccatcc cattaagttg tgctgactga    6180
ttatgttgca aatccagtg tcgtgattac ctccaacatc gcacgcgaat ttcgccatgg     6240
ctgggaaacc caaattcttc ggtcgtccat caaactctga agtcatttca acaccaaact    6300
caacagctat catagaaaaa tatggcgggg ttgcgttttt tagacattgc aagaccattt    6360
gtcagctgga tcccggaagt tgaacttcct tatgaaaact gggggttcga tgaaaagctg    6420
atttactcat ttttcactgc tgccatctat ttgattctgt ccctgcctat atacggtgtc    6480
aaatcctctg aagtcgtgga cccagttccc catttgcgtt ctgccttagg gagtgagaag    6540
ggaacattgc tggagcttgg gttactgcct gtgattactt cggcatttat cttgcagttg    6600
ttggctggtt ggaaagtttt caaagtaaac tttgatctgg ttagtgacag aatattgttc    6660
caaactttgc aaaagatcac ttcagtcgtt atcagcatcg tatatgctgt tcttctcaca    6720
ttttgtgact actttactcc aggtgtgtcc actgataacg tcttgtggtc ccaatttctg    6780
atcatcttac agatagtggt ggtcaacttc ttggttactc tactcgttga agtcattgac    6840
aaggattacg gattttcttc aggagctcta ttgttgcttg cggtttattc cgccaccaac    6900
ttcgttttg gcacgattgg tcttagcacc gtcaacacct ccagatcgaa cgaatctatt    6960
ggtgctctga ttcaattatt ccgcaatttg agctctaaac caattggtgt tgccatatat    7020
gactccttct tcagagtaaa ccttcctaac ttgactcaat tttatctggg gattgccatt    7080
atttgtgttt gtctgttctt gaataatgca agatacgaag taccaattaa gccaaacaag    7140
gttcgtgcca tggcctcagc ttacccaatc aagctacttt tcaatggttc tttgccactt    7200
ctgtacacgt ggactgtgct gtacaacttg aaccttattg gtttctttgt cttcaagctt    7260
accaactttt ctcttttagg gaacttcaaa gtggacccat tcggcaacaa ctactacgaa    7320
attacatctg gactgctgta tttattgact cctactttca acgctgaagc tggacttta    7380
cccaatgttg ctaagccatt tgttttcatt gccttctatg ttggtgttag cactttcttt    7440
gctagatcgt ggtccaacat taacgggtcg tcaggcaagg acattgccaa gtttttcaag    7500
gctcaaggaa tctcattgtt aggaaaaaga gatgcctctg tgtctaaaga gtttaacacc    7560
ctagttcctg ttgcttctgc ctctggagct ttcctattgt cttttccagt tgccgtcgct    7620
gagttattgg gtggctctgg tgttccaacc tctatcggaa tcggtctttt gagtggtttg    7680
gctattttgg aaactgtttt gcaagaatgg caacagtctg gaggtgcctc acagttctcc    7740
caatacttcc agacttctta ggtttagaaa tccttgaaga ctatccagac attcaccgc    7800
acctcaattt accttctaca tacatcacat attctataga ggagagttcc attgctcgta    7860
ctgaacccca caccactctt ctttataccc tacaaactct tcgtccaact caatggcgtc    7920
attcgtgtcg gtatagacaa taatggtacc ccagtccatt tcaaagttgt cttttttcgat    7980
atccatgatt aatttgggca ttatttgaag ttcgaactgt tttcctggca ctttagcttt    8040
```

```
gatgatcgtt tgatatattt catccttgga gttatacagt agtggctttc ctcccaggtg    8100
gtatcgtaaa acctgggaag gattgtgctc aagagccaac tccctttaca acctcactca    8160
agtccgttag agggcgcgcc gcacatgaag ctgtacatgg aaggcacggt gaataaccac    8220
cacttcaaat gcaccagcga gggtgagggt aaaccgtatg aaggcaccca aacgatgcgt    8280
atcaaagttg ttgagggtgg cccgttgccg tttgcgttcg acattttagc gacgagcttt    8340
atgtatggct ctcgtacgtt tatcaagtac ccgaagggta ttccggactt tttcaaacaa    8400
tcttttccag agggtttcac ctgggagcgc gtgactcgct acgaagatgg cggcgtcgtg    8460
accgcaacgc aggataccte cctggaagat ggctgcctgg tctaccacgt tcaggtccgt    8520
ggtgtcaatt tcccgagcaa tggtccggtt atgcagaaga aaccctgggt ttgggaaccg    8580
aacaccgaga tgttgtatcc tgcagatggt ggcctggaag gtcgcagcga catggcattg    8640
aaactggtcg gtggcggcca tctgagctgt agcttcgtga ccacgtatcg ttcgaagaaa    8700
acggtcggta acatcaaaat gccgggtatt cacgcgttg accaccgtct ggtgcgcatt    8760
aaagaagccg acaaagagac ttacgtggag caacatgaag tagccgttgc gaaatttgct    8820
ggtttgggcg gtggtatgga cgaactgtac agttccttat catctggcga atcggaccca    8880
caagagcact gggttccgtt ttacattcca ggaagagttt cagtaatgtc ttgtttcttt    8940
tgttgcagtg gtgagccatt ttgacttcgt gaaagtttct ttagaatagt tgttccaga    9000 ggccaaacat tccacccgta gtaaagtgca agcgtaggaa gaccaagact ggcataaatc    9060
aggtataagt gtcgagcact ggcaggtgat cttctgaaag tttctactag cagataagat    9120
ccagtagtca tgcatatggc aacaatgtac cgtgtggatc taagaacgcg tcctactaac    9180
cttcgcattc gttggtccag tttgttgtta tcgatcaacg tgacaaggtt gtcgattccg    9240
cgtaagcatg catacccaag gacgcctgtt gcaattccaa gtgagccagt tccaacaatc    9300
tttgtaatat tagagcactt cattgtgttg cgcttgaaag taaaatgcga acaaattaag    9360
agataatctc gaaaccgcga cttcaaacgc caatatgatg tgcggcacac aataagcgtt    9420
catatccgct gggtgacttt ctcgctttaa aaaattatcc gaaaaaattt ttgacggcta    9480
gctcagtcct aggtacgcta gcattaaaga ggagaaaatg actactcttg atgacacagc    9540
ctacagatat aggacatcag ttccgggtga cgcagaggct atcgaagcct tggacggttc    9600
attcactact gatacggtgt ttagagtcac cgctacaggt gatggcttca ccttgagaga    9660
ggttcctgta gacccaccct taacgaaagt tttccctgat gacgaatcgg atgacgagtc    9720
tgatgctggt gaggacggtg accctgattc cagaacattt gtcgcatacg gagatgatgg    9780
tgacctggct ggctttgttg tggtgtccta cagcggatgg aatcgtagac tcacagttga    9840
ggacatcgaa gttgcacctg aacatcgtgg tcacggtgtt ggtcgtgcac tgatgggact    9900
ggcaacagag tttgctagag aaagaggagc cggacatttg tggttagaag tgaccaatgt    9960
caacgctcct gctattcacg catataggcg aatgggtttc actttgtgcg gtcttgatac   10020
tgctttgtat gacggaactg cttctgatgg tgaacaagct ctttacatga gtatgccatg   10080
tccatagcac gtccgacggc ggcccacggg tcccaggcct cggagatccg tcccccttt    10140 cctttgtcga tatcatgtaa ttagttatgt cacgcttaca ttcacgccct ccccccacat   10200
ccgctctaac cgaaaaggaa ggagttagac aacctgaagt ctaggtccct atttattttt   10260
ttatagttat gttagtatta agaacgttat ttatatttca aattttttct ttttttctgt   10320
acagacgcgt gtacgcatgt aacattatac tgaaaacctt gcttgagaag gttttgggac   10380
```

```
gctcgaaggc tttaatttgc aagctccgaa taacttcgta tagcatacat tataccttgt    10440
tattacagcg gccgcaaata ttttatctga ttaataagat gatcttcttg agatcgtttt    10500
ggtctgcgcg taatctcttg ctctgaaaac gaaaaaaccg ccttgcaggg cggttttttcg   10560 aaggttctct gagctaccaa ctctttgaac cgaggtaact ggcttggagg agcgcagtca    10620
ccaaaacttg tcctttcagt ttagccttaa ccggcgcatg acttcaagac taactcctct    10680
aaatcaatta ccagtggctg ctgccagtgg tgcttttgca tgtctttccg ggttggactc    10740
aagacgatag ttaccggata aggcgcagcg gtcggactga acgggggggtt cgtgcataca   10800 gtccagcttg gagcgaactg cctacccgga actgagtgtc aggcgtggaa tgagacaaac    10860
gcggccataa cagcggaatg acaccggtaa accgaaaggc aggaacagga gagcgcacga    10920
gggagccgcc aggggggaaac gcctggtatc tttatagtcc tgtcgggttt cgccaccact   10980
gatttgagcg tcagatttcg tgatgcttgt caggggggcg gagcctatgg aaaaacggct    11040
ttgccgcggc cctctcactt ccctgttaag tatcttcctg gcatcttcca ggaaatctcc    11100
gccccgttcg taagccattt ccgctcgccg cagtcgaacg accgagcgta gcgagtcagt    11160
gagcgaggaa gcggaatata tcctgtatca catattctgc tgacgcaccg gtgcagcctt    11220
ttttctcctg ccacatgaag cacttcactg acaccctcat cagtgccaac atagtaagcc    11280
agtatacact ccgctagcgc tgatgtccgg cggtgcgacg tc                       11322
```

<210> SEQ ID NO 97
<211> LENGTH: 888
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97

```
caactttctg ccgccaatct cctttccatt caaattctct acaacaaggc aggcttcgtc      60
cgttgatgtg aagtttgcaa agccaaaacc acgaaaaaca ccattgtcaa aatggtagtt    120
gaaggcataa ggcaaaggca agctaaaactt tgtcataacg tctaaaagtt gctcttttt     180 tatggcaaaa gggatgttct ttatcacaat agcagtggga atgacatctt catcatcatt    240
cgtatcatca ataccatcga gttctgaatc caaaggtttc tgttgttggg ataaggcatc    300
agattctttg agcaggtcgt ccttggcgtc ctcctctaga tgaaatttgc catcgttagg    360
aggtgagtat tgggaaacgt tgacttgttg ctcaatccaa ggatcaacgt tgaccatcgg    420
attgccgttc tgaggagaca gccaggcatt ataccgtggt tgaccggcgt ttacgcgcag    480
aggattgttg ctggtgttgt tgacagaaga cgcatacccca gacgctgcgg atgacatcga    540
cgaaattgaa gggcgacgtt gcatacccat ttgttgctga tccaagaaac ttggtgtttc    600
agtcaattgt ctcaggtcca tattgatcaa tgtgttcaac tgtttcaatc tggttccgga    660
gggtggctat tacgacaagc tgtggctact atctaagtgg gagaagtaac ggaacacatt    720
gatgagacac aggaattaca gggcgtgcat ccaccaataa caattagtcg agatttcaac    780
caattacgta agcgctcaac cctttttcg aacacgtatc gagcaaagtc caggtgaaac     840
cttcatccat tatatccaaa gtcgaccgaa gctttaacaa catccata                  888
```

<210> SEQ ID NO 98
<211> LENGTH: 953
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 98

```
agacaagtgg agagtggaca aattcttgat gttaattcgt aagatcctta acaaatcttt      60
agcaaaactg aaaagtgaag actacgatag ggatttactt gaaaaatata ttcaagtttt     120
gtcagaatac ccactccata ttaacgatat tattgtccct agaactatta cgtaccactt     180
gtgtgatatt tatactgatg agttggaaaa ggttatgttt agtgggcttc ctggatttga     240
agaagaagaa gattacgagg aagaagatga agtctcggct cctatcgaaa aaaaaaccag     300
agatactgat aattcagacg atgaggcctc tgataccgat ccagaaacga gtgacgaaga     360
agacgaaggt gagaatactg aaaacgagtc agaagaggaa ccgatcaaac tctctgcgga     420
agaagaaacg gctctgtgga aaacaaagat ggagattatc catgaaactc ctatcgacaa     480
attactctca cctttgtct cattgaagaa agatacctca ataaaccat taaaattgaa      540
aatccaagaa gcagttcttg ctgatccaag actcggcaaa tggaaagtta atcgtaccg      600
aaagcctaaa ccaaaaccaa aacctcttca ggtgctacag aaacagttat acgaacagat     660
caaatataaa aagggtaaag cagtcacagg tgaagacgac gatgaactca agacgaaga     720
cgaagatgac gatgacgagg tcatctcgga gagtgaagct gataactctg atgaagaaga     780
agatgaagaa tggaatggct ttggaactat ctagaataca tatgtaaaac catatcaggc     840
aataacaatt tctcgctatt tgcatccca acacctcgac cgacgtgttc agttcgaccc      900
tttacctaca gtgtctttaa ctcccatttg gatctcctaa ataacctaca caa            953
```

<210> SEQ ID NO 99
<211> LENGTH: 991
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99

```
tctgaacggg tctttgagct gtctgtgtca tcaaacatat cttcatctgt agttgtattg      60
ttttctttta tcactaggag tccatccttc tggatggctg tcttgcactt atttagccac     120
tccaaaaatg ccgggtctgg agatgaccg cagcaccatt gacaccatat cagagagtat     180
cgagactcct ctggtttcca gtcttgcatg ggaatttcat aaatgtctcc tatcttacct     240
tgttccatca gtgtttgtag ttccaccctc atctggtcga caaatggttt aactggttcc     300
aataaatcaa ccttatcaca aactttatgc agaaaatctc ttgtcacgcg gccaataccg     360
gcaccaaagt ctataccata tttgattttg tcaggatcgt tagagaaacg actctttaac     420
tttcttaaaa aggtcatcga tccaacaaca tctgcttttg gaaccgaagt tgtctcaccg     480
tacccaccca aaactccgtc gacagatgct gggacgctgt tccagtattt cagggcatcg     540
tcatagttga tcaaactgtc cacctgttta gggtcatccc cattatgttc tgtcattgtg     600
gtaaaaatgg gatacagtga tatattgaag gggaatggtt ataagagcct acctgagaaa     660
taaaattatt atgcgccatc cgacatccag aaaaattgat gaaagattgg ctattgttga     720
cggttcttga tcccaaaaaa aaaaaaaaac aagaaatgct gccgtcctag ttttgcttca     780
aagaatggtt tcgtgctatg ccattcccaa cccaaagagc tgtcccatcc cattaagttg     840
tgctgactga ttatgttgca caatccagtg tcgtgattac ctccaacatc gcacgcgaat     900
ttcgccatgg ctgggaaacc caaattcttc ggtcgtccat caaactctga agtcatttca     960
```

```
acaccaaact caacagctat catagaaaaa t                                  991
```

<210> SEQ ID NO 100
<211> LENGTH: 460
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100

```
gacctatatt taaacaggtt tcatcatatc tgtactatat ttacaagtcc actgcgttta    60
ggtatatact aaagacattc aagaagcaca tccacaactt gtgcaagtcc tgtcaaatgt   120
actagatgct tttcagaaca tcctgcggtt tgaggagatt cctgaatttc ccagtcccaa   180
gtctttctct tgtagaggtc tttgagttct tgtgaatgct gaattggggt tcttacctca   240
atttctatta gtgggaaatg ctttcccaca attatttgca atgggatccc ggcaacttta   300
ctttgcttca acttatgtcc catactgaac tttccgtcac ggttgtcaac ttgaacgtcg   360
aatgagctca gtatttcggt gacagtgtct agattctttt tacttgatgt tttattcgaa   420
agtagcgtga tttgatatgg tgcgataatt tgtggccagg                         460
```

<210> SEQ ID NO 101
<211> LENGTH: 492
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101

```
aagtttaggt ttgaatacaa tgtgtatgct taattatatt cacttcgttt cattgatttt    60
tgctatccct gttgtgcgtt aatcatctct atcgtgatcc tctcaagttg cacctcaaat   120
agaagacaac ttatggaggt gtactaccca atatcagtct tgacgtttct agtttcgttg   180
tatgctgcat accaatttca gttcttccgt agtgttttga gcataggctt gtttacccgt   240
cttctttaca ctctgatatg agcacccttat caaacctctt atcacagctg aaaggagaag   300
gcggtggtgg ttcttctggt cagaatcggc ccagaactgt ggatcctgct gttgcaagat   360
tgaaagcaga aaggaagatg gaaagagaga agcaagctct taaagaggct cagcaagccc   420
aggaagctcg ggaaaggcga agaattagtc atgctaccca gataggtttg agaccaacca   480
gtaaagctcc ca                                                       492
```

<210> SEQ ID NO 102
<211> LENGTH: 371
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102

```
gtttagaaat ccttgaagac tatccagaca ttcacccgca cctcaattta ccttctacat    60
acatcacata ttctatagag gagagttcca ttgctcgtac tgaaccccac accactcttc   120
tttatcccct acaaactctt cgtccaactc aatggcgtca ttcgtgtcgg tatagacaat   180
aatggtaccc cagtccattt caaagttgtc tttttcgata tccatgatta atttgggcat   240
tatttgaagt tcgaactgtt ttcctggcac tttagctttg atgatcgttt gatatatttc   300
```

```
atccttggag ttatacagta gtggctttcc tcccaggtgg tatcgtaaaa cctgggaagg    360
attgtgctca a                                                         371

<210> SEQ ID NO 103
<211> LENGTH: 1487
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
ttcagtaatg tcttgtttct tttgttgcag tggtgagcca ttttgacttc gtgaaagttt     60
ctttagaata gttgtttcca gaggccaaac attccacccg tagtaaagtg caagcgtagg    120
aagaccaaga ctggcataaa tcaggtataa gtgtcgagca ctggcaggtg atcttctgaa    180
agtttctact agcagataag atccagtagt catgcatatg caacaatgt accgtgtgga    240 tctaagaacg cgtcctacta accttcgcat tcgttggtcc agtttgttgt tatcgatcaa    300
cgtgacaagg ttgtcgattc cgcgtaagca tgcatacccca aggacgcctg ttgcaattcc    360
aagtgagcca gttccaacaa tctttgtaat attagagcac ttcattgtgt tgcgcttgaa    420
agtaaaatgc gaacaaatta agagataatc tcgaaccgc gacttcaaac gccaatatga    480
tgtgcggcac acaataagcg ttcatatccg ctgggtgact ttctcgcttt aaaaaattat    540
ccgaaaaaat ttttgacggc tagctcagtc ctaggtacgc tagcattaaa gaggagaaaa    600
tgactactct tgatgacaca gcctacagat ataggacatc agttccgggt gacgcagagg    660
ctatcgaagc cttggacggt tcattcacta ctgatacggt gtttagagtc accgctacag    720
gtgatggctt caccttgaga gaggttcctg tagacccacc cttaacgaaa gttttccctg    780
atgacgaatc ggatgacgag tctgatgctg gtgaggacgg tgaccctgat tccagaacat    840
ttgtcgcata cggagatgat ggtgacctgg ctggctttgt tgtggtgtcc tacagcggat    900
ggaatcgtag actcacagtt gaggacatcg aagttgcacc tgaacatcgt ggtcacggtg    960
ttggtcgtgc actgatggga ctggcaacag agtttgctag agaaagagga gccggacatt   1020
tgtggttaga agtgaccaat gtcaacgctc ctgctattca cgcatatagg cgaatgggtt   1080
tcactttgtg cggtcttgat actgctttgt atgacggaac tgcttctgat ggtgaacaag   1140
ctctttacat gagtatgcca tgtccatagc acgtccgacg gcggcccacg ggtcccaggc   1200
ctcggagatc cgtccccctt ttcctttgtc gatatcatgt aattagttat gtcacgctta   1260
cattcacgcc ctccccccac atccgctcta accgaaaagg aaggagttag acaacctgaa   1320
gtctaggtcc ctatttattt ttttatagtt atgttagtat taagaacgtt atttatattt   1380
caaatttttc ttttttttct gtacagacgc gtgtacgcat gtaacattat actgaaaacc   1440
ttgcttgaga aggttttggg acgctcgaag gctttaattt gcaagct                 1487

<210> SEQ ID NO 104
<211> LENGTH: 189
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Met Thr Thr Leu Asp Asp Thr Ala Tyr Arg Tyr Arg Thr Ser Val Pro
1               5                   10                  15
```

```
Gly Asp Ala Glu Ala Ile Glu Ala Leu Asp Gly Ser Phe Thr Thr Asp
            20                  25                  30

Thr Val Phe Arg Val Thr Ala Thr Gly Asp Gly Phe Thr Leu Arg Glu
        35                  40                  45

Val Pro Val Asp Pro Pro Leu Thr Lys Val Phe Pro Asp Asp Glu Ser
 50                  55                  60

Asp Asp Glu Ser Asp Ala Gly Glu Asp Gly Asp Pro Asp Ser Arg Thr
 65                  70                  75                  80

Phe Val Ala Tyr Gly Asp Asp Gly Asp Leu Ala Gly Phe Val Val Val
                85                  90                  95

Ser Tyr Ser Gly Trp Asn Arg Arg Leu Thr Val Glu Asp Ile Glu Val
               100                 105                 110

Ala Pro Glu His Arg Gly His Gly Val Gly Arg Ala Leu Met Gly Leu
            115                 120                 125

Ala Thr Glu Phe Ala Arg Glu Arg Gly Ala Gly His Leu Trp Leu Glu
130                 135                 140

Val Thr Asn Val Asn Ala Pro Ala Ile His Ala Tyr Arg Arg Met Gly
145                 150                 155                 160

Phe Thr Leu Cys Gly Leu Asp Thr Ala Leu Tyr Asp Gly Thr Ala Ser
                165                 170                 175

Asp Gly Glu Gln Ala Leu Tyr Met Ser Met Pro Cys Pro
            180                 185

<210> SEQ ID NO 105
<211> LENGTH: 207
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
gctccagtca acactacaac agaagatgaa acggcacaaa ttccggctga agctgtcatc      60
ggttactcag atttagaagg ggatttcgat gttgctgttt tgccattttc caacagcaca     120
aataacgggt tattgtttat aaatactact attgccagca ttgctgctaa agaagaaggg     180
gtatctctcg agaaaagaga ggctgaa                                        207

<210> SEQ ID NO 106
<211> LENGTH: 69
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Ala Pro Val Asn Thr Thr Thr Glu Asp Glu Thr Ala Gln Ile Pro Ala
 1               5                  10                  15

Glu Ala Val Ile Gly Tyr Ser Asp Leu Glu Gly Asp Phe Asp Val Ala
            20                  25                  30

Val Leu Pro Phe Ser Asn Ser Thr Asn Asn Gly Leu Leu Phe Ile Asn
        35                  40                  45

Thr Thr Ile Ala Ser Ile Ala Ala Lys Glu Glu Gly Val Ser Leu Glu
 50                  55                  60

Lys Arg Glu Ala Glu
65
```

```
<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

His His His His His His His His
1               5
```